United States Patent
Ranum et al.

(10) Patent No.: US 12,360,124 B2
(45) Date of Patent: Jul. 15, 2025

(54) USE AND TREATMENT OF DI-AMINO ACID REPEAT-CONTAINING PROTEINS ASSOCIATED WITH ALS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 18/668,571

(22) Filed: May 20, 2024

(65) Prior Publication Data

US 2024/0393348 A1 Nov. 28, 2024

Related U.S. Application Data

(62) Division of application No. 17/322,604, filed on May 17, 2021, now Pat. No. 12,025,622, which is a division of application No. 16/851,690, filed on Apr. 17, 2020, now Pat. No. 11,035,867, which is a division of application No. 16/362,908, filed on Mar. 25, 2019, now Pat. No. 10,663,475, which is a division of application No. 14/775,278, filed as application No. PCT/US2014/022670 on Mar. 10, 2014, now Pat. No. 10,295,547.

(60) Provisional application No. 61/883,219, filed on Sep. 27, 2013, provisional application No. 61/786,258, filed on Mar. 14, 2013.

(51) Int. Cl.
*A61K 31/155* (2006.01)
*A61K 35/28* (2015.01)
*B01D 21/26* (2006.01)
*C07K 16/18* (2006.01)
*C12Q 1/6883* (2018.01)
*G01N 33/68* (2006.01)

(52) U.S. Cl.
CPC ......... *G01N 33/6896* (2013.01); *A61K 35/28* (2013.01); *B01D 21/262* (2013.01); *C07K 16/18* (2013.01); *C12Q 1/6883* (2013.01); *C07K 2317/34* (2013.01); *C12Q 2600/158* (2013.01); *G01N 2800/2835* (2013.01); *G01N 2800/285* (2013.01)

(58) Field of Classification Search
None
See application file for complete search history.

(56) References Cited

U.S. PATENT DOCUMENTS

| | | |
|---|---|---|
| 5,011,912 A | 4/1991 | Hopp et al. |
| 6,204,008 B1 * | 3/2001 | Borneman ............ C07K 14/415 435/219 |
| 6,342,581 B1 | 1/2002 | Rosen et al. |
| 7,481,997 B1 | 1/2009 | Hardy |
| 8,993,633 B2 | 3/2015 | Megeney et al. |
| 9,448,232 B2 | 9/2016 | Petrucelli et al. |
| 10,295,547 B2 | 5/2019 | Ranum et al. |
| 10,509,045 B2 | 12/2019 | Ranum et al. |
| 10,663,475 B2 | 5/2020 | Ranum et al. |
| 10,940,161 B2 | 3/2021 | Ranum et al. |
| 11,034,974 B2 | 6/2021 | Ling et al. |
| 11,345,911 B2 | 5/2022 | Ranum et al. |
| 12,025,622 B2 | 7/2024 | Ranum et al. |
| 2002/0165355 A1 | 11/2002 | Meheus et al. |
| 2003/0233675 A1 | 12/2003 | Cao et al. |
| 2005/0042657 A1 | 2/2005 | Weese-Mayer et al. |
| 2006/0068434 A1 | 3/2006 | Stoerker |
| 2007/0004729 A1 | 1/2007 | Timmer et al. |
| 2007/0014810 A1 | 1/2007 | Baker et al. |
| 2007/0036760 A1 | 2/2007 | Wilson et al. |
| 2007/0093426 A1 | 4/2007 | Wormser |
| 2008/0227699 A1 | 9/2008 | Chiba et al. |
| 2009/0074721 A1 | 3/2009 | Kim et al. |
| 2009/0143418 A1 | 6/2009 | Dixon et al. |
| 2009/0312395 A1 | 12/2009 | El-Tanani et al. |
| 2010/0298280 A1 | 11/2010 | Kioschis-Schneider et al. |
| 2012/0076785 A1 | 3/2012 | Nikolaev et al. |
| 2012/0094299 A1 | 4/2012 | Ranum et al. |
| 2012/0220534 A1 | 8/2012 | Levin et al. |
| 2013/0115603 A9 | 5/2013 | Ranum et al. |
| 2014/0336133 A1 | 11/2014 | Miller et al. |
| 2015/0361166 A1 | 12/2015 | Edbauer et al. |
| 2016/0025747 A1 | 1/2016 | Ranum et al. |

(Continued)

FOREIGN PATENT DOCUMENTS

| | | |
|---|---|---|
| EP | 2837390 A1 | 2/2015 |
| EP | 2948471 A1 | 12/2015 |

(Continued)

OTHER PUBLICATIONS

Extended European Search Report, mailed Sep. 30, 2016, in connection with Application No. EP 14776090.4.
International Search Report and Written Opinion, mailed Aug. 22, 2014, in connection with Application No. PCT/US2014/022670.
International Preliminary Report on Patentability, mailed Sep. 24, 2015, in connection with Application No. PCT/US2014/022670.
International Search Report and Written Opinion, mailed Sep. 21, 2016, in connection with Application No. PCT/US2016/034738.
International Preliminary Report on Patentability, mailed Dec. 14, 2017, in connection with Application No. PCT/US2016/034738.
Supplementary Partial European Search Report, mailed Oct. 18, 2019, in connection with Application No. EP 17779695.0.
Extended European Search Report, mailed Jan. 7, 2020, in connection with Application No. EP 17779695.0.

(Continued)

*Primary Examiner* — Agnieszka Boesen
(74) *Attorney, Agent, or Firm* — Wolf, Greenfield & Sacks, P.C.

(57) ABSTRACT

Disclosed herein are methods and compositions for identifying and/or treating subjects having or likely to have amyotrophic lateral sclerosis (ALS) or frontotemporal dementia (FTD). Antibodies specific for one or more di-amino acid repeat-containing proteins are also provided herein.

14 Claims, 35 Drawing Sheets

Specification includes a Sequence Listing.

(56) References Cited

U.S. PATENT DOCUMENTS

| | | |
|---|---|---|
| 2016/0096800 A1 | 4/2016 | Walter et al. |
| 2018/0292416 A1 | 10/2018 | Ranum et al. |
| 2019/0142858 A1 | 5/2019 | Ranum et al. |
| 2019/0153445 A1 | 5/2019 | Seow et al. |
| 2019/0285652 A1 | 9/2019 | Ranum et al. |
| 2020/0140846 A1 | 5/2020 | Ranum et al. |
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |
| 2020/0341012 A1 | 10/2020 | Ranum et al. |
| 2021/0236535 A1 | 8/2021 | Ranum et al. |
| 2021/0285970 A1 | 9/2021 | Ranum et al. |
| 2023/0288434 A1 | 9/2023 | Ranum et al. |

FOREIGN PATENT DOCUMENTS

| | | |
|---|---|---|
| EP | 3440100 A1 | 2/2019 |
| JP | 2019-515894 A | 6/2019 |
| WO | WO 2001/75067 A2 | 10/2001 |
| WO | WO 2006/083800 A2 | 8/2006 |
| WO | WO 2010/115033 A2 | 10/2010 |
| WO | WO 2010/132982 A1 | 11/2010 |
| WO | WO 2013/030588 A1 | 3/2013 |
| WO | WO 2014/114303 A1 | 7/2014 |
| WO | WO 2014/114660 A1 | 7/2014 |
| WO | WO 2014/116865 A1 | 7/2014 |
| WO | WO 2014/159247 A1 | 10/2014 |
| WO | WO 2016/025692 A1 | 2/2016 |
| WO | WO 2017/176813 A1 | 10/2017 |
| WO | WO 2018/035408 A1 | 2/2018 |
| WO | WO 2018/195110 A1 | 10/2018 |
| WO | WO 2019/060918 A1 | 3/2019 |

OTHER PUBLICATIONS

Extended European Search Report, mailed Dec. 17, 2020, in connection with Application No. EP 18786964.9.
International Preliminary Report on Patentability, mailed Oct. 31, 2019, in connection with Application No. PCT/US2018/028015.
Extended European Search Report, mailed Nov. 26, 2021, in connection with Application No. EP 18860923.4.
International Search Report and Written Opinion, mailed Jan. 15, 2019, in connection with Application No. PCT/US2018/052913.
International Preliminary Report on Patentability, mailed Apr. 9, 2020, in connection with Application No. PCT/US2018/052913.
Extended European Search Report, mailed Jun. 11, 2021, in connection with Application No. EP 18859783.5.
International Search Report and Written Opinion, mailed Dec. 6, 2018, in connection with Application No. PCT/US2018/052745.
International Preliminary Report on Patentability, mailed Apr. 9, 2020, in connection with Application No. PCT/US2018/052745.
Invitation to Pay Additional Fees, mailed Nov. 30, 2020, in connection with Application No. PCT/US2020/051671.
International Search Report and Written Opinion, mailed Feb. 9, 2021, in connection with Application No. PCT/US2020/051671.
International Preliminary Report on Patentability, mailed Mar. 31, 2022, in connection with Application No. PCT/US2020/051671.
International Search Report and Written Opinion, mailed Dec. 31, 2020, in connection with Application No. PCT/US2020/051670.
International Preliminary Report on Patentability, mailed Apr. 7, 2022, in connection with Application No. PCT/US2020/051670.
Invitation to Pay Additional Fees, mailed Feb. 19, 2021, in connection with Application No. PCT/US2020/054976.
International Search Report and Written Opinion, mailed Apr. 23, 2021, in connection with Application No. PCT/US2020/054976.
International Preliminary Report on Patentability, mailed Apr. 21, 2022, in connection with Application No. PCT/US2020/054976.
[No Author Listed] Amersham ECL Western Blotting Detection Reagent. Retrieved from the internet under https://www.cytivalifesciences.com/en/us/shop/protein-analysis/blotting-and-detection/blotting-standards-and-reagents/amersham-ecl-western-blotting-detection-reagent-p-05748 on Feb. 22, 2022, 6 pages.
[No Author Listed] CRC group Top> L. K. Housing> Query, after sampling and sampling, was conducted, kept still in whole blood ; CRC Corporation, Jun. 30, 2013. https://web.archive.org/web/20130630024235/http://www.crc-group.co.jp/crc/q_and_a/149.html.
[No Author Listed] EBNA1—Epstein-Barr nuclear antigen 1—Epstein-Barr virus (strain GD1) (HHV-4)—EBNA1 gene & protein, Jan. 2018. 2018. Retrieved from the internet under https://www.uniprot.org/uniprot/Q3KSS4 on Sep. 12, 2018. 6 pages.
[No Author Listed], Abstracts. Medizinische Genetik, Berufsverband Nedizinische Genetik, Muchen, DE. Medgen. Mar. 4, 2016; 28(1):84-232. DOI: 10.1007/s11825-016-0083-5.
Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular a-synuclein prevents cell-to-cell aggregate transmission. J Neurosci. Sep. 26, 2012;32(39):13454-69.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Functional genomics in Drosophila models of human disease. Briefings in Functional Genomics. Aug. 22, 2012;11(5):405-415.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.
Duan et al., Generation of polyclonal antiserum for the detection of methylarginine proteins. J Immunol Methods. Mar. 30, 2007;320(1-2):132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.
Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.
Jin et al., Metformin Protects Cells from Mutant Huntingtin Toxicity Through Activation of AMPK and Modulation of Mitochondrial

(56) References Cited

OTHER PUBLICATIONS

Dynamics. Neuromolecular Med. Dec. 2016;18(4):581-592. doi: 10.1007/s12017-016-8412-z. Epub May 25, 2016. Author Manuscript, 19 pages.

Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.

Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone. 0090803.

Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.

Mirkin, Expandable DNA repeats and human disease. Nature. Jun. 21, 2007;447(7147):932-40. doi: 10.1038/nature05977.

Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.

Satoh et al., Dystrophic neurites express C9orf72 in Alzheimer's disease brains. Alzheimers Res Ther. Aug. 16, 2012;4(4):33. doi: 10.1186/alzrt136. 13 pages.

Sha et al., Treatment implications of C9ORF72. Alzheimer's Res Ther. Nov. 27, 2012;4(6):46. doi: 10.1186/alzrt149. eCollection 2012.

Shoesmith et al., Amyotrophic lateral sclerosis: update for family physicians. Can Fam Physician. Dec. 2006;52(12):1563-9.

Trouth et al., Myasthenia gravis: a review. Autoimmune Dis.; 2012:874680. doi: 10.1155/2012/874680. Epub Oct. 31, 2012.

Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.

Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi: 10.1038/srep26120.

William et al., Old friends on new paths: metformin as an early phase treatment in Huntington's Disease?, Medizinische Genetik, 28, pp. 215-216, Mar. 4, 2016 (Mar. 4, 2016) (Abstract).

Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.

Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.

Yu et al., Developing therapeutic antibodies for neurodegenerative disease. Neurotherapeutics. Jul. 2013;10(3):459-72. doi: 10.1007/s13311-013-0187-4.

Zhang et al., Aggregation-prone c9FTD/ALS poly(GA) RAN-translated proteins cause neurotoxicity by inducing ER stress. Acta Neuropathol. 2014;128:505-24.

Zhou et al., Antibodies inhibit transmission and aggregation of C9orf72 poly-GA dipeptide repeat proteins. EMBO Mol Med. May 2017;9(5):687-702. doi: 10.15252/emmm.201607054.

Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas. 1315438110. Epub Nov. 18, 2013.

\* cited by examiner

| | | Case Information | | | | | RAN Inclusions | | | | |
|---|---|---|---|---|---|---|---|---|---|---|---|
| | Case | C9 EXP | Age | Sex/Race | PMD | DX | GP | PA | PR | GR | GA |
| Hippocampus | 1 | + | 59 | F/W | 4 | ALS | +++ | + | + | ++ | ++ |
| | 2 | + | 42 | M/W | 10 | A/F | +++ | + | NA | NA | NA |
| | 3 | + | 74 | F/W | 16 | FTD | +++ | +++* | +++* | ++ | + |
| | 4 | + | 45 | M/W | 3 | ALS | +++ | - | + | ++ | + |
| | 5 | + | 82 | F/W | 17 | FTD | +++ | + | + | ++ | + |
| | 6 | + | 86 | F/W | 10 | A/F | ++ | - | + | ++ | - |
| | 7 | - | 76 | M/W | 7 | ALS | - | - | - | - | - |
| | 8 | - | 55 | M/W | 7.5 | ALS | - | - | NA | NA | NA |
| | 9 | - | 60 | M/W | 16 | CON | - | - | NA | NA | NA |
| | 10 | - | 81 | M/W | 6 | FTD | - | NA | NA | - | - |
| | 11 | - | 83 | M/W | 17 | FTD+ | - | - | - | - | - |
| | 12 | - | 77 | M/W | 16 | CON | - | - | - | - | - |
| Motor Cortex | 1 | + | 59 | F/W | 4 | ALS | +++ | - | - | ++ | ++ |
| | 2 | + | 42 | M/W | 10 | A/F | +++ | + | + | + | - |
| | 7 | - | 76 | M/W | 7 | ALS | - | - | - | - | - |
| | 8 | - | 55 | M/W | 7.5 | ALS | - | - | - | - | - |
| | 9 | - | 60 | M/W | 16 | CON | - | - | - | - | - |
| Spinal Cord | 2 | + | 42 | M/W | 6 | A/F | + | - | - | - | - |
| | 13 | + | 53 | M/W | 10 | ALS | + | - | - | - | - |
| | 14 | + | 55 | F/W | ? | A/F | + | - | - | - | - |
| | 7 | - | 76 | M/W | 7 | ALS | - | - | - | - | - |
| | 8 | - | 55 | M/W | 7.5 | ALS | - | - | - | - | - |
| | 9 | - | 60 | M/W | 16 | CON | - | - | - | - | - |
| | 15 | - | 64 | F/W | 0 | ALS | - | - | - | - | - |
| | 16 | - | 79 | M/W | 33 | ALS | - | - | - | - | - |
| | 17 | - | 79 | M/W | 10 | ALS | - | - | - | - | - |

(-) no inclusions, (+) occasional, (++) moderate, (+++) numerous inclusions. (.) Variable staining from section to section. DX =diagnosis. FTD=frontrotemporal dementia, ALS=amyotrophic lateral sclerosis. F=female, M-Male, PMD=post-mortem interval. NA = not available. HIPPO=hippocampus, M Cortex = motor cortex. The apparent differences in the frequencies of the various inclusions may reflect differences in protein conformation and epitope availability or differences in the affinities of these antibodies.

FIG. 18

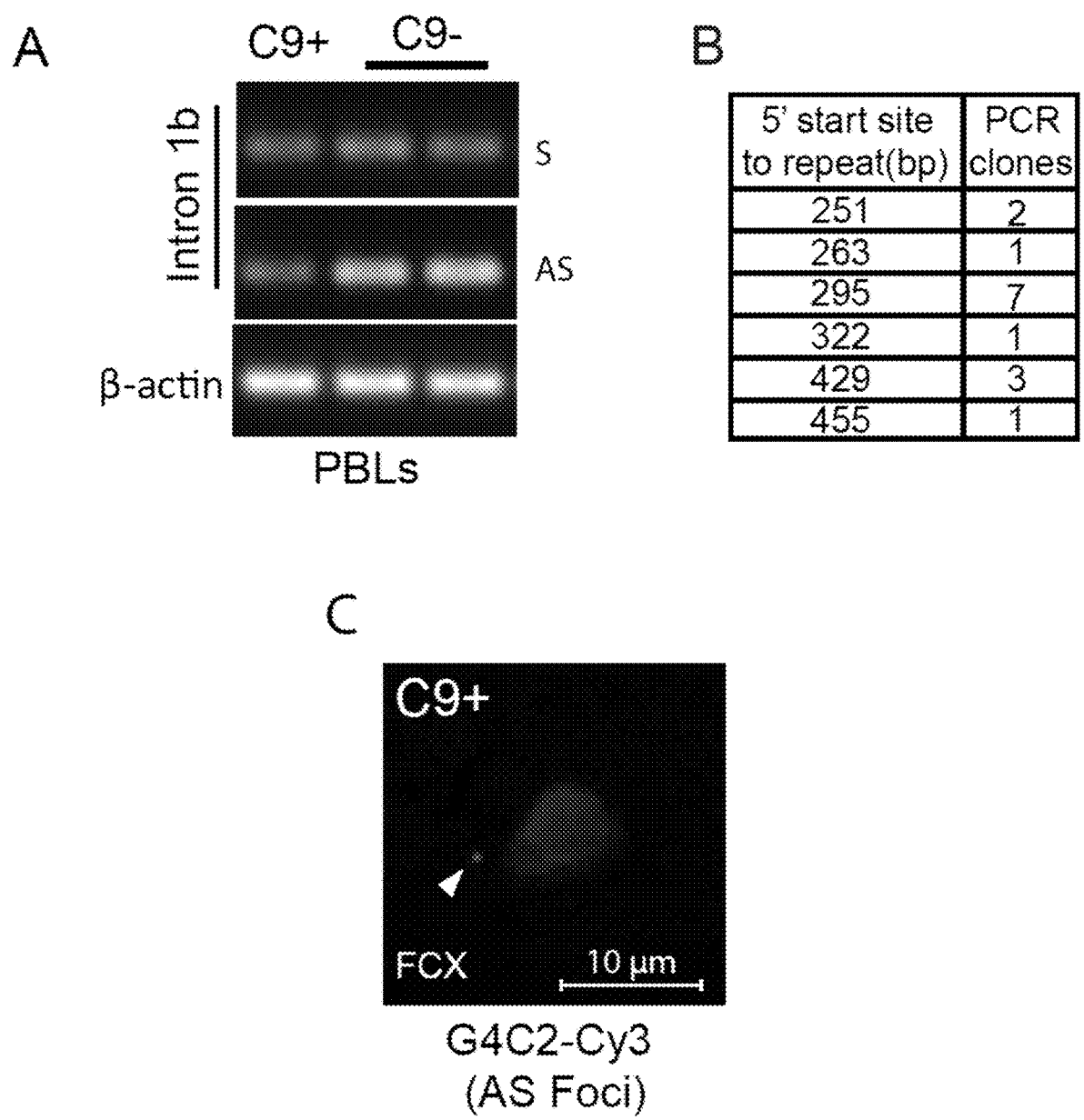
FIG. 19A-C

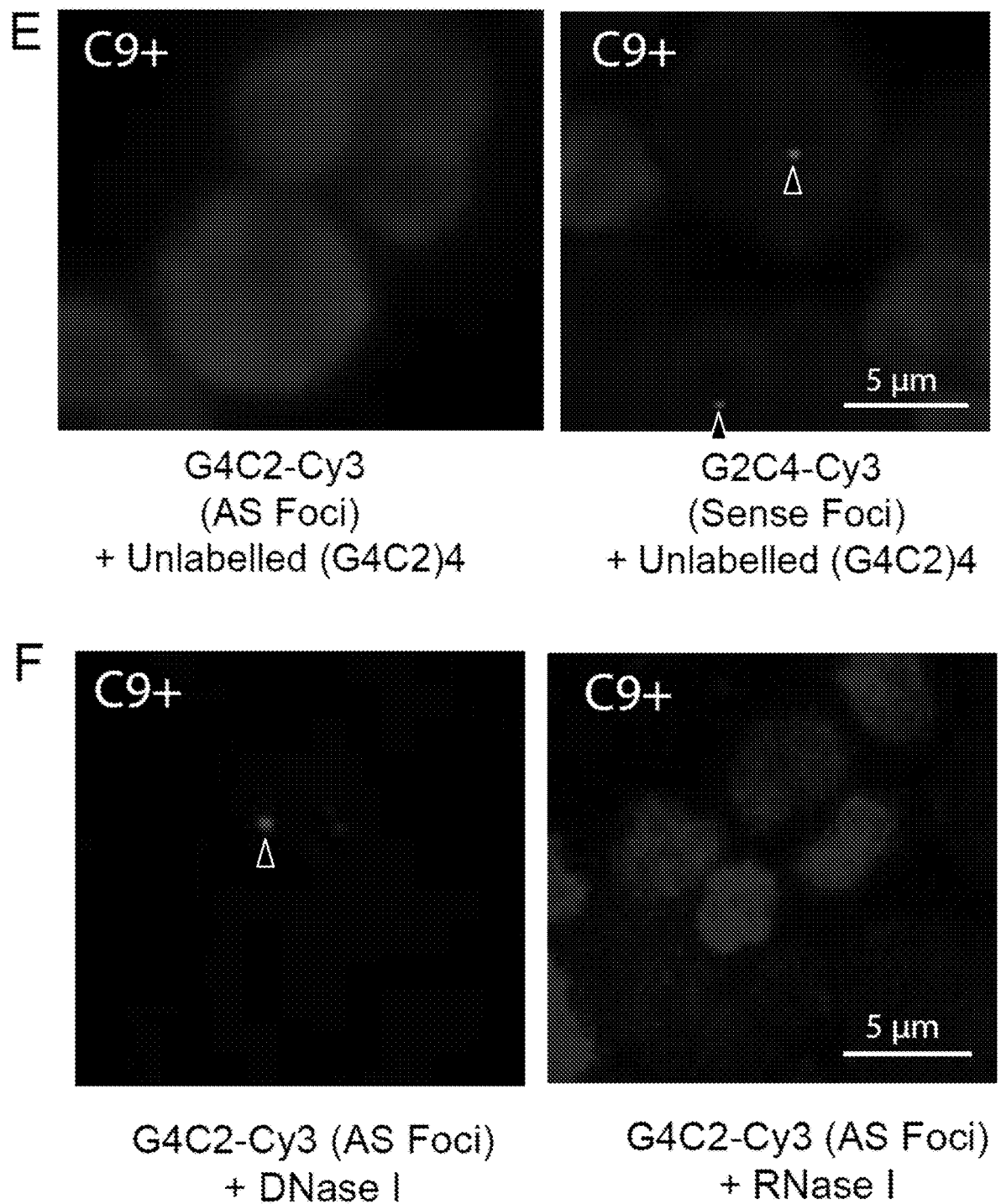
FIG. 19E-F

A
(G4C2)EXP-3T | CMV | 6xStops | (GGGGCC)EXP | Flag(GP)-HA(GR)-Myc(GA) | polyA |
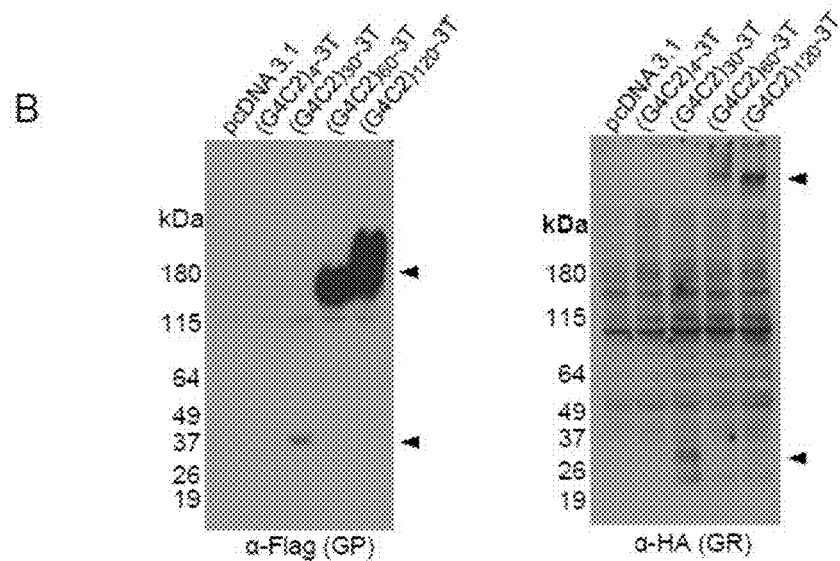
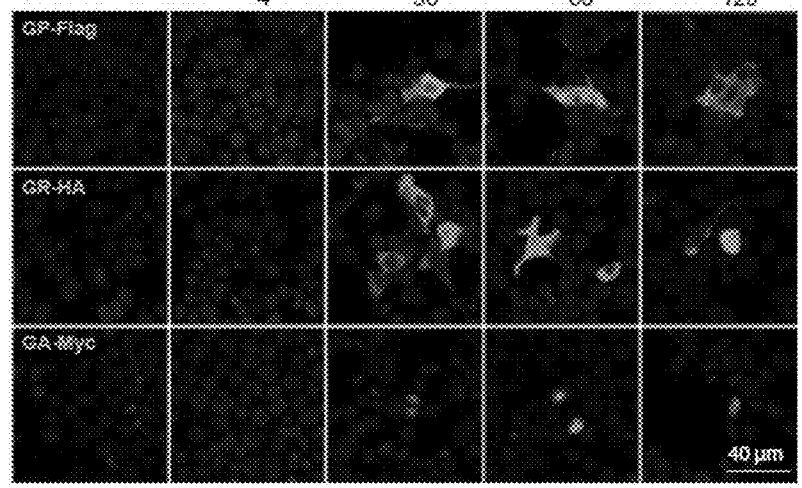
*FIG. 20*

G₂C₄ strand

Frame 1
*GEPPLLPAPLPGSRTPNSHPPGCRLLTHPLATACASAAAGAGTATAAPPRARPRARPQHAPAPA
PAPAPAPAPAPAPA(PA)₁ₓₚPAPAPSARLLSSRACYRLRLFPSLFSSG*

Frame 2
MQAIPPVARGESPTPSFGQRNERESKNASSSEESPRFYPRLFPAAEPQTATRQDAASSLTHSPPP
APPPPRAQAPQPQPRPGPAPGPAPTTPRPRPRPRPRPRPRPRPR(PR)₁ₓₚPRPRPLARDS*

Frame 3
MRGKVKMRRALRRAPASTRASSRQPNPKQPPARMPPPHSPTRHRLRLRRRGRRHRNRSPAPGPPP
GPPRPRPGPGPGPGPGPGPGPGP(GP)₁ₓₚGPGP*

G₄C₂ strand

Frame 1
*GPGPGPGPGPGPGPGPGP(GP)₁ₓₚGPGPGRGRGGPGGGPGAGLRLRCLRPRRRRRRRMRVGE*

Frame 2
*RLTRRKQGGKQPQPVASSGTQESRARGRGRGRGRGRGRGRGRGR(GR)₁ₓₚGRGRGVVGAGPGAG
PGRGCGCGACARGGGGAGGGEWVSEEAASWRVAVWGSAAGKRRG*

Frame 3
*QALELRSRALGAGAGAGAGAGAGAGAGAGA(GA)₁ₓₚGAGAWSGRARGRARGGAAVAVPAPAAAE
AQAVASG*

FIG. 21

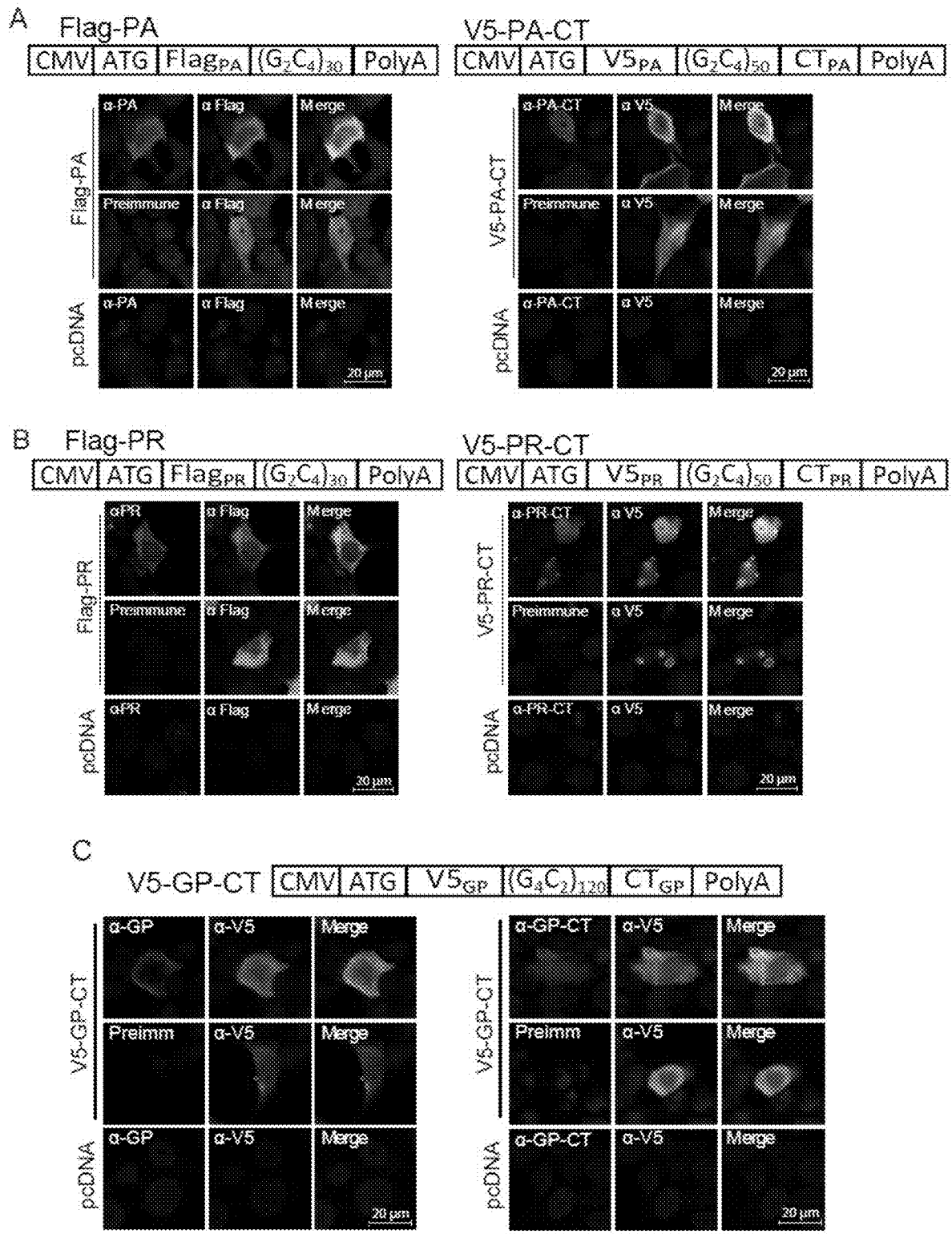
FIG. 22A-C

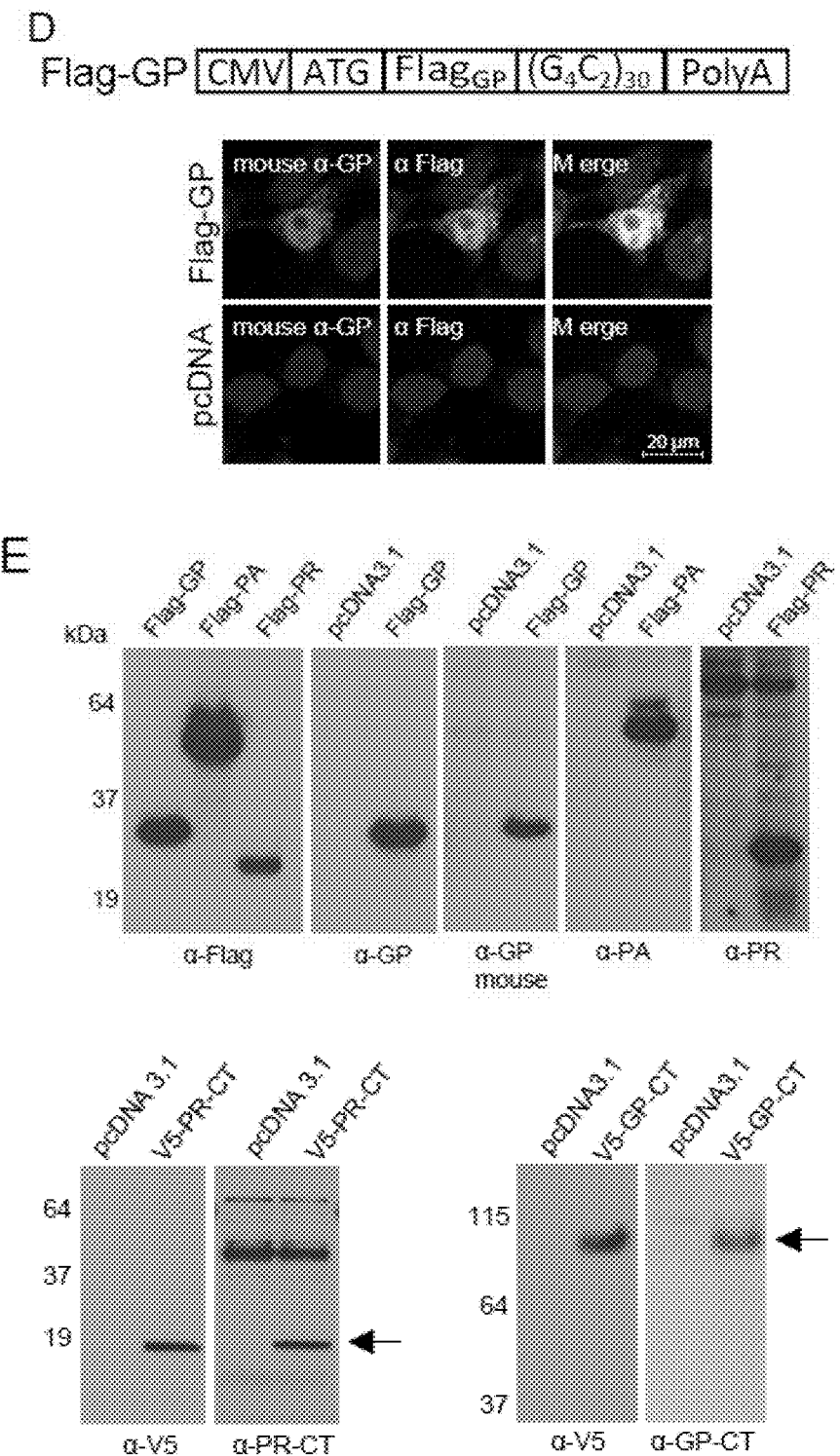
FIG. 22D-E

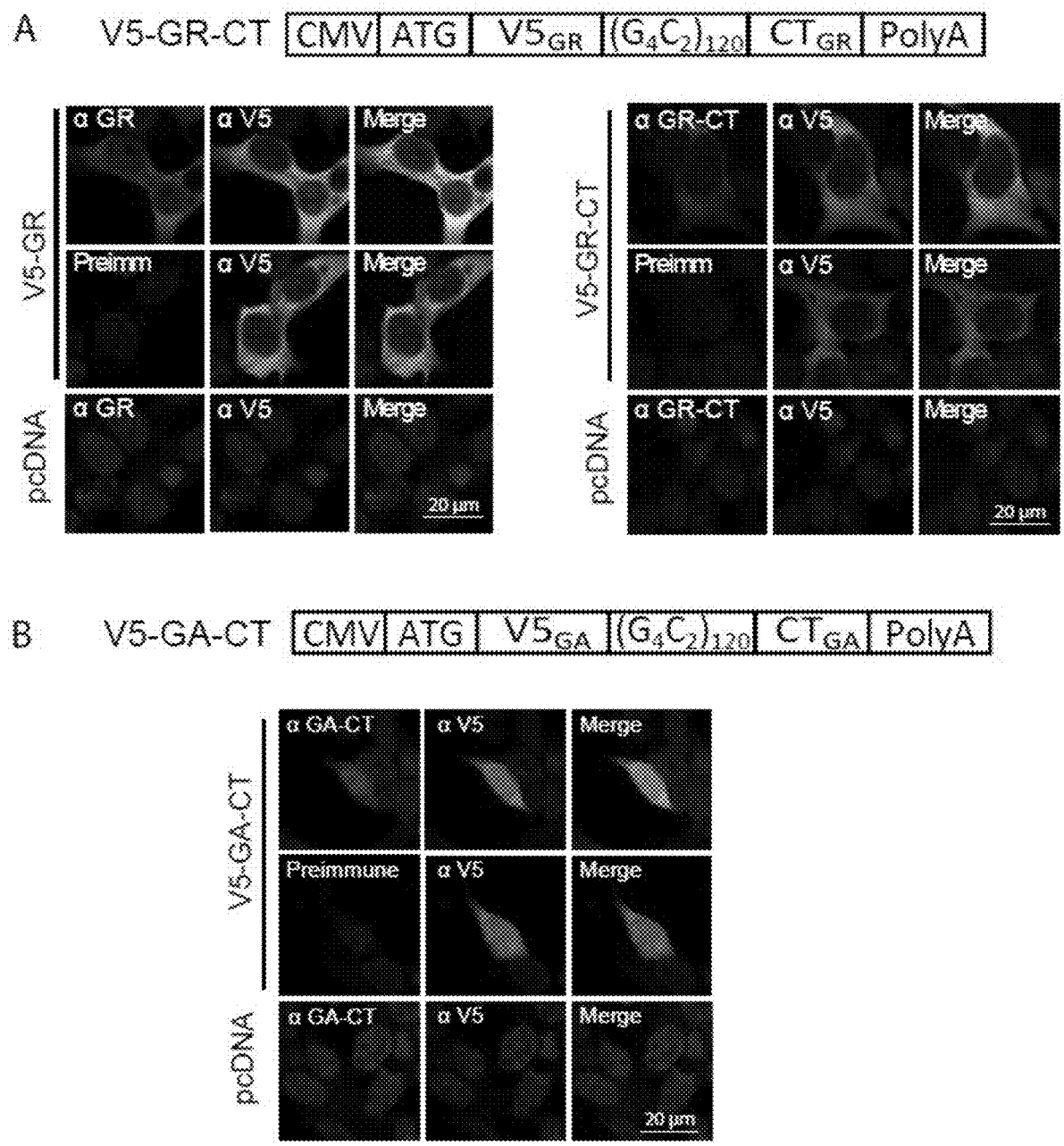
FIG. 23A-B

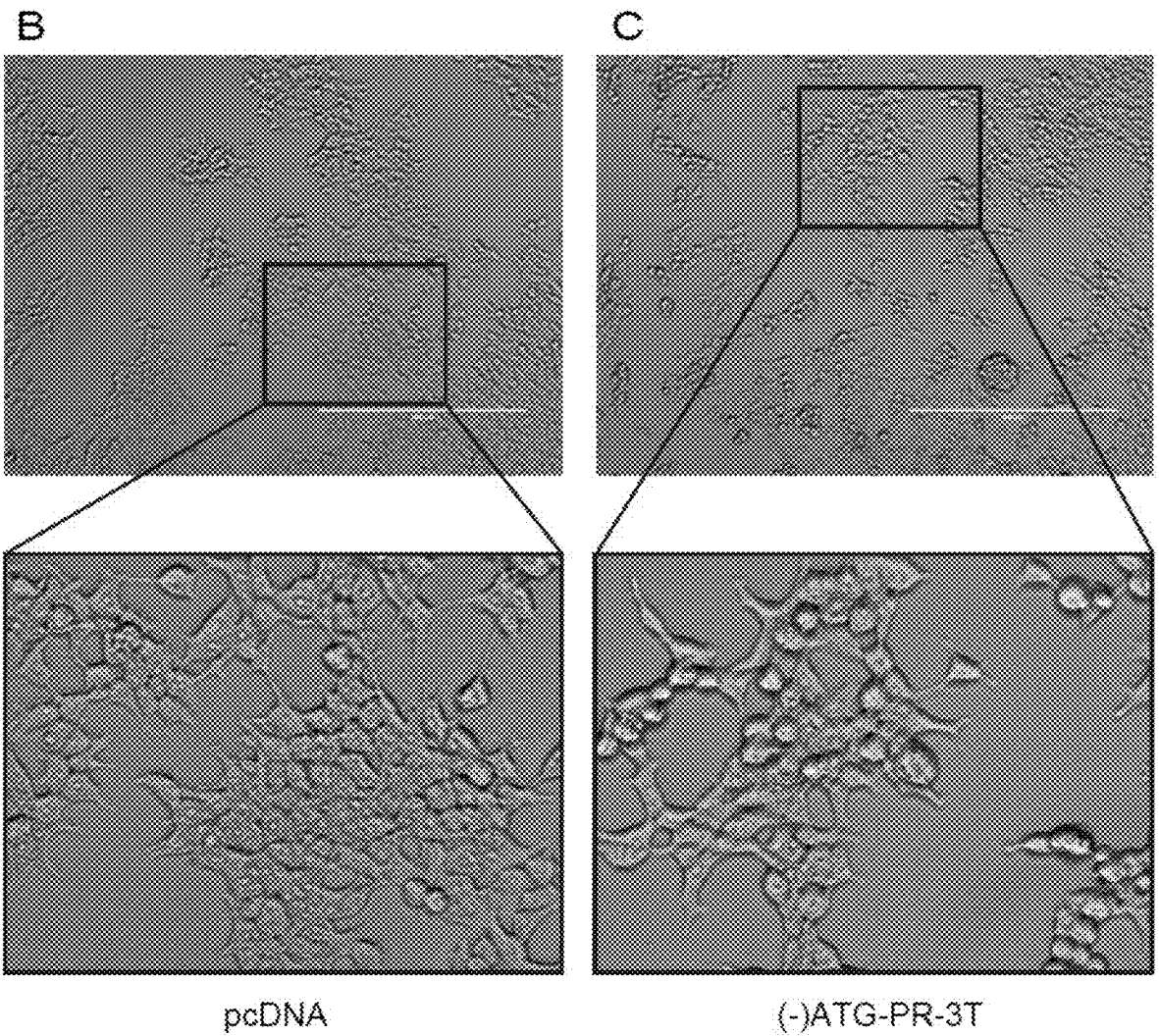
FIG. 26B-C

| Primer Name | Primer Sequence (5' to 3') |
|---|---|
| ASORF-F | AGTCGCTAGAGGCGAAAGC |
| ASORF-R | CGAGTGGGTGAGTGAGGAG |
| LK-ASORF-R | CGACTGGAGCACGAGGACACTGACGAGTGGGTGAGTGAGGAG |
| LK-ASORF-F | CGACTGGAGCACGAGGACACTGAAGTCGCTAGAGGCGAAAGC |
| 1a-F | GCCCACGTAAAAGATGACGC |
| 1a-R | CCTCCTAAACCCACACCTGC |
| LK-1a-R | CGACTGGAGCACGAGGACACTGACCTCCTAAACCCACACCTGC |
| LK-1a-F | CGACTGGAGCACGAGGACACTGAGCCCACGTAAAAGATGACGC |
| LK | CGACTGGAGCACGAGGACACTGA |
| 5'GSP1 | GCTTTCGCCTCTAGCGACT |
| 5'GSP2 | TCTAGCGACTGGTGGAATTGCCT |
| 3'GSP1 | CTGCGGTTGTTTCCCTCCTT |
| 3'GSP2 | TTTCTTGTTCACCCTCAGCGA |
| ACTB3 | CTGGAACGGTGAAGGTGACA |
| ACTB4 | GGGAGAGGACTGGGCCATT |
| 3xTag-Fw | ACGACATCGATTACAAGGACG |
| 3xTag-RV | ATCAGCTTCTGCTCGCTATG |

*FIG. 27*

| Strand | Antigen | ID # | Sequence | Species | IB | IHC | IF |
|---|---|---|---|---|---|---|---|
| AS-G₂C₄ | poly(PA) | H3152 | H2N-APAPAPAPAPAPAPACKKKK-amide | Rabbit | Y | Y | Y |
| | PA C-term | H3159 | Ac-CYRLRLFPSLFSSG-OH | Rabbit | Y | Y | Y |
| | poly(PR) | H3150 | Ac-RPRPRPRPRPRPRPRC-amide | Rabbit | Y | Y | Y |
| | PR C-term | H3162 | Ac-CRPRPLARDS-OH | Rabbit | Y | Y | Y |
| Both Strands | poly(GP) | H3154 | H2N-GPGPGPGPGPGPGPGPGCKK-amide | Rabbit | Y | Y | Y |
| | poly(GP) | F3M1 | H2N-GPGPGPGPGPGPGPGCKK-amide | Mouse | Y | Y | Y |
| S-G₄C₂ | GP C-term | H3157 | Ac-CRRRRWRVGE-OH | Rabbit | Y | Y | Y |
| | poly(GR) | H3148 | Ac-RGRGRGRGRGRGRGRGC-amide | Rabbit | Y | Y | Y |
| | GR C-term | H3160 | Ac-CRVAVWGSAAGKRRG-OH | Rabbit | Y | Y | Y |
| | GA C-term | H3164 | Ac-CSGRARGRARGGA-amide | Rabbit | Y | Y | Y |

Summary of sense and antisense antibodies including antigen recognized, identification number (ID#), and peptide sequence used for injections in rabbits or mice. Detection of recombinant proteins by various methods is summarized on right. IB=immunoblot, IHC=immunohistochemistry, IF=immunofluorescence, Y=yes, N=no, AS=Antisense, S=Sense.

*FIG. 28*

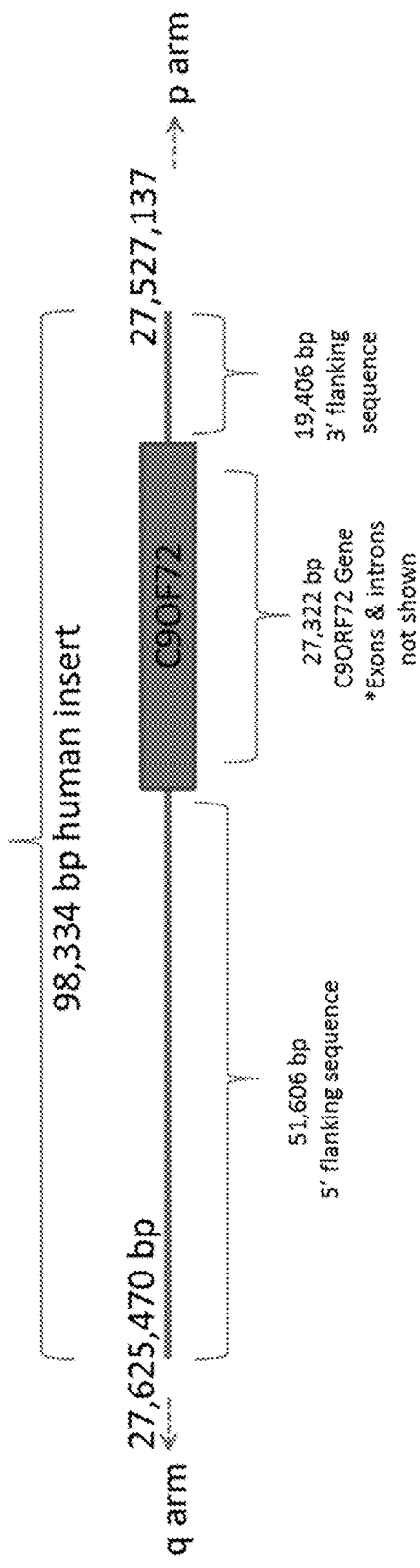

*Map of BAC insert used to make mouse models*

1) BAC insert extends from bp27,625,470 to 27,527,137 of human genome reference sequence on Chromosome 9.
2) The insert was cloned from a patient with ~800 GGGGCC repeats - size estimate above does not include extra repeats from this patient.
3) BAC insert DNA contains about 800 repeats in some clone preps but is very unstable
4) BAC repeat size in the mice is ~500 repeats but this varies between progeny and may grow or shrink in size as mouse colony is expanded and additional generations of mice are propagated in the laboratory.
5) BAC expansion mice express both sense and antisense versions of the C9ORF72 gene

*FIG. 29*

SEQUENCE LISTING

```
Sequence total quantity: 65
SEQ ID NO: 1           moltype = AA  length = 31
FEATURE                Location/Qualifiers
REGION                 1..31
                       note = Synthetic polypeptide
source                 1..31
                       mol_type = protein
                       organism = synthetic construct
SEQUENCE: 1
WSGRARGRAR GGAAVAVPAP AAAEAQAVAS G                                  31

SEQ ID NO: 2           moltype = AA  length = 34
FEATURE                Location/Qualifiers
REGION                 1..34
                       note = Synthetic polypeptide
source                 1..34
                       mol_type = protein
                       organism = synthetic construct
SEQUENCE: 2
GRGRGGPGGG PGAGLRLRCL RPRRRRRRRW RVGE                               34

SEQ ID NO: 3           moltype = AA  length = 54
FEATURE                Location/Qualifiers
REGION                 1..54
                       note = Synthetic polypeptide
source                 1..54
                       mol_type = protein
                       organism = synthetic construct
SEQUENCE: 3
GVVGAGPGAG PGRGCGCGAC ARGGGGAGGG EWVSEEAASW RVAVWGSAAG KRRG         54

SEQ ID NO: 4           moltype = AA  length = 24
FEATURE                Location/Qualifiers
REGION                 1..24
                       note = Synthetic polypeptide
source                 1..24
                       mol_type = protein
                       organism = synthetic construct
SEQUENCE: 4
PSARLLSSRA CYRLRLFPSL FSSG                                          24

SEQ ID NO: 5           moltype = AA  length = 6
FEATURE                Location/Qualifiers
REGION                 1..6
                       note = Synthetic polypeptide
source                 1..6
                       mol_type = protein
                       organism = synthetic construct
SEQUENCE: 5
PLARDS                                                              6

SEQ ID NO: 6           moltype = DNA  length = 780
FEATURE                Location/Qualifiers
source                 1..780
                       mol_type = genomic DNA
                       organism = Homo sapiens
SEQUENCE: 6
ccccatttcg ctagcctcgt gagaaaacgt catcgcacat agaaaacaga cagacgtaac   60
ctacggtgtc ccgctaggaa agagaggtgc gtcaaacagc gacaagttcc gcccacgtaa   120
aagatgacgc ttggtgtgtc agccgtccct gctgccggt  tgcttctctt ttgggggcgg   180
ggtctagcaa gagcaggtgt gggtttagga ggtgtgtgtt tttgttttc  ccaccctctc   240
tccccactac ttgctctcac agtactcgct gagggtgaac aagaaaagac ctgataaaga   300
```

```
ttaaccagaa gaaaacaagg agggaaacaa ccgcagcctg tagcaagctc tggaactcag   360
gagtcgcgcg ctaggggccg gggccgggge cggggcgtgg tcggggcggg ccccggggcg   420
ggcccgggge ggggctgcgg ttgcggtgcc tgcccccgcg gcggcggagg cgcaggcggt   480
ggcgagtggg tgagtgagga ggcggcatcc tggcgggtgg ctgtttgggg ttcggctgcc   540
gggaagaggc gcgggtagaa gcggggggctc tcctcagage tcgacgcatt tttactttcc   600
ctctcatttc tctgaccgaa gctgggtgtc gggctttcgc ctctagcgac tggtggaatt   660
gcctgcatcc gggccccggg cttcccggcg gcggcggcgg cggcggcggc cagggacaa    720
gggatgggga tctggcctct tccttgcttt cccgccctca gtacccgagc tgtctccttc   780

SEQ ID NO: 7                moltype = DNA     length = 780
FEATURE                     Location/Qualifiers
source                      1..780
                            mol_type = genomic DNA
                            organism = Homo sapiens
SEQUENCE: 7
gaaggagaca gctcgggtac tgagggcggg aaagcaagga agaggccaga tccccatccc    60
ttgtccctgc gccgccgccg ccgccgccgc cgccgggaag cccggggccc ggatgcaggc   120
aattccacca gtcgctagag gcgaaagccc gacacccagc ttcggtcaga gaaatgagag   180
ggaaagtaaa aatgcgtcga gctctgagga gagcccccgc ttctaccgc gcctcttccc    240
ggcagccgaa ccccaaacag ccacccgcca ggatgccgcc tcctcactca cccactcgcc   300
accgcctgcg cctccgccgc cgcgggcgca ggcaccgcaa ccgcagcccc gccccgggcc   360
cgccccgggg cccgccccga cacgccccg gccccgcctag ccgcgcgactc             420
ctgagttcca gagcttgcta caggctgcgg ttgtttccct ccttgttttc ttctggttaa   480
tctttatcag gtcttttctt gttcaccctc agcgagtact gtgagagcaa gtagtgggaa   540
gagagggtgg gaaaaacaaa aacacacacc tcctaaaccc acacctgctc ttgctagacc   600
ccgccccaa aagagaagca accgggcagc agggacggct gacacaccaa gcgtcatctt   660
ttacgtgggc ggaacttgtc gctgtttgac gcacctctct ttcctagcgg gacaccgtag   720
gttacgtctg tctgttttct atgtgcgatg acgtttctc acgaggctag cgaaatgggg   780

SEQ ID NO: 8                moltype = AA     length = 33
FEATURE                     Location/Qualifiers
REGION                      1..33
                            note = Synthetic polypeptide
REPEAT                      1..2
                            note = GA repeats
source                      1..33
                            mol_type = protein
                            organism = synthetic construct
SEQUENCE: 8
GAWSGRARGR ARGGAAVAVP APAAAEAQAV ASG                                 33

SEQ ID NO: 9                moltype = AA     length = 34
FEATURE                     Location/Qualifiers
REGION                      1..34
                            note = Synthetic polypeptide
REPEAT                      1..2
                            note = AG repeats
source                      1..34
                            mol_type = protein
                            organism = synthetic construct
SEQUENCE: 9
AGAWSGRARG RARGGAAVAV PAPAAAEAQA VASG                                34

SEQ ID NO: 10               moltype = AA     length = 36
FEATURE                     Location/Qualifiers
REGION                      1..36
                            note = Synthetic polypeptide
REPEAT                      1..2
                            note = GP repeats
source                      1..36
                            mol_type = protein
                            organism = synthetic construct
SEQUENCE: 10
GPGRGRGGPG GGPGAGLRLR CLRPRRRRRR RWRVGE                              36

SEQ ID NO: 11               moltype = AA     length = 37
FEATURE                     Location/Qualifiers
REGION                      1..37
                            note = Synthetic polypeptide
REPEAT                      1..2
                            note = PG repeats
source                      1..37
                            mol_type = protein
                            organism = synthetic construct
SEQUENCE: 11
PGPGRGRGGP GGGPGAGLRL RCLRPRRRRR RRWRVGE                             37

SEQ ID NO: 12               moltype = AA     length = 56
FEATURE                     Location/Qualifiers
```

```
REGION                  1..56
                        note = Synthetic polypeptide
REPEAT                  1..2
                        note = GR repeats
source                  1..56
                        mol_type = protein
                        organism = synthetic construct
SEQUENCE: 12
GRGVVGAGPG AGPGRGCGCG ACARGGGGAG GGEWVSEEAA SWRVAVWGSA AGKRRG         56

SEQ ID NO: 13           moltype = AA   length = 57
FEATURE                 Location/Qualifiers
REGION                  1..57
                        note = Synthetic polypeptide
REPEAT                  1..2
                        note = RG repeats
source                  1..57
                        mol_type = protein
                        organism = synthetic construct
SEQUENCE: 13
RGRGVVGAGP GAGPGRGCGC GACARGGGGA GGGEWVSEEA ASWRVAVWGS AAGKRRG        57

SEQ ID NO: 14           moltype = AA   length = 27
FEATURE                 Location/Qualifiers
REGION                  1..27
                        note = Synthetic polypeptide
REPEAT                  1..2
                        note = AP repeats
source                  1..27
                        mol_type = protein
                        organism = synthetic construct
SEQUENCE: 14
APAPSARLLS SRACYRLRLF PSLFSSG                                         27

SEQ ID NO: 15           moltype = AA   length = 26
FEATURE                 Location/Qualifiers
REGION                  1..26
                        note = Synthetic polypeptide
source                  1..26
                        mol_type = protein
                        organism = synthetic construct
SEQUENCE: 15
PAPSARLLSS RACYRLRLFP SLFSSG                                          26

SEQ ID NO: 16           moltype = AA   length = 8
FEATURE                 Location/Qualifiers
REGION                  1..8
                        note = Synthetic polypeptide
REPEAT                  1..2
                        note = PR repeats
source                  1..8
                        mol_type = protein
                        organism = synthetic construct
SEQUENCE: 16
PRPLARDS                                                              8

SEQ ID NO: 17           moltype = AA   length = 9
FEATURE                 Location/Qualifiers
REGION                  1..9
                        note = Synthetic polypeptide
REPEAT                  1..2
                        note = RP repeats
source                  1..9
                        mol_type = protein
                        organism = synthetic construct
SEQUENCE: 17
RPRPLARDS                                                             9

SEQ ID NO: 18           moltype = AA   length = 18
FEATURE                 Location/Qualifiers
REGION                  1..18
                        note = Synthetic polypeptide
source                  1..18
                        mol_type = protein
                        organism = synthetic construct
SEQUENCE: 18
RGRGRGRGRG RGRGRGRC                                                   18

SEQ ID NO: 19           moltype = AA   length = 18
```

-continued

```
FEATURE                 Location/Qualifiers
REGION                  1..18
                        note = Synthetic polypeptide
source                  1..18
                        mol_type = protein
                        organism = synthetic construct
SEQUENCE: 19
RPRPRPRPRP RPRPRPRC                                                       18

SEQ ID NO: 20           moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 20
APAPAPAPAP APAPACKKKK                                                     20

SEQ ID NO: 21           moltype = AA  length = 20
FEATURE                 Location/Qualifiers
REGION                  1..20
                        note = Synthetic polypeptide
source                  1..20
                        mol_type = protein
                        organism = synthetic construct
SEQUENCE: 21
GPGPGPGPGP GPGPGPGCKK                                                     20

SEQ ID NO: 22           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 22
CRRRRWRVGE                                                                10

SEQ ID NO: 23           moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 23
CYRLRLFPSL FSSG                                                           14

SEQ ID NO: 24           moltype = AA  length = 15
FEATURE                 Location/Qualifiers
REGION                  1..15
                        note = Synthetic polypeptide
source                  1..15
                        mol_type = protein
                        organism = synthetic construct
SEQUENCE: 24
CRVAVWGSAA GKRRG                                                          15

SEQ ID NO: 25           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 25
CRPRPLARDS                                                                10

SEQ ID NO: 26           moltype = AA  length = 13
FEATURE                 Location/Qualifiers
REGION                  1..13
                        note = Synthetic polypeptide
source                  1..13
                        mol_type = protein
                        organism = synthetic construct
SEQUENCE: 26
CSGRARGRAR GGA                                                            13
```

```
SEQ ID NO: 27              moltype = AA   length = 32
FEATURE                    Location/Qualifiers
REGION                     1..32
                           note = Synthetic polypeptide
source                     1..32
                           mol_type = protein
                           organism = synthetic construct
SEQUENCE: 27
AWSGRARGRA RGGAAVAVPA PAAAEAQAVA SG                                      32

SEQ ID NO: 28              moltype = AA   length = 35
FEATURE                    Location/Qualifiers
REGION                     1..35
                           note = Synthetic polypeptide
source                     1..35
                           mol_type = protein
                           organism = synthetic construct
SEQUENCE: 28
PGRGRGGPGG GPGAGLRLRC LRPRRRRRRR WRVGE                                   35

SEQ ID NO: 29              moltype = AA   length = 55
FEATURE                    Location/Qualifiers
REGION                     1..55
                           note = Synthetic polypeptide
source                     1..55
                           mol_type = protein
                           organism = synthetic construct
SEQUENCE: 29
RGVVGAGPGA GPGRGCGCGA CARGGGGAGG GEWVSEEAAS WRVAVWGSAA GKRRG             55

SEQ ID NO: 30              moltype = AA   length = 25
FEATURE                    Location/Qualifiers
REGION                     1..25
                           note = Synthetic polypeptide
source                     1..25
                           mol_type = protein
                           organism = synthetic construct
SEQUENCE: 30
APSARLLSSR ACYRLRLFPS LFSSG                                              25

SEQ ID NO: 31              moltype = AA   length = 7
FEATURE                    Location/Qualifiers
REGION                     1..7
                           note = Synthetic polypeptide
source                     1..7
                           mol_type = protein
                           organism = synthetic construct
SEQUENCE: 31
RPLARDS                                                                  7

SEQ ID NO: 32              moltype = AA   length = 99
FEATURE                    Location/Qualifiers
REGION                     1..99
                           note = Synthetic polypeptide
REPEAT                     92..93
                           note = PR repeats
source                     1..99
                           mol_type = protein
                           organism = synthetic construct
SEQUENCE: 32
MQAIPPVARG ESPTPSFGQR NERESKNASS SEESPRFYPR LFPAAEPQTA TRQDAASSLT        60
HSPPPAPPPP RAQAPQPQPR PGPAPGPAPT TPRPLARDS                               99

SEQ ID NO: 33              moltype = AA   length = 74
FEATURE                    Location/Qualifiers
REGION                     1..74
                           note = Synthetic polypeptide
REPEAT                     73..74
                           note = GP repeats
source                     1..74
                           mol_type = protein
                           organism = synthetic construct
SEQUENCE: 33
MRGKVKMRRA LRRAPASTRA SSRQPNPKQP PARMPPPHSP TRHRLRLRRR GRRHRNRSPA        60
PGPPPGPPRP RPGP                                                         74

SEQ ID NO: 34              moltype = AA   length = 68
FEATURE                    Location/Qualifiers
REGION                     1..68
```

```
                        note = Synthetic polypeptide
REPEAT                  67..68
                        note = GP repeats
source                  1..68
                        mol_type = protein
                        organism = synthetic construct
SEQUENCE: 34
MRRALRRAPA STRASSRQPN PKQPPARMPP PHSPTRHRLR LRRRGRRHRN RSPAPGPPPG   60
PPRPRPGP                                                            68

SEQ ID NO: 35           moltype = AA   length = 41
FEATURE                 Location/Qualifiers
REGION                  1..41
                        note = Synthetic polypeptide
REPEAT                  40..41
                        note = GP repeats
source                  1..41
                        mol_type = protein
                        organism = synthetic construct
SEQUENCE: 35
MPPPHSPTRH RLRLRRRGRR HRNRSPAPGP PPGPPRPRPG P                       41

SEQ ID NO: 36           moltype = DNA   length = 19
FEATURE                 Location/Qualifiers
misc_feature            1..19
                        note = Synthetic polynucleotide
source                  1..19
                        mol_type = other DNA
                        organism = synthetic construct
SEQUENCE: 36
agtcgctaga ggcgaaagc                                                19

SEQ ID NO: 37           moltype = DNA   length = 19
FEATURE                 Location/Qualifiers
misc_feature            1..19
                        note = Synthetic polynucleotide
source                  1..19
                        mol_type = other DNA
                        organism = synthetic construct
SEQUENCE: 37
cgagtgggtg agtgaggag                                                19

SEQ ID NO: 38           moltype = DNA   length = 42
FEATURE                 Location/Qualifiers
misc_feature            1..42
                        note = Synthetic polynucleotide
source                  1..42
                        mol_type = other DNA
                        organism = synthetic construct
SEQUENCE: 38
cgactggagc acgaggacac tgaagtcgct agaggcgaaa gc                      42

SEQ ID NO: 39           moltype = DNA   length = 42
FEATURE                 Location/Qualifiers
misc_feature            1..42
                        note = Synthetic polynucleotide
source                  1..42
                        mol_type = other DNA
                        organism = synthetic construct
SEQUENCE: 39
cgactggagc acgaggacac tgacgagtgg gtgagtgagg ag                      42

SEQ ID NO: 40           moltype = DNA   length = 23
FEATURE                 Location/Qualifiers
misc_feature            1..23
                        note = Synthetic polynucleotide
source                  1..23
                        mol_type = other DNA
                        organism = synthetic construct
SEQUENCE: 40
cgactggagc acgaggacac tga                                           23

SEQ ID NO: 41           moltype = AA   length = 91
FEATURE                 Location/Qualifiers
REGION                  1..91
                        note = Synthetic polypeptide
source                  1..91
                        mol_type = protein
                        organism = synthetic construct
```

```
SEQUENCE: 41
MQAIPPVARG ESPTPSFGQR NERESKNASS SEESPRFYPR LFPAAEPQTA TRQDAASSLT    60
HSPPPAPPPP RAQAPQPQPR PGPAPGPAPT T                                  91

SEQ ID NO: 42           moltype = AA   length = 72
FEATURE                 Location/Qualifiers
REGION                  1..72
                        note = Synthetic polypeptide
source                  1..72
                        mol_type = protein
                        organism = synthetic construct
SEQUENCE: 42
MRGKVKMRRA LRRAPASTRA SSRQPNPKQP PARMPPPHSP TRHRLRLRRR GRRHRNRSPA    60
PGPPPGPPRP RP                                                       72

SEQ ID NO: 43           moltype = AA   length = 66
FEATURE                 Location/Qualifiers
REGION                  1..66
                        note = Synthetic polypeptide
source                  1..66
                        mol_type = protein
                        organism = synthetic construct
SEQUENCE: 43
MRRALRRAPA STRASSRQPN PKQPPARMPP PHSPTRHRLR LRRRGRRHRN RSPAPGPPPG    60
PPRPRP                                                              66

SEQ ID NO: 44           moltype = AA   length = 39
FEATURE                 Location/Qualifiers
REGION                  1..39
                        note = Synthetic polypeptide
source                  1..39
                        mol_type = protein
                        organism = synthetic construct
SEQUENCE: 44
MPPPHSPTRH RLRLRRRGRR HRNRSPAPGP PGPPRPRP                            39

SEQ ID NO: 45           moltype = DNA   length = 20
FEATURE                 Location/Qualifiers
misc_feature            1..20
                        note = Synthetic polynucleotide
source                  1..20
                        mol_type = other DNA
                        organism = synthetic construct
SEQUENCE: 45
gcccacgtaa aagatgacgc                                               20

SEQ ID NO: 46           moltype = DNA   length = 20
FEATURE                 Location/Qualifiers
misc_feature            1..20
                        note = Synthetic polynucleotide
source                  1..20
                        mol_type = other DNA
                        organism = synthetic construct
SEQUENCE: 46
cctcctaaac ccacacctgc                                               20

SEQ ID NO: 47           moltype = DNA   length = 43
FEATURE                 Location/Qualifiers
misc_feature            1..43
                        note = Synthetic polynucleotide
source                  1..43
                        mol_type = other DNA
                        organism = synthetic construct
SEQUENCE: 47
cgactggagc acgaggacac tgacctccta aacccacacc tgc                     43

SEQ ID NO: 48           moltype = DNA   length = 23
FEATURE                 Location/Qualifiers
misc_feature            1..23
                        note = Synthetic polynucleotide
source                  1..23
                        mol_type = other DNA
                        organism = synthetic construct
SEQUENCE: 48
cgactggagc acgaggacac tga                                           23

SEQ ID NO: 49           moltype = DNA   length = 19
FEATURE                 Location/Qualifiers
misc_feature            1..19
```

```
                        note = Synthetic polynucleotide
source                  1..19
                        mol_type = other DNA
                        organism = synthetic construct
SEQUENCE: 49
gctttcgcct ctagcgact                                                 19

SEQ ID NO: 50           moltype = DNA  length = 23
FEATURE                 Location/Qualifiers
misc_feature            1..23
                        note = Synthetic polynucleotide
source                  1..23
                        mol_type = other DNA
                        organism = synthetic construct
SEQUENCE: 50
tctagcgact ggtggaattg cct                                            23

SEQ ID NO: 51           moltype = DNA  length = 20
FEATURE                 Location/Qualifiers
misc_feature            1..20
                        note = Synthetic polynucleotide
source                  1..20
                        mol_type = other DNA
                        organism = synthetic construct
SEQUENCE: 51
ctgcggttgt ttccctcctt                                                20

SEQ ID NO: 52           moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 52
tttcttgttc accctcagcg a                                              21

SEQ ID NO: 53           moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 53
ctgggaacgg tgaaggtgac a                                              21

SEQ ID NO: 54           moltype = DNA  length = 19
FEATURE                 Location/Qualifiers
misc_feature            1..19
                        note = Synthetic polynucleotide
source                  1..19
                        mol_type = other DNA
                        organism = synthetic construct
SEQUENCE: 54
gggagaggac tgggccatt                                                 19

SEQ ID NO: 55           moltype = DNA  length = 21
FEATURE                 Location/Qualifiers
misc_feature            1..21
                        note = Synthetic polynucleotide
source                  1..21
                        mol_type = other DNA
                        organism = synthetic construct
SEQUENCE: 55
acgacatcga ttacaaggac g                                              21

SEQ ID NO: 56           moltype = DNA  length = 20
FEATURE                 Location/Qualifiers
misc_feature            1..20
                        note = Synthetic polynucleotide
source                  1..20
                        mol_type = other DNA
                        organism = synthetic construct
SEQUENCE: 56
atcagcttct gctcgctatg                                                20

SEQ ID NO: 57           moltype = AA  length = 106
FEATURE                 Location/Qualifiers
```

```
REGION                  1..106
                        note = Synthetic polypeptide
REPEAT                  78..79
                        note = AP repeats
source                  1..106
                        mol_type = protein
                        organism = synthetic construct
SEQUENCE: 57
GEPPLLPLPL PGSRTPNSHP PGCRLLTHPL ATACASAAAG AGTATAAPPR ARPRARPDHA    60
PAPAPAPAPA PAPAPAPAPP APASARLLSS RACYRLRLFP SLFSSG                  106

SEQ ID NO: 58           moltype = AA   length = 119
FEATURE                 Location/Qualifiers
REGION                  1..119
                        note = Synthetic polypeptide
REPEAT                  108..109
                        note = PR repeats
source                  1..119
                        mol_type = protein
                        organism = synthetic construct
SEQUENCE: 58
MQAIPPVARG ESPTPSFGQR NERESKNASS SEESPRFYPR LFPAAEPQTA TRQDAASSLT    60
HSPPPAPPPP RAQAPQPQPR PGPAPGPAPT TPRPRPRPRP RPRPRPRPRP RPRPLARDS    119

SEQ ID NO: 59           moltype = AA   length = 94
FEATURE                 Location/Qualifiers
REGION                  1..94
                        note = Synthetic polypeptide
REPEAT                  89..90
                        note = GP repeats
source                  1..94
                        mol_type = protein
                        organism = synthetic construct
SEQUENCE: 59
MRGKVKMRRA LRRAPASTRA SSRQPNPKQP PARMPPPHSP TRHRLRLRRR GRRHRNRSPA    60
PGPPPGPPRP RPGPGPGPGP GPGPGPGPGP GPGP                                94

SEQ ID NO: 60           moltype = AA   length = 56
FEATURE                 Location/Qualifiers
REGION                  1..56
                        note = Synthetic polypeptide
REPEAT                  17..18
                        note = GP repeats
source                  1..56
                        mol_type = protein
                        organism = synthetic construct
SEQUENCE: 60
GPGPGPGPGP GPGPGPGPGP GPGRGRGGPG GGPGAGLRLR CLRPRRRRRR RWRVGE        56

SEQ ID NO: 61           moltype = AA   length = 98
FEATURE                 Location/Qualifiers
REGION                  1..98
                        note = Synthetic polypeptide
REPEAT                  39..40
                        note = GR repeats
source                  1..98
                        mol_type = protein
                        organism = synthetic construct
SEQUENCE: 61
RLTRRKQGGK QPQPVASSGT QESRARGRGR GRGRGRGRGR GRGRGVVGAG PGAGPGRGCG    60
CGACARGGGG AGGGEWVSEE AASWRVAVWG SAAGKRRG                             98

SEQ ID NO: 62           moltype = AA   length = 65
FEATURE                 Location/Qualifiers
REGION                  1..65
                        note = Synthetic polypeptide
REPEAT                  29..30
                        note = GA repeats
source                  1..65
                        mol_type = protein
                        organism = synthetic construct
SEQUENCE: 62
QALELRSRAL GAGAGAGAGA GAGAGAGAGA GAGAWSGRAR GRARGGAAVA VPAPAAAEAQ    60
AVASG                                                                 65

SEQ ID NO: 63           moltype = DNA   length = 98334
FEATURE                 Location/Qualifiers
repeat_region           51933..51938
                        note = GGGGCC repeats
```

| source | 1..98334 |
| --- | --- |
| | mol_type = genomic DNA |
| | organism = Homo sapiens |

SEQUENCE: 63

```
aagcttgata atattatcaa atattagata aatgtaatat tagaagaaaa cttttttgaa   60
aagatatata aaaataattt cattcaaaat ttttatattt aatttaaatt tttaatgaaa  120
atatatctaa gttttgtacg ctttaaatgt aattatgttt gataatttaa tcatttacta  180
ttcgttctct attgctgccc taacaaatta ccatagttca gtggcttaca aaacacaaat  240
ttattatctt accattctgt gagtcaaaat tccaaaatag gtgtcactag gctaaaatga  300
aggactgcat ttcttcctgc aggctccagg agagatctat gtcttactct tttcggcttc  360
taaaggctgc ccacattcct cgactagtgg cgtccctcct tcgtctctaa acccagcaac  420
aacaggttga gtcctcatgt cacatctttc ttacctttct gtcatctcat ctcgctgact  480
gctgctggga aaaattctcc acttttaagg gctatcatga ttagactatg cccactagat  540
aatacaagat ctcagatcct taacttccat cacatctgca aagtcgcttt tgcctcataa  600
aagagtctga ggtttagacg ggagatctta agggggctat taatatgcct accataatca  660
ctgagaataa gtacaagtta agattataat agcaatagaa tatacaaacg tgaagctcca  720
aaagaacaac aacaacaaaa aaggtgaaca ggaaaaagaa actgaaaatc tttaaaaagg  780
cagtctgttt aaatctataa aaactggaaa aaaatgagag tggacaaata tctggtaagc  840
atgatggact taaaatttgt gactagggca ttacatttt tatattaata taatgaagat  900
tgaattactg atcaaaacaa ttaaaaagca agagaactat tctcatcaaa tctgcaacac  960
gaaaagttca gacaaaattc caacaacttc acattctgaa ctaaatgagg actaattacc  1020
agttcagca atgagaatat atgaggtcct ccgtttgcac tttgccaggg atctgaaaac  1080
gttgggagta ggtcggcttc accctgaagc cagaccatcg acagccagtt ttccctcct  1140
tctccaccca caggtcttag gccctcatcc ttcccagcct cagaactagt ctccaaagaa  1200
gaggaaagtt agaggagaga gtaaatcgtt gaataggatg aaggagatgt gggaaaaga  1260
aaaagagagg ctgcaagaga gagggtccca gggataactc tgctcttgga agggtggcca  1320
cagtcatgtg gtcccaagag gcaacaacaa gcttaggaag ccagagaaac cagttacaat  1380
cactgctact cttttcgatt ctgtgttgtt taagaaatat cacccgccag gagttctcca  1440
gaaacatttt ccctgattcc atgtaagtgc tcaaccagtg aatggtaatc ccattttggt  1500
ttagtctgta ccatcccta ttccaaaata aagggaaata tggtgggttt atatcttaaa  1560
ttttctactt tactaaactc aagggaaata gccaagcaaa aacgaaagct gagactcttg  1620
ctaattatcc tttccataga atgtttgcta aaattccttg tcaaggaagg aataacaaag  1680
ctagtccacg ctctgtatag ggtgtttcca attagttata ctttaaagta taagtattta  1740
acaaaatcta taaattttgt taattattta cttgtagtga aaaatgagcc attctcaagc  1800
aaatcacttt ttattacaca ttccagaaga taaccataaa aggacattta ttatagcaaa  1860
aataaccaca tctggatgga acttcaatca ccagtattta ctaaataaat gcccagaaaa  1920
aaaatagttc atctttaatt tcagtcatca ttaataaaag ctgaagtacc tcttcagatc  1980
ttttgatcat ttttctgttgg attgttttct ttttactgag ttgcaaatgc tcttttatata  2040
ttttggatac aaagctttat cacataggca ttttgcaagt attttttcca agttttttta  2100
tcttttcatt tatttaataa tatctttcaa agaacgggaa tttttataatt tttatgaagt  2160
ccatttataa tttttttctt tatgggttgg tggggttgg gggttgtgtt gtcctaagaa  2220
atcttggctc aacacaaaaa gattagtttc tatattttct tctagaagtt ttatagtacg  2280
atctcagatc catttcagat gatgaataag cacataaaaa aaggtactc atcgttagtc  2340
attagagaaa tgcatattaa aaccataagg aaatactact atatacatat attagatagg  2400
atgaagagca actggaatct catacagtgc tgattgaaat gcaaaatggc aaaacaactt  2460
tagaaaccaa tttggaagca gctgtactga catgaatttt tgagctggaa gaatcttaga  2520
aaaagaatac tttaccacct cccccattct cttcacccct gggaactgtt aaatgaggaa  2580
attgtggttc aaggaggaac ttgtctatat gctttctcag cttttcccgtg gtaattacca  2640
tcttgataat ataacgtaat gtatgtatat gttatcaaat aatataatat cttcatcata  2700
tatttatcat cttcataatg ttagctgtct agtggtaact tttttttgct ctttattgcc  2760
tccctctttt ttccctcttt gttgtttttt gtcatacaat tatgatatat gtgtatatat  2820
tctcactgta aagatgtaaa caacacaaag attattgaac aaatcacgaa agtaaccctt  2880
ccttcattct taccctatcc aaccctcatc tcctcagaag aatacaccat tttagttgta  2940
aatgtttttc tagctctttt tcaatgtttc tacctatatg catgtatgta taatgtatat  3000
acatacatat atacacatat attgatatat acatatatag aggtatggtt ttttaactta  3060
aatggaattg cattgtggat attgtcctat gacttgcttt caaccaaatt atatgtcttg  3120
gaaatacata catatattta aaaaatatgt tatgtatatg taacatacta tatgtgcata  3180
atatatatta catagatata ataaggccta ggaagaaatt gtgtgcaacc tctagtacat  3240
cttcctctat atctactgta catacataca acccattctt ttttaattt ttttattttt  3300
ttagacagaa tcttgctctg tcgcccaggc tggagtgcag tggcacaatc tcggctcact  3360
gcaagctcca cctcctgggt tcacgccatt ctcctgcctc agcctcccaa gtagctggga  3420
atacaggcac ctgccatcag gcccagctaa ttttttttg tatttttagt acagatgggg  3480
tttcaccgtg ttagccagga tggtctccat ctcctgacct cgtgatccgc ccaccttcatc  3540
ctcccaaagt gctgggattt acaggcgtga gccaccgcca gccattgcag  3600
agtagtccaa aatatggatg gactgtagct taattactta ttctcccatt gatagacact  3660
taggactttt ctaattttta aatttaaaa atatgctgca attaacaaac attcttgtgt  3720
atcttttgc tgtatgtatg catatttctt tagtatgggt tttggaagag gaatcacaaa  3780
ggaggcatag aatataaata ttttttattt gaaaaataca gttgtaattt aataacccac  3840
caaaagactc tcaagttta gattcacatc aacagttgtaa gaacatgtct gttttactgc  3900
atccttaccc ccactggtta taatactttt aattaacaat cttatggatg aagaatacta  3960
tcgcaatgtt gttttaatgc attttttcaa ttactagtga gattgaacat taattctttt  4020
attttatgga tcactggctt ttctccttct gtgaactacc tgttcacatc ctctgctttt  4080
cagctcttga gctgttatct ttttcttatt gatttatatg agctctttat atattcaaga  4140
tgttaatcat ttgtattta ttctatatggc aatgattttc ttccaaacca atgcttgtct  4200
tttatttatt tatttattta tttatttatt tgagaccgag tctcgctctg tcgcccaggc  4260
tggagtgcag tggcgcgatc tcggctcact gcaagctccg cctcccgggt tcacgccatt  4320
ctcctgcctc agcctcctga gtaggtggga ctacaggcgc ccgctgccac acccggctaa  4380
ttttttgtat ttttagtaga cagggtttt caccgtgtta gccaggatgc tctctatctc  4440
ctgacctcgt gatccgcccg cctcggcctt ccaaagtggg cggattacag gcatgagcca  4500
```

```
ccacgcctgg ccaatgcttg tctttttatc tctgtttatg gcatctttca tactatggac  4560
atttttattt ttatttttta tgttgattta ttcttgaatt gtatacatgt taattatacc  4620
taagttattg taatacccct aaagccaagt tctacacata tatttaattt gctttcccaa  4680
taggtctctg agggaacaca ttttttcaaa tcactttgtt tcatcttttt taggtgttga  4740
tcaattatta aggagtttga aataatcatt taaacgagat tcttcagatg aaaacataaa  4800
gacatttatc gggtcagagc attggtcggt tcacatactc aggatcagtg gcctgggtgg  4860
gcaggcactg ggtgaatgga gagctgcagg tattggaaga gagcccagtt ggatatgtag  4920
tttccaaaga tcatcaaggc agacaaccaa agggaaaccg tgggaaacac ctgctttggg  4980
ccatctaaga tgagatgata aagtaaggaa agagttgagc ccaacacagt gatagccaat  5040
ctgaaagcgg gcagaactga caagaccaaa caagtggctgc aggcagccag  5100
ccaccacagg gacagcgtgt actccaggga caagctcaag gctataggta gttagttcaa  5160
ggctactagg gtgagaagag caggaactga gttctatacc agtgcttctc aaaactaatg  5220
tgcatcctaa tcacctggaa atcttgtaaa aatgtagatt ctgattcagt gagtctgaag  5280
cagagcttaa gatactacat gcttaacaag agcctagttg atgctgacac tgctggtccc  5340
tggagctctc tttgagtagc aggcttctgg aaggcttgtg tcactaagca cagagaagcc  5400
tcacttatca aatctgcacc aaaacaggaa aactaatgtg aagaataatg tgatgcacac  5460
gtcagagcat gaggcagttg ctttgtccct gaggttgcgc tccagatggc ttcctaagat  5520
gcgacaggct gatcttgtgc gtgggggtcc cggaggcttg ggcacgggga gagacaggac  5580
ctcagaggct gggagacagg cagagacaga agagtgacat cctgctgctt ttgaatttgc  5640
acattctgta gaataataac agcagtaaac tgttacacaa tatctattct cagcatcttg  5700
aagccctttc acatattgtt acttccatta atggggccct tgctgctat ttctacttt  5760
ctcttcagct atcaacaata tggctttcca cacctccatc agacagtagc cagatgaaat  5820
aaaatgtgcc agaatgaaaa cttgttcatt tgtctacttt ttgccaagac tagacaggca  5880
ggaaattgaa tgtatttta cagaaaaggt tttcaaaact ttttcccctc tgtggctcat  5940
ttaggtaaac taaaaggcat aagacccacc taaaacatgg gttcccgctt tttattggag  6000
aaagaacata gtactttaaa aaaatacata aaataataaa aaggaaagac aaagataatg  6060
aaggttgtac atggtaccaa atttttgtat cccataataa cacatgagta gatcactact  6120
aagtaggttt tagtgacata taggaaacat taaaatctac agaaatttgc attattttct  6180
gtcaaaaagg atcatttcac agcctttcag ggggaaccca ttgcccacag gaactcatgc  6240
attccatgct ttgaggatca ctagatctaa gaagccttcc ttggaggttc tagcctccaa  6300
cccttatttt agtaaaagaa gctccagttt tatctgtttc taagtcagac taccacacaa  6360
cattgggctt aaagaaaggt ttccagggct aaagcagact ttgaggatta ctaattccga  6420
gttaaatttc tgtgtattat ctctggattt gacttattca cactggacta tcactcataa  6480
atatacataa tacagagtta actatttaaa tttataaaga gagtattttc ctttttatg  6540
agcaaaacat gctgccaact acttggacca catactgatc cataaatact gacagctttg  6600
taattggaaa taataaatac acactaatga agcatctcaa aagggaagag ccacaggtaa  6660
tctgagtgat taggcattca tgttaggtta ggctttgatc attgttttta atcgcaattt  6720
cattgcagtg catctataaa tccatgtcca gaagtatgaa gtggttctat agtaagaata  6780
agatgctaca gataatgcga ctaaataaga cactatagt aatgacacag attcaagtct  6840
tattgttgat gggaagaggt caataatgga tgatataata tactacagca atgagaatta  6900
ttgaatgttt tccagactca cttgtataat tggccataac agcaaacaaa aaacaggttc  6960
tgatagcaaa atgatataca gtactaacaa aggtgaatct tgaggtgaac cttctcttta  7020
taagtttaaa tagtttaccc ccgaccttt cccatagtag aacagcctaa aaagtatctt  7080
tcagtagaat gctagtgctt atgaggtttt cttaagatat cattttttcaa ttaaaattta  7140
tttcacaaaa gactcacatc cttgccagcc ttcagggtga gtgttgattc aggctgtgtc  7200
caacggcaac gatgagtgaa cttctcaccc tcagaatcac atgagcattc ctgagatgtt  7260
ttatcagagt gataccaact tcattattag aatattgagt ccctattttcc tatattcaat  7320
gtcctttcaa gccctaactt tgtccggggtt gaaggcaaag atccaaataa tcacatttgt  7380
ctttgataac tgaaactggg agaactggga ctgtctcaag agttctacgt gactgtaggt  7440
tgcaagtact gtggttgcat ctccaaatat taaccaatcc cagtgacaat tcaatgggt  7500
ctcctgaacc atgatcctca tgtctccagt gaaggaaatg ggcaaagggg attcaaaaat  7560
cccttttgga ggaataggaa acttctgctt tccttcattt cataacattt gcgatggaac  7620
aaaggctttt ttagaatgga gcaaccagat cctttttgg gggaatcagc ttaaatgtcc  7680
cttcttctca tactacttt atctatgtga tcctattctt ttctgttgtg gattgaatca  7740
tgtccctcaa aaagattgaa tttagatgt gctctaaatt caatgtggaa aaatttggac  7800
acagaggcag acacacaggg agaaccccgt gtgacaatgg aggaagagga tgcatttatg  7860
ctgccacaag ccaaggaaca ccaaagatt tcagcagcca ccagaagcta ggataaaggc  7920
atggcacatc actccctctg agcccccaaa aggagccaag actgctaata ctctgatctc  7980
ggacttctgg cctgaaacag tgagaaaata aggttctgtt gtttcaagct acccagcttg  8040
cggtattttg tcacagaagc acaaggaatc aagtacattt tcttttctcag cacttgtgat  8100
aatttgattt tttctttact cagtggttgt ttcacaccta tgtccccatc agactgtaag  8160
cttaaagaga cctggatctg gtctgtcttc accactgttg attcattacc agcacagtgc  8220
ctggcccatg gtcactgaat aaacgtttgt tgagagaatg aatgtgctta accagaagta  8280
ctattgacct attaggccaa gttcaaggtg cctaacagct cagctgtgaa ggataccctc  8340
cctttcagtc ctctgttaca tatgtccctg atagatgtgt tatttgtatc tcctcctggc  8400
cctcaagttt gtttgagggc aggaccctt tttgtatatc tgtagagctt cgtagtacct  8460
aaatactact ttgcatatat aataaagttt cgataaaat tcattaaata aagaaataaa  8520
tgaaatgact aagttttcta agatgttaca actagattga agatatttag ctcattattt  8580
aacaagaaaa ctatggttaa ttatggtgtc ctgtgtgaaa atggttatag tttgtttttt  8640
aattaatata agcatgtatg tgcattatca gtatacacaa tttgtggtat gagtgttttg  8700
tgtccctgca cacagaccac ggaaatcctg agaaacaaac tgccacccca gagcaggtgc  8760
ctaacacaga gactttaat cctaaagtt tttctataac taagcaatgt ttttcaat  8820
gcaataacac tgatatgcag acatattgat tgtccactca caaagccatt cctcaatatc  8880
attacaacat gcctcttga atgtcattaa aaatagatgt ctcattttc taggacaagt  8940
tggctgaagt tctgcttgaa aactggtaat agaaaataca atttctcaac ccgctttggc  9000
cttttaattc tgttctacaa ccttgccagt tcactttcaa agtcagggga tgcatccttgc  9060
aaaaccatga catcttttga gtaactcctt ctgttcttaa cacatattcc caggagctta  9120
ataaatattg tttttgcaac ttgttagtg gcaaataat gagtccttgg tgtatgctta  9180
tcctctgctt tgctattaga aagatatat tcagactgtt ttaaacaaat taattcaagg  9240
```

```
gcagggaaca gtcctaaaac ctgttaaaat tcaaatactt ggtcactgta tgtgcagcat   9300
gtgtgttcta gaaagtccta ttattttaaa atataaattg aatcttgttg agaaattaat   9360
gtcatatgaa tatattaata actgaaatgc tgccaagttt acaaaaagcc ctcaatgaaa   9420
ctgtgacctt gtatagacaa gggcctgtgg agggacattt ttaaaccatc tctttttta    9480
tttcctcatg agatctacaa tgtaagtgca ttaaagttga ttaatgaatt gcagtgcaac   9540
ttttcctgcc tcttttgcct ttcatttgtc tatatttcaa gcttcactga agtgatagat   9600
tttgggcttt gccacattgt cctctgattg cttccctctg ctcctccttt tcctagtgaa   9660
tctttgtttt actggtggaa aaatctacat cttttgtatct tggcatttta ctttcacatt   9720
atctcataga ttttatttca agttgctata aagttatcaa cttttatttt taactaatat   9780
tattttaac aattagaaaa ttgttgacca ggtaattcca gcactttggg aagctgaagc    9840
gggaggatca cgtgagccca ggagctcgag accagcctgg gcaatgcaag agactgtct    9900
ctacaaaata taaaaataca ttagccaggt ttggcggtgc atgcctgggg tccagctatt   9960
caggaagctg aggtgggagg atcacttgag ctggagaggt tgaggctgca gtgagcagtg  10020
atcgcaccac tgcactccag tctgggtgac agaggagaac cctatctgca aaaaaggaa   10080
aagaagagga ttttgctggc aagatggctg aataggaata gctccgttct gcagctccca  10140
gtgagatcaa tgcagaaggc aggtgatttc tgcatttcca acagaggtac ctggttcatc  10200
tcactgggac tggttggacg gtgggtgcag cccatggagg gtgagcagaa gtagggtggg  10260
gcgttgcctc actcaggaag tgcaagggggt ccctcttctg gccaagtgaa gccgtcaggg  10320
actgtgccat aagaacagtg cactctggtc caggctttc ccacagtctt tgcaacccac  10380
agaccaggag ataacaagcg tgcctatgc caccagggcc cggggtttca agcacaaaac  10440
tgggtggcca tttgggcaga catcaagcta gctgcaggag ttttttatttt catacccag    10500
tggtgcctgg aacgccagtg agacagaacc gttcactccc ggtgataagg ggcagaatcc  10560
agggagccaa gtggtctggc ttggcgggtc ccacacccac ggcgcccagc aagctaagat  10620
ccactggctt gaaactctcg cttccagcac agcagtctga ggtccacctg agacgcccgg  10680
gcttggtgtg ggaggggca tccaccattg ctgaggcttg agtaggcggt tttaccctca  10740
cggtgtaaac aaagctgcct ggaaggtcca gctgggcaca gcccaccaca gctcaccaag  10800
gccgctgtgg ccagagtgcc ctctctggatt cctcctctct gggcaaggca tctctgaaaa  10860
aaaggcagca gcgccagtca gagacttata gataaaaccc ccatcaccct gggacagagc  10920
acctcaggga aggagtggct gtgggtgcag tttcagcaga tttaaacgtt cctgcctgac  10980
agctctgaga gagcaacaga tctcccagca cagcgttcaa gctctgttaa agatcagact  11040
gcctcctcaa gtgggtccct gactcccatg tctcctgatt gagagacacc tcccagtagg  11100
ggctgacaaa cacctcataa aggagagctc cagctggcat ctggcaggtg ccctctggg  11160
acgaagcttc cagaggaagg aacaggcagc aatctttgct gttctgcagt ctcagctgat  11220
gatacccagt caaacaggtc ctggagtgga cctccagcaa actccagcag acctgcacca  11280
gaggggcctg accgttagaa ggaaaattaa caaatagaaa ggaatagtat caacatcaac  11340
aaaaaggacg tccactcaga gaccccatcc aaaagtcacc aacatcaaag accaaaggta  11400
gataaatcca caaagatggg gagaaaccag tgcaaaaaag tctgaaaatt ccaaaaacca  11460
gaacgcctct tctcctccaa agaatcacca ctcctcacta gcaaggtaac aaaactggac  11520
agagaatgag tttgacaaat tcacagaatt agtgttcaga aggtgggcaa taacaaactc  11580
ctccaagcta acggagcatg caaggaagct aagaaccttg aaaaaagtta gagcaattgc  11640
taactagaat aaccagttta gagaagaaca taaatgacct gatggagctg aaaaacacag  11700
cacgagaact ttgtgaagca tacacaagta tcaatagcca aatcgatcac gtggaagaaa  11760
ggatatcaga gattaaagat caacttaatg aaataaattg agagaacaa attagagaaa  11820
aaagaatgaa aaggaatgaa caaagcctcc aagcaatata ggactatgtg aaaagaccaa  11880
atctatgttt gactggtgta ccagaaagtg acggggagca tggaaccaag ctggaaaaca  11940
ctcttcagga tattatccag gagaacgtcc ccaacctagc aaaacaggcc aacatttaaa  12000
ttcaagaaat acagacaaca ccacaaagat actcctcgag aagaccaacc ccaagacaca  12060
taatcgtcag attcaccaag gttgaaatga agaaaaaaat gttaagggca gccagagaga  12120
aaggtcaggt tacccacaaa ggaagcccat cagactaaca gcagatctct ctgcagaaac  12180
cctacaagcc agaagagagt gggggccaat attcaacatt tttaaagaaa agaattttca  12240
acccagaatt tcatgtccag ccaaactaag cttcataagt gaaggagaaa taaaatcctt  12300
tacagacaac caaatgctga gagattttgt caacagcaag cgtgccttac aagagctcct  12360
gaaggaagca ctaaacgtgg aaaggaacaa tcggtaccag ccactgcaaa agcacaccaa  12420
attttaaagt ccattgacac tatgaaaaaa ctgcatcaac taacaggcaa ataaccagc   12480
tagcatcata atgacaggat caaattaacc ttaattaagt tagccttaaa tgtaaacggg  12540
ctaaatgccc cagttaaaag acacagactg gccaccgtgt aaagagtaa agacccatca   12600
gtgtgctata ttcaggagac ccatctcaca tgaaaagaca cacataggct caaaataaag  12660
ggatggagga atatttacta agcaaatggg aagcaaagaa aacaaaaagc aggggttgca  12720
atcctagtct ctgataaaac agactttaaa ccaacaaaga tcaaaataga caacaagggg  12780
cattacataa tggtaaaggg atcaatgcaa caagaacagc taactatcct aaatatatat  12840
gcacccaata caggagcacc cagattcata agcaagttc ttagagacct acaaagagac  12900
ttagactccc acacaataat aatgggagac tttaacactc cactgtcaat attagacaga  12960
tcaatgagat aggaaattaa caaggatact caggacttga actcagttct ggatcaagtg  13020
gtcctaatag atacctacag aactctccac cccaaactaa cagaatttac attcttctca  13080
gcaccacatc gcacttattc taaaattcac cacatagttg gaagtaaaac actcctcagc  13140
aaatgcaaaa gaacggaaat cataacagtc tcttagacca cagtgcagtc aaattagaac  13200
tcaggattaa gaaactcact caaaaccgca caactacatg gaaactgaac ctgttcctga  13260
atgactactg ggtaaataat gaaatgaagg gcaaaataaa gaagttcttt gaaaccaatg  13320
acaacaaaca cacaatgtac cagaatctct gggacacatt taaagcagtg ttaagagggga  13380
aatttatagc actagatgcc caaaaaagaa agcagaaaag atctaaaatc gacaccctag  13440
catcacaatt aaaagaacta gagaagcaag agcaaacaaa ttcaaaagct agcagaagac  13500
aataaataag atcagagcag aactgaagag gagagagaca tgaaaaccc ttcaaaaaaa    13560
tcaatgaatc caggagctgg ttttttgaag agattgacaa acagataga ccactagcca   13620
gacaataaag aaggagagaa gaatcaaata gatgcaataa aaatgataa ggggggtatc    13680
accactgatc ccacagaaat acaaactacc atcagagaga atactataaa caactacaca  13740
aataaactag aaaatctaga agaaatggat aaattcctgg acacatacac cctcccaagt  13800
ctaaaccagg aagaagttga atccctgaat agaccaataa caagttctga aattcaggta  13860
gtaattaata gcctaccaac caaaaaaagt ccaggaccag acagattcac agccgaattc  13920
tatcagaggt acaaacagga gctggtacca ttccttctga aactattcca atagaaaaag  13980
```

```
agggaatcct ccctaactga ttgtatgaag ccagcatcat cgtgatacca aaacctggca   14040
gagacacaac aaaaaaaaga aattttcagg ccaatatccc tgatgaacat tgatgcgaaa   14100
atcctcaata aaatactggc aagcggaatc cagcagcgca tcaaaaagct tatccgccag   14160
gatcaagtcg gcttcatctc tgggatgcaa ggctggttca acatacgcaa atcaataaac   14220
catcattctc agcaaattat cacaagaaca gaaaaccaaa caccgcatgt tctcactcat   14280
aagagggagt tgaacaatga gaacacgtgg acccaaggag gggaacatca catactgcgg   14340
cctgtcgagg gatttggggt tgagggagtg atagcattag gagaaatacc taatgtaggt   14400
aacaggttga tgggtgcagc aaaccacaat gcgatgtgta tacctaccta acaaacctgc   14460
acgttctgca catgcactcc agaacttaaa gtataataat aaaaggcgct gcctcaggat   14520
gtaaagtgta acaagggggc tggggtgggc agcgtgggcc tctgagacct ttggttgccc   14580
gtgtccgcag ctcgccccgc agccggctcc acaatggtcc gctccgtttg ccacgtgcgg   14640
attcgggttc cagactgaag gctgcgtgtt ctctgccgcc cacagcccaa gtttattgtg   14700
gcaaccgccg gagcagcctt ccccgctgtg gaggagcctg gggctacccc tcagcggtat   14760
tggggggctgg tcctggggga gctaagcagg gttgtgccga cactgcctga aagtgtgaga   14820
ccagactcta atccttatgg ttttccatgg gagttggtga tatgtgcagc tgtacatgga   14880
ttttttgctg ttctcttttt ttgtgtggag aagttttaga tcggttggga gtcggcttta   14940
tgtgggaaga gaaaaaaagc ttgctgtaat gctttctgga ctaattgaag aaaagcataa   15000
actacttgaa aaatttagcc atgttcaaaa agagtatgaa ggctatgaag tagagtcatc   15060
tttaaagaat gccagctttg agaaggaggc aacctgtgaa aagctaaaca ggtccaattc   15120
tgaacttgag gatgaaatac tctgtctaga aaaagagtta aaataagaga aatctaaaca   15180
ttctgaacaa ggtgaattga tggtggatat ttgcaaaagg atacagtctc tagaagatga   15240
gtcaaaatcc ctcaaatgac aagtagctga agccaaaatg aacttgacga tatttcaaat   15300
gaatgaagaa cgactgaaga tagcaataaa agatgctttg aatgaaaatt ctcaactcca   15360
ggaaaacgag agacagcttt tgcaagaagc tgaggtatgg aaagaacaag tgagtgaact   15420
taataaacag aaaataacat ttgaagactc caaagtacat gcagaacaag ttctaaatga   15480
taaagaaaat cacatcaaga ctctgaacgc ttgctaaaaa tgaaagatca ggctgctatg   15540
cttggagaag acataacgga tgatggtaac ttggaattag aaatgaacag tgaatcggaa   15600
aatggtgctt acttagataa tcctccgaaa ggagctctga agaaactgat ttatgctgct   15660
aagttaaatg cttcttaaa aaccttacaa ggagaaagaa accaaattta tagtcagtta   15720
tctgaagttg ataaaggaag agcttacaga gcatattaaa aatcttcaga ctgaacaagc   15780
atctttgcag tcagaaaaca cacatttga aagtgagaat cagaagcttc aacaaaaact   15840
taaagtaatg attgaatttt atcaagaaaa tgaaatgaaa ctccagagga aattaacagt   15900
agatgaaatt accggttaga aaggaagaa aaactttcta aagtacacga aaagatcagc   15960
cgtgccactg aagagttgga gacctataga aagtgagcca aagatcttga agaagagttg   16020
gcgagaacta ttcattctta tcaaggatgg attatttccc acgagaaaaa agcacataat   16080
aattggttgg cagcttggac tgctgaaaga aacctcaatg gttaaggaa agaaagtgct   16140
cacaacagac aaaaattaac tgaagcagag tttaaatttg aactttaga aaaagatcct   16200
tatgcacttc atgttccaaa tacagcattt ggcagagagc attccccata tggtccctca   16260
ccactgggtc ggccttcatc ctaaacaaga gcttttctct gagggcccac tgagactctc   16320
atctttgcta acaggaggag gaggaagagg ctcaagaggt ccagggaatc ctctggacca   16380
tcagattacc aatgaaagag gagaatcaag atgtgacagg ttaaccaatc ctcacagggc   16440
ttctctgaca ctgggtccct gtcacctcca tgggaacagg accgtaggat gatgtttctt   16500
ccaccaggac aatcatatcc tgattcagct cttcctccac aaaggcaaga cagattttat   16560
tctaattctg gcacactgtc tggaccagca gaactcagaa ggtttaatat gacttctttg   16620
gataaagtgg atgggtcaat gctttcagaa atggaatcca gcagaaatga taccaaagat   16680
gaccttggta atttaaatgt gcctgattca tctctccctg ctgaaaatga agcaactggc   16740
ccttactttt ctcctccacc tcttgctcca atcagagctc cattgtttcc ggggataca   16800
aggagcctgt tcatgagaag aggacctcct ttccccccac ctcctccagg aaccatgttt   16860
ggagcttctc aagattattt tccaccaagg gatttcccag atccaccaca tgctccattt   16920
gcaatgaaaa atgtctatcc agcgaggcgt ttcctcctta cctttcccca aaacctggat   16980
ttttcccat aaaccccaca ttctgaaggt agaagtgagt tccctgcagg gctgattctg   17040
ccttcaaatg agcctgctac tgaacatcca gaaccacacc aagaaacctg acaatattt   17100
tgctctcttc aaaagtaatt ttgactgatc tcatttttcag tttaagtaac tgctgttact   17160
taagtgatta cactttttgct cccactgaag cttaatggaa ttataattct caggatagtg   17220
ttttctaaat aaagatgatt taaatatgaa tcttatgagt aaatttattc cattttatgt   17280
tattctggaa agtataacta ttttaatttg ataaactaat ccacgattat ataaacaata   17340
atgggagttt tatatatgta atcttgcagg tagggaggct ttaaattata aaggttgtgt   17400
ctttatgcca agaactgtat taactgtggt tgtagacaaa tgtgaaagta attttatgct   17460
tcattaaata aatttagtt gattttttt taaaaaaaaga aaatggttaa tctatcattt   17520
aggtgcatca tcagttgttt aaccattctc tcttactgaa cattgggttg tttaaaaagt   17580
gttgttattt ttgaatcatg gttcagtgaa caattttgga cacataactt tttatctgat   17640
gagttatttc ctaaggatcc agctcagaaa ctcagcacat aaacctaata agaaaaaaac   17700
aatttgaagt ggctaacctc ttatcccaat aaaaatgttg tatttatgtt tggatttaga   17760
tgcctttcag tggtcatacc ttcacctaac ttttatgagt ttctactttta acatgtagag   17820
tgactgttta aatcacctaa actcactgag ttttaagttc cttttttattc aacaagactg   17880
gattgtatgt tccagctcct caaacttagt taccaaccac catcctagag aagtgaattc   17940
acatgaggcc tgtccagaag aacaatctcc ctttcagtgt cctcatgcat gcagtgacca   18000
gagccaaacc ttgataaatt atggaaaaag taacacat tctggaagag ccatgaaaga   18060
tccagatcat ctggtgctgg ataagaatat taatgagcg gctgggcgcg gtggctcacg   18120
cctgtaatcc tagcacttg ggaggccgag gcgggcggaa catggaggtca ggagatcgag   18180
accatcctgg ctaacacggt gaaacccgt ctctactgaa aatacaaaaa attagccggg   18240
catggtggcg ggcgcctgta gtcccagcta cacgagaggc tgaggcagga gaatggcgtg   18300
aacccggga gcagagcttg tagtgagccc agatggcgcc attgcacttg agcctgggcg   18360
acagagtgag actccgtttc aaaaaaaaaa aaaaagaat attaatggac aaaaagatta   18420
atgaaagaac atattgaagc atccaattac ctggtgtctg ctcaaatgag gaatcggtga   18480
gataggtcag ttagcagtca agatttataa aagagacgat ggccttggga ggggctgccc   18540
tactcgactt tttaatggct agaagctatt aagggctaag ccagaaccct tcagtatggt   18600
tcagtgagga tcccaatttg gggtccaaaa gtaaatgaca actcccagga accattaaga   18660
ataaaaatca tggagcatta ctgagaattt atgttatcta agtctgagga aaattaatgt   18720
```

```
taaggaagct tcaaaagtc taatatttac accgaattcc agggcaccat gctctaagac   18780
aaagcactct ggtcctgccc ctctcctttc ctcatgtttt ttggttcttg ggatccttaa   18840
gggtcaatgt tattcttaaa atacagagca tcctggaaac taaaaaagtg aagatattc    18900
aaattctaat gaatgtactg gcagtattgt agatcatgga gtataacata aagacaagaa   18960
tccctagcct cttccaccat actttgtaat ggtaaggaga aaggatagaa ttttgagaag   19020
tctgggaaga caatgtatga taacatctgg agaagctctg cataagttac tttgttcag    19080
gcttaagaaa aattctagct tgccctgca ctgtcatcag gtatcatgaa agtaaataaa    19140
acctttaaag attcttcaag ccagcagact tctatcttct ctatactatc ctgtgatcct   19200
aaactcttaa cagttactac gtataatttc cctacatttg ctactagtat tttatcatac   19260
acaatattac actcaatatt tcaaagtgg atgattcatc tcccgaagag actgcaaaat    19320
tcatgagtta agatttgaga atactatttt agacaagatt tagtcagatt ttagagagtt   19380
agaaacctgt aacaattctc taacaatact gcttctcctt ttgtgtatta aggaattttt   19440
gtctatcaaa gatagtacga ggtagaccag aagtaactt gccttcaaaa tgtctggaat    19500
gtaaaatggc aacagtagta tttggggact tcgtagggga tggccaatat acacccattc   19560
ttagaggtac tgatgatata atgtataaga caaaatcaag tggtctccat caccatataa   19620
tgtttaaaat ggcaaagagg gagcagaaca aacaccctt gcaaatctct tcatagaatc    19680
taccgtaata aacttgtact tgcttaaagt gtgtctcttc agtggtctta ttaccactac   19740
tttggggaaa atgaggctgc ttaaaagatt aacagacatt acattttaca tatctgtggc   19800
agagaaaaca ctatgtattc accaaaccac ttcttttcct tcccagtcac tcggaaagag   19860
gtcatttctt tgtcccctt catctaattg aggtgccgtg actacttcta gacaggcaat   19920
gtgagcagaa ggtatgcacg ccacgtatag gcctggtctt caaaaatccc tcagatatga    19980
tcttcttctc tcgtctcttt catggacaaa ctacaggcca tgtaataagg atggtggggt   20040
tccaaactga aagagcctgg atttctgatt tactgttttg agaagagttc accagggaaa   20100
cagcctggaa atacgcacag gaaaatatgc acaggaccct gtgtgagcaa gatataaaga   20160
tctattacat ggtgccatta aggtgagagt attgtgctta tagtatccag cattaattat   20220
cctcactact acaacttctt tgtatccatc atgtggaaaa gtagagtatt taataaatga   20280
ttattgagtt tattacctt tttatattcc aatcattgct aattgtacgt tacctcattt    20340
caaggtaaag gtgaccaagg gctaaagcag tgctatccaa accaagccag acatcaaaat   20400
cacacaaaac cttttgaaaa tacaactttg aagatgccat tcacatagat atttattcag   20460
tgggttttca aatggaaccc tggaatctac agtcttaac aaggcttccc aagttattct   20520
gatatacagc aggcaaatct gagaaccact ggacaagaag aaaataaagg ctatatcttt   20580
cgacaacaaa gacaatgcct taaacataga atgtattcaa ttaaagcttg tagaaagata   20640
ggtttgtgaa caggcacagg gactagcctc gagcaaatta ataagggcag caatgttttt   20700
cactgaaacc attattcccc ctattttatt tcttctgggg ctctgtgttt cctttctcct   20760
atcaaaatcc attctaaggt tggaggttgg gggtatctct tgcctactcc atacagcaag   20820
gaataaaatt agtatttctc gaactatctg tgacagcaga cccattgtag gccagtactt   20880
ttgtaaaatg caataaaaat taacttctag agaatgaaat tttaaaatca cagacattca   20940
aaatacaaat tccaattttt ttattattaa ctgtaagaaa tttaaaatta aatctcaata   21000
aataaaatta aagcaaacat aagatagaaa aaaataagca ttatggattg gcccagtctg   21060
caaactgtat acactttgcc aaacatgggc ataaattact aagaagcaaa atcttccatc   21120
tgtaaacatt tccatttcca ttgacaatat gtgtgaggga aaggagggat gcttctgttt   21180
tagaatgcca ggcgtcagct aacaagtgac aaatacgtat tgagactgag atctccccag   21240
cctctcagta gtcagcaaga acatgttgag gcctctgttt ttgactaaaa aattggccag   21300
tgcatgggca acatgcatag gtcctgaatg aaaaaaatag cagcagcaga aatttaaag    21360
aattttcaca gctaggccac agtaaattct caagcccttc atcagaagcc actgtggggc   21420
ctcatttatg cctttgtttt tattaaattg gatgtgatct taagattctt ctgtcaaaat   21480
tccactagca tgtgaaggca ccaaaagttt aaaatgtaaa attaacccaa gttaagctat   21540
tccattatta agcaatagca gatatatttg ttattatatg agaagaaagt taacaggag    21600
ctaagattga tgttactgat aagaaacaga aacaagactt taaaattaaa taaatgaatt   21660
atttatttaa taagaaccaa ttgacagatt ctcgataaag actgtaagat gtcttaaaac   21720
attaggtgta tggagataac atttgtaact ttgacaattt atatgatgag aaaaatcaat   21780
gaatgttatt gtttattggc agagttctag aattacaatt ccatcattct gttttgggga   21840
agtttccctt gaagtaaatg ataacaggc ttgaaatagt acacctcagc attttgttta    21900
taaaactgtg gaataggtaa ggtttgtatt gtaactgaac ccaggttcag ctgcttgctg   21960
ctctaaagct agacataaga gaggaaggtt ggtgggagga aaagcgattt taatcggaga   22020
agcagcaaac caagaagatg gtgaacaata gtcacagaac catcttaaat tttaaaattt   22080
accatagagt gttcaaagga aaacttggta tgggaggcat gcaggagggg tgcaggggc    22140
ggggtctgtg tgtcttgttc caatggctat ctcagatagt cacccatctg gaggtctagt   22200
tggtattatt ttgaattcag cccagtggtg gtggactgtc agtgactcct cgctaagcag   22260
gaggattctg cactcagggc tccatgcatg gtttgtttca agattggcct ctggaatttc   22320
tcaagcaaga acataattaa ataagcaggc attgccagag gggagtgtct ggaaaggaaa   22380
ggaatgaaga gatgaaagga aagtgggtgg ttaaactata ttttaaaac tgaggttccc    22440
agttatagta tgtttcgcac gctccccca ttttagcacc cctgacagaa tttagtaatc     22500
tcctcatctt gtcctctact tcaggtcccc tatctgtcct tgtactctcc agggtttcct   22560
tttcttcttc acgaccttcc ttccctgcaa tttttataagc tattcctatc ccagtgattt   22620
agtttcagct tataaaactg tgtctttgcc attgtaatca aattgaaggg cctctgcttc   22680
atggttggat tctgtgacca ggagactctt acgaggagtt ggccaggtct ctgttaggaa   22740
agcaaaaaag aacaatggag gcaattatcc cattgatttc agctataaat cctatttgc    22800
ctgaattgtc tgaacgatga gtattctgtg aaaatgctgc tctctagtgc aatagaactg   22860
caaataatgc acatctattt cttataatct catccaacat acccacagag attcagatct   22920
aacaaaacag aggtgatttg gttattgaat cataatataa atgtgggaa gagagggaa     22980
atttcaagcc tgaggaaact gtagtaggag taagtatgct gtgtttaaga ggtcacagat   23040
aaaattaata ttaccaatcc atcaataggc aattactaat agcttactac acacacagga   23100
ataaaatgtg aagacagagg aagtgtaaaa tggagcccac aactctacgg agttgttttgc   23160
aatttggtct ggtagaaagc tatgaaataa ggaagtacat gattgagagc tagagaatgt    23220
ggcacaggct ctgaacccgg accgttcaat gtagtaagct ctagcacac tggacacttg    23280
caatgtggct tgtccaaact gacatgtgct ttaagtataa aatataatcc agatttctaa   23340
gacttcaaaa aaaatggaaa tatctcatta ataatcttaa gttattaca ggtagaaatg    23400
atagattaaa taaactatat tgtcaaaatt catttgatct gtttctacag tataacaaac   23460
```

```
ttacttgtgt ggtttgcatt ttatttctac tggataacat ggctttaaaa atggtatttt   23520
agaggaagga aagcttggta gagaatggac taatccggat ccctggaaga aatggacctt   23580
gaatgggtct tgatgacttg gagaggcaga gagagaaaaa gaaaagtcaa acatagggaa   23640
ttggttgata aaatgaaggt gaggggagaa ggaacagagg gaggagaaga tccagtttga   23700
gggatattac agcgagcagc ctgagaaaga aggataaaga aggagagaaa aaatgcaagg   23760
gaagtaaccc ttcaaagcca gtcgaagtt tctgggttcc tcagcagcca gaaaagaagc   23820
cgttgaaaag atctgagtaa cggagattct ggacgaaaac tgaagttatg gaagggaagt   23880
ttagacatgg gttattaaac gctttagcgc attagaagtt tcttatgtaa tcactaaatt   23940
cagatcctga aataatgcca caagaactat acagctcagc cacccaattc aataagaagt   24000
tacagcacag tctcacacat atccaattaa ccttggcctt tagtcaacat ctgggttcct   24060
tttgtcattt tcaaatacta tcacccagag gtgctatgat ttatattggg gaggggatta   24120
aaagaaaata agtaagttgg tgataagaaa aagctttcag atgattccat ctgaattaac   24180
agccctcttt agttgtctag gaaagaggat gcttttctt gaaagtgctt tgaaatgatg   24240
atgtgcttgt tagtaaacat caattatttt caaatcgtaa tgtttgcaag tttgtcttcc   24300
tgtagctcac cctttatgta ggtccagaat atgattgtca caaatatctg ggtgagcaag   24360
actatgaaat gtggtcataa agtcaagtgat tatttctaaa ctcatctttg tcactcgtag   24420
tgcttcacaa agcacctttt cctggactac aattcatttt aattgatccc atcagcacta   24480
tatctgtatc ctgagtgact tcacaatacc ctctatttca agagaaacca atcaggttat   24540
gggtttgtta gtaataaaaa ttaccaagga gcagtttgtg gatggtaaaa gcaatgcaaa   24600
ttctaaagag aagtcataag agcaataata agcatcctcc tcacttcttg gaagtgaaca   24660
attccaagct ccctgaagca acacttaacc tatcatatta aacagtaatg gacaaatatt   24720
agaaatgttg atgtcagctt tcagaatctg tgggcatcaa aacatcactt aagttctccg   24780
aagtattctc tgtcaagttt ccttctacag tattcttttc ctactaggac agagccttaa   24840
gccctagaag aataaattg cttgtgtgtt aattatttgt ttactggttc attccagagt   24900
gtgagctgga aaaaggggga agtgtcataa atagttttt atggcccatg gttttcaac   24960
tacgtcacta ttggtagcag tttccactgc aggatctatt tgcaaagcct aggaaattag   25020
cattaagcaa gctgctagga agacttcaac agtaactagg ccacaggcct cacacatttt   25080
tcctccaccc cagcctcctc tggagagtac ttgctaaacc tctgtgacac ataatgaagc   25140
aaagaaagtg atagaacaac agaattacac gggcagatcc ttgtttcttc ttctctctct   25200
aaagaattcc tttggactgaa aagcagttta tttttggagga gtgagaaagt ggtgacagaa   25260
ttagaagggc ctgggagggc ttcattttag gagacagttt taggctgaaa agagatttca   25320
tgagtgtgat ttacctgagg tgactttttgg gggctcttat aaaaaggaag ttcatgctga   25380
atgggaggtg gcttctgaga tgcagattct ggtgagctaa gagggctcgg taaagaggag   25440
gcaggagtta agtagcgtga actatgcagt agcagccttc ttccccccctt gcttggggca   25500
ggtcatcaca acccttctca ataaagggg ccaggaacca ctaggaataa atgggcattt   25560
gcacttcagg tgaaacccat ttgtcataac tgcttggact ttaagcttac aaataaaaag   25620
aaccacatat ttcccttgc agcttgattt agttaatgtc atttgagaa agaaagaaga   25680
cattgttatc ccgtcccttt ttttttttttt ttttttttt tatgaagaga ctgggactca   25740
gagaagtcaa gtgattttcc cagaaccaga aaacacagaa gtagcagagc tgagatgact   25800
actccggtct tctgattcca aattccaaat tcattcttct aagcgatttc ccaaaacggg   25860
aaatgggttt atcttctatt tatgggaagt gatagtggta ttctatttag agaacttata   25920
taaaatctta ctttaaaata aataatattt caaaagtaa gcttaattta aagaaaataa   25980
tcaagaaagt ctggtatatt tttacaaata taccaaatga ccttgctcta aaatacatct   26040
actttccagc aagccaaagt gaaacaattt gaaataagtg gcatttactg accactccc   26100
aaagttcaca caaagaggt agtactctaa cttaaatata caaggtgaag aaatagctta   26160
ctcagcctgt tgggcttcct cttctacact cttgggaaat gccctccgtg ttaaccaaga   26220
attctcaggc cttggaggga gttttccatt ctcagtaaac tgagattgca gttgcggaaa   26280
ttaagaggta tctgtccagc acttcattcc cttaaggtca ggatctgtgc ttttaataat   26340
gacaattagc taacatatac aattaagcca tgcaaatgaa gtaagagaaa gctagaggag   26400
aaattcagga gccagttgcc tttttccgac atcttgtaca aatagtgttc aaaggactaa   26460
ttcaaaagat gggattcttc gcttgaaccc aggaggtgga gtttgcagtg agcggagatc   26520
gctccactgc actccagcct gggtgacaaa gtgagacccc atccaaaaaa aaaaaaaaa   26580
aaaaaaaaaa aagatgggat tctttttttaa aaaataaatt ttactgcgta tttttaaggt   26640
atacaacgtg atgttataag atggatatag atagtgaaaa ggtaactgta gtgaagcaaa   26700
ttaacatatt catcatctca catagttatc ttttatttgt tttgttttga tgggattttt   26760
aagatagtag aaaaggaatgg tagacaataa acatttgagg gaaagtgggg ctttgtagaa   26820
ctcctaaaat gacagcacgc acaaatgtcc ccattatgtc taaagggtaa ctcgttccta   26880
cttctaggga cagctgaggg acatcaatgt aaatttctaa atgacttcct gaactttta   26940
tttttatttt ttgtattttt agaggaaatt ataataacat caagccacct ctggaccata   27000
tcgctgctga tatcatcagc aaatggcact attcctaaat cctaagatgc acttttccct   27060
tcacatttca acatttgtga aactcgattg tacctacacc tgatttttata tacaatgcag   27120
ccttttcctttt tcttttgtca ttgcatctta cgcctgattt ctccttggaa ttgagtaaat   27180
ataatgctta catgtgttaa taagaattga ggtcactcat aatttttgaa atatgccacc   27240
aaatataagc cttttctacat attgttgact ttgaagtcat ttctttttt aactactaaa   27300
caataacact ttttgttgag aaaaattgca tatgaacaag agaccaagca ggtagagaga   27360
aaaaaacttt taataatcaa gagaatgtta ctgtgtccca aaggctaaag tcaccttact   27420
atcaagagag aaggacagga acagagagaa ccaggtaaat tacgaattga aaattccatg   27480
gttcatttat cttttatttt aattaattcca tttgtgtgat tgtgttgacc acaaggtcat   27540
aatgttactc ttcatactgc cttctcatgt aaattataaa taagtttta tgctaatgat   27600
ttatggagta agctattcat ctttccgaca gagagttacc tacaaagaaa taattattct   27660
acctctgaga tgaaatatca tgaaaggagt ggtttccaga tattttgact tttaaaagct   27720
taaagaatat atgtagtata aaattctaaa gcagcaaaa ttaatccttt tagcaatcaa   27780
gatagcggct acttttggtg agaaggacaa ggtagtgata gagaagggggc tcaggggtct   27840
ttcctgaaga cagtgaggtg ggaaatggta tttccttga cctggatggt gattaaacag   27900
atgtgtttac tttgtgataa ttgactaggc tgtgcaccta tgaactgcat acttttccat   27960
atatgtactg tattccttata cttaaaaga agttaaaaaa taaatgcaac agatatagga   28020
cttcctatat tactcgttga ccaaaaaaat ggattcattt ttctttcagg taaaacgtac   28080
tagtggttt aatattatat tgaccaggga gtaaatgttt accttaggaa ccttaatctt   28140
gatgttctcc aaagtcatta tctgttctttt ctgattatca gaatagagta tatctctata   28200
```

```
taaatgaaaa tttctggtca ttctcaaaaa ataacactaa gcatgaaaat cagaaatatt  28260
gatcttgttt tgtaatgatg tttctattga tgtgaagtag tttctagtag agttgctgtc  28320
ctaacacaca aatgaaattg cactgtttgg aagacacaac tgtgaatgac ttgcttcagt  28380
aaggaatttc caacatgatg gtttagggat agaggtgctc gattcctctg tctccggtta  28440
cccaggttat tgaggacagg gaggtcaata agtaatgccc tcctcccacc catagcacaa  28500
aacagagcgg ggttcagaga ataggtaagg ctttggccag ggtgttgagg agacttacat  28560
ccctgggaac cagtcagaat gggggcgctg aaaacaatgt tttaaattct agcacccagc  28620
aacatatgtg tgaagattaa atgtactcgt gctaaattca cttgctccat tactgaattt  28680
gggtggtgtc tgttaaagat gggaacaaag gcattcaggt cctggtatct tctaccactc  28740
ccagcatgaa cagactcatg tcagtgggta agggatggta tttcccgaga aggctttgaa  28800
ctcttgtagt gggtcaaata atggccccc acttaaaaat gttcatgtcc aaatccctgg  28860
aagctgtgaa aaggggtttt tgcacatgta attaagtcaa agatattgaa attagatcat  28920
cctggattac ataggtgggc cctacattta atgacaagta tcctcataac agaagaggag  28980
aaggtgatgt gagatttgga gcagcagaga ttggaggtgat gtggccacca atcaaggaaa  29040
ccaaggactt ccagcagcca ccagaagctg gaagaggcaa ggaaggactc ttccctaaag  29100
cctttaaagg agcacagccc tactaacacc ttgcttttgg gctctggccc gcaaaactgt  29160
gaaaggatac attgctgtta tttgaagcca cagttcgtag taaatttatt acagcagccc  29220
tagaaactga tacaactcct aaatacaccc ttagcaacac tgctcaacaa gaagtaggca  29280
atttcctcct gactgaaaaa tactgatact gttatgggat ccttgggggt gttgcttttc  29340
tgtccagaaa cctctgtggc ggtggcacct ttgcatgagt tttgctcggg tccactgggc  29400
ccactcatcc tggcaggctg cgctcagctg acactactgg cgtggatccc atgcctccaa  29460
agagactgga gcgaagcggt gagggatgtg tgaggaaggt gggtggggt ctggcacaca  29520
gtcaggctca atggctgcta cagcgggatg ggcagcttca ggtgctggca cgggtgctgg  29580
ctcactgcaa ggctgtggct gcaccaagca gcgcagcaac ggaacgcatt ggtgcctgga  29640
aacttggaga ctccaggaac ctcagggctc caaaaggcaa atcacagccc tagcttcggg  29700
agctcccagg tctgggctgc caaagggctg cagctcttct ctcctctctc tctcttcgct  29760
cctctccctt tctctcttca ctcctccctc tttctctctt cactcctcct gtcgcctatg  29820
aacagcgaat tcaaccttcc agttttcaga ctaggaatgc tggagttgtc cttgattact  29880
ctgaattgtt cactccgcat atgggcactg aggatacgtt gatgaactac acagacaaaa  29940
aggatagaaa ttcctgtcaa gactacattc aatagggatg aagcaggcaa taatgaataa  30000
acatactaag ttgaatatga ctatttaaat atatataaca catatgactt gtataatgtt  30060
aaatatttta agtttttaa attcttccct tcatagattt tacattatag tagaagaggc  30120
attttttgttg ttgttctttt tgttttggat tcagagggta aatgtgcggg gttgttacat  30180
gggtatattg cataatgctg atgatggtcc catcacccag gtggtaaaca tagtacgtaa  30240
taggtgaatt tttagcccgt gcttccctct cccatctagt cgtcctgagt gtttatcgtt  30300
gctacgttta tgtcaatgtg tattcaatat ttagctccca cttataattg agaatatgca  30360
gtatttcgtt ttttgttctc gtgttaattt gtttaggata atggcctaca aagaacatga  30420
tttcattatt tttatggaca tgtagtattt catggtcatt atgtaccacg gtttctttat  30480
acaatcccac tgttgatggg caccttaggtt gattctattg ctgttgtgaa tagggctgca  30540
atgaacatac aagtgcatgt atcttttttgg taacaaaaat tttatatttg gattacccag  30600
tagaattgct gggttgaata atagtttttgg tttaagttct ctgagaaatc tccaaactgc  30660
tttccacagt agctgaacta atttacattt ccactagcag tgtataagcg ttctctttttc  30720
tccacaatct tttcaccagc atctgttatg ttttggcttt taatagcct tttgatgact  30780
gtgaaatggt atctcactgt ggtttggatt tccattctc taatgattag tgaatgttga  30840
gcattttttt catatgttta ttggccgttt gtatgtcttc ttttgataag cgtctgttca  30900
tgtccttttac acattttcaa ttaaaatatt tgttttttgc ttgctgattt aagttctttg  30960
tatattctgg aaattagatc tttgtcagat gcatagtttg caaatatttt ctcccattct  31020
gtagcctgtt tactctgttg gtaatttctt ttgctgtaca gaaactcttt aattaggtcc  31080
cacttgccta tttttagttt tgttgcaatt attctctgga acttagccat aaaattgttttg  31140
ccaaagccaa cgtggagaag gatattttct aggttttctt ctaggatttt atagtttaag  31200
ttttacattt aaatcttttaa tccatcttga gttaattttt gtatatgttg agaagcagga  31260
gtctaatttc attcttctgc ataggggctag ccattatctt ggcaccattt attgaataga  31320
gagtcctttc cttattgctt atttctgtca atttttgttga atatcagatc gtcgtaggtg  31380
tatgggtcca tttctgggtt ttctattctg ttctattttgt ctctgtgtct gttttttgtac  31440
cagaaccatg ctgcttggtt actgtagcct tttagtatag tttgaagttg ggtaatgtga  31500
tgtctctggc ttcgttcttt ttgcttagga ttgctttggc tattcaggct ccttttttggt  31560
tccatatgaa ttttagaata ttttttctgat tctgtgaaaa atgacttgat attttgctag  31620
ggatagcatt ggagtggtaa cttgctttgg acagtgtggc cattttaatg atattgatta  31680
ttccaatcca tgagcatgga gtattttttat atttattcag tcatcttgat ttcttttcag  31740
agtgttttgt agttcaccct gtagaacatt tcacttccat ggttagatgt attcctattt  31800
tgtggctatt gtaaatggca ttgtattttt tttatttgg ccctaaacta gaatgttatt  31860
ggtgtataga attgctactg attttgtac attgattttg tatccttaaa ctttactgaa  31920
gttatttatc agttctagga gacttttgga gaagtcttta gggttttcta tgtatgaaat  31980
catatcatca gcaaagagag acagtttgac ttcttcttcc ttttggatgc catttatttc  32040
tttctcttgc ctagttgctc tgactaggac ttccagggca atgctgaata gaagtggtga  32100
gagtgggcat ccttgtcttg ttccagtact caagagaaat gcttccagca tttacctgtt  32160
tagtatgatg ttggctgtgg tttgtcatag gtggatctta ttattctaag gtatattcct  32220
ttgatgccta gcctgtcgag ggtttttaat catgaatgga tattgaattt tattgaaggt  32280
tttttctgaa actattgaga tgatcatatg gtttttgttt tttcattctg tttatgtggt  32340
gaatcacact tattgatttg ttatgttgaa ccagccttgc atcccaggaa taaagcctac  32400
ttgattgttg tgaattaact ttttgatgtg cttcttgatt tagtttgctc atattttgtt  32460
gaggattttc gtgtttatgt taatcagaga tattgtcctg aagttttctt ttttcattgt  32520
gtctctggca gattttgata tcaggatgat gctggcattg tagaatgagt tagggaggag  32580
ccctctcct taatattatg gaatagtttc agtaagatta ctatcagttc ttctttgtat  32640
gcttggtaga attcagttgt gaatccatcc ggtccaggc taaatttggt tggtaggttt  32700
tttattactg attcaatttt ggaacttgtt ataggtctgt tcaagttttc acttccgtcc  32760
tggttcaatc ttgggaggtt gtatgttttcc aggaatttat ccattcctc tagatttcct  32820
actttgtgtg catagaggtg ttcataacgg tctctgaaaa tctttggcat ttctgtggga  32880
ttggtcgtaa tgtcattttt gtcatttctt gtgctttttg gaacttctgt ctgttttttcc  32940
```

```
tcgttttct  agctagcagt  ctattagtct  tgtttattct  tatgaaaaac  caactcttg   33000
tttcactaac  attttatgga  cttttgcatc  tcaattttat  ttagtcatta  tctgatttta  33060
gttatgtctt  ttcctctgct  agctgtgaga  ttgaattgtg  ctctttttt   ctagttcctc  33120
tagtgttatg  ttagattgtt  tagttgagat  ctttctaacc  tcttgatgaa  ggcattttag  33180
cactataaac  tttcctctta  acactgcttt  tgctacatcc  caaagatttt  ggaaagttgt  33240
gtctctattt  tcattaattt  caaataattt  tttgatttct  gccttaattt  cattgttcac  33300
ccaacagtta  ttcgggagca  tgtggcttaa  tttccatgct  tttgtgtagt  tttgagagat  33360
cttcttggta  ttgatttcta  ttgttatttc  actatgattt  gagagtggcc  tttgtatgat  33420
tttaattttt  tttaatttat  tgagacttgc  tttatgactg  agcatgtggg  gcaatcttag  33480
aatacgttcc  atgtgcatat  gagaagaatg  tgtgttctgt  cattgttggc  ttgagtatcc  33540
tagagaggtc  tattaggtcc  aactggtcaa  gtgtcaagtt  taattccaga  attccttcgt  33600
cagttttctg  cctcagtgat  ctgtctaatg  ctatcagtgg  agtgataaag  cccccactaa  33660
tattgtgctg  ccatctacgt  tttattgtag  gccaataatt  tgttttatga  atctgagtgc  33720
tccagtgttg  ggtgcatata  tgtttagaat  agttaagtct  ttttgttcaa  ttgaacctt   33780
tatcatttta  taatgccctt  ctttgtcctt  cctgattgtt  gttggtttaa  agtatgtttt  33840
aatctgattt  aagggtagca  actcctgctc  tttttttgtt  ttcatttgca  tggtagatct  33900
ttcttcattc  tttcactttg  agcctgtgag  tgtcattcat  gtaggatgca  tcttctgaaa  33960
acagcagaca  gttgtgtctt  gtctttttat  ccagcttacc  actttatgca  ttttaaaggg  34020
agagtgtaga  ctgtttacat  ttaggggttag  cattgacatg  tgagattttg  ctcctgtcat  34080
tgtgttgttt  agctggttgt  tttgtagact  tcattgtgta  ataagtgtat  ttttattggt  34140
agcaggtttc  gtctttcatt  tccatgttta  gcaatcactt  acgatttcc   tgtaagaatc  34200
atctggtggt  aatgaatctc  cttgtgtgct  gcttgtctga  gaaggattgt  atttctcctt  34260
cacttatgaa  actcagtttg  gtgggatatg  agttcttggt  tgaaatttat  tttctttaat  34320
aatgctgaaa  atataggccc  cccatatct   tctggcttgt  aaggtttctg  ctgacagaac  34380
tgttgctggc  ctgatgaggt  tcttttttgta  ggtgacctga  cctttctcac  tagctgcctt  34440
aacaatttt   tcttttgcat  tgaccttggt  gaatcatatg  tgac        ttggcaatgg  34500
ttgtcttgta  tagtgtctca  caggagttct  ctgtatttct  tgaatttgta  tgcccacctc  34560
tctggtgaga  taggggaaat  tttcatggac  tgcatcctca  gatgtatgtt  ctaagttgct  34620
tactctcttt  ctcaggaatg  actgtgagtc  atagacttgg  tctctttaca  taacctcata  34680
aatcttgaag  gttttgttca  tgttttaaat  tcttttttct  ttattttttgt  ccaaccaagt  34740
tgattcaaat  aactggtctt  caaactctga  gattctttcc  tcagcttggt  ctgttctgct  34800
gttaatgcct  ctgactatat  tatgaaattt  ttgaagttga  tccctcaatt  tctgaagttc  34860
agttttgttc  tttcttaaaa  tagctatttc  atctttaagc  tctttgatca  tttttctgga  34920
ttccttgagt  tccttgtatt  gggtttcaat  gatctcctgg  atcttgatgt  acttccttgc  34980
catccagatt  ctgaattcta  tgtatgtcat  ttgagtcatt  ttaatctggt  taaaatcctt  35040
tgctggagga  cttgtgtgtt  tgtctggagg  taaggagaca  ccagcttttt  tgaattgcta  35100
gagttcttga  gatgactctt  taacatatga  gggctggtgt  tccattaaca  atagtgtaca  35160
ttgagtatag  tcagttggct  tcattctgag  tgctttcaaa  gggccaaagc  tctgtacagc  35220
atctttattt  gtggctagat  ttttgcttta  ggttcacag   gtgctgtata  ttggaaaaat  35280
gtttttggtg  ttgtcatttg  gggtgcaatc  cagtaggtca  tgcttaagag  tggtagctgg  35340
cagataggct  cttactcagt  ccacagctct  tttgtatttt  ggtgcagtcc  tcagtagtgc  35400
tctgtggtgg  tagggagaga  tgaccccctc  accagataca  ttcctgggcc  ttggggagc   35460
cctctcttat  tactggcact  gcacctgcat  ttcatttatt  aggtgtcctg  ggctgcaggg  35520
tgccctcagg  cagaggctgc  ggctggaaaa  tagaccatac  ccttccctgg  ctggccctgc  35580
acaaggaggc  acaccctgtt  cctgagccag  tccatgaacc  cagctgtctc  acccctctca  35640
gtgttctgag  agtaggggat  cccccactgc  ttgagcacca  tgagccctc   ctggctacag  35700
gcagtgggga  taggtatagt  ctctcaaccc  actgtccaac  tgatttccag  ggtaacagag  35760
agctgtgcct  gcccacagag  ttcaggcaga  ggccaggcca  ttgtgctgga  agctgatgct  35820
aagccttgtc  tgatgatggg  gagtgaagca  atgtaacggc  tccctaactg  tggcttctct  35880
cagggctatg  gcagctggca  tgagactgct  ccaggtccaa  ggcctgtggg  acttcctgtg  35940
gacttgagtt  ttgcctctgc  aaacactcca  gcaactctct  atgtcagtct  agaggccag   36000
ggacacggat  caggtattgg  gatgaagggg  ttctccagtt  cccaggattt  cacaggtccc  36060
tgtgaaagt   gaggatcccc  caggggctct  cactcactca  ccctttctct  atgttgggga  36120
gcttccctg   gctccatgcc  catcttgggt  ggccagctgc  ccagcttcac  tcttccctgt  36180
tctctgtgtc  ccctcactcc  cttaattgtc  ctgatatcgt  tccttaggtg  atctacttgc  36240
agaggcagtg  tttactcgcc  acttgttttc  tctctgtgag  agtagcacac  actagctgct  36300
actcatctag  catcttgaat  tcttcccatc  tgaaaaagtt  tcaactgcaa  tcacagttaa  36360
agaaatacaa  aaacaatagc  actctaagtt  acaacttctc  acctatagaa  ttcaaaaaca  36420
tccaaatgat  taactaaaca  tttgtttggt  agatctgtgg  gaaaacatga  attccttgtg  36480
aattactgga  gaaatgaaa   atgatgcaac  acttatggaa  gaaaatttgg  ggatttttgg  36540
ggggagggg   aacaatatat  ttaaaactat  aaatgcattt  atcctagcaa  ttctatgaat  36600
ggggatttat  cttagggtac  acctgcacac  ttaggaaata  atgtatgcag  tcattcatta  36660
cagaattgtt  tgtaatagca  acaacctgaa  aagcaactca  tatatcctc   catcacacag  36720
ggactggttt  catgactacg  gttcatgaat  atctctgcagc  ccttagaaag  aatgaggaag  36780
tggccgggca  cggtggctca  tgcctgtaat  cccagcactt  gggaggccg   aggcgggtgg  36840
atcacgaggt  caggagatca  agaccatcct  ggctaacacg  gtgaaacccc  gtctctacta  36900
aaaacaatac  aaaaaaatta  gccaggcagg  cgcctatagt  cccagctatt  cgggaggctg  36960
aggcggaga   atggcatgaa  cccggaggc   agagcttgca  gtgagccgag  ataacgcac   37020
tgcactccat  ccagcctggg  cgacagagcg  agactccgtc  aaaaaaaaa   aaaaagagga  37080
agttctctat  gcgctgacat  ggaaggaaga  cagatggttg  aatgaaaaaa  gtacataatt  37140
agccataaag  tgtaagactt  tttgtctaaa  aagaagggt   gatataattg  catatttata  37200
ttttcttcca  tttatattaa  gagataataa  aggtacacaa  attggctaga  ataaagtggt  37260
ttcctataaa  gggtaagagt  aattgagtgg  atgaagacta  gggttaggga  tagatttctc  37320
agtgtattca  ttttaatata  tgtattcatt  ttatatatgt  actaattttt  atatatgtat  37380
ttattttata  ttttgatttt  cttaacataa  atatatatt   ccttcataaa  attaaacttg  37440
atacatttt   gattactaga  tatgtagaaa  gcattatgtt  cagtaccaca  gtaatacttt  37500
caaaccagct  acaattagta  tttatgagca  tctatgtgcc  agacattgtg  ttctgctttg  37560
gttggtgggg  gtagaggagg  aaaggaaacc  atggcttaca  taggagtgga  agtccttgtct  37620
ttcactttgc  acctctctcc  ttcagaccta  gcataaatat  gaccttaggg  gaggcagaac  37680
```

```
acatatgata aagagataac tagcaagaga cataatagta gctaaataaa tactgaagga  37740
aaaattcagg aagaggtagg aaggatatgc ctcatcactt ccacctgtta agaaaaactt  37800
tagacattct tgccaatatt ccttattgcc tgtcttttga acaaatgcca ttatcactag  37860
agtgaaatga tatttcattg tagttttgat ttgcatttct ctcatgatcg gtgatgttga  37920
gcacctttt atatacctgt ttgccatttg tatgtctttct cttgaaaaat gtctattcag  37980
atctttgccc atttttaaat ggcgtaatac attttttcct attgagttgt ttgagttctt  38040
tatatattct ggttattaat cccttgtcag atgaataatt tgcaaatatt ttctcccatt  38100
ctgaggatta ccagaggctc agaggggtaa tggtggtggg ggagaataaa aatggttaat  38160
gagtacaaaa atatagatag gagtaataag atctagtatc tgatagcaca acagggtaat  38220
tacagccaac aaaaatttat tgtgcatttc aaaataacta agagtataat tggaatgtct  38280
gtaacacaaa gaagcaataa atgcttgagg tgatgtgagg ggatggatat ctaatttacc  38340
ttgatgtgat tattacatat tgtatgcctg catcaaaata gctcatgtat cttataagta  38400
tatacaccta ttatgtaccc attaaatttt ttaagaactt taaacaaatc aaatttaaca  38460
gagtttaatt gggcaaagaa tgatttgagg atcaggcaac ccccagaaac agaagaggtt  38520
caaagcaact cagtgctgtc acatggttgg agaggattta tgggcagaaa agggaaagag  38580
agatacagaa aatggaagtg aggtacacaa acagctggat tggttacagc ttgccatttg  38640
cgttatttga acataatctg aacagttggc tgtctttgct tgaccaaaac ttggtgtttg  38700
gtacaagagc agattacagt ctatttacac atccagttag tttacagttc actatacacg  38760
aagaagaaac ctttaagcag aacttaaaat atgcaaagag gaagctttaa gttaaactta  38820
atttaacaca cccaattatc aaaaaatgag tagctctgca aaagtggatt ttcctggtca  38880
tctttggtac ttccttaaaa aagagaaaag tagtactcac gataaaaaaa aaaagtcct  38940
caagtcttta ttttattcct ttccaattta aaatgttaca tcatctgagg aaggtttttc  39000
cctttgaccg cttcataga catttcttct gcatggggttg gccagaatca gaagagtaat  39060
tgtaactttc tgttcttgtc ctacagttac aaagcggttt cactttgtaa atgctctttg  39120
gatggcagga accaagcagc catgaaaaga ggagttacac cttttaagga gtcattccat  39180
catgactctc aggactggaa catgaattac tgaatgacc tctttggcac agataggcca  39240
cccttgaaag gtgttccaag ctaggaactc actaccactg ttacatcgat gcaactctgt  39300
gagaagtttt tatctggtga tggaaaatct catctcttca acacactgac tactaccagt  39360
ctcagaaccc tgtaaacaag attcattcat ctcaaattgg gttaaagcag tcaccctgcc  39420
ttacattagt ttggaataag gatgtggga tggtggtaga ggaggggagt ggatgatgat  39480
tttttattg ttatttgatt ctaaagaaac ttctatacat tttgcattta aaataattat  39540
gttttaaca atgtttggat taattcaaaa taggatatta tatcctatta tattaaatat  39600
actatttaat catcttgttg accaaatgca acttaaacat gtaaatggt aaatagcata  39660
ataattgtct tctaagcctg cactataaag tatttcagtg gcctcattat taaaggacca  39720
aggtgcccaa agaaacaaaa tttagtaatc ataaacaaga gacaaaccta cttctttttcc  39780
cccagagttc tggccacatt gaaataaggt gtttgaatgc ttaataagaa ttattttggc  39840
ccacacagtg gctcatgcct gtaatctcag cactttggga tgccaaggtg agcagatcac  39900
ttgaggccag gagttcaaga ccagcgtggc caacgtggtg aaaacccatc tctactaaaa  39960
atacaaaaat tagcccggtg tggtggtaca cgcctatagt cccagctact cgggagactg  40020
aggtgggaga atcacttgaa cccgggaggc caaggctgca atatcgagat cacaccactg  40080
cactctagcc tgggcaacag agtgagagtg agactctttc tcggaaaaaa aaaaaaagaa  40140
ttattttgaa caaagtgctg tcacctaagt tagcaaaact ccaagcaagg ttttttggctc  40200
tgtaaggaaa gaattagcct actcatttgg aaatttagtg gtgttttgtaa tgcagaaagt  40260
gacagtgaga ctggaaaggg attggctttg gggcttgttc tgctttataa ataaatga  40320
atcttctcca acatgaagta atgtgaatta aaaaaaaaaa atctgtcctt agagtacaaa  40380
attacttcat aacccaatct gcatttctcc actccaagca tattttctgg gagttctact  40440
tagagagtga aagctgctgt gtgtgtgata ttaattttta acaaacactt ggcaaactga  40500
gctggactat gtataagcta ccctagacta agcatgaatt tgaactgcac ttttttatggt  40560
gtttttttcca caatgacatt atttaggcat ttaaagttat ctgaactgca atttttttgtt  40620
cttttttttt taatttgact ttttaaaaaa aattattcct gaataaagag gcagtttgta  40680
aaaactcgag aactgtgaga gataattgaa tctttgtgta gcaaaactag aagggtgttg  40740
ggtatctgct ctttatcaaa tggaccactt actttttcttt tcttttttgc cctgtgttca  40800
gaaaacaaat gtgcgtgtct cctgatttat aatgtatagt tcattaatgg agaaagtgct  40860
tgagaattag atcctaatgt catttcccat gcagcatctt cattcttttc taaagcacta  40920
tttggtaaaa acaactgata gtcgtcagag gtgatcagca atgtttgagc actatttcct  40980
ttttatatcc tgcacatgga atatggacag gcaaacaaat catttccaag taagaaaata  41040
aattttgagg gagttaatac tataatttga aagtaataac ctcctattta tccatctagt  41100
ttgttgttct gtactaaatt atttgtgcat gtctctgtgt ctataattta tgtgaaactt  41160
tgcacaatct taaataggac aaaatagaca ttctgtaatt tcccaggcaa gctatttaag  41220
gtgactatct ctctacatat ttgagatgaa aaacaataac atgacaatcc atcccttctt  41280
aggtttttgt aagcagactt actacctgtg actcagttttt gttctcacag ggtactaatt  41340
aatccttcac gataataact tgtcaaattc cattacttct gtaaaggcaa tactttatat  41400
ttgtttgtat tcaaatttta aactgatgtt aaatgccgtg ggtgcaactg caggttaaaa  41460
atatgtgttt gaatctctta ttctttttgc ttggcaatgt atgaaataac tgctctttct  41520
agaaatcttg atgatgaagt ggcctgttgt tttgtcaccct aaaaatgcaa taatgttcaa  41580
attaagcttt tctttattaa catcacttga ttgtgtgcca tatttagagc ttagtgaaat  41640
tttaatctac acattgatta aatacatttt attattctt gttctaatg ggaacttctt  41700
ttgttctaa tgggaactt cttaaattaa attacatcca acatttatta aagacctaaa  41760
acataggcaa ttactgtgct tagaggaaaa gcgcagacga aagtgaatca gacaagttcc  41820
ctgccctccg gaagctttca gtctagtgat gagaaagacg tatacacacc ttatgttgat  41880
ttaaaaaaaa aaaagctct tacctggttg ctggcatatg aaagtgttag ttacagatct  41940
gccccaaact aaaggtgtca cctcgagtaa atctcttttcc ctttccctt caatctcttc  42000
atctataaac taggggttgg gaatacattt attaacaaac acaaattgag cgtctaccat  42060
agtgataatag tagctaaact tactgagcaa ttaccatggg gccagggtatca agataaaccc  42120
tttatgatgg taacctcatt taatcctcaa agcaattcca ttttcaagag gaggaaattg  42180
aggctcaaaa atgttaagta actccccaa ggatgcaaag tgattgagcc agaattcaag  42240
actaggttgg tttgactcca aaactcatgc cattaaaccc tattgtgtca ctgcaaacaa  42300
ctctaatagt ttcaaattat tagttctatt aatattat taccattatt tgcccccaaa  42360
atgtaaaatg taaatacaaa gagtttggtt tttgtattac tagtggaggt taaaggtgca  42420
```

-continued

```
caatggaatt attcaaactg ggaaaatcca ggaagacttc atggaggagg cagcatatgg   42480
ctgcagttaa taaggtttgc tcacacaaaa tggagaggtg aggacatttc aggcagagag   42540
aattatatga gaggttacag agcagtaaac agtcatgcgt ctgcaagatc aaagggaaag   42600
ggcggtaaga gagaagcttg aaagtcaagt ggagccagat tgtggaaaaa ctagagagtc   42660
atgccaaggt ccttgacata tagaaaatgg gaagcccctg aaaggtgaag aacatgagag   42720
tgaaatgatt agtaactttt tggtttagga cttgtttctt ttgtgttttg gttgctttct   42780
tgtttttgttt tgttttgtggt ttttaaattt acaaccaata agaatattta gtaaggtttc   42840
caaatacatc atgaatatat aaaactagcc tgactcaagg ataataattc tgggtagttg   42900
gagtgaagtt tcaatcagct acgtggcatt tgctaatcat ctgatatgag ctaacaataa   42960
aggagttaac aaataaactg tcagcctaca gtccagggtc tcaaatagca tgtgacatag   43020
ttgagaagca gtttttccata tcatacatga aataactaaa gaaactactt acaaagcact   43080
ataccagtaa ctacaataaa atacaactat acatgcaaaa taatgctgaa agctgcaagt   43140
agaggggtaa agctaggcca gttgctcagg gaaccattct gaagtggatt tgggaagtat   43200
gtctagaagg ggagccattg ctgtgagagt gctgaggctc atctgctact agtccccccac   43260
tactcaggca tatggtaggt cagtaacaaa accatcattg tgcactgttc tttccatcta   43320
aattccatca aattatgacc aacctatcaa ggtactagtt caaattctct cttcctctat   43380
aagctagtgg tcttctctaa aatttaagaa gatcgtgctc atcttcctac ttcttgttct   43440
cttcttctg tgtttttctga ggctgcaatg aactaggaac ttcctctccc cagaactctg   43500
tattccaggc cttagatcac tcaaaactgt tgcttataaa gtgcagagaa tcaacagaga   43560
aggaatagag gttaatgtct ggtcaaagat gtgattctct tgttgaaaag ttcattagct   43620
tattatttat agaatcataa gtcccaggaa aaaccaaaag gaaatatata ttggatccta   43680
atgatattct cttttttttct ttttcttttt ccccccactcc attgcccagg ctggagtgca   43740
gtggcataat ctcagctcac tgcaacctcc acctcccggg ttcaagggac tctcctgcct   43800
cagccttcca agtagatggg attacaggca tgtgccacca catctggcta attttttttt   43860
gtatttttag tagagatggg gtttcaccat gttagtcagg ctggtgttga actcctgacc   43920
tcaaatgatc caccagcctc ggcctcccag tgtgctgagga ttgcaggcgt gagccaccac   43980
acccggcctg atattctctt gcaagggcat tgtttacatt gtctatcatc agaactgtag   44040
agtgttggct ccaggcacag aaccccctaga gttttgtaaa ccatttatat cacactggca   44100
accagaagta actttatata ctcaagaatc aagatttcac ctagaagtac ctcaggtagg   44160
tgttggttca ttcacattcc aaccaaaaga taatgtacca taaagtgcat accgcctagt   44220
ccgtaatgat taaggcaacc acataaaatc tcattattta aaagaaatta agtccaggca   44280
cggtggctca cacctgtaat ctcagcactt cgggaggcca aggagggcag atcacctgag   44340
gttgggagtt tgagaccagc ctgatcaaca tggagaaatc ccatctctac taaaaataca   44400
aaattagcgg ggcatggtgg tgcatgccta taatcccagc tactcaggag gctgaggcag   44460
gagaatcact tgaacccagg aggtggaggt tgagatccgtg ccattgcact ccagcctgga   44520
caacaagagt gaaactctgt ctcaaaaaag aaaaaaagaa aaagaaatta aatgcactat   44580
ggtttatgga gcggtattcc tcctccatgt cctacataag atctttcaca tgccagtcac   44640
agttaaaatct aatttgctgt aatctggata aatgggagct aatcaacaag ctctcagctc   44700
tagctctgaa tcagcagcag atattgcatt tttgaaatac actaatagca agaatgcctt   44760
cctgacaaca actggcattt ttgacacagc aggaagttta tctggattct gatataaatag   44820
ttattggaat catacatagg tacatagttt aaaaggctaa taagtcattt gttattgctt   44880
ttattatctc tgcatagtta gtaaaattga gattagaacc acttctcgaa tgtactgttc   44940
taaatcctta gcttgcttga tcacacatga ccctcacaat gatcctagga gaaattattc   45000
tgcatgccat tttgtagctg gggaaactga ggcacagaga aatacagtac tgcccaaaat   45060
gtcataacta atcaaaggca aagacaatac tcacaccagc tctgattcca gagcccactc   45120
tcttaaccat atgcttttct gcttcccctag ttgtagagtc ttttttgtatg actgcattaa   45180
ttatatgtga agagttcaaa aatttctata taaggtcttt taagggtgtc attctggttg   45240
aaaatggagg actaggcttc tcacttgaag acatatttct gtagaaaaac ctattttcat   45300
ttagatgcta cagttacttg atgtggttaa taaaccagtt aacagagtat gaaaaggata   45360
agggttaaag ccctcccaag ccatcttcca tgctgctaat atgaatcaca ttactagata   45420
cttaaatatc attttctctt tggttcccag aagactgcat atatgctaga atatttgtcc   45480
tcctcttttta ccctttcagg caataaagta ttttggacca ctgtactatg ttataattat   45540
tgtttctctc ctgattttttt tgctccaatc taatgaaaga catacaagct actatactgc   45600
tacacaatga ctaaatacct gttggattag gtgggggaaa gatacacagt cactggctag   45660
aaagcatcat gcatacagag ccattttcac catatatttt atttctcatg atcatgtaga   45720
atttaggctt tggtgttgat tatttctctc ttaggaaaca tagttgtttc agggttgata   45780
tcacaaaaaa acagaaaaac ctattcgaga aaaggaaaat tatttgtctg taggccaaat   45840
tttgaagtag gaaaacctgc ttttggagtt gtattccoct cccaggcact taatccaagt   45900
tccagtctta ttctaaactg gggatgctag tattaaccac cataggagtt atctgagatg   45960
agttatcatc aacttggtac caggttgttg tcctctggac tcagtgagct ctagaattgc   46020
atgaaactgg cctaatttat caaagtatgt agccttgggt aaataattca agctctcaga   46080
ggtccagtta tctcctctgt aaaacatatc tacatcctag ggatgacaat atctacatcc   46140
tagagatgtc aggaggatta agtgtaattt ttttttaattg tatgtattta aaatgggcaa   46200
cataatgttt tgatatacac gtgtatagtg attactacag tcaagcaaat taacatatcc   46260
atcatttcat agctaccttt tatgtatgtg ataagattat ctaaaatcta ttctcttacc   46320
aaatttccag tatacaatat tgatatggtt tgatccatat ccccatccaa atctcatgtt   46380
cagttgcaat ccccaacgtt ggagatggag cctggttgga ggtgattgga tcacagggtgt   46440
ggcttctaat ggttcagcac catcctttct tggtactgta tagtgagtaa gttctcacga   46500
gatctggttg tttaaaagtg tgtaacacct ccccacttt ccctcctctc gttcctcctg   46560
ctcccgctat gtgaagtgcc agctccctct ttgccttccg ccatgattgt aagttctctg   46620
aggcatcccc agaagctgat gctgccatgc ttcctataca gcctgcagaa ccatgagtca   46680
attaaacctc ttttctttgt aaattaccca gtctcaagta tttctttata gcaatgcaag   46740
aatggactaa tacagaaaat tgttactgag aagaagggca ttgctataaa gatacctgaa   46800
aatgtagaag tgactttgga accggctaac aggcagaagt tgaaacattt tagagggctc   46860
agaagaagac agaaagatga gagaaagttt ggaactcgct aggaacttgt tgagtggttg   46920
taaccaaaat actgatagtg atatagacag tgaagtccag gctgaggagg tctcagatgg   46980
aaatgagaaa tttattggga atgagtaaag gtcaggtttg ctatgcttta gcaaagagct   47040
tagctgcatt gttcctctgt tctagggatc tgtgaaatct tagacttaag aatgatgatt   47100
tagggtatct ggcagaagaa atttctaagc agcagagtgt tcaagaagta acctagctgc   47160
```

```
ttctaatagc ctatgctcat aggcatgagc acagaaatga cctgaaattg gaacttacac   47220
ttaaaaggga agcagagcat aaaagtttgt aaattttgca gcctggccat gtggtagtaa   47280
agaaaagctc gttctcagga gaggaagtca agcaggctgc ataaatttgc ataactaaaa   47340
ggaaggcaag ggctgataac caaaacaatg gggagaaaga ctcataggac taacaggcat   47400
tttattttat tttatttta ttttattatt attatacttt aagttttagg gtacatgtgc   47460
acaatgtgca ggttagttgc atatgtatac atgtgccatg ctggtgtgct gcacccatta   47520
actcgtcatt tagcattagg tatatctcct aatgctatcc ctcccccctc cccaccccca   47580
caacagtccc cagagtgtga tgttcccctt cctgtgtcca tgtgttctca ttgttcaatt   47640
cccacctatg agtgagaaca tgtggtgttt ggttttttga ccttgcaata gtttactgag   47700
aatgacgatt tccaatttca tccatgtccc tacaaaggac atgaactcat catttttat   47760
ggctgcatag tattccatgg tgtatatgtg ccacattttc ttaatccagt ctatcactgt   47820
tggacatttg ggttggttcc aagtctttgc tattgtgaat agtgccacaa taaacatagt   47880
gtgcatgtgt ctttatagca gcaggattta tagtcctttg ggtatatacc cagtgatggg   47940
atggctgggt caaatggtat ttctagttct agatccctga ggaatcgcca cactgacttc   48000
cacaatggtt gaactagttt acagtccac caacagtgta aaagtgttcc taataggcat   48060
tttaggcttt catggtggtc cctctcatca caggccccga ggcctaggag gactgaatca   48120
tttcctgggc caggcctagg gccctgctc cctcttacag ccttgggact ctgctccctg   48180
aatcccagct gctcaaaggg gcccaggtac tgttacagta ggtagctaat caggcatgag   48240
tggggtaaga gagaagtccc caccaccac caggaatgtc aggcaaccat cagatgatgg   48300
tcaggcagtt gtcatactgc ctctctaaaa tagtaattgg ttgcagccag caccagggag   48360
aggcaacttc tcaatagata gaaacacctg aaattggtaa ctgggcgctt ccaataagat   48420
ctcaggaact gagagagtgg gcttaacatg cacattaaga ggcaaaatgg tgaagtatga   48480
cctttgggggg cattccaccg gaaaaggggaa gaaagcctca ggtaagcatg tatacaactc   48540
cagtaaacac actgcacacg ctcaccttcc aagtgcaagc agggcaccat gcatgcggca   48600
agctcaccct tagggaagga ccaagggaaa gggggcacaag atgtcagaag taggccagtg   48660
tataagatcc taggttcaag gtcaaacagg gcacttgacc tccaaggtgc ccacttgggc   48720
ctcttccaaa tgtactttcc tttcattcct gttctaaagc ttttttaataa actttactc   48780
ctgctctgaa acttgtcgca gtctcttttt ctgccttatg cctcttggtc aaattctttc   48840
ttctgaggag gcaagaattg aggttgctgc agacccacat ggatttgcag ctggtaactc   48900
agataacttt caccagtaag aatacagttc aggctgctgc ttcacagggt gccaggcata   48960
agccttggtg gcttccataa gctgtgaagc cggcgggcgc acataatgga agagttgagg   49020
cttaagaagc tctgcctaga tttagagga tgtatgaaaa agcctggatg tccagacaga   49080
agcctgttac tgggggtggaa tcctcatgga gaacatctac tagggaagca aggagaagaa   49140
atgtggggtt gcagccccca cagagagtcc cctggggcac tgcctagcag agctatgaca   49200
agacagccac cgtcctccag acccccagaat ggtagatcca ccaacaactt gcaccctgca   49260
gcctggaaaa gctgcaagca ctcaatgcta gcccatgaga gcagctgtgg gagatgaacc   49320
ctggaaaacc acaggggtgg ttctgcccaa ggttttggga gcccactcat tgcatcagtg   49380
ttccctgggt gtgagtcaaa ggagattatt tcagagcttt aacatttaat gactgcccgg   49440
ctggcttca gacttgcaat ggggccctat agcctctttc tttggcaga tttctccctt   49500
tcggaatggc agtatctgcc caatgcctat accccattg tatctttgaa gcaattacct   49560
tgttttgat tttacaggtt cataggtaga agggactagc ttcgtctcag gtgagacttg   49620
ggactttgga cttttgaatg aatgctggat cgagttaaga ctttggggaa ctgttggtaa   49680
ggcacgacag tattttgcaa tatgagaagg acattagatt tgggaggggc cagagttgga   49740
ataacatggt ttggatctct gtccccaccc aaatctcatg ttcaactgta atccccagtg   49800
ttggaggttg ggcctggtgg gaggtgagtg gattatgggg tggcttctaa tggttttgta   49860
cagtcccctc ttggtactat atagtgagtt ctgacaagat ctagttgttt aaacgtatgt   49920
agcacctccc atttctctct tccccccagtt cctgccatgt gaagtctggg gtctccctat   49980
gccttccatc atgattttaa gttccctatg gcctgcccag aagctgatcc agccatgctt   50040
cttgtacagc ctgcagaact gtgagccatt aaacttttct ttataaatta cccagtttca   50100
gttattctt tatagcagtg taagaatgga ctaacacaat tattaacgct agtcctcatg   50160
ttgtacatta aatctctaga tgtattagac gtaactgcaa ctttgtaccc taccctacaa   50220
ttttctttcc ccccaagccc cccaaccaag ggtctactct gttctataa attcagttgt   50280
tttttaattc cacgtataag tgaagtacaa ctcagtgtag aaacttggta aatgctagct   50340
acttgttata agctgtcagt caaaataaaa atacagagat gaatctctaa attaagtgat   50400
ttatttggga agaaagaatt gcaattaggg catacatgta gatcagatgg tcttcggtat   50460
atccacacaa caaagaaaag ggggaggttt tgttaaaaaa gagaaatgtt acatagtgct   50520
ctttgagaaa attcattggc actattaagg atctgaggag ctggtgagtt caactggtg   50580
agtgatggtg gtagataaaa ttagagctgc agcaggtcat tttagcaact attagataaa   50640
actggtctca ggtcacaacg ggcagttgca gcagctggac ttggagagaa ttacactgtg   50700
ggagcagtgt catttgtcct aagtgctttt ctacccccta ccccccactat tttagttggg   50760
tataaaaga atgacccaat ttgtatgatc aactttcaca aagcatagaa cagtaggaaa   50820
agggtctgtt tctgcagaag gtgtagacgt tgagagccat tttgtgtatt tattcctccc   50880
tttcttcctc ggtgaatgat taaaacgttc tgtgtgattt ttagtgatga aaaagattaa   50940
atgctactca ctgtagtaag tgccatctca cacttgcaga tcaaaaggca cacagttttaa   51000
aaaaccttg tttttttaca catctgagtg gtgtaaatgc tactcatctg tagtaagtgg   51060
aatctataca cctgcagacc aaaagacgca aggtttcaaa aatctttgtg ttttttacac   51120
atcaaacaga atggtacgtt tttcaaaagt taaaaaaaaa caactcatcc acatattgca   51180
actagcaaaa atgacattcc ccagtgtgaa aatcatgtct gagagaattc ttacatgtaa   51240
aggcaaaatt gcgatgactt tgcagggggac cgtggggatc ccgccccag tgccggagct   51300
gtccccctacc agggtttgca gtggagtttt gaatgcactt aacagtgtct tacggtaaaa   51360
acaaaattc atccaccaat tatgtgttga gcgcccactg cctaccaagc acaaacaaaa   51420
ccattcaaaa ccacgaaatc gtcttcactt tctccagatc cagcagcctc ccctattaag   51480
gttcgcacac gctattgcgc caacgctcct ccagagcggg tcttaagata aagaacagg   51540
acaagttgcc ccgcccatt tcgctagcct cgtgagaagaa cgtcatcgca catagaaaaa   51600
agacagacgt aacctacggt gtcccgctag gaaagagagg tgcgtcaaac agcgacaagt   51660
tccgcccacg taaagatga cgcttggtgt gtcagccgtc cctgctgccc ggttgcttct   51720
cttttggggg cggggtctag caagagcagg tgtgggttta ggaggtgtgt gttttttgttt   51780
tcccacccct ctctccccac tacttgctct cacagtactc gctgagggtg aacaagaaaa   51840
gacctgataa agattaacca gaagaaaaca aggagggaaa caaccgcagc ctgtagcaag   51900
```

```
ctctggaact caggagtcgc gcgctagggg ccggggccgg ggccggggcg tggtcgggc    51960
gggcccgggg gcgggcccgg ggcggggctg cggttgcggt gcctgcgccc gcggcggcgg    52020
aggcgcaggc ggtggcgagt gggtgagtga ggaggcggca tcctggcggg tggctgtttg    52080
gggttcggct gccgggaaga ggcgcgggta gaagcggggg ctctcctcag agctcgacgc    52140
attttactt tccctctcat ttctctgacc gaagctgggt gtcgggcttt cgcctctagc    52200
gactggtgga attgcctgca tccgggcccc gggcttccg gcggcggcgg cggcggcggc    52260
ggcgcaggga caaggatgg ggatctggcc tcttccttgc tttcccgccc tcagtacccg    52320
agctgtctcc ttcccgggga cccgctggga gcgctgccgc tgcgggctcg agaaaaggga    52380
gcctcgggta ctgagaggcc tcgcctgggg gaaggccgga gggtgggcgg cgcgcggctt    52440
ctgcggacca agtcggggtt cgctaggaac ccgagacggt ccctgccggc gaggagatca    52500
tgcgggatga gatgggggtg tggagacgcc tgcacaattt cagcccaagc ttctagagag    52560
tggtgatgac ttgcatatga gggcagcaat gcaagtcggt gtgctcccca ttctgtggga    52620
catgacctgg ttgcttcaca gctccgagat gacacagact tgcttaaagg aagtgactat    52680
tgtgacttgg gcatcacttg actgatggta atcagttgtc taaagaagtg cacagattac    52740
atgtccgtgt gctcattggg tctatctggc cgcgttgaac accaccaggc tttgtattca    52800
gaaacaggag ggaggtcctg cactttccca ggaggggtgg cccttcaga tgcaatcgag    52860
attgttaggc tctgggagag tagttgcctg gttgtgcag ttggtaaatt tctattcaaa    52920
cagttgccat gcaccagttg ttcacaacaa gggtacgtaa tctgtctgac attacttcta    52980
cttttgtaca aaggatcaaa aaaaaaaag atactgttaa gatatgattt ttctcagact    53040
ttgggaaact tttaacataa tctgtgaata tcacagaaac aagactatca tatagggat    53100
attaataacc tggagtcaga atacttgaaa tacggtgtca tttgacacgg gcattgttgt    53160
caccacctct gccaaggcct gccactttag gaaaaccctg aatcagttgc aaactgctac    53220
atgctgatag tacatctgaa acaagaacga gagtaattac cacattccag attgttcact    53280
aagccagcat ttacctgctc caggaaaaaa ttacaagcac cttatgaagt tgataaaata    53340
ttttgtttgg ctatgttggc actccacaat ttgcttcag agaacaaag taaaccaagg    53400
aggacttctg tttttcaagt ctgccctcgg gttcatttct acgttaatta gatagttccc    53460
aggaggacta ggttagccta cctattgtct gagaaacttg gaactgtgag aaatggccag    53520
atagtgatat gaacttcacc ttccagtcct ccctgatgtt gaagattgag aaagtgttgt    53580
gaactttctg gtactgtaaa cagttcactg tccttgaagt ggtcctgggc agctcctgtt    53640
gtggaaagtg gacggtttag gatcctgctt ctctttgggc taggagaaaa taaacagcat    53700
ggttacaagt attgagagcc aggttggaga aggtggctta cacctgtaat gccagagctt    53760
tgggaggcgg aggcaagagg atcacttgaa gccaggagtt caagctcaac ctgggcaacg    53820
tagaccctgt ctctacaaaa aattaaaaac ttagccgggc gtggtgatgt gcacctgtag    53880
tcctagctac ttgggaggct gaggcaggag ggtcatttga gcccaagagt ttgaagttac    53940
cgagagctat gatcctgcca gtgcattcca gcctggatga caaaacgaga ccctgtctct    54000
aaaaaacaag aagtgagggc tttatgattg tagaattttc actacaatag cagtggacca    54060
accacctttc taaataccaa tcagggaaga gatggttgat tttttaacag acgtttaaag    54120
aaaagcaaa acctcaaact tagcactcta ctaacagttt tagcagatgt taattaatgt    54180
aatcatgtct gcatgtatgg gattatttcc agaaagtgta ttgggaaacc tctcatgaac    54240
cctgtgagca agccaccgtc tcactcaatt tgaatcttgg cttccctcaa aagactggct    54300
aatgtttggt aactctctgg agtagacagc actacatgta cgtaagatag gtacataaac    54360
aactattggt tttgagctga ttttttttcag ctgcatttgc atgtatggat ttttctcacc    54420
aaagacgatg acttcaagta ttagtaaaat aattgtacag ctctcctgat tactacttcta    54480
tgtgacattt catttcccag gctatttctt ttggtaggat ttaaaactaa gcaattcagt    54540
atgatctttg tccttcattt tctttcttat tctttttgtt tgtttgtttg tttgtttttt    54600
tcttgaggca gagtctctct ctgtcgccca ggctggagtg cagtggcgcc atctcagctc    54660
attgcaacct ctgccaccct ccggttcaag agattctcct gcctcagcct cccgagtagc    54720
tgggattaca ggtgtccacc accacacccg gctaattttt tgtatttta gtagaggtagc    54780
ggtttcacca tgttggccag gctggtcttg agctcctgac ctcaggtgat ccacctgcct    54840
cggcctacca aagagctggg ataacaggtg tgacccacca tgcccggccc atttttttt    54900
tcttattctg ttaggagtga gagtgtaact agcagtataa tagttcaatt ttcacaacgt    54960
ggtaaaagtt tccctataat tcaatcagat tttgctccag ggttcagttc tgttttagga    55020
aatacttta ttttcagttt aatgatgaaa tattagagtt gtaatattgc ctttatgatt    55080
atccaccttt ttaacctaaa agaatgaaag aaaaatatgt ttgcaatata attttatggt    55140
tgtatgttaa cttaattcat tatgttggcc tccagtttgc tgttgttagt tatgacagca    55200
gtagtgtcat taccatttca attcagatta cattcctata tttgatcatt gtaaactgac    55260
tgcttacatt gtattaaaaa cagtggatat tttaaagaag ctgtacggct tatatctagt    55320
gctgtctctt aagactatta aattgataca acatatttaa aagtaaatat tacctaaatg    55380
aattttgaa attacaaata cacgtgttaa aactgtcgtt gtgttcaacc atttctgtac    55440
atacttagag ttaactgttt tgccaggctc tgtatgccta ctcataatat gataaaagca    55500
ctcatctaat gctctgtaaa tagaagtcag tgctttccat cagactgaac tctcttgaca    55560
agatgtggat gaaattcttt aagtaaaatt gtttactttg tcatacattt acagatcaaa    55620
tgttagctcc caaagcaatc atatggcaaa gataggtata tcatagtttg cctattagct    55680
gcttttgtatt gctattatta taaatagact tcacagtttt agacttgctt aggtgaaatt    55740
gcaattcttt ttactttcag tcttagataa caagtcttca attatagtac aatcacacat    55800
tgcttaggaa tgcatcatta ggcgattttt tcattatgca aacatcatag agtgtactta    55860
cacaaaccta gatagtatag cctttatgta cctaggccgt atggtatagt ctgttgctcc    55920
taggccacaa acctgtacaa ctgttactgt actgaatact atagacagtt gtaacacagt    55980
ggtaaatatt tatctaaata tactaaaaca gagaaaaggt acagtaaaag tatggtataa    56040
aagataatgg tatacctgtg taggccactt accacgaatg gagcttgcag gactagaagt    56100
tgctctgggt gagtcagtga gtgagtggtg aattaatgtg aaggcctaga acactgtaca    56160
ccactgtaga ctataaacac agtacgctga agctacacca aatttatctt aacagttttt    56220
cttcaataaa aaattataac tttttaactt tgtaaacttt ttaattttt aactttaaa     56280
atacttagct tgaaacacaa atacattgta tagctataca aaatattttt ttcttttgtat    56340
ccttattcta gaagcttttt tctattttct atttttaatt tttttttta cttgttagtc    56400
gttttttgtta aaaactaaaa cacacacact ttcacctagg catagacagg attaggatca    56460
tcagtatcac tcccttccac ctcactgcct tccacctcca catcttgtcc cactggaagg    56520
ttttaggggg caataacaca catgtagctg tcacctatga taacagtgct ttctgttgaa    56580
tacctcctga aggacttgcc tgaggctgtt ttacatttaa cttaaaaaaa aaaaagtag    56640
```

```
aaggagtgca ctctaaaata acaataaaag gcatagtata gtgaatacat aaaccagcaa   56700
tgtagtagtt tattatcaag tgttgtacac tgtaataatt gtatgtgcta tactttaaat   56760
aacttgcaaa atagtactaa gaccttatga tggttacagt gtcactaagg caatagcata   56820
tttttcaggtc cattgtaatc taatgggact accatcatat atgcagtcta ccattgactg   56880
aaacgttaca tggcacataa ctgtatttgc aagaatgatt tgtttttacat taatatcaca   56940
taggatgtac cttttttagag tggtatgttt atgtggatta agatgtacaa gttgagcaag   57000
gggaccaaga gccctgggtt ctgtcttgga tgtgagcgtt tatgttcttc tcctcatgtc   57060
tgttttctca ttaaattcaa aggcttgaac gggcccatt tagcccttct gttttctacg   57120
tgttctaaat aactaaagct tttaaattct agccatttag tgtagaactc tctttgcagt   57180
gatgaaatgc tgtattggtt tcttggctag catattaaat atttttatct ttgtcttgat   57240
acttcaatgt cgtttttaaac atcaggatcg ggcttcagta ttctcataac cagagagttc   57300
actgaggata caggactgtt tgcccatttt ttgttatggc tccagacttg tggtatttcc   57360
atgtctttttt ttttttttt ttttttgacc ttttagcggc tttaaagtat ttctgttgtt   57420
aggtgttgta ttactttttct aagattactt aacaaagcac cacaaactga gtggctttaa   57480
acaacagcaa tttattctct cacaattcta gaagctagaa gtccgaaatc aaagtgttga   57540
caggggcatg atcttcaaga gagaagactc tttccttgcc tcttcctggc ttctggtggt   57600
taccagcaat cctgagtgtt cctttcttgc cttgtagttt caacaatcca gtatctgcct   57660
tttgtcttca catggctgtc taccatttgt ctctgtgtct ccaaatctct ctccttataa   57720
acacagcagt tattggatta ggccccactc taatccagta tgaccccatt ttaacatgat   57780
tacacttatt tctagataag gtcacattca cgtacaccaa gggttaggaa ttgaacatat   57840
cttttttgggg gacacaattc aacccacaag tgtcagtctc tagctgagcc tttcccttcc   57900
tgtttttctc cttttttagtt gctatgggtt agggggccaaa tctccagtca tactagaatt   57960
gcacatggac tggatatttg ggaatactgc gggtctattc tatgagcttt agtatgtaac   58020
atttaatatc agtgtaaaga agcccttttt taagttattt ctttgaatttt ctaaatgtat   58080
gccctgaata taagtaacaa gttaccatgt cttgtaaaat gatcatatca acaaacattt   58140
aatgtgcacc tactgtgcta gttgaatgtc tttatcctga taggagataa caggattcca   58200
catctttgac ttaagaggac aaaccaaata tgtctaaatc atttgggggtt ttgatggata   58260
tctttaaatt gctgaaccta atcattggtt tcatatgtca ttgtttagat atctccggag   58320
catttggata atgtgacagt tggaatgcag tgatgtcgac tctttgccca ccgccatctc   58380
cagctgttgc caagacagag attgctttaa gtggcaaatc accttttatta gcagctactt   58440
ttgcttactg ggacaatatt cttggtccta gagtaaggca catttgggct ccaaagacag   58500
aacaggtact tctcagtgat ggagaaataa cttttcttgc caaccacact ctaaatggag   58560
aaatccttcg aaatgcagag agtggtgcta tagatgtaaa gttttttgtc ttgtctgaaa   58620
agggagtgat tattgtttca ttaatctttg atggaaactg gaatggggat cgcagcacat   58680
atggactatc aattatactt ccacagacag aacttagttg ctacctccca cttcatagag   58740
tgtgtgttga tagattaaca catataatcc ggaaaggaag aatatggatg cataaggtaa   58800
gtgattttttc agcttattaa tcatgttaac ctatctgttg aaagcttatt ttctggtaca   58860
tataaatcttt atttttttaa ttatatgcag tgaacatcaa acaataaatg ttatttattt   58920
tgcatttacc ctattagata caaatacatc tggtctgata cctgtcatct tcatattaac   58980
tgtggaaggt acgaaatggt agctccacat tatagatgaa aagctaaagc ttagacaaat   59040
aaagaaactt ttagaccctg gattcttctt gggagccttt gactctaata ccttttgttt   59100
cccctttcatt gcacaattct gtcttttgct tactactatg tgtaagtata acagttcaaa   59160
gtaatagttt cataagctgt tggtcatgta gcctttgtc tcttttaacct cttttgccaag   59220
ttcccaggtt cataaaatga ggaggttgaa tggaatggtt cccaagagaa ttcctttttaa   59280
tcttacagaa attattgttt tcctaaatcc tgtagttgaa tatataatgc tatttacatt   59340
tcagtatagt tttgatgtat ctaaagaaca cattgaattc tccttcctgt gttccagttt   59400
gatactaacc tgaaagtcca ttaagcatta ccagtttaaa aaggcttttg cccaaatagta   59460
aggaaaaata atatctttta aaagaataat tttttactat gtttgcaggc ttacttcctt   59520
ttttctcaca ttatgaaact cttaaaatca ggagaatctt ttaaacaaca tcataatgtt   59580
taatttgaaa agtgcaagtc attctttttcc tttttgaaac tatgcagatg ttacattgac   59640
tgtttttctgt gaagttatct tttttttcact gcagaataaa ggttgttttg atttttatttt   59700
gtattgttta tgagaacatg catttgttgg gttaatttcc taccccctgcc cccatttttt   59760
ccctaaagta gaaagtattt ttcttgtgaa ctaaattact acacaagaac atgtctattg   59820
aaaaataagc aagtatcaaa atgttgtggg ttgttttttt aaataaattt tctcttgctc   59880
aggaaagaca agaaaatgtc cagaagatta tcttagaagg cacagagga atggaagatc   59940
aggtatatgc aaattgcata ctgtcaaatg tttttctcac agcatgtatc tgtataaggt   60000
tgatggctac atttgtcaag gccttggaga catacgaata agcctttaat ggagcttttta   60060
tggaggtgta cagaataaac tggaggaaga tttccatatc ttaaacccaa agagttaaat   60120
cagtaaacaa aggaaaaatag taattgcatc tacaaattaa tatttgctcc ctttttttt   60180
ctgtttgccc agaataaaatt tggataact tgttcatagt aaaaaataaaa aaaattgtct   60240
ctgatatgtt ctttaaggta ctacttctcg aacctttccc tagaagtagc tgtaacagaa   60300
ggagagcata tgtaccctg aggtatctgt ctggggtgta ggccaggtc cacacaatat   60360
ttcttctaag tcttatgttg tatcgttaag actcatgcaa tttacatttt attccataac   60420
tattttagta ttaaaatttg tcagtgatat ttcttaccct ctcctctagg aaaatgtgcc   60480
atgtttatcc cttggctttg aatgcccctc aggaacagac actaagagtt tgagaagcat   60540
ggttacaagg gtgtggcttc ccctgcggaa actaagtaca gactatttca ctgtaaagca   60600
gagaagttct tttgaaggag aatctccagt gaagaaagag ttcttcactt ttacttccat   60660
ttcctcttgt gggtgcccct caatgctcct tgtaaaactc caatattttta aacatggctg   60720
tttgcctttt ctttgcttct tttttagcatg aatgagacag atgatacttt aaaaaagtaa   60780
ttaaaaaaaa aaacttgtga aaatacatgg ccataataca gaaccaata caatgatctc   60840
ctttaccaaa ttgttatgtt tgtacttttg tagatagctt tccaattcag agacagttat   60900
tctgtgtaaa ggtctgactt aacaagaaaa gatttcccctt tacccaaaga atcccagtcc   60960
ttatttgctg gtcaataagc agggtcccca ggaatggggt aactttcagc accctctaac   61020
ccactagtta ttagtagact aattaagtaa acttatcgca agttgaggaa acttaagacc   61080
aactaaaatt ctgcttttac tgggattttg ttttttcaaa ccagaaacct ttacttaagt   61140
tgactactat taatgaattt tggtctctct ttaagtgct cttcttaaaa atgttatctt   61200
actgctgaga agttcaagtt tgggaagtac aaggaggaat agaaacttaa gagattttct   61260
tttagagcct cttctgtatt tagccctgta ggattttttt tttttttttt tttttggtg   61320
ttgttgagct tcagtgaggc tattcattca cttatactga taatgtctga gatactgtga   61380
```

```
atgaaatact atgtatgctt aaacctaaga ggaaatattt tcccaaaatt attcttcccg   61440
aaaaggagga gttgccttt  gattgagttc ttgcaaatct cacaacgact ttattttgaa   61500
caatactgtt tggggatgat gcattagttt gaaacaactt cagttgtagc tgtcatctga   61560
taaaattgct tcacagggaa ggaaatttaa cacggatcta gtcattattc ttgttagatt   61620
gaatgtgtga attgtaattg taaacaggca tgataattat tactttaaaa actaaaaaca   61680
gtgaatagtt agttgtggag gttactaaag gatggttttt ttttaaataa aactttcagc   61740
attatgcaaa tgggcatatg gcttaggata aaacttccag aagtagcatc acatttaaat   61800
tctcaagcaa cttaataata tggggctctg aaaaactggt taaggttact ccaaaaatgg   61860
ccctgggtct gacaaagatt ctaacttaaa gatgcttatg aagactttga gtaaaatcat   61920
ttcataaaat aagtgaggaa aaacaactag tattaaattc atcttaaata atgtatgatt   61980
taaaaaatat gtttagctaa aaatgcatag tcatttgaca atttcattta tatctcaaaa   62040
aatttactta accaagttgg tcacaaaact gatgagactg tggtggtag  tgaataaatg   62100
agggaccatc catatttgag acactttaca tttgtgatgt gttatactga attttcagtt   62160
tctatctata gactacaaat ttcaaaatta caatttcaag atgtaataag tagtaatatc   62220
ttgaaatagc tctaaaggga attttttctgt tttattgatt cttaaaatat atgtgctgat   62280
tttgatttgc atttgggtag attatacttt tatgagtatg gaggttaggt attgattcaa   62340
gttttcctta cctatttggt aaggatttca aagtcttttt gtgcttggtt ttcctcattt   62400
ttaaatatga aatattga  tgacctttaa caaattttt  ttatctcaaa ttttaaagga   62460
gatcttttct aaaagaggca tgatgactta atcattgcat gtaacagtaa acgataaacc   62520
aatgattcca tactctctaa agaataaaag tgagctttag ggccgggcat ggtcagaaat   62580
ttgacaccaa cctggccaac atggcgaaac cccgtctcta ctaaaaatac aaaaatcagc   62640
cgggcatggt ggcggcacct agtcccag  ctacttggga ggtgagaca ggagagtcac   62700
ttgaacctgg gaggagaggt tgcagtgagc tgagatcacg ccattgcact ccagcctgag   62760
caatgaaagc aaaactccat ctcaaaaaaa aaaaagaaa  agaagaata aaagtgagct   62820
ttggattgca tataaatcct ttagacatgt agtagacttg tttgatactg tgtttgaaca   62880
aattacgaag tattttcatc aaagaatgtt attgtttgat gttatttta ttttttattg    62940
cccagcttct ctcatattac gtgatttct  tcacttcatg tcactttatt gtgcagggtc   63000
agagtattat tccaatgctt actggagaag tgattcctgt aatggaactg ctttcatcta   63060
tgaaatcaca cagtgttcct gaagaaatag atgtaagttt aaatgagagc aattatacac   63120
tttatgagtt ttttggggtt ataagttat  tatgtatat  attaatattc taattttaat   63180
agtaaggact ttgtcataca tactattcac atacagtatt agccacttta gcaaataagc   63240
acacacaaaa tcctggattt tatgcaaaa  cagaggcatt tttgatcagt gatgacaaaa   63300
ttaaattcat tttgtttatt tcattacttt tataattcct aaaagtggga ggatcccagc   63360
tcttatagga gcaattaata tttaatgtag tgtcttttga aacaaaacta tgtgccaaag   63420
tagtaaccat taatgaagt  ttacttgtag tcacaaattt agtttcctta atcatttgtt   63480
gaggacgttt tgaatcacac actatgagtg ttaagagata cctttaggaa actattcttg   63540
ttgttttctg atttttgtcat ttaggttagt ctcctgattc tgacagctca gaagaggaag   63600
ttgttcttgt aaaaattgtt taacctgctt gaccagcttt cacattgtt cttctgaagt    63660
ttatggtagt gcacagagat tgttttttgg ggagtcttga ttctcggaaa tgaaggcagt   63720
gtgttatatt gaatccagac ttccgaaaac ttgtatatta aaagtgttat ttcaacacta   63780
tgttacagcc agactaattt ttttattttt tgatgcattt tagatagctg atacagtact   63840
caatgatgat gatattggtg acagctgtca tgaaggcttt cttctcaagt aagaattttt   63900
cttttcataa aagctggatg aagcagatac catcttatgc tcacctatga caagatttgg   63960
aagaaagaaa ataacagact gtctacttag attgttctag ggacattacg tatttgaact   64020
gttgcttaaa tttgtgttat tttcactca  ttatatttct atatatattt ggtgttattc   64080
catttgctat ttaaagaaac cgagtttcca tcccagacaa gaaatcatgg ccccttgctt   64140
gattctggtt tcttgttta  cttctcatta aagctaacag aatcctttca tattaagttg   64200
tactgtagat gaacttaagt tatttaggcg tagaacaaaa ttattcatat ttatactgat   64260
ctttttccat ccagcagtgg agtttagtac ttaaagtttt gtgcccttaa accagactcc   64320
ctggattaat gctgtgtacc cgtgggcaag gtgcctgaat tctctataca cctatttcct   64380
catctgtaaa atggcaataa tagtaatagt acctaatgtg tagggttgtt ataagcattg   64440
agtaagataa ataatataaa gcacttagaa cagtgcctgg aacataaaaa cacttaataa   64500
tagctcatag ctaacatttc ctatttacat ttcttctaga aatagccagt atttgttgag   64560
tgcctacatg ttagttcctt tactagttgc tttacatgta ttatcttata ttctgttta   64620
aagttttctt acagttacag attttcatga aattttactt ttaataaaag agaagtaaaa   64680
gtataaagta ttcactttta tgttcacagt cttttccttt aggctcatga tggagtcatca  64740
gaggcatgag tgtgtttaac ctaagagcct taatggcttg aatcagaagc actttagtcc   64800
tgtatctgtt cagtgtcagc ctttcataca tcattttaaa tcccatttga ctttaagtaa   64860
gtcacttaat ctctctacat gtcaatttct tcagctataa aatgatgtga tttcaataaa   64920
taaatacatt aattaaatga tattatactg actaattggg ctgttttaag gctcaataag   64980
aaaatttctg tgaaaggtct ctagaaaatg taggttccta tacaaataaa agataacatt   65040
gtgcttatag cttcggtgtt tatcatataa agctattctg agttatttga agagctcacc   65100
tactttttt  tgttttagt  ttgttaaatt gttttatagg caatgttttt aatctgttt    65160
ctttaactta cgatgccatc agctcacact tgcaaacctg ttgctgttcc gttgtagtag   65220
gtagcagtgc agagaaagta aataaggtag tttatttat  aatctagcaa atgatttgac   65280
tctttaagac tgatgatata tcatggattg tcatttaaat ggtaggttgc aattaaaatg   65340
atctagtagt ataaggaggc aatgtaatct catcaaattg ctaagacacc ttgtggcaac   65400
agtgagtttg aaataaactg agtaagaatc attatcagt  ttattttgat agctcggaaa   65460
taccagtgtc agtagtgtat aaatgttt  gagaatatat taaaatcaga tatataaaa    65520
aaattactct tctatttccc aatgttatct ttaacaaatc tgaagatagt catgtacttt   65580
tggtagtagt tccaaagaaa tgttatttgt ttattcatct tgatttcatt gtcttcgctt   65640
tccttctaaa tctgtccctt ctagggagct attgggatta agtggtcatt gattattata   65700
ctttattcag taatgtttct gacccttcc  ttcagtgcta cttgagttaa ttaaggatta   65760
atgaacagtt acatttccaa gcattagcta ataaactaaa ggattttgca cttttctca    65820
ctgaccatta gttagaaaga gttcagagat aagtatgtgt atctttcaat ttcagcaaac   65880
ctaatttttt aaaaaaagtt ttacatagga aatatgttgg aaatgatact ttacaaagat   65940
attcataatt tttttttgta atcagctact ttgtatattt acatgagcct taatttatat   66000
ttctcatata accatttatg agagcttagt atacctgtgt cattatattg catctacgaa   66060
ctagtgacct tattccttct gttacctcaa acaggtggct ttccatctgt gatctcccaaa  66120
```

```
gccttaggtt gcacagagtg actgccgagc tgctttatga agggagaaag gctccatagt   66180
tggagtgttt tttttttttt tttttaaacat ttttcccatc ctccatcctc ttgagggaga   66240
atagcttacc ttttatcttg ttttaatttg agaaagaagt tgccaccact ctaggttgaa   66300
aaccactcct ttaacataat aactgtggat atggtttgaa tttcaagata gttacatgcc   66360
tttttatttt tcctaataga gctgtaggtc aaatattatt agaatcagat ttctaaatcc   66420
cacccaatga cctgcttatt ttaaatcaaa ttcataatt aattctcttc tttttggagg     66480
atctggacat tctttgatat ttcttacaac gaatttcatg tgtagaccca ctaaacagaa   66540
gctataaaag ttgcatggtc aaataagtct gagaaagtct gcagatgata taattcacct   66600
gaagagtcac agtatgtagc caaatgttaa aggttttgag atgccataca gtaaatttac   66660
caagcatttt ctaaatttat ttgaccacag aatccctatt ttaagcaaca actgttacat   66720
cccatggatt ccaggtgact aaagaatact tatttcttag gatatgtttt attgataata   66780
acaattaaaa tttcagatat ctttcataag caaatcagtg gtcttttac ttcatgtttt     66840
aatgctaaaa tattttcttt tatagatagt cagaacatta tgccttttttc tgactccagc  66900
agagagaaaa tgctccaggt tatgtgaagc agaatcatca tttaaatatg agtcagggct   66960
ctttgtacaa ggcctgctaa aggtatagtt tctagttatc acaagtgaaa ccacttttct    67020
aaaatcattt tgagactct ttatagacaa atcttaaata ttagcattta atgtatctca     67080
tattgacatg cccagagact gacttccttt acacagttct gcacatagac tatatgtctt   67140
atggatttat agttagtatc atcagtgaaa caccatagaa taccctttgt gttccaggtg   67200
ggtccctgtt cctacatgtc tagcctcagg acttttttttt ttttaacaca tgcttaaatc  67260
aggttgcaca tcaaaaataa gatcatttct ttttaactaa atagatttga atttttattga  67320
aaaaaaattt taaacatctt taagaagctt ataggattta agcaattcct atgtatgtgt   67380
actaaaatat atatatttct atatataata tatattagaa aaaaattgta ttttttcttttt 67440
atttgagtct actgtcaagg agcaaaacag agaaatgtaa attagcaatt atttataata   67500
cttaaaggga agaaagttgt tcaccttgtt gaatctatta ttgttatttc aattatagtc   67560
ccaagacgtg aagaaatagc tttcctaatg gttatgtgat tgtctcatag tgactacttt   67620
cttgaggatg tagccacggc aaaatgaaat aaaaaaattt gcaaatacaa                67680
gttatattag gcttttgtgc atttcaata atgtgctgct atgaactcag aatgatagta     67740
tttaaatata gaaactagtt aaaggaaacg tagtttctat ttgagttata catatctgta   67800
aattagaact tctcctgtta aaggcataat aaagtgctta atacttttgt ttcctcagca   67860
ccctctcatt taattatata attttagttc tgaaaggggac ctataccaga tgcctagagg  67920
aaatttcaaa actatgatct aatgaaaaaa tatttaatag ttctccatgc aaatacaaat   67980
catatagttt tccagaaaat acctttgaca ttatacaaag atgattatca cagcattata   68040
atagtaaaaa aatggaaata gcctcttcct tctgttctgt tcatagcaca gtgcctcata   68100
cgcagtaggt tattattaca tggtaactgg ctaccccaac tgattaggaa agaagtaaat   68160
ttgttttata aaaatacata ctcattgagg tgcatagaat aattaagaaa ttaaaagaca   68220
cttgtaattt tgaatccagt gaatacccac tgttaatatt tggtatatct ctttctagtc   68280
ttttttttccc ttttgcatgt atttttcttta agactcccac ccccactgga tcatctctgc  68340
atgttctaat ctgctttttt cacagcagat tctaagcctc tttgaatatc aacacaaact   68400
tcaacaactt catctataga tgccaaataa taaattcatt tttatttact taaccacttc   68460
ctttggatgc ttaggtcatt ctgatgtttt gctattgaaa ccaatgctat actgaacact   68520
tctgtcacta aaacttttgca cacactcatg aatagcttct taggataaat ttttagagat  68580
ggatttgcta aatcagagac catttttttaa aattaaaaaa caattattca tatcgtttgg  68640
catgtaagac agtaaatttt cctttttattt tgacaggatt caactggaag ctttgtgcta  68700
cctttccggc aagtcatgta tgctccatat cccaccacac acatagatgt ggatgtcaat   68760
actgtgaagc agatgccacc ctgtcatgaa catatttata atcagcgtag atacatgaga   68820
tccgagctga cagccttctg gagagccact tcagaagaag acatggctca ggatacgatc   68880
atctacactg acgaaagctt tactcctaga ttgtacgtaa tgctctgcct gctggtactg   68940
tagtcaagca atatgaaatt gtgtcttttta cgaataaaaa caaaacagaa gttgcattta   69000
aaaagaaaga aatattacca gcagaattat gcttgaagaa acatttaatc aagcattttt   69060
ttcttaaatg ttcttctttt tccatacaat tgtgtttacc ctaaaatagg taagattaac   69120
ccttaaagta aatatttaac tatttgttta ataaatatat attgagctcc taggcactgt   69180
tctaggtacc gggcttaata gtggccaacc agacagcccc agcccagcc cctacattgt    69240
gtatagtcta ttatgtaaca gttattgaat ggacttatta acaaaccaa agaagtaatt   69300
ctaagtcttt ttttttcttga catatgaata taaaatacag caaaactgtt aaaatatatt   69360
aatggaacat ttttttactt tgcattttat attgttattc acttcttatt tttttttaaa  69420
aaaaaaagcc tgaacagtaa attcaaaagg aaaagtaatg ataattaatt gttgagcatg  69480
gacccaactt gaaaaaaaaa atgatgatga taaatctata atcctaaaac cctaagtaaa  69540
cacttaaaag atgttctgaa atcaggaaaa gaattatagt atacttttgt gtttctcttt  69600
tatcagttga aaaaaggcac agtagctcat gcctgtaaga acagagcttt gggagtgcaa  69660
ggcaggcgga tcacttgagg ccaggagttc cagaccagcc tgggcaacat agtgaaaccc  69720
catctctaca aaaatataaaa aagaattatt ggaatgtgtt tctgtgtgcc tgtaatccta  69780
gctattccga aagctgaggc aggaggatct tttgagccca ggagtttgag gttacaggga   69840
gttatgatgt gccagtgtac tccagcctgg ggaacaccga gactctgtct tatttaaaaa   69900
aaaaaaaaaa aaaatgcttg caataatgcc tggcacataa aagtaacag taagtgttaa   69960
ctgtaataac ccaggtctaa gtgtgtaagg caatagaaaa attggggcaa ataagcctga   70020
cctatgtatc tacagaatca gtttgagctt aggtaacaga cctgtggagc accagtaatt   70080
acacagtaag tgttaaccaa aagcatagaa taggaatatc ttgttcaagg gacccccagc   70140
cttatacatc tcaaggtgca gaaagtgac ttaatatagg cccattttt tcctagttct      70200
ccagagtttt tattggttct tgagaaagta gtagggaat gttttagaaa atgaattggt    70260
ccaactgaaa ttcatgtcca gtaagttttt atatattggt aaattttagt agacatgtag   70320
aagttttcta attaatctgt gccttgaaac attttctttt ttcctaaagt gcttagtatt   70380
ttttccgttt tttgattggt tacttgggag ctttttttgag gaaatttagt gaactgcaga   70440
atgggtttgc aaccatttgg tatttttgtt ttgtttttta gaggatgtat gtgtattttta  70500
acatttctta atcattttta gccagtcatg tttgtttttgc tgatttgaca aactacagtt   70560
agacagctat tctcatttttg ctgatcatga caaaataata tcctgaattt ttaaatttttg  70620
catccagctc taaattttct aaacataaaa ttgtccaaaa aatagtattt tcagccacta   70680
gattgtgtgt taagtctatt gtcacagagt cattttactt ttaagtatat gttttacat    70740
gttaattatg tttgttattt ttaatttaa cttttttaaaa taattccagt cactgccaat   70800
acatgaaaaa ttggtcactg gaattttttt tttgactttt attttaggtt catgtgtaca   70860
```

```
tgtgcaggtg tgttatacag gtaaattgcg tgtcatgagg gtttggtgta caggtgattt    70920
cattacccag gtaataagca tagtacccaa taggtagttt tttgatcctc acccttctcc    70980
caccctcaag taggccctgg tgttgctgtt tccttctttg tgtccatgta tactcagtgt    71040
ttagctccca cttagaagtg agaacatgcg gtagttggtt ttctgttcct ggattagttc    71100
acttaggata atgacctcta gctccatctg gtttttatgg ctgcatagta ttccatggtg    71160
tatatgtatc acattttctt tatccagtct accattgata ggcatttagg ttgattccct    71220
gtctttgtta tcatgaatag tgcctgtgatg aacatacaca tgcatgtgtc tttatggtag    71280
aaaaatttgt attcctttag gtacatatag aataatgggg ttgctagggt gaatggtagt    71340
tctattttca gttatttgag aaatcttcaa actgcttttc ataatagcta aactaattta    71400
cagtcccgcc agcagtgtat aagtgttccc ttttctccac aaccttgcca acatctgtga    71460
ttttttgact ttttaataat agccattcct agagaattga tttgcaattc tctattagtg    71520
atattaagca ttttttcata tgcttttttag ctgtctgtat atattcttct gaaaaatttt    71580
catgtccttt gcccagtttg tagtgggggtg ggttgttttt tgcttgttaa ttagttttaa    71640
gttccttcca gattctgcat atccctttgt tggatacatg gtttgcagat attttttctcc    71700
cattgtgtag gttgtctttt actctgttga tagtttcttt tgccatgcag gagctcgtta    71760
ggtcccattt tgtgtttgttt ttgttgcagt tgcttttggc gtcttcatca taaaatctgt    71820
gccagggcct atgtccagaa tggtatttcc taggttgtct tccagggttt ttacaatttt    71880
agattttacg tttatgtctt taatccatct tgagttgatt tttgtatatg gcacaaggaa    71940
ggggtccagt ttcactccaa ttcctatggc tagcaattat cccagcacca tttattgaat    72000
acggagtcct ttccccattg cttgtttttt gtcaactttg ttgaagatca gatggttgta    72060
agtgtgtggc tttatttctt ggctctctat tctccattgg tctatgtgtc tgttttata    72120
acagtaccct gctgttcagg ttcctatagc tttttagtat aaaatcggct aatgtgatgc    72180
ctccagcttt gttcttttttg cttaggattg ctttggctat ttgggctcct tttttgggtcc    72240
atattaattt taaaacagtt ttttctggtt ttgtgaagga tatcattggt agtttatagg    72300
aatagcattg aatctgtaga ttgctttggg cagtatggcc attttaacaa tattaattct    72360
tcctatctat gaatatggaa tgttttttcca tgtgttttgg tcatctcttt atacctgatg    72420
tataaagaaa agctggtatt attcctactc aatctgttcc aaaaaattga ggaggaggaa    72480
ctcttcccta atgaggccag catcattctg ataccaaaac ctggcagaga cacaacagaa    72540
aaaagaaaac ttcaggccaa tatccttgat gaatatagat gcaaaatcc tcaacaaaat    72600
actagcaaac caaatccagc agcacatcaa aaagctgatc tactttgatc aagtaggctt    72660
tatccctggg atgcaaggtt ggttcaacat acacaaatca ataagtgtga ttcatcacat    72720
aaacagagct aaaaacaaaa accacaagat tatctcaata ggtagagaaa aggttgtcaa    72780
taaaatttaa catcctccat gttaaaaacc ttcagtaggt caggtgtagt gactcacacc    72840
tgtaatccca gcactttggg aggccaaggc gggcatatct cttaagccca ggagttcaag    72900
acgagcctag gcagcatggt gaaaccccat ctctacaaaa aaaaaaaaaa aaaaaatta    72960
gcttggtatg gtgacatgca cctatagtcc cagctattca ggaggttgag gtgggaggat    73020
tgtttgagcc cgggaggcag aggttggcag cgagctgaga tcatgccacc gcactccagc    73080
ctgggcaacg gagtgagacc ctgtctcaaa aagaaaaat cacaaacaat cctaaacaaa    73140
ctaggcattg aaggaacatg cctcaaaaaa ataagaaacc tctatgacag acccatagcc    73200
aatatcttac caaatgggca aaagctggaa gtattctcct tgagaaccgt aacaagacaa    73260
ggatgtccac tctcaccact ccttttcagc atagttctgg aagtcctagc cagagcaatc    73320
aggaaagaga agaaagaaa gacattcaga taggaagaga agagtcaaa ctatttctgt    73380
ttgcaggcag tataattctg tacctagaaa atctcatagt ctctgcccag aaactcctaa    73440
atctgttaaa aatttcagca aagttttggc attctctata ctccaacacc ttccaaagtg    73500
agagcaaaat caagaacaca gtcccattca caatagccgc aaaacgaata aaatacctag    73560
gaatccagct aaccagggag gtgaaagatc tctatgagaa ttacaaaaca ctgctgaaag    73620
aaatcagaga tgcacaaaac aaatggaaat gttcttttt aacaccttgc tttatctaat    73680
tcacttatga tgaagatact cattcagtgg aacaggtata ataagtccac tcgattaaat    73740
ataagcctta ttctctttcc agagcccaag aaggggcact atcagtgccc agtcaataat    73800
gacgaaatgc taatattttt cccctttacg gtttctttct tctgtagtgt ggtacactcg    73860
tttcttaaga taaggaaact tgaactacct tcctgttttgc ttctacacat acccattctg    73920
tttttttgcc actctggtca ggtataggat gatccctacc actttcagtt aaaaactcct    73980
cctcttacta aatgttctct taccctctgg cctgagtaga acctagggaa aatgaaagag    74040
aaaaagatga aagggaggtg gggcctggga agggaataag tagtcctgtt tgtttgtgtg    74100
tttgctttag cacctgctat atcctaggtg ctgtgttagg cacacattat tttaagtggc    74160
cattatatta ctactactca ctctggtcgt tgccaaggta ggtagtactt tcttggatag    74220
ttggttcatg ttacttacag atggtgggct tgttgaggca aacccagtgg ataatcatcg    74280
gagtgtgttc tctaatctca ctcaaatttt tcttcacatt ttttggtttg ttttggtttt    74340
tgatggtagt ggcttatttt tgttgctggt ttgtttttttg tttttttttg agatggcaag    74400
aattggtagt tttatttatt aattgcctaa gggtctctac tttttttaaa agatgagagt    74460
agtaaaatag attgatagat acatacatac ccttactggg gactgcttat attctttaga    74520
gaaaaaatta catattagcc tgacaaacac cagtaaaatg taaatatatc cttgagtaaa    74580
taaatgaatg tatattttgt gtctccaaat atatatatct atattcttac aaatgtgttt    74640
atatgtaata tcaatttata agaacttaaa atgttggctc aagtgaggga ttgtggaagg    74700
tagcattata tggccatttc aacatttgaa ctttttttctt ttcttcattt tcttcttttc    74760
ttcaggaata ttttttcaaga tgtcttacac agagacactc tagtgaaagc cttcctggat    74820
caggtaaatg ttgaacttga gattgtcaga gtgaatgata tgcatgtttt tctttttaa    74880
tatatcctac aattgcctgtt ctatatattt atattccct ggatcatgcc ccagagttct    74940
gctcagcaat tgcagttaag ttagttacac tacagttcctc agaagagtct gtgagggcat    75000
gtcaagtgca tcattacatt ggttgcctct tgtcctagat ttatgcttcg ggaattcaga    75060
cctttgttta caatataata aatattattg ctatctttta aagatataat aataagatat    75120
aaagttgacc acaactactg ttttttgaaa catagaattc ctggtttaca tgtatcaaag    75180
tgaaatctga cttagctttt acagatataa tatatacata tatatatcct gcaatgcttg    75240
tactatatat gtagtacaag tatatatata tgttgtgtg tgtatatata tatagtacga    75300
gcatatatac atattaccag cattgtagga tatatatatg tttatatatt aaaaaaaagt    75360
tataaactta aaaccctatt atgttatgta gagtatatgt tatatatgat atgtaaaata    75420
tataacatat actctatgat agagtgtaat atattttta tatatttt aacatttata    75480
aaatgataga attaagaatt gagtcctaat ctgtttatt aggtgctttt tgtagtgtct    75540
ggtctttcta aagtgtctaa atgatttttc cttttgactt attaatgggg aagagcctgt    75600
```

```
atattaacaa ttaagagtgc agcattccat acgtcaaaca acaaacattt taattcaagc  75660
attaacctat aacaagtaag ttttttttt tttttgaga agggaggtt gtttatttgc    75720
ctgaaatgac tcaaaaatat ttttgaaaca tagtgtactt atttaaataa catctttatt 75780
gtttcattct tttaaaaaat atctacttaa ttacacagtt gaaggaaatc gtagattata  75840
tggaacttat ttcttaatat attacagttt gttataataa cattctgggg atcaggccag  75900
gaaactgtgt catagataaa gctttgaaat aatgagatcc ttatgtttac tagaaatttt  75960
ggattgagat ctatgaggtc tgtgacatat tgcgaagttc aaggaaaatt cgtaggcctg  76020
gaatttcatg cttctcaagc tgacataaaa tccctcccac tctccacctc atcatatgca  76080
cacattctac tcctacccac ccactccacc ccctgcaaaa gtacaggtat atgaatgtct  76140
caaaaccata ggctcatctt ctaggagctt caatgttatt tgaagatttg ggcagaaaaa  76200
attaagtaat acgaaataac ttatgtatga gttttaaaag tgaagtaaac atggatgtat  76260
tctgaagtag aatgcaaaat ttgaatgcat ttttaaagat aaattagaaa acttctaaaa  76320
actgtcgat tgtctgggcc tggtggctta tgcctgtaat cccagcactt tgggagtccg   76380
aggtgggtgg atcacaaggt caggagatcg agaccatcct gccaacatgg tgaaaccccg  76440
tctctactaa gtatacaaaa attagctggg cgtggcagcg tgtgcctgta atcccagcta  76500
cctgggaggc tgaggcagga gaatcgcttg aacccaggag gtgtaggttg cagtgagtca  76560
agatcgcgcc actgcacttt agcctggtga cagagctaga ctccgtctca aaaaaaaaaa  76620
aaaatatcag attgttccta cacctgtgc ttctatacca cactcctgtt agggggcatc   76680
agtggaaatg gttaaggaga tgtttagtgt gtattgtctg ccaagcactg tcaacactgt  76740
catagaaact tctgtacgag tagaatgtga gcaaattatg tgttgaaatg gttcctctcc  76800
ctgcaggtct ttcagctgaa acctggctta tctctcagaa gtactttcct tgcacagttt  76860
ctacttgtcc tcacagaaa agccttgaca ctaataataa atatagaaga cgatacgtga   76920
gtaaaactcc tacacggaag aaaaacctttt gtacattgtt tttttgtttt gtttcctttg  76980
tacatttct atatcataat tttgtgcttc cttttttttt tttttttttt tttttttcca   77040
ttattttag gcagaaggga aaaagcccct taaatctctc tcggaacctg aagatagacc   77100
ttgatttaac agcagagggc gatcttaaca taataatgac tctggctgag aaaattaaac  77160
caggcctaca ctcttttatc tttgaagac ctttctacac tagtgtgcaa gaacgagatg    77220
ttctaatgac ttttttaaatg tgtaacttaa taagccatt ccatcacaat catgatcgct   77280
ggtaaagtag ctcagtggtg tggggaaacg ttccctgga tcatactcca gaattctgct    77340
ctcagcaatt gcagttaagt aagttacact acagttctca caagagcctg tgaggggatg  77400
tcaggtgcat cattacattg ggtgtctctt ttcctagatt tatgcttttg ggatacagac   77460
ctatgtttac aatataataa atattattgc tatctttta agatataata ataggatgta    77520
aacttgacca caactactgt ttttttgaaa tacatgattc atggtttaca tgtgtcaagg  77580
tgaaatctga gttggctttt acagatagtt gactttctat cttttggcat tcttttggtgt  77640
gtagaattac tgtaatactt ctgcaatcaa ctgaaaacta gagcctttaa atgatttcaa   77700
ttccacagaa agaaagtgag cttgaacata ggatgagctt tagaaagaaa attgatcaag  77760
cagatgttta attggaattg attattagat cctactttgt ggatttagtc cctgggattc  77820
agtctgtaga aatgtctaat agttctctat agtccttgtt cctggtgaac cacagttagg   77880
gtgttttgtt tattttattg ttcttgctat tgttgatatt ctatgtagtt gagctctgta   77940
aaaggaaatt gtattttatg ttttagtaat tgttgccaac tttttaaatt aattttcatt   78000
attttgagc caaattgaaa tgtgcacctc ctgtgccttt tttctcctta gaaaatctaa    78060
ttacttggaa caagttcaga tttcactggt cagtcatttt catcttgttt tcttcttgct   78120
aagtcttacc atgtacctgc tttggcaatc attgcaactc tgagattata aatgcctta    78180
gagaatatac taactaataa gatctttttt tcagaaacag aaaatagttc cttgagtact   78240
tccttcttgc atttctgcct atgttttga agttgttgct gtttgcctgc aataggctat    78300
aaggaatagc aggagaaatt ttactgaagt gctgtttttcc taggtgctac tttggcagag  78360
ctaagttatc tttttgttttc ttaatgcgtt tggaccattt tgctggctat aaaataactg   78420
attaatataa ttctaacaca atgttgacat tgtagttaca caaacacaaa taaatatttt   78480
atttaaaatt ctggaagtaa tataaaaggg aaaatatatt tataagaaag ggataaaggt   78540
aatagagccc ttctgccccc cacccaccaa atttacacaa caaaatgaca tgttcgaatg  78600
tgaaaggtca taatagcttt cccatcatga atcagaaaga tgtggacagc ttgatgtttt   78660
agacaaccac tgaactagat gactgttgta ctgtagctca gtcatttaaa aaatatataa   78720
atactacctt gtagtgtccc atactgtgtt ttttacatgg tagattctta tttaagtgct  78780
aactggttat tttctttggc tggtttattg tactgttata cagaatgtaa gttgtacagt  78840
gaaataagtt attaaagcat gtgtaaacat tgttatatat cttttctcct aaatgggaaa  78900
ttttgaataa aatatatttg aaattttgcc tctttcagtt gttcattcag aaaaaaatac   78960
tatgatattt gaagactgat cagcttctgt tcagctgaca gtcatgctgg atctaaactt   79020
tttttaaaat taattttgtc ttttcaaaga aaaatatttt aaagaagctt tataatataa   79080
tcttatgtta aaaaaacttt ctgcttaact tctcggattt catttttgatt tttcaaatta  79140
tatattaata tttcaaatgt aaaatactat ttagataaat tgttttttaaa cattcttatt  79200
attataaatat taatataacc taaactgaag ttattcatcc caggtatcta atacatgtat   79260
ccaaagtaaa aatccaagga atctgaacac tttcatctgc aaagctagga ataggtttga  79320
cattttcact ccaagaaaaa gttttttttt gaaaatagaa tagttgggat gagaggtttc   79380
tttaaagaa gactaactga tcacattact atgattctca aagaagaaac caaaacttca    79440
tataatacta taaagtaaat ataaaatagt tccttctata gtatatttct ataatgctac   79500
agtttaaaca gatcactctt atataatact attttgattt tgatgtagaa ttgcacaaat   79560
tgatatttct cctatgatct gcagggtata gcttaaagta acaaaacag tcaaccacct    79620
ccatttaaca cacagtaaca ctatgggact agttttatta cttccatttt acaaatgagg  79680
aaactaaagc ttaaagatgt gtaatacacc gcccaaggtc acacagctgg taaaggtgga  79740
tttcatccca gacagttaca gtcattgcca tgggcacagc tcctaactta gtaactccat  79800
gtaactggta ctcagtgtag ctgaattgaa aggagagtaa ggaagcaggt tttacaggtc   79860
tacttgcact attcagagcc cgagtgtgaa tccctgctgt gctgcttgga gaagttactt   79920
aacctatgca aggttcattt tgtaaatatt ggaaatggag tgataatacg tacttcacca   79980
gaggtttaa tgagacctta tacgatcctt agttcagtac gttcagttga cttcataaat    80040
gcttttcat ccaatctgac aatctccagc ttgtaattgg ggcatttaga acatttaata    80100
tgattattgg catggtaggt taaagctgtc atcttgctgt tttctatttg ttcttttgtt   80160
tttctcctta cttttggatt tttttattct actatgtctt ttctattgtc ttattaacta   80220
tactcttgaa tttattttag tggttgtttt agggttatac ctcttctaa tttaccagtt    80280
tataaccagt ttatatacta cttgacatat agcttaagaa acttactgtt gttgtcttttt  80340
```

```
tgctgttatg gtcttaacgt ttttatttct acaaacatta taaactccac actttattgt   80400
tttttaattt tacttataca gtcaattatc ttttaaagat atttaaatat aaacattcaa   80460
aacaccccaa ttaaaagtca gagattgtta ataccacatg atctcactta cacacagaat   80520
tgaaaaactt ggaactcata gaagcagaga gtaaaaacat ggttaccagg tgctggggag   80580
aggcggtggg ctggggagat gttggtcaaa gttagacagg aggaataagt tcaagagatc   80640
tattgtacaa cttattcagt tagatagag gaataagcta aagatcaaga gatctattgt   80700
acaatgtgac tataaccaac aacatatatt gtacacttga aaattgctaa cagtatcttt   80760
taagtgttct ctctacaaat aaatatgtga ggtaatgtat atattaatta actgtagtca   80820
tttcacaatg tatacttatt tcaaaacatc atattgtatg ctataaatat atacaactta   80880
tattttcaa ttttagaaat gtccttaaaa aatcagattt tcagatcaga taaaaaagca    80940
agacccaact atatgctgcc aacaggaaac acaccttaaa aataaaggac gaacaaacag   81000
attaaaagta aaaggatgga gaaaagatac atcatattgg taattagaag aaaactggag   81060
tgacaatatg aaacaaaata gatttcagag caaagaatat taccaggggt aaaaatgttc   81120
attttataat gataaaagag tcagttcagc aaaaggatat aacagtccta aatgttttt    81180
cacctcatag ctgtgtcaaa atagatgaag caaaaactga tagaactgta agaagtagac   81240
aagtccacaa ttatgtttgg agattttttt tttttttttt tttgtcgccc aggctggagt   81300
gcagtggcag gatctcagct cactgcaagc tccgcctccc aggttcacgc cattctcctg   81360
cttcagcctc cccagtagct gggactacag gcggccacca ccacgcctgg ctaattttt    81420
tgtattttta gtagacacgg ggtttcaccg tgttagccag gatggtctcg atctcctgac   81480
ctcgtgatct gcctgcctcg gcctcccaaa gtgctgggat tacaggcatg agccactgca   81540
cgcagcctgg agattttaat atcctttcaa tgtttagtag aacaagaata cacaaaatca   81600
gtaaggatat agaagattag aacaagacta tcaaacaatt tgacttaaat gacatttgta   81660
gagcacagca gtcccaaca acaataaatc acacatctt tccaagagta catgaaacat     81720
gtaccaagat agaccgtatt ttgagccatg aaacaaatct tgataaattt aaaaggattc   81780
aagtcataga aaatatgttc tctgaccaca atggaattaa attattaacc aataacaaat   81840
atctgggaaa acctcaaaaa cttgacacc agcgttttta aagactaaa taattctaa     81900
attatctgtg ttgggggaa aagagaaatg gattagagag caaaaaggg atcagagtgc    81960
tgtggtacga tttttatgaa gagtggaaca gaatctgcct ttggcgtttc cccactacag   82020
cccattcttc acattgataa cagcatgatc cttctaaaat taaatctaac gatcacttct   82080
gcttaatggc tctccaacac ttacagaatt aggtccaaaa ttctagcaca gttctgttc    82140
atctttctaa ccttcttcc cacaggtcta gctagtacgt attcttta ttgcatttat      82200
tacactattc ctttgcttat ctatctcccc acctaggcta aagaacaaga ttcttgtctt   82260
tttcatttt gtgtctcagt gcctagcatg gtgccaggca cacagcatgc ttccagtaaa    82320
tgttagctgg atgatgtaa tgagtatatt aaatattaat ttatttgttt ttccccaaaa    82380
agaattattt cctgcaaatc aaggaaattg ctttctttat ataatcaaaa acttattttc   82440
ccagaagatt cttcattaaa aattaagcct atgcacaacc tagctctaaa gtttcaaaga   82500
ttttaggcag caattttca atcttttga agtaatacat ttgaatcttt tcaaatttct    82560
gtttctgcat ttgtgccaca ccatctcatc tcttgctgaa atgttttttgt taaattaatt  82620
gcttgataaa ttgctaagta cttttcatca gaccaattag gacaatagta agtatccatc   82680
tgtggagcgc ggacattcaa gaaatctgat ccagtattta gaaagtcatt cctgagctga   82740
gttggctcaa actggcacct tctggcttt tgcttgtgggt gggggaatgtg gaatgctttg   82800
aaagctgaat gagtttgtca gttttaaaa ttcccttatg gctaaaggaa aacaacattc    82860
attgtttaaa aacaccattg tttgttttt ctgcttttt gttctttgga gcctgaatct     82920
gcaaaaacac tcacacccag cattttgctt catgtaccac tcctaagatg tttttagaga   82980
cttgaatagt gtctccgcac tacttttttat tgtgattgtt cagaatgttc ataacaaatg   83040
gtaaaaagtc agttttagtg ctcaaattga gttttatgga gaaagaccat aatttatgtt   83100
tgtcattgta aattgatagg agaattttttg gaagttttgca tcctagaacc agatttccaa  83160
ggctcagatc cttattttct cacttcctag ctgtgtgacc ttagacaagg tattaaacct   83220
gtctgtgctg cctcagtgtc ctcatctatt cttttaagagt aagaatagaa cctacccgat  83280
agagtcactt gaagattaag tgggttagta aattcagaat gcttggaaca gtaactagca   83340
cagaataagt gtccaataaa attgggttgc agctattatc agtattattc ctgtcataat   83400
catcatcacc attaagcaat taaatgtaga gttccaaaat ttgattatga aactacagtt   83460
atacagccat gattcccggt gataccacgt cagtaacaag attatttcct tagcttgagc   83520
cagtcactac ctcattgcat gtggcagagt gtgttgccgt aggcaaatgt cattgtaggg   83580
aatgaaaaaa aaattgcctg tgagctgctc tccagaggcc tcatcccatt ttcccatcgt   83640
ccactttact ccatctccac tgccactatt aggaccttat catttcttgt ctagattaat   83700
tcaacagctt ccttccttct agtctccatg atttcaccca ctagccatcc cctcccctt    83760
gcccaatttt ctccatttat ggtagagtga tcttctaat aggaaactcc tgacttgcct    83820
taaaaagccc tcattgaggc cggacgtggt ggctcatgcc tgtaatccca gcacttgggg   83880
aggccgagc aggtggatca cgaggtcaag agattgagac atcgtgact aacacagtga     83940
aaccccatct gtactaaaaa tacaagaaat tagccaggcg tggtggcggg tgcctgtagt   84000
cgcagctact ggggaggctg aggcaggaga atggcgtgaa cccgggaggc agagcttgca   84060
gtgagccgag attgcgccac tgcactccag cctgggcgac agagtgagac tccgtctcaa   84120
aaaaaaaaag ccctcattga caaccttcaa cccacaatgc atggtgaagc acaggagcct   84180
tggggatctg ccccccagcac acctctccac ccttgtctct cactgctcct gccttcatgg  84240
agagccctga tgaactattt gtagtttccc ctgactcacc ttgctgttac tgggcctgtg   84300
tgcgtgttgc tcccactacc tgcaatacgc ttacccactt cacctgggtg aactttactt   84360
aggattcacc ttaggtgggc atcatgttct tccaggcccc tcctctaact tttagttgag   84420
agtattccag acttaaggct ccatgggata gggatcttc ctatgcacca gcttattccc    84480
aactgcctgg cacgtaatgc atttattaaa tatatattga attgattacc ctacttgggg   84540
ctcttgtttg cttctacact tacagttcta gcatagcact taactcatta tcatgcatca   84600
ttattatggg tttgttttgt ctcccattag actgtgagct ccacaaggct gtgtccttgt   84660
cttatacatc attgtatttc cagcttccaa catagtgctt gccatgacac aggaagtcag   84720
taagctctga atgaatgaat atgtatctaca taccattaat ctgaggttta aagttttccc  84780
aaattctgaa gcaaggggat ttacggactt ccctgacaat ttttggatgt catcccaatg   84840
ataccactaa catttaaagg gacagcttgc atatatacat ttttctggat ggcagttttt   84900
tttcccacag gcttcatcag atatttctcc atagccttcc tcagattctc aaaggggtct   84960
ctgattcccc caaaagataa gaaactgtca taaaaaatta tttctaaata tcaattgtta   85020
aataaaatgt ttgcaaagca gcctgatgaa tcatttcagg ccacttgacc ccgatgagtt   85080
```

```
agagagtttg tgctctgcaa tctgactgct tccagcagtc tcactgctgc tggactgtgg   85140
cacttccaat tggcagcagg gcaagtttct tctggatgaa tattctgtca tagggggtccc   85200
ccttccacac atacctgtag gagcagtttg aaactcatat gcatggtctt cctggttcta   85260
ggcacatgag tcatttaagc tgctggagcc aggaccagct agtatgctag cccggcattc   85320
agaaagttaa aatttggggt caaaactgag aaccttcttt gatccacctt ggccagacat   85380
tttctctggc ttccattaat agcctcaaca tttttttttt ttctggccta gacccacaca   85440
ggcaagagac cagagcttct ctaaggagct aagggaaagc acattttaaa aataacttga   85500
gcaaatgaat tcatctggca aaagcaaccc cactacgtaa aataaacctt tttagtttcg   85560
caatagcagt tcctgaaaat gtaaacaacc tcagggtcta catgcactga atcatttgct   85620
gaacagaaag tccctggtcc aaattctgca agaataaaca ccttacaaaa ctaggggtca   85680
atgaccttca tatgggaaca aggagggtgt gggggggcagc aacccaccct gaggacaatg   85740
agaaagtctt gagacttgat attcaaaatg ctggctttct aaaccaaaaa ctggcatgag   85800
tggagggaga aggggagggt gggcacagtc tatgcctcag gctcttgctc agaccctacc   85860
aggcccctgc cttccctagg gaaagcgaga gtctactcac tgtcatgaag ccagaggaag   85920
gccctgcagg tttcactgtg tgttctgttg acaagatgat ggttccattg aaactgtaat   85980
aacatacttg gccaactaag cccatacgat cgtagtaact ttgtacccag tcctagcttt   86040
tcaaacataa tgataaatatg ttcttctaa tgtggcccat actgttctaa tgaacttatg   86100
ctgagttttt ctgagtacta gaataatatt cgccataaat aatagatata attattctca   86160
tttaatattt gcgtagctct tctttaaagc agaaagtatt ttctcattcc ttactagaac   86220
cttttctgtgt gaggagcact gagctagaac ccatatctta gaatggtcag aatttggaga   86280
aattcaggga aaaggcactg gactcatttt taaagactag aaaatgcaac ctccagaaaa   86340
agattcaaga gttttttact cccagagatg taggaaagat tggagtaaat cttaatatta   86400
tatttcaggt aaacaaagga tcactgtcaa aatagcagca tttattgagt aatggctgtg   86460
tgccaggtac tttacagttt cacatttaac cctcataata accttgtaaa gtggatatcc   86520
cctcagtaca tgatgagaac actgaagctt aggttaaatg attgtccaaa tcggacaatc   86580
attttcaaaa tctccccctt ttttctcct ttcttatctg caaggcagat tgcccttcc    86640
ctttcagtga aacttgtgca tgaccacatg actctctttg gccaatgaaa catgaacaag   86700
cagcgtttat cactttcaga tggaaggctt tgcatgagct ttgcctcctt ttcactctgc   86760
cacagtggcc actaacattc cagatagtgg cgctctgcag gctaggtcct atagtgggag   86820
ctatgggcag agccccttt cccaccccca tcaagatgtg catgctgcat aagccatgca   86880
ttaatctttg cagtttaag ccactaagtt ttggagttat attaatcatt aatcatggtt   86940
ctcaagagaa acagagtggg ggagtggtat tcattatggg aattggctta catgattatg   87000
gaagctgagt agtcccccag tctgctgttt ttgagctgga gaactagagg agccagtggt   87060
ataattcagc ccaagcctga aggcctgaga aatgggatgg gggaattggg agggtgggtg   87120
tgctagggta ggataagtcc tgaagttcaa aggccagcca gaaggtggat gtttcagcac   87180
cagaagagag agcaaattcg ctttttcttct gcctttttgt cctctctggg ccctcaatgg   87240
attggatgat gccctcccac attggtaagg gtggatcttc tatactcagt ctgctaattt   87300
cttccagaaa catcttcaca gacacatcca gaaataatgt tttaccagct atctcggtat   87360
cccttagcct agtccatatt taaaaattaa tgatcacaag cagttgtttg tttccacagc   87420
aaaacctggg tgacagacca agtgacccag atgactagaa tttgaccttc ttttgttgcc   87480
cacaccatac tctgaactaa catgctgtgc tgccttccaa gtggagaatg atggctaagt   87540
atcttctacc taatttgagt cacagaaaaa aaaaaaaaag gttattaact gcagtgacaa   87600
gaattgtgat tccccagggg gcagatcaag actgatagat aagagaagtg aggaacatct   87660
ggggaatgtc cattgaaaat ttactcagaa gagaagaata attaatataa taatatgata   87720
tattgaatta taataaataa tattttgatg tatttccttc caggcatgtt taagtttatag  87780
actttgagta tattttctca aagggggttc tatgtaagag actattctt aatatagttc    87840
ctagcttgga attgctcttg ctggtttaag ctgagctat tttattacag acttcacaac     87900
aataacgttt tccttcacta gtcagtacac aagatggtct tcatttccag tttggaatcc   87960
cacactatca gagcctgaga caaggactag tatgcagtta gtttgtttgg gaggtgattc   88020
caggaagtgg gaatgagaga tcagtcagcc tgcaacacga aggaggaaaa gtcaatataa   88080
ggatgaattt ggcaattggc cgtttcatgc aactggggct aaattttgct tggctctctca   88140
agaaatgtaa agaatgcctc ccgtaattgc tcacctcaag tatttattca ttggctctca   88200
tgctccattg gttgtccatg agaactttag ccctccctcg ctgcagcaca gacactgtgc   88260
tttctcctag gctgagcaag ctcctgcatc tgtggaaacc gtcccggggc agatagtgaa   88320
ataatgactg ctgcgtgctt gagatctggg aaagaggcca catcataagt gcactgaaat   88380
cagagatgtg tcaagagatg tgacacaggg catctgaggt gtctactgca ccagctataa   88440
ctccctaaac gctaatctca gttcttacag aggggatgga tgcaagggaa cagtcatgat   88500
tgagagcacc gaagaagctc tgtatgaacc ttaggcaagt ttcctaatct ccaaaatgaa   88560
ggtaataata cccaccatcc aagatcttcg ggaggaatag atgaactaat gtatgtgaaa   88620
atgtccagca caggtcctaa cccatagtag gtgctcacca aatgttagtt ccctgccctc   88680
cacgttgtgt gtatccggag ctgcactaga tgctgaggca aatggtctca aatgtacttt   88740
aacacttaat gactgagatt ttttctgagc tgcctacagg ttattgacta tattcattat   88800
taataataat atatatggcc acttcaggca actgggggcta aattttgctt ggctctctaa   88860
gaaatgtaaa gaatgcctcc tgtaattgct cacctcaagt atttattcat tggctctcgt   88920
gctttattgg ttgtccctga ggactttagc cctctctcac tgcagcacag acactctgct   88980
ttctccagt ttctgtggca agtgacagga gcccacctca aactaaagca aaagggactt    89040
cattggctct tgtagctagg aattccaggg ttggcactgg ctttgggcac tactggatgc   89100
aggaattcaa acaatgtctt caactctttc ttttggtgtt tctctcagct gtgcttctct   89160
tgtcgtttct ttttcccatt ttacagataa gttcatccgt aactgagaga ggtgaaaagg   89220
ggatggctgc agagaactct ggcttatatc atccttgctt gctgacctca aggtccatgt   89280
ataaattctc agagaagaag ccctctggtt ggtgatgctt ggaacatgcc ctggagggtg   89340
ggccccttga agtggagctt gctggaacca catgggctgg agcaaggcgc tagggccaga   89400
agagagaggt aggcagggct gctggccagg cactcttcac caagcaaagg caagaggagg   89460
ggcatgattg aggcagtgat acagaaagca gacagtagga tgcgtgccaa gtgtgccgtt   89520
acttgctacc tgtggttgat gggagagtca caccacattt aggaggagag aatccatttg   89580
ccacttctga caatgccaca agaatcacat atttcatcca gaggttgaat ttggcccatg   89640
ctgagcttta aaatacagag ctgtcttgga acaatggctc agtacattca tttggtgtcc   89700
aacaaagcct gcctctgttg ccttccctct ctctgtgtgc ccttcaagat cttcattgtg   89760
ctttggggag agaaagagaa aatgtcatat cagggtagct caccccatgt gtcctggact   89820
```

```
caggaaaaga gtatcttatc accttactct tttgttatta taaaaaataa agttgaacgt   89880
cttcaaataa aataaagaag tatagaaaaa attttaaatt aacctgttat gattctacct   89940
agagaaccat tgtcaacatc ttggtatatg tacttccaga tactttccta tgaatatata   90000
cattgtagat tttttaatat taaaaggcta tcatgctgct ttgtatacag gctttcttta   90060
ctgatatgta atataataca cagacaaata tacaaatcct aagccatcaa ctcattgaat   90120
ttttattcat tgtttttaat acctgcattg tgttccattg ttaggctatg tcacaacata   90180
tttaattaag cccctattga tgaatattaa tttactctat ttgccagttc attccagtcc   90240
aacatttatt gagtgtctac ttacgggcca ggcactcttg tattcatcaa gatcaccaca   90300
ttatctgtat cagttattta ttgccacaat aaaactgcat aacaaatcac tccaaaatgt   90360
agcaccttaa aactacaact acttattatt tctcaagagt caatgggtca gctgagcagt   90420
tctgccgata ggggtcaagg tcaacacatt tcaactagac tacttgtaaa aagaatgag    90480
tgtctgggta ggtgtgttct tctaaaaata aaacaaggaa tgaggaaatt gcaggtagga   90540
taagagggg ggttggcaac caaaccccac aaaaggcaga caaattttaa ggaaacatta    90600
tgccagactc ctatgtcatc atccaagtag atgcagtgaa gtataacctg gggcgtagta   90660
gggtaggagt ggggagagca gaggagaagg aagggagatt gcttttcatc acttttggat   90720
tccctaataa cagacatgac tgccagtatt aaaatttaac aaaggatatc tgatcattaa   90780
ttttcctgta taagtcactg gtgatcttca acatctctcc ctcccttcct cccttccttc   90840
ctcccaccct cccttccttc cttctttcct cttttgcttt caacttcctt ttctcgtttc   90900
cttttgcttt ctttctcttc tccctttttt ctgtcactct gggcgtatgt agtagtgtaa   90960
aaaggttgac agagaaatca aatataacag gagcagggcc ctgagaaaag cacctggcat   91020
cctgtaggca aaccattgtt tctaaaagaa gggactgaga gattgaggag ctcaggacat   91080
tgccaaatga acaaggcaag cacattatt cagtaccaaa caacggaaa acggcctttc     91140
caaataactg acctataaaa cagccttttc acaagagtac cgtaattact ggccaacagc   91200
aacaatgaaa aacaactccc aaacaaagaa atatttctgg attaaaagcc atgagatctg   91260
gattctaaca agctgtgctc ctcaaactac aagtacaaaa tctggctcta aactaacaag   91320
ctatgagcct caaactgatg actgacatgt ttgggtctcc atctcctttct tgggggttgg   91380
ggtcttagag acccttttcc acgccctgat tctcttacta gtgtgtatgc tttccttttg   91440
acttctcatg ctgaccgtct gagcaggagt gagaagcaat ttcaaaggaa aacatcgttt   91500
atcatctgct gaaagaaacc aaaaagaaca caggaaaaca aaaagacaag gaaagggaat   91560
gaaaatgtaa ttcattttat taaaaagaag aattattctt ctgggacact ggatagaaac   91620
cttaatgagt tacctagcta tcataaatcc tctaacagag aagagaagag aaagaaacaa   91680
agacggaaga gggcaggata aaagaaagaa aaaaggaagg gaaaatgaa ggaaggaagt     91740
tatctattca tttctacaga gactctgctg agcagtagac aagaagactt gggaaaaatt   91800
taactgaaac ttttccaaaa atcttttcag agggattttt tccctctgaa aagcatcatt   91860
agaggctgtt caatacccaa ggcaagcctc tttcatatta cttactgtac atgaaacact   91920
catgcaattg aggctagcca gaggccattt agaaattcaa taattattca acccaagggg   91980
cttttccaaat ggtgaagtag cttcttaaga ggaaattaat attgagcagt atagcaaacc    92040
taattggaat cttgagaaaa tagttctgtg tcgttagaac agctagaggc taaagaagat   92100
caggttggat gataccttca tttttgtctc tttccttaat tatgatgtaa agggaaaaat   92160
cttgtttatt ttctatgcca ggagggtaga gggtgatttg gagaggttcc aagtttatca   92220
aaatctacct tcagtctggc agtagaaaag tttacttcct tcatttcttt cctatagaca   92280
ttcaaagaga gctaaggaga tccaaaaacc ttttttttcta tatttgcaat gcaaggcagt    92340
tgggaattaa tgactgattt gttggtgagg gcagtggaga tgtgatcacaa aagcagtaaa   92400
gctgtgtttc tcaaagagag aaagtctctt tgagatcttc attattttac tatttagaag   92460
agaaaggggc gttatatcac gttggaagca tccatgagtc actagtctct tctctatctt   92520
tctatgcctt tctgtattaa ttactttgaa agcacaacat tccaaaccca ttgagcacac   92580
agtggtctga tttctccact tgtgaaaggt gctaaagtct cactgtagga ttaatttggg   92640
ggtccaggct atgggcttgt agatatgact accttagact ttggttctcc tggcaactaa   92700
cccttttttgg atcgtatcta agttgacctg tttcacagtg agagaactcc tctccattac   92760
tcagaatact gaggcagatc acaagtgtac cacacctggc taatgttaag ccagacagaa   92820
acatcaggct catctcttga gaagaagggt cgcttattaa ggatacaaac tattttttt    92880
ttttttttttt gagacagggt ctcattgccc aggttagagt gcagtggtgc aatcatagct   92940
cactgcagcc tcaaccacat gggtattttt aaataagaaa aaaataccat ctgatagata   93000
tgaaggagca ttgggtcact ataaacaaaa cagattctaa gagcaggaag aaagagtaca   93060
gtctctttc aataattttt tttaaactt gggaaagaac actcactcta ttcctataga    93120
ccagaaagca gataattgtc cattatgatt ccacatgaca ctatcttgtt cagctgtcac   93180
tgaaacaact ttgaacactg tcatatgttc ttcccagctc ctgaactctg accttttat     93240
gccttagttc cactttcaca aaagggatt gatgtaatgt gcatttcaga ggaaacgact     93300
atagacattt agtgtcatta taaatgttga gaagtatgct ggcagaaatt atgccttaag   93360
atcatatatg gattcttgta tggtttgaaa ttgcttaaaa gatatatatg atctctaaaa   93420
tgtgtgtgta tatatatatg atgtcttctt atatatctat atgtgatata tttatatata   93480
tataaatctg tgtatatcac atatataaat ttgctgttat ttgaattgcc attacctcag   93540
tgcttagggg aagccatgca cgtttgtttc ttttcagtac ccagagttaa ttaacataag   93600
ttatcacaga agctcccata acattgaga caatttctct ataccctgta ctatttaagg     93660
ttttgaaaac aaaacagaag caggtaagga ggaagtacgc tttactattg aagatttatt    93720
aggtacacat ttagatttgt gaactcacat tgcttaggat gaaagggact cttgaggatg   93780
tctgctgttt gttagtgaac tgcctgtaac aattacaatt agcacacaca tgagcacaat   93840
gaactgggta gtcagactca gccaaaatga atagaaatag cctcttacca aatttactt    93900
gagtagccct tggactctga gcactgctgc ccagagcaat atgactgtag gtccaagttt   93960
gtcaatgact atgcaaatgt gctttcttcg cttttactct attgtcatct gtctattaca   94020
atgttgctat ggtgacacct ttccaatatc cctgtgcttc tttggtatcc tctaagggga   94080
agctgtaatg aagtggcttg gcaaaagaat cctcttggaa ttttttttt ttcatatgct    94140
actgaaaacc agcatgattt tcctcttatg ggaaatgtat aaagtatgag ttggaaatga   94200
tggaaattaa tgtgtactga cttgggcaag gaatgtgaat gttattcatt ctgttccaaa   94260
ctacctgaaa atattctctt tctgttccta ctttccagga gataacatct taagggacac   94320
tgaagcttgt gcgtgtgtga gtagaacacg tgctggggc cttgagctc atgagggagg     94380
ggctacatgt cggtggggtg ataactgtat gctggaaaca atgataggtg gtgaccctgg   94440
agcacttacc atgtgacagg tgttatgcta agcatgttgt atgcattcct tcattgaatg   94500
acagctacct atattatcct cattttataa gatgaggtaa cagagcttca gaaaggttag   94560
```

```
actcagctgc tatgggtctg tctgactctg gtgttcttcc tcttaaaaac tggggcactt   94620
tggaaatgag attcctcggt gatgaacaga aatattgctt agcggctgta tttttgtatc   94680
tggcagtttt cccatatttg agtcttatat tcacaatcgg tatctttaca ttacacaaaa   94740
gtgacacaga attagagtca tttaatccag ggttgatatc attaagtcat gactatttat   94800
taaatgtttc ttacaatatc tgagatgata ttgcaaaaga tgtaagtgat tttagaagtt   94860
ctcacttcgt agttagttgc agaaacctct tttggaggag ggatgttttc tctatatatc   94920
ctaatttcta cttaatatat ttccacacct cttttgaagtg tgtagtaaga atggtaaaat   94980
gcagtacttc gtcatttggt acagttcaat caatatgcat taagatgtga tcatatgggt   95040
aatagaaaaa tgtgaaagat ccaattcttt ttctccagaa ggcaggaagc tcatatttga   95100
tttctgttac tataaactat aaaaacgttt caaatgtagt ttacccgtaa ccatcaccct   95160
gcaagggtga tattgctccc cgccaattta cggaggagaa tactgaggct ttaaggttgt   95220
agatagacca agaccacaca agtagagagt ggcgggctgt gggttgagct ttaaaatcca   95280
ggttcatcca tgactcccag tgtgttctag taaatccact agaatctgag tattttccaa   95340
tgatttatgc tccgctctgt gtcaggcagt tcatgtatt tttcaacaat cagaaaatcc   95400
tggggaaggc aaactgtttc cccctctcta ggtgccttgg aagtggccgt tgtggaccca   95460
gagatcatcc tttctgatct gacaccttct tcactgccct ggcccagtgt cttttctgca   95520
aggctggaag cccccttaga ctggtcatgt cccatctctt tccggaggga agatgatccc   95580
aaagacgact ttttctctcca cggtgctgcc ataccgcagg cggccgccag gggtccccgc   95640
tcggcgtccc cgccgagacag tcgagccccg gccggctgcg cggcgcgctg ggtgcatgag   95700
ggggctgctc cggagcgacg gcggctgcag ctggagccag gcgctcgccc gtccgccggt   95760
tggctcgccg ggacctcgcg caccggcggc agagtcccct gcgtggattg gcaagcgacg   95820
ccccacctgc cccgagctca ccattttctt tcgcgctggc tgcagctgac ccggcgaagg   95880
gagccgaccg ggcctgggc tggaggtaaa accccacggt gagtaagaac ccgctccaag   95940
ctaggggagg cggcgcagcc cggtggctgc tcgctcccga tctcgcccgg gcgggcggcg   96000
aggtttgggg cgcacctggg cgcgggtgca agaaggtgcg ggaggcggcg gaccggtctt   96060
ctgcccgccg gccacgggct tccggggctg gagtcctcct cagaccctg ccggcgcctg   96120
ggtttctggc cggctcctcg tgtgcacttc ccggcaggaa caagggtcgc ccactttcca   96180
ccccgggatc ttgatttgtc cttgatttga aaagatataa atcaataaga tcgtccttct   96240
ttcgggggtgc aagactccga gcccatcccc agccgcggac gcctgcaggg tgcgtgttgg   96300
gctgtgggtg gcgggaagac aaacttttac aaaagtgcgc ctgggctggg ggacaacgct   96360
tgggcgtcct gatcctgagg gaggagtctc ggcttgggc agcgtagggg aagtccgcac   96420
cgtcagccag gtcgccccg gggctgacga tgcctcacgg aggtggggag cgtgtaaagg   96480
ccgtacaaat cgccgcttaac tttggggcca acaactgtca aacatctgga atcccagccc   96540
ctcccttttcc ctgaactggg gaagaaggtg aaaaccctt aagtttttctt tgattgcccc   96600
ttcccaccctt cagaccctg ctgggagggt aaagcgccga cccctggtgc ctggcaagta   96660
ccagagactc taaatctctc gggatccccc ccctcgcgct cttttcctgac cctctccct   96720
aaccctcccc acagagatct ctctacgcag ccgactgaga tcgtggcgaa tggcttttg   96780
tttctccgcg tttccctat tgtttgcctt tccaacatct ggcgggcctt ggggagagaa   96840
ggaagccct ctggtccccc tccccggccc ccacgccagg tccggcaggg gatcccagct   96900
gggaaagtgg aggagcccga cccccagcgag gccgccccac cccgcccttg tggttagagg   96960
gcggagggaa agttgttcct tccccgcctc gctgctgcc tgtggcccag ggcgcatttc   97020
tcagatctca gcccaggcgc gccgcaaagg ctcaaatccg agaaggtgct gctttcgaga   97080
cagtggaagc gcgttccgcc ccaatccaga gcgtccagtg gttggttcca gaggatttca   97140
atctctagcc aaaggcgttg gggctgggc gctgctaggg cagtggggagg ggatcggggc   97200
acctttggta ggcggaaagc tgagattctg gggtccacaa gtttccaagg gcgggagggc   97260
aggctagtcg ccaaaaagag aacgaagatg caaataacga ggaagcctta tgacgttgcc   97320
tggaaatagt agtgtggtgg ttcactccgg aatgaacgtg gagttctggc tttgagtacc   97380
gctccaagtt taaatcccaa gtcccctttc ttcattgtag aaaagagga ctcagacgac   97440
gcaacacaga tacggctaga gcacagttcc tgcttccacg tcccagaaa caagtggctt   97500
aggatggtcc cgagttcccc tgtgggtgcg cttgttgggt tgcaggcggc cctgtttccc   97560
tgcacaagtc agatgcttac acattgtgtt cattcttagt gtggattatt gattaaagaa   97620
ctggggcaaa agcaaagtag ctactctgag aagtcagggt ccccagatgg tgcccagcga   97680
gttgtcttgc ctctgagggg aggctgactg agactgtgca cctgttagaa cctatgctac   97740
cccatagcct tgcagttgac ttgctgttgc cagcttttcc tgtgggatcc ccaatgagtc   97800
cctcttccaa ggaagctcaa ttacacttttt gattcctcca caacccaggg gaagaaagag   97860
gcttctgtag gaacattatg atctatgtac ccactcagac attgtcagtg gataccagaa   97920
gcttggctct gcacagctct gagagttttc cctttgcgaa ctcaacagaa cttttgagtt   97980
tccatttaac ataaaagaag tgagactgct aagccaggaa tgcgacacat agagcacttt   98040
ctctagtgat ttctggggtat tatatctctt taccttccca accggtggaac caggaaaaga   98100
aaaaaagca acatctttga agtactgcaa ggcactttac aaacattttca ttatgaaaat   98160
gatcccaag gaaggattcc tttgaaattt agcagcagca acccagaagc aacaaaaag   98220
accaaagtta ctcaagaagt acccaaaggc atcattaaca aaataaaaga gcatttcttg   98280
tcttggccta cccccgctaag gaaaacaggg taattatagt ggaagttaag cttg         98334
```

```
SEQ ID NO: 64          moltype = DNA   length = 28
FEATURE                Location/Qualifiers
misc_feature           1..28
                       note = Synthetic polynucleotide
source                 1..28
                       mol_type = other DNA
                       organism = synthetic construct
SEQUENCE: 64
cccggggccg gggccggggc cggggccc                                          28

SEQ ID NO: 65          moltype = DNA   length = 212
FEATURE                Location/Qualifiers
misc_feature           1..212
                       note = Synthetic polynucleotide
source                 1..212
```

```
                  mol_type = other DNA
                  organism = synthetic construct
SEQUENCE: 65
cccggggccg gggcccgggg cccgggccc ggggcccggg gcccggggcc cggggcccgg    60
ggcccggggc ccggggcccg gggcccgggg cccggggccc ggggcccggg gcccggggcc   120
cggggcccgg ggcccggggc ccggggcccg gggcccgggg cccggggccc ggggcccggg   180
gcccggggcc cggggcccgg ggcccggggc cc                                 212
```

USE AND TREATMENT OF DI-AMINO ACID REPEAT-CONTAINING PROTEINS ASSOCIATED WITH ALS

CROSS-REFERENCE TO RELATED APPLICATIONS

This application is a Divisional Application of U.S. application Ser. No. 17/322,604, filed May 17, 2021, which is a Divisional Application of U.S. application Ser. No. 16/851,690, filed Apr. 17, 2020, which is a Divisional Application of U.S. application Ser. No. 16/362,908, filed Mar. 25, 2019 and issued as U.S. Pat. No. 10,663,475, which is a Divisional Application of U.S. application Ser. No. 14/775,278, filed Sep. 11, 2015 and issued as U.S. Pat. No. 10,295,547, which is a national stage filing under 35 U.S.C. § 371 of International PCT application PCT/US2014/022670, filed Mar. 10, 2014, which claims the benefit of the filing date of U.S. Provisional Application No. 61/786,258, filed Mar. 14, 2013, and the benefit of the filing date of U.S. Provisional Application No. 61/883,219, filed Sep. 27, 2013. The entire contents of each of these referenced applications are incorporated by reference herein.

FEDERALLY SPONSORED RESEARCH OR DEVELOPMENT

This invention was made with government support under NS058901 and NS040389, awarded by the National Institutes of Health. The Government has certain rights in the invention.

REFERENCE TO AN ELECTRONIC SEQUENCE LISTING

The contents of the electronic sequence listing (U120270062US06-SEQ-KZM.xml; Size: 190,397 bytes; and Date of Creation: Mar. 5, 2024) is herein incorporated by reference in its entirety.

BACKGROUND OF THE INVENTION

Expansion of a GGGGCC hexanucleotide sequence within the intron of the human C9ORF72 gene is associated with both amyotrophic lateral sclerosis and frontotemporal dementia in humans. Amyotrophic lateral sclerosis (ALS) is a debilitating disease with varied etiology characterized by rapidly progressing weakness, muscle atrophy, muscle spasticity, difficulty speaking (dysarthria), difficulty swallowing (dysphagia), and difficulty breathing (dyspnea). Although the order and rate of symptoms varies from person to person, eventually most subjects are not able to walk, get out of bed on their own, or use their hands and arms. Most subjects with ALS will eventually die from respiratory failure, usually within three to five years from the onset of symptoms. Riluzole (Rilutek) is the only currently available treatment for ALS and only slows progression and increases survival to a modest extent. Frontotemporal dementia (FTD) is also a devastating group of disorders resulting from atrophy or shrinkage of the frontal and temporal lobes of the brain. This shrinkage or atrophy results in severe behavioral changes. There is currently no cure for FTD and limited medications for managing the symptoms of FTD. New methods for diagnosing and treating ALS and/or FTD would greatly benefit ALS and FTD subjects.

SUMMARY OF THE INVENTION

Expansion of a GGGGCC hexanucleotide sequence within the intron of the human C9ORF72 gene is associated with both amyotrophic lateral sclerosis and frontotemporal dementia in humans. As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. These sense and anti-sense transcripts were found to be translated to produce di-amino acid repeat-containing proteins. The sense transcript (containing 5'-GGGGCC-3' hexanucleotide repeats) was found to be translated through repeat-associated non-ATG (RAN) translation such that poly-(Gly-Ala), poly-(Gly-Pro), and poly-(Gly-Arg) proteins were produced. The anti-sense transcript (containing 5'-GGCCCC-3' hexanucleotide repeats) was found to be translated through repeat-associated non-ATG (RAN) translation such that poly-(Pro-Ala), poly-(Pro-Arg), and poly-(Gly-Pro) proteins were produced. Additionally, the anti-sense transcript was found to be translated through ATG-initiated translation to produce Met . . . poly-(Pro-Arg) and Met . . . poly-(Gly-Pro) proteins.

These di-amino acid repeat-containing proteins were found to be present in ALS subject blood samples. Accordingly, aspects of the disclosure relate to a method of detection of di-amino acid-repeat containing protein levels in sample (e.g., blood) obtained from a subject, the method comprising measuring di-amino acid-repeat-containing protein levels in the sample of the subject. In some aspects, detection of di-amino acid-repeat containing protein levels may identify (or diagnose) or aid in identification (or aid in diagnosis) of a subject having ALS or FTD or likely to develop ALS or FTD. Alternatively or additionally, detection of di-amino acid-repeat containing protein levels, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject. Aspects of the disclosure also relate to treatment of a subject having ALS or FTD by decreasing or stabilizing di-amino acid-repeat-containing protein levels in the blood of the subject.

Additionally, expression of the anti-sense transcript (containing 5'-GGCCCC-3' hexanucleotide repeats) was found to be highly elevated in subjects having the expanded GGGGCC hexanucleotide repeat compared to controls. Foci of sense and anti-sense transcripts were also detectable using fluorescent in situ hybridization (FISH) in brain and blood cells of patients having the expanded GGGGCC hexanucleotide repeat sequence within the intron of the C9ORF72 gene. Thus, other aspects of the disclosure relate to a method of detection of a hexanucleotide repeat-containing transcript, the method comprising measuring a level a hexanucleotide repeat-containing transcript and/or measuring the presence or absence of a hexanucleotide repeat-containing transcript focus. In some aspects, detection of a hexanucleotide repeat-containing transcript may identify (or diagnose) or aid in identification (or aid in diagnosis) of a subject as having ALS or FTD or likely to develop ALS or FTD. Alternatively or additionally, detection of a hexanucleotide repeat-containing transcript, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject.

In some aspects, the disclosure relates to a method for identifying a subject as having ALS or FTD or likely to develop ALS or FTD, the method comprising determining, in a blood sample obtained from a subject, a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid repeat-containing proteins that is elevated compared to a control level indicates that the subject has ALS or FTD or is likely to develop ALS or FTD. In some embodiments, the level of the one or more di-amino acid repeat-containing proteins is determined by performing an assay. In some embodiments, the assay comprises an immuno-based assay. In some embodiments, the immuno-based assay comprises an isolated antibody specific for an antigen comprising a sequence as set for in Tables 1, 2, or 3. In some embodiments, the immuno-based assay comprises an isolated antibody specific for the C-terminus of the one or more di-amino acid repeat-containing protein.

In some embodiments, the method further comprises identifying the subject as having ALS or FTD or likely to develop ALS or FTD if the level of the di-amino acid repeat-containing protein is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant.

In some embodiments, the one or more di-amino acid repeat-containing proteins is selected from the poly-(Pro-Ala), poly-(Pro-Arg), Met . . . poly-(Pro-Arg) or Met . . . poly-(Gly-Pro) protein. In some embodiments, the one or more di-amino acid repeat-containing proteins is two or more di-amino acid repeat-containing proteins.

Other aspects of the disclosure relate to a method for treating a subject with ALS or FTD, the method comprising decreasing or preventing an increase in a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein in the blood of the subject. In some embodiments, decreasing or preventing an increase of the level of one or more di-amino acid repeat-containing proteins comprises removing the one or more di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, the bone marrow transplantation is an allogeneic bone marrow transplantation.

In yet another aspect, the disclosure relates to an isolated antibody specific for one or more di-amino acid repeat proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. In some embodiments, the di-amino acid repeat protein is selected from a poly-(Pro-Ala), poly-(Pro-Arg), Met . . . poly-(Pro-Arg) or Met . . . poly-(Gly-Pro) protein. In some embodiments, the isolated antibody is specific for an antigen comprising a sequence or fragment of a sequence as set for in Tables 1, 2, or 3.

Other aspects of the disclosure relate to a method for identifying a subject as having ALS or FTD or likely to develop ALS or FTD, the method comprising determining, in a sample obtained from a subject, a level of a 5' GGGGCC-3' hexanucleotide repeat-containing RNA and/or a 5'-GGCCCC-3' hexanucleotide repeat-containing RNA, wherein a level of the 5'-GGGGCC-3' hexanucleotide repeat-containing RNA and/or a 5'-GGCCCC-3' hexanucleotide repeat-containing RNA that is elevated compared to a control level indicates that the subject has ALS or FTD or is likely to develop ALS or FTD. In some embodiments, the level is determined by performing an assay. In some embodiments, the assay comprises a nucleic acid-based assay, such as in-situ hybridization (e.g., FISH) or RT-PCR (e.g., quantitative RT-PCR or strand specific quantitative RT-PCR). In some embodiments, the method further comprises identifying the subject as having ALS or FTD or likely to develop ALS or FTD if the level of a 5'-GGGGCC-3' hexanucleotide repeat-containing RNA and/or a 5'-GGCCCC-3' hexanucleotide repeat-containing RNA is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant. In some embodiments, the level of a 5'-GGGGCC-3' hexanucleotide repeat-containing RNA and/or a 5'-GGCCCC-3' hexanucleotide repeat-containing RNA is a level of a 5'-GGCCCC-3' hexanucleotide repeat-containing RNA.

Yet other aspects of the disclosure relate to a method for identifying a subject as having ALS or FTD or likely to develop ALS or FTD, the method comprising determining, in a sample obtained from a subject, the presence or absence of foci containing 5'-GGGGCC-3' hexanucleotide repeat-expansion-containing RNA and/or a 5'-GGCCCC-3' hexanucleotide repeat-expansion-containing RNA, wherein the presence of the foci of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. In some embodiments, presence or absence of foci or elevated C9ORF72 sense or antisense RNA levels is determined by performing an assay. In some embodiments, the assay comprises a nucleic acid-based assay, such as strand specific RT-PCR or in-situ hybridization (e.g., FISH).

Yet other aspects of the disclosure relate to transgenic mice. In some embodiments, the transgenic mouse comprises a human C9ORF72 gene and optionally human flanking sequences. In some embodiments, the transgenic mouse comprises SEQ ID NO: 63.

These and other aspects are described in more detail herein and illustrated by the non-limiting figures and examples.

BRIEF DESCRIPTION OF THE DRAWINGS

The drawings are first described.

FIG. 18 is a table summarizing histopathological findings in C9ORF72 positive ALS/FTD cases and controls.

FIGS. 19A-19F are a series of images and datasets. (A) shows strand-specific RT-PCR detection of sense(S) and antisense (AS) transcripts (across intron 1) of PBLs of C9(+) patient and normal controls. (B) is a summary of 5' RACE products. (C) shows FISH staining of frontal cortex from a C9(+) case showing an example of cytoplasmic RNA foci. (D) shows FISH staining of peripheral blood leukocytes showing the accumulation of antisense (AS) $G_2C_4$ and sense(S) $G_4C_2$ RNA foci in C9(+) but not C9(−) cells. (E) shows antisense foci specificity assay showing excess unlabeled $(G_4C_2)_4$ oligo blocks labeling of G4C2-Cy3 antisense (AS) but not $G_2C_4$-Cy3 labeled sense foci. (F) shows additional controls for antisense RNA foci showing expected DNase I resistance and RNase I sensitivity.

FIG. 20 is a series of images of in vitro evidence for RAN translation of the sense GGGGCC repeat expansion. (A) shows constructs containing varying GGGGCC repeat lengths with upstream 6X Stop cassette and 3' tags in each reading frame. Immunoblots (B) and/or immunofluorescence staining (C) showing RAN translation occurs in all three frames (GP, GR, GA) in cells transfected with constructs containing 30, 60 and 120 repeats.

FIG. 21 is a schematic of putative protein products in sense and antisense directions for all reading frames SEQ ID NOs: 57-62, from top to bottom. Underlined sequences were used to generate polyclonal antibodies. *=Stop codon.

FIGS. 22A-22E are a series of images showing validation of dual antibodies to detect putative polyPA, polyPR, polyGP proteins by immunofluorescence and protein blot (A-D Top): Schematic diagrams of constructs expressing ATG-initiated N-terminal epitope-tagged (V5 or Flag) repeat proteins with or without endogenous C-terminal sequences. (A-D Bottom panels), co-localization of α-Flag or α-V5 staining in transfected HEK293T cells with staining using the following newly developed antibodies: (A) α-PA or α-PA-CT (antisense); (B) α-PR or α-PR-CT (C) rabbit α-GP or α-GP-CT (sense); (D) mouse α-GP. Similar staining was not seen in preimmune or pcDNA3.1 empty vector controls; (E) Corresponding immunoblots showing six of the seven antibodies tested also detect recombinant proteins by Western.

FIGS. 23A-23C are a series of images showing validation of additional sense repeat and C-terminal polyclonal antibodies. (A, B Top): Schematic diagrams of constructs expressing ATG-initiated N-terminal V5-epitope tagged GR or GA repeat proteins with endogenous C-terminal sequences. (A-B Bottom panels), co-localization of α-V5 staining in transfected HEK293T cells with α-GR, α-GR-CT and α-GP-CT respectively. Similar staining was not seen in preimmune or pcDNA3.1 empty vector controls. (C) α-GR detection of recombinant protein in Flag-GR transfected cells by protein blot.

FIGS. 26A-26D are a graph and a series showing images RAN translation and PR protein expression affect cell viability. (A) qRT-PCR shows expression of expansion transcripts are similar in HEK293T cells transfected with (−)ATG-PR-3T and (+)ATG-PR-3T constructs. (B-D) Bright-field microscopy images showing changes in cell morphology in cells expressing RNA and RAN proteins from (−)ATG-PR-3T constructs compared to empty vector control (pcDNA3.1) and worsening effects in (+)ATG-PR-3T cells expressing increased levels of PR protein.

FIG. 27 is a table describing primers used for RT-PCR and RACE (SEQ ID NOs: 17 of them (in order. SEQ ID NOs: 36, 37, 39, 38, 45-47, 40, 48-56).

FIG. 28 is a table describing novel sense and antisense antibodies. (in order SEQ ID NOs: 20, 23, 19, 25, 21, 21, 22, 18).

FIG. 29 is a schematic of the BAC insert used to make transgenic mice.

DETAILED DESCRIPTION OF THE INVENTION

Figure 1:
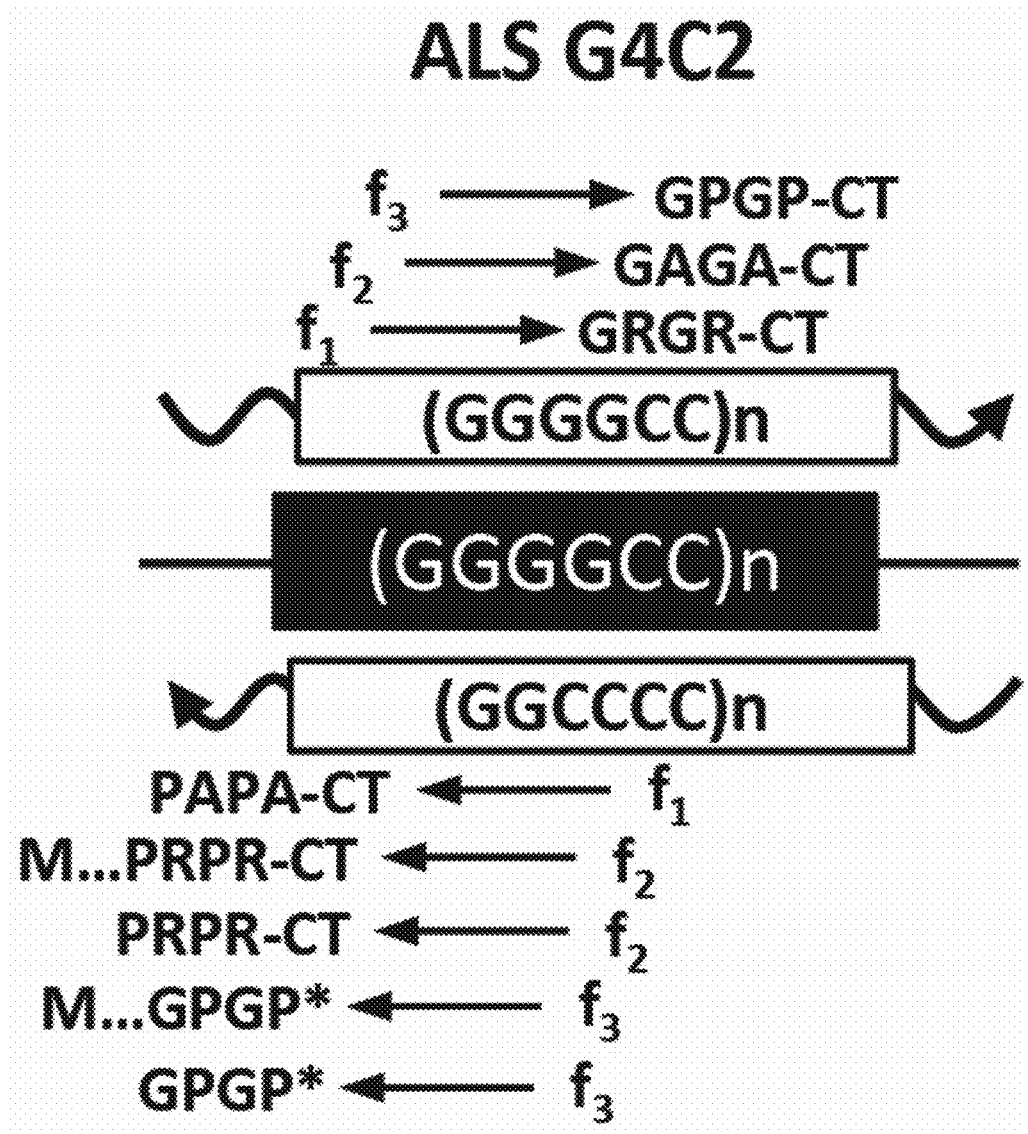
FIG. 1 is a drawing showing that transcripts are produced in the sense and anti-sense direction on the C9ORF72 gene, and that repeat-associated non-ATG (RAN) translation proteins are translated in all three reading-frames from both the sense and anti-sense C9ORF72 transcripts. The drawing also shows that Met . . . poly-(Pro-Arg) and Met . . . poly-(Gly-Pro) proteins are translated through ATG-initiated translation on the anti-sense transcript. CT=predicted to and/or shown to contain a c-terminal domain. *=end of protein (due to stop codon). M=Methionine.

Well-established rules of translational initiation have been used as a cornerstone in molecular biology to understand gene expression and to predict the consequences of disease causing mutations. In general, microsatellite expansion mutations (e.g., CAG, CTG) located in predicted coding- and non-coding regions have been thought to cause disease by protein gain-, or loss-, of-function or RNA gain-of-function mechanisms. It has been previously reported that the canonical rules of translation do not apply for CTG·CAG repeat expansions and that CAG and CUG expansion transcripts express homopolymeric expansion proteins in all three frames without an AUG start codon (see, e.g., T. Zu et al., Non-ATG-initiated translation directed by microsatellite expansions. PNAS 108, 260 (2011)). This translation independent of an AUG start codon is termed repeat-associated non-ATG (RAN) translation. RAN translation is hairpin dependent and occurs without frameshifting or RNA editing. RAN translation has been observed from trinucleotide, tetranucleotide, and pentanucleotide repeats associated with myotonic dystrophy 1, myotonic dystrophy 2, spinocerebellar ataxia type 3, spinocerebellar ataxia type 8 and Huntington disease (see PCT publication WO/2010/115033, which is incorporated herein by reference).

Expansion of a GGGGCC hexanucleotide repeat within the intron of the C9ORF72 gene has been previously associated with both amyotrophic lateral sclerosis and frontotemporal dementia. As described herein, it has been found that this expanded hexanucleotide repeat is contained within RNA transcripts expressed in both the sense and anti-sense direction from the C9ORF72 locus. These hexanucleotide repeat-containing transcripts were found to undergo RAN translation such that poly-(Gly-Ala), poly-(Gly-Pro), poly-(Gly-Arg), poly-(Pro-Ala), or poly-(Pro-Arg) proteins were produced, depending on the frame of the hexanucleotide repeat being read from the RNA (5'-GGGGCC-3', 5'-GGGCCG-3', and 5'-GGCCGG-3' on the sense transcript, 5' GGCCCC-3', 5'-GCCCCG-3', and 5'-CCCCGG-3' on the anti-sense transcript, see FIG. 1). In addition, the anti-sense transcript was found to be translated through ATG-initiated translation to produce Met . . . poly-(Pro-Arg) and Met . . . poly-(Gly-Pro) proteins. These RAN and ATG-initiated proteins are referred to as di-amino acid-repeat-containing proteins herein. The sense and anti-sense hexanucleotide repeat-containing transcripts are referred to herein as 5'-GGGGCC-3' hexanucleotide repeat-containing RNA (sense) and 5'-GGCCCC-3' hexanucleotide repeat-containing RNA (anti-sense).

As further described herein, these di-amino acid-repeat-containing proteins unexpectedly were found to be present in blood samples from subjects with ALS. Additionally, expression of the anti-sense 5'-GGCCCC-3' hexanucleotide repeat-containing RNA transcript was found to be highly elevated in subjects having a C9ORF72 gene containing the expanded GGGGCC hexanucleotide repeat sequence. Further, foci of both the sense and anti-sense hexanucleotide repeat-expansion-containing RNA transcripts were found to be present in subjects having a C9OR/72 gene containing the expanded GGGGCC hexanucleotide repeat sequence. Without wishing to be bound by theory or mechanism, it is believed that di-amino acid-repeat-containing proteins in the blood of subjects with ALS accumulate within the brain parenchyma over time, leading to neuroinflammatory changes, CNS dysfunction, and neuronal death. Accordingly, aspects of the disclosure relate to identification of a subject as having ALS or likely to develop ALS by providing novel assays for determining di-amino acid-repeat-containing protein levels in the blood of the subject and/or hexanucleotide repeat-containing RNA levels in a sample from the subject. Aspects of the disclosure also relate to treatment of a subject having ALS or FTD by decreasing or stabilizing di-amino acid-repeat-containing protein levels in the blood of the subject.

Identification of a Subject Having ALS or FTD or Likely to Develop ALS or FTD

Aspects of the disclosure relate to identification of a subject having ALS or FTD or likely to develop ALS or FTD based on a level of one or more di-amino acid-repeat-containing proteins in a blood sample from a subject. In some embodiments, a method comprises, determining, in a blood sample obtained from a subject, a level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid-repeat-containing proteins that is elevated compared to a control level indicates that the subject has ALS or FTD or is likely to develop ALS or FTD. In some embodiments, a level of one or more di-amino acid-repeat-containing proteins is determined by performing an assay. Non-limiting assays are described herein.

Other aspects of the disclosure relate to identification of a subject having ALS or FTD or likely to develop ALS or FTD based on a level of a 5'-GGGCC-3' hexanucleotide repeat-containing RNA and/or a 5'-GGCCCC-3' hexanucleotide repeat-containing RNA in a sample from a subject. In some embodiments, identification of a subject having ALS or FTD or likely to develop ALS or FTD is based on a level of a 5'-GGCCCC-3' hexanucleotide repeat-containing RNA in a sample from a subject. The sample may be, e.g., a fluid or tissue sample obtained from the subject. In some embodiments, a method comprises, determining, in a sample obtained from a subject, a level of a 5'-GGGGCC-3' hexanucleotide repeat-containing RNA and/or a 5'-GGCCCC-3' hexanucleotide repeat-containing RNA, wherein a level of the hexanucleotide repeat-containing RNA that is elevated compared to a control level indicates that the subject has ALS or FTD or is likely to develop ALS or FTD. In some embodiments, a level of a hexanucleotide repeat-containing RNA is determined by performing an assay. Non-limiting assays are described herein.

Yet other aspects of the disclosure relate to identification of a subject having ALS or FTD or likely to develop ALS or FTD based on the presence or absence of RNA foci containing a 5'-GGGGCC-3' hexanucleotide repeat-expansion-containing RNA and/or a 5'-GGCCCC-3' hexanucleotide repeat-expansion-containing RNA in a sample from a subject, wherein the presence of the focus of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. As used herein, a focus of a 5'-GGGGCC-3' hexanucleotide repeat-expansion-containing RNA and/or a 5'-GGCCCC-3' hexanucleotide repeat-expansion-containing RNA refers to an area of accumulation of the 5'-GGGGCC-3' hexanucleotide repeat-expansion-containing RNA and/or the 5'-GGCCCC-3' hexanucleotide repeat-expansion-containing RNA, which may be detectable using a nucleic acid-based assay, such as FISH. In some embodiments, the focus may be, e.g., 0.1 to 2 micrometers in diameter, 0.1 to 1.5 micrometers in diameter, or 0.1 to 1 micrometers in diameter. In some embodiments, the focus may be at least 0.1 micrometers in diameter. It is to be appreciated that a sample may contain more than one focus and that each focus may be a different size. For example, one focus may be 0.2 micrometers in diameter, while second focus may be 1 micrometer in diameter. Non-limiting examples of foci and methods detecting such foci are provided in Example 3.

It is to be understood that a subject may be identified based on a level of one or more di-amino acid-repeat-containing proteins, a level of a hexanucleotide repeat-expansion containing RNA, the presence or absence of a hexanucleotide repeat-expansion containing RNA, or any combination thereof. In some embodiments, the method further comprises identifying the subject as having ALS or FTD or likely to develop ALS or FTD if the level of the di-amino acid-repeat-containing protein or hexanucleotide repeat-containing RNA is elevated compared to a control level. In some embodiments, the method further comprises identifying the subject as having ALS or FTD or likely to develop ALS or FTD if the focus or foci of the hexanucleotide repeat-expansion-containing RNA are present in the sample. In some embodiments, the method further comprises identifying the subject as not having ALS or FTD or unlikely to develop ALS or FTD if the level of the di-amino acid-repeat-containing protein or hexanucleotide repeat-containing RNA is decreased or the same compared to a control level. In some embodiments, the method further comprises identifying the subject as not having ALS or FTD or unlikely to develop ALS or FTD if the focus or foci of the hexanucleotide repeat-expansion-containing RNA are absent in the sample.

In some embodiments, a level of one or more di-amino acid-repeat-containing proteins or the identity of a subject may be recorded. In some embodiments, recordation comprises inputting a level or identity of subject into a computer, such as a medical record database.

Other aspects of the disclosure relate to treatment of a subject identified as having ALS or FTD or likely to develop ALS or FTD. As used herein, "treat" or "treatment" refers to (a) preventing or delaying the onset of ALS or FTD; (b) reducing the severity of ALS or FTD; (c) reducing or preventing development of symptoms characteristic of ALS or FTD; (d) preventing worsening of symptoms characteristic of ALS or FTD; and/or (e) reducing or preventing recurrence of ALS or FTD symptoms in subjects that were previously symptomatic for ALS or FTD.

In some embodiments, treatment comprises administering an effective amount of a known ALS therapeutic agent, such as Riluzole (Rilutek. Sanofi-Aventis), to a subject identified as having ALS. In some embodiments, treatment comprises administering an effective amount of a known FTD therapeutic agent, such as trazodone (Desyrel, Oleptro) or a selective serotonin reuptake inhibitor (SSRI), to a subject identified as having FTD. In some embodiments, treatment comprises administering an effective amount of a therapeutic agent, such as baclofen, diazepam, phenytoin, trihexyphenidyl and/or amitriptyline, which reduces one or more symptoms of ALS or FTD in a subject identified as having ALS or FTD. In some embodiments, treatment comprises one or more of physical therapy, occupational therapy, or speech therapy. In some embodiments, treatment comprises a method as described herein for decreasing or stabilizing di-amino acid-repeat-containing protein levels in the blood of the subject, such as bone marrow transplantation or plasmapheresis. In some embodiments, treatment comprises any combination of the above-mentioned treatments or any other treatments described herein.

An effective amount is a dosage of a therapeutic agent sufficient to provide a medically desirable result, such as treatment of ALS or FTD. The effective amount will vary with the age and physical condition of the subject being treated, the severity of ALS or FTD in the subject, the duration of the treatment, the nature of any concurrent therapy, the specific route of administration and the like factors within the knowledge and expertise of the health practitioner.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Other aspects of the disclosure relate to methods for monitoring responsiveness to a treatment in a subject having ALS or FTD or suspected of having ALS or FTD. In some embodiments, the method comprises: determining, in a blood sample obtained from the subject at a first time point, a first level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein; and determining, in a blood sample obtained from the subject at a second time point, a second level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a second level that is elevated or the same compared to a first level indicates that the subject is unresponsive or likely unresponsive to treatment and wherein a second level that is decreased compared to a first level indicates that the subject is responsive or likely responsive to treatment. In some embodiments, the first blood sample is obtained before treatment of the subject and the second blood sample is obtained during or after treatment of the subject. This method may also be performed by determining a level of a hexanucleotide repeat-containing RNA or the presence or absence of a focus or foci of a hexanucleotide repeat-expansion-containing RNA in addition to or in place of the level of di-amino acid protein.

As used herein, "elevated" means that the level of one or more di-amino acid-repeat-containing proteins or a hexanucleotide repeat-containing RNA is above a control level, such as a pre-determined threshold or a level of one or more di-amino acid-repeat-containing proteins or a hexanucleotide repeat-containing RNA in a control sample. Controls and control levels are described in detail herein. An elevated level includes a level that is, for example, 1%, 5%, 10%, 20%, 30%, 40%, 50%, 60%, 70%, 80%, 90%, 100%, 150%, 200%, 300%, 400%, 500%, or more above a control level. An elevated level also includes increasing a phenomenon from a zero state (e.g., no or undetectable di-amino acid-repeat-containing protein expression or hexanucleotide repeat-containing RNA expression) to a non-zero state (e.g., some or detectable di-amino acid-repeat-containing protein expression or hexanucleotide repeat-containing RNA).

As used herein, "decreased" means that the level of one or more di-amino acid-repeat-containing proteins or a hexanucleotide repeat-containing RNA is below a control level, such as a pre-determined threshold or a level of one or more di-amino acid-repeat-containing proteins or a hexanucleotide repeat-containing RNA in a control sample. Controls and control levels are described in detail herein. A decreased level includes a level that is, for example, 1%, 5%, 10%, 20%, 30%, 40%, 50%, 60%, 70%, 80%, 90%, 100%, 150%, 200%, 300%, 400%, 500%, or more below a control level. A decreased level also includes decreasing a phenomenon from a non-zero state (e.g., some or detectable di-amino acid-repeat-containing protein expression or hexanucleotide repeat-containing RNA) to a zero state (e.g., no or undetectable di-amino acid-repeat-containing protein expression or hexanucleotide repeat-containing RNA expression).

Hexanucleotide Repeat-Containing RNAs and Di-Amino Acid Repeat-Containing Proteins As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. The GenBank Gene ID for the human C9ORF72 gene is 203228. Both the sense and anti-sense hexanucleotide repeat-containing transcripts were found to undergo translation independent of an AUG start codon (repeat-associated non-ATG (RAN) translation) such that poly-(Gly-Ala), poly-(Gly-Pro), poly-(Gly-Arg), poly-(Pro-Ala), or poly-(Pro-Arg) di-amino acid repeat-containing proteins were produced, depending on the frame of the hexanucleotide repeat being read (5'-GGGGCC-3', 5'-GGGCCG-3', and 5'-GGCCGG-3' on the sense transcript. 5'-GGCCCC-3', 5'-GCCCCG-3', and 5'-CCCCGG-3' on the anti-sense transcript, see FIG. 1). In addition, the anti-sense hexanucleotide repeat-containing transcript was found to be translated through ATG-initiated translation to produce Met . . . poly-(Pro-Arg) and Met . . . poly-(Gly-Pro) proteins.

Accordingly, aspects of the invention relate to the sense and anti-sense RNAs containing an expanded hexanucleotide repeat and uses thereof. The sense RNA is a 5'-GGGGCC-3' hexanucleotide repeat-containing RNA and the anti-sense RNA is a 5'-GGCCCC-3' hexanucleotide repeat-containing RNA.

The 5'-GGGGCC-3' and 5'GGCCCC-3' hexanucleotide repeat-containing RNAs comprise a repeat nucleic acid sequence of the formula $(GGGGCC)_x$ or $(GGCCCC)_x$, respectively, where X may be at least 10, at least 20, at least 25, or at least 30, or in a range selected from 10-100,000, 10-50,000, 10-5,000, 20-1,000, 20-100,000, 20-50,000, 20-5,000, 20-1,000, 25-100,000, 25-50.000, 25-5,000, or 25-1,000. The hexanucleotide repeat-containing RNA may further comprise additional N- and/or C-terminal nucleic acids. In some embodiments, an N-terminal nucleic sequence comprises a nucleic acid sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal nucleic acid sequence comprises a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript.

additional C-terminal sequence. Methods described herein may comprise use of a poly-(Gly-Pro) protein translated from the sense strand, the anti-sense strand, or both. Antibodies described herein may be specific for a poly-(Gly-Pro) protein translated from the sense strand, the anti-sense strand, or both.

Each di-amino acid repeat-containing protein comprises a repeat amino acid sequence, which contains a di-amino acid repeat unit of the formula $(YZ)_x$, where X can be from 2-10,000, 5-10,000, 2-5,000, 5-5,000, 2-1000, 5-1000, 5-500, 5-300, 5-200, 10-500, 10-300, or 10-200. The di-amino acid repeat unit for each di-amino acid repeat-containing protein is provided in Table 1.

TABLE 1

Di-Amino Acid-Repeat-Containing Proteins

| Di-Amino Acid-Repeat-Containing Protein | Di-Amino Acid Repeat Unit | Predicted C-terminus |
|---|---|---|
| poly-(Gly-Ala) | $(GA)_x$ or $(AG)_x$ | WSGRARGRARGGAAVAVPAPAAAEAQA VASG (SEQ ID NO: 1) or AWSGRARGRARGGAAVAVPAPAAAEAQ AVASG (SEQ ID NO: 27) |
| poly-(Gly-Pro) | $(GP)_x$ or $(PG)_x$ | GRGRGGPGGGPGAGLRLRCLRPRRRRRR RWRVGE (SEQ ID NO: 2, sense), PGRGRGGPGGGPGAGLRLRCLRPRRRRRR RWRVGE (SEQ ID NO: 28, sense) or none (anti-sense) |
| poly-(Gly-Arg) | $(GR)_x$ or $(RG)_x$ | GVVGAGPGAGPGRGCGCGACARGGGGA GGGEWVSEEAASWRVAVWGSAAGKRRG (SEQ ID NO: 3) or RGVVGAGPGAGPGRGCGCGACARGGGG AGGGEWVSEEAASWRVAVWGSAAGKRR G (SEQ ID NO: 29) |
| poly-(Pro-Ala) | $(AP)_x$ or $(PA)_x$ | PSARLLSSRACYRLRLFPSLESSG (SEQ ID NO: 4) OR APSARLLSSRACYRLRLFPSLESSG (SEQ ID NO: 30) |
| poly-(Pro-Arg) | $(PR)_x$ or $(RP)_x$ | PLARDS (SEQ ID NO: 5) or RPLARDS (SEQ ID NO: 31) |
| Met . . . poly-(Pro-Arg) | $(PR)_x$ | PLARDS (SEQ ID NO: 5) |
| Met . . . poly-(Gly-Pro) | $(GP)_x$ | None | x = number of repeats of the sequence in the parentheses

Other aspects of the invention relate to one or more di-amino acid repeat-containing proteins and uses thereof. The one or more di-amino acid repeat-containing proteins are selected from poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) proteins.

The sense 5'-GGGGCC-3' hexanucleotide repeat-containing RNA and the anti-sense 5'-GGCCCC-3' hexanucleotide repeat-containing RNA both encode poly-(Gly-Pro) proteins. Accordingly a poly-(Gly-Pro) protein may include a protein translated from the sense strand, the anti-sense strand, or both. It is predicted that the C-terminus of the sense and anti-sense translated poly-(Gly-Pro) proteins may differ (see Table 1). Accordingly, a sense poly-(Gly-Pro) protein may comprise the poly-(Gly-Pro) a C-terminal sequence as described in Table 1, while an anti-sense poly-(Gly-Pro) protein may comprise the repeat region with no additional C-terminal sequence.

Each di-amino acid repeat-containing protein may further comprise an N- and/or C-terminal amino acid sequence that comprises a non-di-amino acid repeat sequence. In some embodiments, a N-terminal amino acid sequence comprises an amino acid sequence translated from a nucleotide sequence of a C9ORF72 RNA transcript, such as a nucleotide sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal amino acid sequence comprises an amino acid sequence translated from a nucleotide sequence of a C9ORF72 RNA transcript, such as a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript. Such a nucleotide sequence downstream of the 5'-GGGGCC-3' or 5'-GGCCCC-3' hexanucleotide repeat may be translated until a stop codon or multiple stop codons are reached.

A portion of a C9ORF72 gene sequence (sense and anti-sense) is shown below. The 5'-GGGGCC-3' or 5'-GGCCCC-3' hexanucleotide repeat is underlined and in bold. The nucleotide sequence upstream of the 5'-GGGGCC-3' or 5'-GGCCCC-3' hexanucleotide repeat precedes the underlined and bolded sequence. The nucleotide sequence downstream of the 5'-GGGGCC-3' or 5'-GGCCCC-3' hexanucleotide repeat follows the underlined and bolded sequence. It is to be understood that this 5'-GGGGCC-3' or 5'-GGCCCC-3' hexanucleotide repeat can be repeated more than the number of times present in these sequences.

C9ORF72 (Partial Sequence, Sense)

(SEQ ID NO: 6)
CCCCATTTCGCTAGCCTCGTGAGAAAACGTCATCGCACATAGAAAACAG

ACAGACGTAACCTACGGTGTCCCGCTAGGAAAGAGAGGTGCGTCAAACA

GCGACAAGTTCCCCCCACGTAAAAGATGACGCTTGGTGTGTCAGCCGTC

CCTGCTGCCCGGTTGCTTCTCTTTTGGGGCGGGGTCTAGCAAGAGCAG

GTGTGGGTTAGGAGGTGTGTGTTTTTGTTTTTCCCACCCTCTCTCCCC

ACTACTTGCTCTCACAGTACTCGCTGAGGGTGAACAAGAAAAGACCTGA

TAAAGATTAACCAGAAGAAAACAAGGAGGGAAACAACCGCAGCCTGTAG

CAAGCTCTGGAACTCAGGAGTCGCGCGCTAGGGGCCGGGGCCGGGGCCG

GGGCGTGGTCGGGGCGGGCCCGGGGGGGCCCGGGGCGGGGCTGCGGTT

GCGGTGCCTGCGCCCGCGGCGGCGGAGGCGCAGGCGGTGGCGAGTGGGT

GAGTGAGGAGGCGGCATCCTGGCGGGTGGCTGTTTGGGGTTCGGCTGCC

GGGAAGAGGCGCGGGTAGAAGCGGGGGCTCTCCTCAGAGCTCGACGCAT

TTTTACTTTCCCTCTCATTTCTCTGACCGAAGCTGGGTGTCGGGCTTTC

GCCTCTAGCGACTGGTGGAATTGCCTGCATCCGGGCCCCGGGCTTCCCG

GCGGCGGCGGCGGCGGCGGCGCAGGGACAAGGGATGGGGATCTGGC

CTCTTCCTTGCTTTCCCGCCCTCAGTACCCGAGCTGTCTCCTTC

C9ORF72 (Partial Sequence, Anti-Sense)

(SEQ ID NO: 7)
GAAGGAGACAGCTCGGGTACTGAGGGGGGGAAAGCAAGGAAGAGGCCAG

ATCCCCATCCCTTGTCCCTGCGCCGCCGCCGCCGCCGCCGCCGCCGGGA

AGCCCGGGGCCCGGATGCAGGCAATTCCACCAGTCGCTAGAGGCGAAAG

CCCGACACCCAGCTTCGGTCAGAGAAATGAGAGGGAAAGTAAAAATGCG

TCGAGCTCTGAGGAGAGCCCCCGCTTCTACCCGCGCCTCTTCCCGGCAG

CCGAACCCCAAACAGCCACCCGCCAGGATGCCGCCTCCTCACTCACCCA

CTCGCCACCGCCTGCGCCTCCGCCGCCGCGGGCGCAGGCACCGCAACCG

CAGCCCCGCCCCGGGCCCGCCCCCGGGCCCGCCCCGACCACGCC<u>CCGGC</u>

<u>CCCGGCCCCGGCCCC</u>TAGCGCGCGACTCCTGAGTTCCAGAGCTTGCTAC

AGGCTGCGGTTGTTTCCCTCCTTGTTTTCTTCTGGTTAATCTTTATCAG

GTCTTTTCTTGTTCACCCTCAGCGAGTACTGTGAGAGCAAGTAGTGGGG

AGAGAGGGTGGGAAAAACAAAAACACACACCTCCTAAACCCACACCTGC

TCTTGCTAGACCCCGCCCCCAAAAGAGAAGCAACCGGGCAGCAGGGACG

GCTGACACACCAAGCGTCATCTTTTACGTGGGCGGAACTTGTCGCTGTT

TGACGCACCTCTCTTTCCTAGCGGGACACCGTAGGTTACGTCTGTCTGT

TTTCTATGTGCGATGACGTTTTCTCACGAGGCTAGCGAAATGGGG

In some embodiments, a Met . . . poly-(Pro-Arg) or Met . . . poly-(Gly-Pro) protein comprises an N-terminal amino acid sequence comprising an N-terminal methionine. In some embodiments, a Met . . . poly-(Pro-Arg) protein comprises an N-terminal amino acid sequence comprising MQAIPPVARGESPTPSFGQRNERESKNASS-SEESPRFYPRLFPAAEPQTATRQDAASSL THSPP-PAPPPPRAQAPQPQPRPGPAPGPAPTT (SEQ ID NO: 41) or a fragment thereof, wherein the sequence is N-terminal to a poly-(Pro-Arg) repeat amino acid sequence. In some embodiments, a Met . . . poly-(Gly-Pro) protein comprises an N-terminal amino acid sequence comprising (SEQ ID NO: 42)
MRGKVKMRRALRRAPASTRASSRQPNPKQPPARMPPPHSPTRHRLRLRR

RGRRHRNRSPAPGPPPGPPRPRP, (SEQ ID NO: 43)
MRRALRRAPASTRASSRQPNPKQPPARMPPPHSPTRHRLRLRRRGRRHR

NRSPAPGPPPGPPRPRP, (SEQ ID NO: 44)
MPPPHSPTRHRLRLRRRGRRHRNRSPAPGPPPGPPRPRP, or a fragment thereof, wherein the sequence is N-terminal to a poly-(Gly-Pro) repeat amino acid sequence.

In some embodiments, a C-terminal amino acid sequence comprises a C-terminus amino acid sequence shown in Table 1 or a fragment of a C-terminus amino acid sequence shown in Table 1. It is to be understood that C-terminal amino acid sequences other than those in Table 1 are also contemplated.

Exemplary di-amino acid repeat-containing proteins may comprise a sequence provided in Table 2.

TABLE 2

```
(GA)ₓWSGRARGRARGGAAVAVPAPAAAEAQAVASG (SEQ ID NO: 8)

(AG)ₓAWSGRARGRARGGAAVAVPAPAAAEAQAVASG (SEQ ID NO: 9)

(GP)ₓGRGRGGPGGGPGAGLRLRCLRPRRRRRRRWRVGE (SEQ ID NO: 10)

(PG)ₓPGRGRGGPGGGPGAGLRLRCLRPRRRRRRRWRVGE (SEQ ID NO: 11)

(GP)ₓ

(PG)ₓ

(GR)ₓGVVGAGPGAGPGRGCGCGACARGGGGAGGGEWVSEEAASWRVAVWG
SAAGKRRG (SEQ ID NO: 12)

(RG)ₓRGVVGAGPGAGPGRGCGCGACARGGGGAGGGEWVSEEAASWRVAVW
GSAAGKRRG (SEQ ID NO: 13)

(AP)ₓAPSARLLSSRACYRLRLFPSLESSG (SEQ ID NO: 14)

(PA)ₓPSARLLSSRACYRLRLFPSLFSSG (SEQ ID NO: 15)

(PR)ₓPLARDS (SEQ ID NO: 16)

(RP)ₓRPLARDS (SEQ ID NO: 17)

MQAIPPVARGESPTPSFGQRNERESKNASSSEESPRFYPRLFPAAEPQTATRQDA
ASSLTHSPPPAPPPPRAQAPQPQPRPGPAPGPAPTT(PR)xPLARDS (SEQ ID NO:
32)

MRGKVKMRRALRRAPASTRASSRQPNPKQPPARMPPPHSPTRHRLRLRRRGR
RHRNRSPAPGPPPGPPRPRP(GP)x (SEQ ID NO: 33)

MRRALRRAPASTRASSROPNPKQPPARMPPPHSPTRHRLRLRRRGRRHRNRSP
APGPPPGPPRPRP(GP)x (SEQ ID NO: 34)

MPPPHSPTRHRLRLRRRGRRHRNRSPAPGPPPGPPRPRP(GP)x (SEQ ID NO: 35)
``` x = a number between 2-10,000, 5-10,000, 2-5,000, 5-5,000, 2-1000, 5-1000, 5-500, 5-300, 5-200, 10-500, 10-300, or 10-200.

In some embodiments, the one or more di-amino acid repeat-containing proteins are selected from the poly-(Pro-Ala), poly-(Gly-Pro), poly-(Pro-Arg), Met . . . poly-(Pro-Arg) or Met . . . poly-(Gly-Pro) protein. In some embodiments, the one or more di-amino acid repeat-containing proteins are selected from the poly-(Pro-Ala), poly-(Pro-Arg) protein, Met . . . poly-(Pro-Arg) or Met . . . poly-(Gly-Pro) protein.

In some embodiments, the one or more di-amino acid repeat-containing proteins is two or more, three or more, four or more, or five or more, or six or more, seven or more, or eight di-amino acid repeat-containing proteins.

Subjects

Aspects of the disclosure relate to identification and treatment of a subject, such as a human, with ALS or FTD or likely to develop ALS or FTD. In some embodiments, a subject may have ALS. In some embodiments, a subject may have one or more symptoms of ALS, such as difficulty breathing, difficulty swallowing, muscle cramps, muscle contractions, muscle weakness, paralysis, speech problems, or weight loss. In some embodiments, a subject may not have any symptoms of ALS. In some embodiments, a subject may have a family history of ALS.

In some embodiments, a subject may have frontotemporal dementia (FTD). In some embodiments, a subject may have one or more symptoms of FTD, such as lethargy, aspontaneity, disinhibition, loss of empathy and other interpersonal skills, apathy, progressive nonfluent aphasia, semantic dementia, binge eating, compulsive behavior, tremor, rigidity, muscle spasms, poor coordination, difficulty swallowing, and muscle weakness. In some embodiments, a subject may not have any symptoms of FTD. In some embodiments, a subject may have a family history of FTD.

In some embodiments, a subject may have GGGGCC hexanucleotide repeats within one or both alleles of a C9ORF72 gene (NCBI Entrez Gene ID: 203228). In some embodiments. GGGGCC hexanucleotide repeats are within a promoter and/or intron of the C9ORF72 gene. In some embodiments, the number of GGGGCC hexanucleotide repeats is greater than 25, 50, 100, 150, 200, 250, 300, 500, 5,000, 10,000 or more. The number of repeats may be detected using any assay known in the art, e.g., using as a nucleic acid-based assay such as a southern blot (see, e.g., Dejesus-Hernandez et al. Expanded GGGGCC hexanucleotide repeat in noncoding region of C9ORF72 causes chromosome 9p-linked FTD and ALS. Neuron 72, 245 (2011); Renton et al. A hexanucleotide repeat expansion in C9ORF72 is the cause of chromosome 9p21-linked ALS-FTD. Neuron 72, 257 (2011); and Gijselink et al. A C9orf72 promoter repeat expansion in a Flanders-Belgian cohort with disorders of the frontotemporal lobar degeneration-amyotrophic lateral sclerosis spectrum: A gene identification study. Lancet Neurol. 11, 54 (2011)).

Controls and Control Levels

Aspects of the disclosure relate to comparison of a level of one or more di-amino acid repeat-containing proteins and/or hexanucleotide repeat-containing RNAs to a control level. In some embodiments, the control level is a level of one or more di-amino acid repeat-containing proteins and/or hexanucleotide repeat-containing RNAs in sample, such as a fluid sample or tissue sample, obtained from a healthy subject or population of healthy subjects. In some embodiments, the sample is a blood sample. As used herein, a healthy subject is a subject that is apparently free of disease and has no history of disease, such as ALS or FTD. In some embodiments, a healthy subject is a subject that has 25 or fewer GGGGCC hexanucleotide repeats within a C9ORF72 gene.

In some embodiments, a control level is a level of one or more di-amino acid repeat-containing proteins and/or hexanucleotide repeat-containing RNAs that is undetectable or below a background/noise level obtained using standard methods of detection (e.g., Western blot, qPCR, northern blot, or immunohistochemistry). Such a level could be obtained, for example, by measuring a level of one or more di-amino acid repeat-containing proteins and/or hexanucleotide repeat-containing RNAs in a sample that is known to be free of the di-amino acid repeat-containing proteins and/or hexanucleotide repeat-containing RNAs.

The disclosure also involves comparing the level of one or more di-amino acid repeat-containing proteins and/or hexanucleotide repeat-containing RNAs with a predetermined level or value, such that a control level need not be measured every time. The predetermined level or value can take a variety of forms. It can be single cut-off value, such as a median or mean. It can be established based upon comparative groups, such as where one defined group is known not to have ALS or FTD and another defined group is known to have ALS or FTD. It can be a range, for example, where the tested population is divided equally (or unequally) into groups, such as a subject that has 25 or fewer GGGGCC hexanucleotide repeats, a subject that has 25-50 GGGGCC hexanucleotide repeats, and a subject that has 50 or more GGGGCC hexanucleotide repeats.

Samples

Aspects of the disclosure relate to determining a level of one or more di-amino acid repeat-containing proteins in a blood sample (e.g., whole blood, plasma, or serum) obtained from a subject. The blood sample may be obtained by any method known in the art, e.g., using a needle or fingerprick device. The blood may be processed before use in the methods described herein. Such processing includes, for example, addition of an anti-coagulant, removal of blood cells, and/or freezing of the blood. However, it should be appreciated that other samples may be used, such as a tissue sample (e.g., brain tissue) or other fluid samples such as saliva, or urine.

Other aspects of the disclosure relate to determining a level of hexanucleotide repeat-containing RNA in sample obtained from a subject. The sample may be a fluid or tissue sample. In some embodiments, the tissue sample is brain tissue. In some embodiments, the fluid sample is blood (e.g., whole blood, plasma, or serum), saliva, or urine. In some embodiments, the fluid sample is a blood sample (e.g., whole blood, plasma, or serum).

Assays

Aspects of the disclosure relate to performing an assay to determine a level or presence/absence of one or more di-amino acid repeat-containing proteins and/or hexanucleotide repeat-containing RNAs. Assays known in the art for detecting proteins and RNAs (see, e.g., Molecular Cloning: A Laboratory Manual, J. Sambrook, et al., eds., Third Edition. Cold Spring Harbor Laboratory Press, Cold Spring Harbor, New York, 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York) can be used alone or in combination with, techniques and compositions described herein for measuring a di-amino acid repeat-containing protein level.

Assays for detecting protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are well-known in the art. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329, all of which are incorporated herein by reference in their entirety.

Any suitable binding partner for a di-amino acid repeat-containing protein is contemplated for detection of a di-amino acid repeat-containing protein level. In some embodiments, the binding partner is any molecule that binds specifically to a di-amino acid repeat-containing protein as described herein. As described herein, "binds specifically to a di-amino acid repeat-containing protein" means that the molecule is more likely to bind to a portion of or the entirety of a di-amino acid repeat-containing protein than to a portion of or the entirety of a non-di-amino acid repeat-containing protein.

In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Binding partners also include other peptide molecules and aptamers that bind specifically to a di-amino acid repeat-containing protein. Methods for producing peptide molecules and aptamers are well known in the art (see, e.g., published US Patent Application No. 2009/0075834, U.S. Pat. Nos. 7,435,542, 7,807,351, and 7,239,742). The binding partner may comprise a label including, but not limited to, a fluorescent, enzymatic, affinity or isotopic label.

In some embodiments, an assay comprises an immuno-based assay. In some embodiments, the immuno-based assay comprises an isolated antibody specific for one or more di-amino acid repeat-containing proteins. In some embodiments, the isolated antibody specific for one or more di-amino acid repeat-containing proteins is an isolated antibody as described herein in further detail. In some embodiments, the isolated antibody specific for one or more di-amino acid repeat-containing proteins is an isolated antibody specific for an antigen or sequence, or a fragment of an antigen or sequence described in Table 1, Table 2 or Table 3.

Accordingly, a di-amino acid repeat-containing binding partner (e.g., a di-amino acid repeat-containing-specific antibody) can be labeled with a detectable moiety.

Assays for detecting RNA include, but are not limited to, hybridization-based assays such as Northern blot analysis, RT-PCR, sequencing technology, RNA in situ hybridization (using e.g., DNA or RNA probes to hybridize to RNA molecules present in the sample as in FISH), in situ RT-PCR (e.g., as described in Nuovo G J, et al. Am J Surg Pathol.

1993, 17:683-90; Komminoth P, et al. Pathol Res Pract. 1994, 190:1017-25), and oligonucleotide microarray (e.g., by hybridization of polynucleotide sequences derived from a sample to oligonucleotides attached to a solid surface (e.g., a glass wafer) with addressable locations, such as an Affymetrix microarray (Affymetrix®, Santa Clara, CA)). Methods for designing nucleic acid binding partners, such as probes, are well known in the art. In some embodiments, the nucleic acid binding partners bind to a part of or an entire nucleic acid sequence of a hexanucleotide repeat-containing RNA provided herein.

Treatment

As described herein, it was found that di-amino acid repeat-containing proteins were present in samples of blood from patients with ALS. Without wishing to be bound by theory or mechanism, it is believed that di-amino acid repeat-containing proteins in the blood of subjects with ALS accumulate within the brain parenchyma over time, leading to neuroinflammatory changes, CNS dysfunction, and neuronal death. Accordingly, aspects of the disclosure relate to treatment of a subject having ALS or PTD by decreasing or stabilizing di-amino acid repeat-containing protein levels in the blood of the subject.

In some embodiments, decreasing or preventing an increase of the level of one or more di-amino acid repeat-containing proteins comprises removing the one or more (e.g., 1, 2, 3, 4, 5, 6, 7 or 8) di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, it may be advantageous to decrease or prevent an increase of the level of all di-amino acid repeat-containing proteins expressed by a subject. Accordingly, in some embodiments, a method comprises decreasing or preventing an increase of the level of all forms of di-amino acid repeat-containing proteins expressed by a subject.

In some embodiments, the one or more di-amino acid repeat-containing from the blood of the subject is removed using a hematopoietic stem cell (HSC) transplantation. HSC transplantation is the transplantation of hematopoietic stem cells, usually derived from bone marrow, peripheral blood, or umbilical cord blood, into a subject. The source of hematopoietic stem cells may be allogeneic (e.g., from a donor such as a healthy subject). Methods of HSC transplantation are well known in the art (see, e.g., Bishop M R, Pavletic S Z. Hematopoietic stem cell transplantation. In: Abeloff M D, Armitage J O, Niederhuber J E, Kastan M B, McKena W G, eds. Clinical Oncology. 4th ed. Philadelphia, Pa: Elsevier Churchill Livingstone; 2008: chap 32; and Vose J M. Pavletic S Z. Hematopoietic stem cell transplantation. In: Goldman L, Schafer A I. Cecil Medicine. 24th ed. Philadelphia, Pa: Saunders Elsevier; 2011: chap 181).

In order to prepare a subject for HSC transplantation, the HSCs present in the subject may be removed or depleted so that the transplanted cells can become the dominant HSC population in the subject. HSCs in the subject may be depleted, for example, by treating the subject with a chemotherapy, radiation, or both in order to cause the HSC cells of the subject to undergo apoptosis or cell cycle arrest.

In allogeneic HSC transplantation, the HSCs are obtained from a donor. The donor is preferably a healthy subject, such as a subject that is apparently free of disease and has no history of disease, such as ALS or FTD. It is preferable that the donor is HLA-compatible with the subject receiving the transplant in order to reduce the risk of graft versus host disease. HLA-compatibility can be determined, e.g., using HLA typing. HLA typing generally involves examination of at least 8 HLA markers: two A, two B, two C, and two DRB1 markers, and optionally also two DQ markers. HLA typing can be accomplished, e.g., through a blood test. HLA allele identities can be determined using serology or a nucleic acid-based assay. Generally, a match of at least 4-6 markers between host and donor is preferred. In some embodiments, the donor is a subject that has 25 or fewer GGGGCC hexanucleotide repeats within a C9ORF72 gene.

HSCs can be obtained from a donor using any method known in the art. Exemplary methods include bone marrow harvest and leukapheresis (see, e.g., Transfusion. 2003 February; 43(2):259-64. Leukapheresis after high-dose chemotherapy and autologous peripheral blood progenitor cell transplantation: a novel approach to harvest a second autograft. Schwella N, Braun A, Ahrens N, Rick O, Salama A). In a bone marrow harvest, the bone marrow is typically removed from the back of one or both hip bones of the donor. Leukapheresis involves separation of HSCs from blood obtained from the donor using, e.g., continuous flow centrifugation or filtering. The growth factor G-CSF may be administered to the donor to stimulate the growth of new HSCs so that more HSCs are present in the blood. Once obtained, the allogeneic HSCs are then administered to the subject receiving the transplant. Any suitable method of administration known in the art is contemplated, e.g., by central venous catheter.

In some embodiments, during or after HSC transplantation, the subject receiving the HSC transplant may receive additional treatments and/or therapies, such as antibiotics, antifungals, antivirals, blood transfusions and/or immunosuppressive therapies. Such treatments and/or therapies may help to prevent infection and/or graft versus host disease during a HSC transplant recovery period.

In some embodiments, the HSC transplantation is bone marrow transplantation. In some embodiments, the bone marrow transplantation is an allogeneic bone marrow transplantation.

Plasmapheresis is a medical procedure that occurs outside the body (an "extracorporeal therapy") and refers to the removal, treatment, and return of (components of) blood plasma from blood circulation. Plasmapheresis is well-known in the art and has been used to treat several diseases including Goodpasture's syndrome, myasthenia gravis, Guillain-Barre syndrome, lupus, and thrombotic thrombocytopeniarpura (see, e.g., Madore, Plasmapheresis Technical aspects and indications, Crit Care Clin 18:375-392, 2002). During plasmapheresis, blood is initially taken out of the body, e.g., through a needle or previously implanted catheter. Plasma is then separated from the blood cells, e.g., by using a cell separator. After plasma separation, the blood cells are combined with a replacement fluid and readministered to the subject. The replacement fluid may be either the separated plasma treated to remove disease-associated components or a replacement plasma (also called plasma exchange).

Exemplary procedures used to separate the plasma from the blood cells include:

1) Discontinuous flow centrifugation: One venous catheter line is used. Typically, one or more batches of blood are removed at a time and centrifuged to separate plasma from blood cells. The blood cells are then combined with the replacement fluid and returned to the subject.
2) Continuous flow centrifugation: Two venous lines are used. Plasma is continuously spun out of the blood and the separated blood cells are fed through a line that combines with a replacement fluid before return to the subject.

3) Plasma filtration: Two venous lines are used. The plasma is filtered using standard hemodialysis equipment, e.g., a parallel-plate or hollow-fiber filter. The separated blood cells are fed through a line that combines with a replacement fluid before return to the subject. The filters usually have pores of 0.2-0.6 μm diameter, sufficient to allow passage of plasma, while retaining cells. Several membrane plasma separators are commercially available (e.g., Plasmaflo from Asahi Medical Co., Ltd., Tokyo, Japan; Plasmax from Toray Industries, Tokyo, Japan; CPS-10 from Baxter. Deerfield. IL, USA; Plasmaflux from Fresenius Medical Care AG, Bad Homburg, Germany; Prisma TPE 2000 from Hospal, Lyon, France).

If the separated plasma is to be used as the replacement fluid, the separated plasma is first treated to decrease the levels of di-amino acid repeat-containing proteins present in the separated plasma. In some embodiments, decreasing the levels of di-amino acid repeat-containing proteins present in the separated plasma comprises contacting the separated plasma with one or more isolated antibodies specific for a di-amino acid repeat-containing protein as described herein, whereby the di-amino acid repeat-containing proteins present in the separated plasma bind to the one or more isolated antibodies. In some embodiments, a binding partner for the one or more isolated antibodies is contacted with the separated plasma. A binding partner for the one or more isolated antibodies may be, for example, a capture moiety such as biotin or streptavidin, protein A, or a secondary antibody specific for the one or more isolated antibodies. Such binding partners allow for the one or more isolated antibodies to be removed from the separated plasma.

In some embodiments, the one or more isolated antibodies are attached to a filter, column, and/or solid support. In such embodiments, the separated plasma is contacted with, the filter, column, and/or solid support, whereby the di-amino acid repeat-containing proteins bind to the isolated antibodies attached to the filter, column and/or solid support. Without wishing to be bound by theory, it is believed that the di-amino acid repeat-containing proteins may form aggregates in the blood. Accordingly, the di-amino acid repeat-containing proteins may be removed from the separated plasma using a filter, such that the aggregates are isolated from the separated plasma.

In some embodiments, a subject expressing one or more di-amino acid repeat-containing proteins may develop autoantibodies. In some embodiments, autoantibodies to one or more di-amino acid repeat-containing proteins may be removed from the separated plasma. Autoantibodies may be removed using any method known in the art, e.g., using a binding partner (e.g., bound to a solid support or attached to a tag) that recognizes the autoantibodies. In some embodiments, the binding partner may be one or more di-amino acid repeat-containing proteins as described herein.

If plasma exchange is to be used, the subject receives replacement plasma. Replacement plasma may be, e.g., donor plasma or a solution of albumin (e.g., 5-70% albumin in saline). An exemplary replacement plasma is 5% albumin combined with 0.9% saline in a 50%: 50% (vol:vol) solution. Medication to keep the blood from clotting (e.g., an anticoagulant such as citrate, acid-citrate dextrose or heparin) may be given to the subject or contacted with the blood of the subject during the procedure.

In some embodiments, decreasing or preventing an increase of the level of one or more di-amino acid repeat-containing proteins comprises decreasing a level of a hexanucleotide repeat-containing RNA. Decreasing a level of a hexanucleotide repeat-containing RNA may comprise administration of an effective amount of an inhibitory nucleic acid molecule such as an shRNA, an siRNA, miRNA, or an antisense nucleic acid molecule that targets the hexanucleotide repeat-containing RNA.

Methods for producing shRNAs, siRNAs, miRNAs, and antisense nucleic acid molecules are well known in the art (see e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition). In some embodiments, a nucleic acid inhibitor comprises or corresponds to at least a portion of sequence of a target hexanucleotide repeat-containing RNA sequence or comprises at least a portion of a sequence complementary to a target hexanucleotide repeat-containing RNA sequence.

In some embodiments, treatment may comprise decreasing or stabilizing a level of an autoantibody to one or more di-amino acid repeat-containing proteins in a subject. A level of autoantibody may be decreased or stabilized using any method known in the art. In some embodiments, decreasing or stabilizing a level of an autoantibody comprises administration of an effective amount of atacicept, belimumab, blisibimod, BR3-Fc, rituximab, ocrelizumab, atumumab, epratuzumab, corticosteroid (e.g., prednisone), mycophenolic acid, methotrexate, cyclophosphamide, azathioprine, and/or cyclosporin. In some embodiments, decreasing or stabilizing a level of an autoantibody comprises plasmapheresis.

Antibodies

Aspects of the disclosure relate to isolated antibodies specific for a di-amino acid repeat-containing protein (e.g., a RAN protein) selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. The isolated antibody may recognize a region or regions of the di-amino acid repeat-containing protein (such as a repeat sequence or the C-terminus) or may recognize the entire di-amino acid repeat-containing protein.

An antibody that "specifically binds" to a target or an epitope is a term understood in, the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically binds to a poly-(Gly-Ala) protein or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically bind to a second target antigen. As such, "specific binding" does not necessarily require (although it can include) exclusive binding. Generally, but not necessarily, reference to binding means specific binding. In some embodiments, antibodies described herein have a suitable binding affinity to a di-amino acid repeat-containing protein (e.g., a RAN protein). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or 105 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2 at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

[Bound]=[N][Free]/(Kd+[Free])

It is not always necessary to make an exact determination of $K_A$, though, since sometimes it is sufficient to obtain a quantitative measurement of affinity. e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the isolated antibody is specific for a di-amino acid repeat-containing protein selected from a poly-(Pro-Ala) poly-(Pro-Arg), Met . . . poly-(Pro-Arg) or Met . . . poly-(Gly-Pro) protein.

In some embodiments, the isolated antibody is specific for an antigen comprising a di-amino acid repeat and/or C-terminus sequence or fragment thereof as defined in Table 1. In some embodiments, the isolated antibody is specific for an antigen comprising a sequence or fragment of a sequence defined in Table 2.

In some embodiments, the isolated antibody is specific for an antigen in Table 3 or in FIG. 28. In some embodiments, an antigen in Table 3 does not contain an N- and/or C-terminal modification.

TABLE 3

Di-Amino Acid Repeat-Containing Protein Antigens

| di-amino acid repeat-containing protein | Label | Antigen | Antigen location in di-amino acid repeat-containing protein |
|---|---|---|---|
| Poly-(Gly-Arg) | GGGGCC F1 repeat | Ac-RGRGRGRGRGRGRGRGRC-amide (SEQ ID NO: 18) | Repeat sequence |
| Poly-(Pro-Arg) | GGGGCC-AS F2 repeat | Ac-RPRPRPRPRPRPRPRPRC-amide (SEQ ID NO: 19) | Repeat sequence |
| Poly-(Pro-Ala) | GGGGCC-AS F1 repeat | H2N-APAPAPAPAPAPAPAPACKKKK-amide (SEQ ID NO: 20) | Repeat sequence |
| Poly-(Gly-Pro) | GGGGCC F3 repeat | H2N-GPGPGPGPGPGPGPGPGCKK-amide (SEQ ID NO: 21) | Repeat sequence |
| Poly-(Gly-Pro) | GGGGCC F3 CT | Ac-CRRRRWRVGE-OH (SEQ ID NO: 22) | C-terminus |
| Poly-(Pro-Ala) | GGGGCC-AS F1 CT | Ac-CYRLRLFPSLFSSG-OH (SEQ ID NO: 23) | C-terminus |
| Poly-(Gly-Arg) | GGGGCC F1 CT | Ac-CRVAVWGSAAGKRRG-OH (SEQ ID NO: 24) | C-terminus |
| Poly-(Pro-Arg) | GGGGCC-AS F2 CT | Ac-CRPRPLARDS-OH (SEQ ID NO: 25) | C-terminus |
| Poly-(Gly-Ala) | GGGGCC F2 CT | Ac-CSGRARGRARGGA-amide (SEQ ID NO: 26) | C-terminus |

F1 = reading frame 1, F2 = reading frame 2, F3 = reading frame 3, AS F1 = anti-sense reading frame 1, AS F2 = anti-sense reading frame 2, AS F3 = anti-sense reading frame 3.

An isolated antibody may be a monoclonal or polyclonal antibody, or an antigen-binding fragment thereof. An antigen-binding fragment thereof includes, for example, an Fab, F(ab)2, F(ab')2, Fv, single chain antibody, Fab fragment, sFab fragment, Fd fragment, scFv, or dAb fragment. Methods for producing polyclonal and monoclonal antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Also encompassed are antibodies made by recombinant means such as chimeric antibodies (variable region and constant region derived from different species) and CDR-grafted antibodies (complementary determining region derived from a different species) as described in U.S. Pat. Nos. 4,816,567 and 5,225,539, which are incorporated herein by reference in their entirety. Also encompassed are humanized antibodies, typically produced by recombinant methods, wherein the human sequences comprise part or all of the antibody. Also included are fully human antibodies, such as those produced in genetically-altered mice (see PCT Application No. 93/12227, which is incorporated herein by reference in its entirety).

In some embodiments, an isolated antibody specific for a di-amino acid repeat-containing protein is a rabbit polyclonal antibody as listed in Table 4.

TABLE 4

Di-Amino Acid Repeat-Containing Protein Rabbit Polyclonal Antibodies

| Antigen | Animal | Titer |
|---|---|---|
| GGGGCC F1 repeat | H3147 | 1,575,500 |
| GGGGCC F1 repeat | H3148 | 1,956,500 |
| GGGGCC-AS F2 repeat | H3149 | 2,399,600 |
| GGGGCC-AS F2 repeat | H3150 | 3,225,000 |
| GGGGCC-AS F1 repeat | H3151 | 660,200 |
| GGGGCC-AS F1 repeat | H3152 | 2,082,600 |
| GGGGCC F3 repeat | H3154 | 752,300 |
| GGGGCC F3 repeat | H3155 | 590,500 |
| GGGGCC F3 CT | H3156 | 231,300 |
| GGGGCC F3 CT | H3157 | 616,700 |
| GGGGCC-AS F1 CT | H3158 | 6,300 |
| GGGGCC-AS F1 CT | H3159 | 32,800 |
| GGGGCC F1 CT | H3160 | 573,900 |
| GGGGCC F1 CT | H3161 | 363,000 |
| GGGGCC-AS F2 CT | H3162 | 2,261,700 |
| GGGGCC-AS F2 CT | H3163 | 176,300 |
| GGGGCC F2 CT | H3164 | 1,549,500 |
| GGGGCC F2 CT | H3165 | 115,700 |

Antibodies may be produced in bacterial cells, e.g., *E. coli*, or eukaryotic cells, such as yeast cells or mammalian cells. In one embodiment, antibodies are produced in mammalian cells. Mammalian host cells for expressing the antibodies or antigen-binding fragments thereof include Chinese Hamster Ovary (CHO cells) (including dhfr-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, and a cell from a transgenic animal, e.g., a transgenic mammal. Antibodies can also be produced by a transgenic animal. For example, U.S. Pat. No. 5,849,992 describes a method of expressing an antibody in the mammary gland of a transgenic mammal.

Isolated antibodies of the disclosure may also have a detectable label attached thereto. The label may be, for example, a fluorescent, enzymatic, affinity or isotopic label. Examples include fluorescein isothiocyanate (FITC) for detection by fluorescence, horseradish peroxidase which allows detection by cleavage of a chromogenic substrate, radioisotopes such as $I^{125}$ for detection by autoradiography and avidin/biotin for antibody detection and affinity purification of antigens and antigen-bearing cells.

Also encompassed by the disclosure are hybridoma cell lines producing a monoclonal antibody specific for a di-amino acid repeat-containing protein selected from a poly-(Gly-Ala), poly-(Oly-Pro), poly-(Gly-Arg), poly-(Pro-Ala), poly-(Pro-Arg) protein, Met . . . poly-(Pro-Arg). Met . . . poly-(Gly-Pro), a C-terminal peptide of a di-amino acid repeat-containing protein as described herein, and/or a combination of two or more thereof.

In some embodiments, an isolated antibody is an isolated auto-antibody obtained from a subject having ALS, wherein the isolated auto-antibody is specific for one or more di-amino acid repeat-containing proteins as described herein.

In some embodiments, an isolated antibody described herein is contained within a buffered solution. In some embodiments, an isolated antibody described herein is attached to a solid support (e.g., the surface of a plate or a bead).

Transgenic Mouse

In another aspect, the disclosure relates to a transgenic mouse comprising a human C9ORF72 gene comprising a GGGGCC hexanucleotide repeat sequence. In some embodiments, the mouse comprises a human C9ORF72 gene comprising a GGGGCC hexanucleotide repeat sequence and flanking human sequences on the 5' and 3' end of the human C9ORF72 gene. In some embodiments, the flanking human sequences on the 5' and 3' end are each independently at least 1 kilobases (kB), at least 5 kB, at least 10 kB, at least 20 kB, at least 30 kB, at least 40 kB, or at least 50 KB in length. In some embodiments, the flanking human sequences on the 5' and 3' end each independently comprise a promoter capable of driving transcription of the human C9ORF72 gene in the sense and anti-sense direction, respectively. Accordingly, in some embodiments, the transgenic mouse expresses both sense and anti-sense transcripts (e.g., 5'-GGGGCC-3' and 5'GGCCCC-3' hexanucleotide repeat-containing RNAs described herein). In some embodiments, the human C9ORF72 gene and flanking sequences comprise the sequence below, wherein (GGGGCC) n indicates the location of the GGGGCC hexanucleotide repeat sequence:

Chr9: 27,527,137-27,625,470 (reverse complement)

(SEQ ID NO. 63)

AAGCTTGATAATATTATCAAATATTAGATAAATGTAATATTAGAAGAAAACTTTTTTGAAAAGATATATAAAAAT

AATTTCATTCAAAATTTTTATATTTAATTTAAATTTTTAATGAAAATATATCTAAGTTTTGTACGCTTTAAATGT

AATTATGTTTGATAATTTAATCATTTACTATTCGTTCTCTATTGCTGCCCTAACAAATTACCATAGTTCAGTGGC

TTACAAAACACAAATTTATTATCTTACCATTCTGTGAGTCAAAATTCCAAAATAGGTGTCACTAGGCTAAAATGA

AGGACTGCATTTCTTCCTGCAGGCTCCAGGAGAGATCTATGTCTTACTCTTTTCGGCTTCTAAAGGCTGCCCACA

-continued

```
TTCCTCGACTAGTGGCGTCCCTCCTTCGTCTCTAAACCCAGCAACAACAGGTTGAGTCCTCATGTCACATCTTTC
TTACCTTTCTGTCATCTCATCTCGCTGACTGCTGCTGGGAAAAATTCTCCACTTTTAAGGGCTATCATGATTAGA
CTATGCCCACTAGATAATACAAGATCTCAGATCCTTAACTTCCATCACATCTGCAAAGTCGCTTTTGCCTCATAA
AAGAGTCTGAGGTTTAGACGGGAGATCTTAAGGGGGCTATTAATATGCCTACCATAATCACTGAGAATAAGTACA
AGTTAAGATTATAATAGCAATAGAATATACAAACGTGAAGCTCCAAAAGAACAACAACAACAAAAAAGGTGAACA
GGAAAAAGAAACTGAAAATCTTTAAAAAGGCAGTCTGTTTAAATCTATAAAAACTGGAAAAAAATGAGAGTGGAC
AAATATCTGGTAAGCATGATGGACTTAAAATTTGTGACTAGGGCATTACATTTTTTATATTAATATAATGAAGAT
TGAATTACTGATCAAAACAATTAAAAAGCAAGAGAACTATTCTCATCAAATCTGCAACACGAAAAGTTCAGACAA
AATTCCAACAACTTCACATTCTGAACTAAATGAGGACTAATTACCAGTTCGAGCAATGAGAATATATGAGGTCCT
CCGTTTGCACTTTGCCAGGGATCTGAAAACGTTGGGAGTAGGTCGGCTTCACCCTGAAGCCAGACCATCGACAGC
CAGTTTTCCCCCCTTCTCCACCCACAGGTCTTTAGGCCCTCATCCTTCCCAGCCTCAGAACTAGTCTCCAAAGAA
GAGGAAAGTTAGAGGAGAGAGTAAATCGTTGAATAGGATGAAGGAGATGTGGGAAAAAGAAAAAGAGAGGCTGCA
AGAGAGAGGGTCCCAGGGATAACTCTGCTCTTGGAAGGGTGGCCACAGTCATGTGGTCCCAAGAGGCAACAACAA
GCTTAGGAAGCCAGAGAAACCAGTTACAATCACTGCTACTCTTTTCGATTCTGTGTTGTTTAAGAAATATCACCC
GCCAGGAGTTCTCCAGAAACATTTTCCCTGATTCCATGTAAGTGCTCAACCAGTGAATGGTAATCCCATTTTGGT
TTAGTCTGTACCATCCCCTATTCCAAAATAAAGGGAAAAATGGTGGGTTTATATCTTAAATTTTCTACTTTACTA
AACTCAAGGGAAATAGCCAAGCAAAAACGAAAGCTGAGACTCTTGCTAATTATCCTTTCCATAGAATGTTTGCTA
AAATTCCTTGTCAAGGAAGGAATAACAAAGCTAGTCCACGCTCTGTATAGGGTGTTTCCAATTAGTTATACTTTA
AAGTATAAGTATTTAACAAAATCTATAAATTTTGTTAATTATTTACTTGTAGTGAAAAATGAGCCATTCTCAAGC
AAATCACTTTTTATTACACATTCCAGAGAATAACCATAAAAGGACATTTATTATAGCAAAAATAACCACATCTGG
ATGGAACTTCAATCACCAGTATTTACTAAATAAATGCCCAGAAAAAAAATAGTTCATCTTTAATTTCAGTCATCA
TTAATAAAAGCTGAAGTACCTCTTCAGATCTTTTGATCATTTTCTGTTGGATTGTTTTCTTTTTACTGAGTTGCA
AATGCTCTTTATATATTTTGGATACAAAGCTTTATCACATAGGCATTTTGCAAGTATTTTTTCCAAGTTTTTTA
CTTTTCATTTATTTAATAATATCTTTCAAAGAACGGGAATTTTATAATTTTTATGAAGTCCATTTATAATTTTT
TCTTTTATGGGTTGGTGGGGGTTGGGGGTTGTGTTGTCCTAAGAAATCTTGGCTCAACACAAAAAGATTAGTTTC
TATATTTTCTTCTAGAAGTTTTATAGTACGATCTCAGATCCATTTCAGATGATGAATAAGCACATAAAAAAAGGA
TACTCATCGTTAGTCATTAGAGAAATGCATATTAAAACCATAAGGAAATACTACTATATACATATATTAGATAGG
ATGAAGAGCAACTGGAATCTCATACAGTGCTGATTGAAATGCAAAATGGCAAAACAACTTTAGAAACCAATTTGG
AAGCAGCTGTACTGACATGGAATTTTGAGCTGGAAGAATCTTAGAAAAAGAATACTTTACCACCTCCCCATTCT
CTTCACCCTGGGGAACTGTTAAATGAGGAAATTGTGGTTCAAGGAGGAACTTGTCTATATGCTTTCTCAGCTTTC
CCGTGGTAATTACCATCTTGATAATATAACGTAATGTATGTATATGTTATCAAATAATATAATATCTTCATCATA
TATTTATCATCTTCATAATGTTAGCTGTCTAGTGGTAACTTTTTTTGCTCTTTATTGCCTCCCTCTTTTTCCC
TCTTTGTTGTTTTTGTCATACAATTATGATATATGTGTATATATTCTCACTGTAAAGATGTAAACAACACAAAG
ATTATTGAACAAATCACGAAAGTAACCCTTCCTTCATTCTTACCCTATCCAACCCTCATCTCCTCAGAAGAATAC
ACCATTTTAGTTGTAAATGTTTTTCTAGCTCTTTTTCAATGTTTCTACCTATATGCATGTATGTATAATGTATAT
ACATACATATATACATACATATTGATATATACATATATAGAGGTATGGTTTTTAACTTAAATGGAATTGCATTG
TGGATATTGTCCTATGACTTGCTTTCAACCAAATTATATGTCTTGGAAATACATACATATATTTAAAAAATATGT
TATGTATATGTAACATACTATATGTGCATAATATATATTACATAGATATAATAAGGCCTAGGAAGAAATTGTGTG
CAACCTCTAGTACATCTTCCTCTATATCTACTGTACATACATACAACCCATTCTTTTTTTAATTTTTTTATTTTT
TTAGACAGAATCTTGCTCTGTCGCCCAGGCTGGAGTGCAGTGGCACAATCTCGGCTCACTGCAAGCTCCACCTCC
```

-continued

```
TGGGTTCACGCCATTCTCCTGCCTCAGCCTCCCAAGTAGCTGGGAATACAGGCACCTGCCATCAGGCCCAGCTAA
TTTTTTTTTGTATTTTTAGTACAGATGGGGTTTCACCGTGTTAGCCAGGATGGTCTCCATCTCCTGACCTCGTGA
TCCGCCCACCTCATCCTCCCAAAGTGCTGGGATTTACAGGCGTGAGCCACCGCGCCCAGCCACAACTCATTGCAG
AGTAGTCCAAAATATGGATGGACTGTAGCTTAATTACTTATTCTCCCATTGATAGACACTTAGGACTTTTCTAAT
TTTTATAATTTAAAAATATGCTGCAATTAACAAACATTCTTGTGTATCTTTTTGCTGTATGTATGCATATTTCTT
TAGTATGGGTTTTGGAAGAGGAATCACAAAGGAGGCATAGAATATAAATATTTTTATTTTGAAAAATACAGTTGT
AATTTAATAACCCACCAAAAGACTCTAACAGTTTAGATTCACATCAACAGTGTAAGAACATGTCTGTTTTACTGC
ATCCTTACCCCCACTGGTTATAATACTTTTAATTAACAATCTTATGGATGAAGAATACTATCGCAATGTTGTTTT
AATGCATTTTTCCAATTACTAGTGAGATTGAACATTAATTCTTTTATTTTATGGATCACTGGCTTTTCTCCTTCT
GTGAACTACCTGTTCACATCCTCTGCTTTTCAGCTCTTGAGCTGTTATCTTTTTCTTATTGATTTATATGAGCTC
TTTATATATTCAAGATGTTAATCATTTGTATTTTATGTATATGGCAATGATTTTCTTCCAAACCAATGCTTGTCT
TTTATTTATTTATTTATTTATTTATTTGAGACCGAGTCTCGCTCTGTCGCCCAGGCTGGAGTGCAGTGGCG
CGATCTCGGCTCACTGCAAGCTCCGCCTCCCGGGTTCACGCCATTCTCCTGCCTCAGCCTCCTGAGTAGGTGGGA
CTACAGGCGCCCGCTGCCACACCCGGCTAATTTTTTGTATTTTTAGTAGAGACAGGGTTTCACCGTGTTAGCCAG
GATGCTCTCTATCTCCTGACCTCGTGATCCGCCCGCCTCGGCCTTCCAAAGTGGTCGGATTACAGGCATGAGCCA
CCACGCCTGGCCAATGCTTGTCTTTTTATCTCTGTTTATGGCATCTTTCATACTATGGACATTTTTATTTTTATT
TTTTATGTTGATTTATTCTTGAATTGTATACATGTTAATTATACCTAAGTTATTGTAATACCCTTAAAGCCAAGT
TCTACACATATATTTAATTTGCTTTCCCAATAGGTCTCTGAGGGAACACATTTTTTCAAATCACTTTGTTTCATC
TTTTTTAGGTGTTGATCAATTATTAAGGAGTTTGAAATAATCATTTAAACGGAATTCTTCAGATGAAAACATAAA
GACATTTATCGGGTCAGAGCATTGGTCGGTTCACATACTCAGGATCAGTGGCCTGGGTGGGCAGGCACTGGGTGA
ATGGAGAGCTGCAGGTATTGGAAGAGAGCCCAGTTGGATATGTAGTTTCCAAAGATCATCAAGGCAGACAACCAA
AGGGAAACCGTGGGAAACACCTGCTTTGGGCCATCTAAGATGAGATGATAAAGTAAGGAAAGAGTTGAGCCCAAC
ACAGTGATAGCCAATCTGAAAGCGGGCAGAACTGACAAGACCAAACAAGTAGGTGAACTGGCTGCAGGCAGCCAG
CCACCACAGGGACAGCGTGTACTCCAGGGACAAGCTCAAGGCTATAGGTAGTTAGTTCAAGGCTACTAGGGTGAG
AAGAGCAGGAACTGAGTTCTATACCAGTGCTTCTCAAAACTAATGTGCATCCTAATCACCTGGAAATCTTGTAAA
AATGTAGATTCTGATTCAGTGAGTCTGAAGCAGAGCTTAAGATACTACATGCTTAACAAGAGCCTAGTTGATGCT
GACACTGCTGGTCCCTGGAGCTCTCTTTGAGTAGCAGGCTTCTGGAAGGCTTGTGTCACTAAGCACAGAGAAGCC
TCACTTATCAAATCTGCACCAAAACAGGAAAACTAATGTGAAGAATAATGTGATGCACACGTCAGAGCATGAGGC
AGTTGCTTTGTCCCTGAGGTTGCGCTCCAGATGGCTTCCTAAGATGCGACAGGCTGATCTTGTGCGTGGGGGTCC
CGGAGGCTTGGGCCACGGGAGAGACAGGACCTCAGAGGCTGGGAGACAGGCAGAGACAGAAGAGTGACATCCTGC
TGCTTTTGAATTTGCACATTCTGTAGAATAATAACAGCAGTAAACTGTTACACAATATCTATTCTCAGCATCTTG
AAGCCCTTTTCACATATTGTTACTTCCATTAATGGGGCCCTTTGCTGCTATTCTACTTTTCTCTTCAGCTATCAA
CAATATGGCTTTCCACACCTCCATCAGACAGTAGCCAGATGAAATAAAATGTGCCAGAATGAAAACTTGTTCATT
TGTCTACTTTTTGCCAAGACTAGACAGGCAGGAAATTGAATGTATTTTTACAGAAAAGGTTTTCAAAACTTTTTC
CCCTCTGTGGCTCATTTAGGTAAACTAAAAGGCATAAGACCCACCTAAAACATGGGTTCCCGCTTTTTATTGGAG
AAAGAACATAGTACTTTAAAAAAATACATAAAATAATAAAAAGGAAAGACAAAGATAATGAAGGTTGTACATGGT
ACCAAATTTTTGTATCCCATAATAACACATGAGTAGATCACTACTAAGTAGGTTTTAGTGACATATAGGAAACAT
TAAAATCTACAGAAATTTGCATTATTTTCTGTCAAAAAGGATCATTTCACAGCCTTTCAGGGGGAACCCATTGCC
CACAGGAACTCATGCATTCCATGCTTTGAGGATCACTAGATCTAAGAAGCCTTCCTTGGAGGTTCTAGCCTCCAA
CCCTTATTTTAGTAAAAGAAGCTCCAGTTTTATCTGTTTCTAAGTCAGACTACCACACAACATTGGGCTTAAAGA
AAGGTTTCCAGGGCTAAAGCAGACTTTGAGGATTACTAATTCCGAGTTAAATTTCTGTGTATTATCTCTGGATTT
```

-continued

```
GACTTATTCACACTGGACTATCACTCATAAATATACATAATACAGAGTTAACTATTTAAATTTATAAAGAGAGTA

TTTTCCTTTTTTATGAGCAAAACATGCTGCCAACTACTTGGACCACATACTGATCCATAAATACTGACAGCTTTG

TAATTGGAAATAATAAATACACACTAATGAAGCATCTCAAAAGGGAAGAGCCACAGGTAATCTGAGTGATTAGGC

ATTCATGTTAGGTTAGGCTTTGATCATTGTTTTTAATCGCAATTTCATTGCAGTGCATCTATAAATCCATGTCCA

GAAGTATGAAGTGGTTCTATAGTAAGAATAAGATGCTACAGATAATGCGACTAAATAAGACACTATAGGTAATGA

CACAGATTCAAGTCTTATTGTTGATGGGAAGAGGTCAATAATGGATGATATAATATACTACAGCAATGAGAATTA

TTGAATGTTTTCCAGACTCACTTGTATAATTGGCCATAACAGCAAACAAAAAACAGGTTCTGATAGCAAAATGAT

ATACAGTACTAACAAAGGTGAATCTTGAGGTGAACCTTCTCTTTATAAGTTTAAATAGTTTACCCCCGACCTTTT

CCCATAGTAGAACAGCCTAAAAGTATCTTTCAGTAGAATGCTAGTGCTTATGAGGTTTTCTTAAGATATCATTT

TTCAATTAAAATTTATTTCACAAAAGACTCACATCCTTGCCAGCCTTCAGGGTGAGTGTTGATTCAGGCTGTGTC

CAACGGCAACGATGAGTGAACTTCTCACCCTCAGAATCACATGAGCATTCCTGAGATGTTTTATCAGAGTGATAC

CAACTTCATTATTAGAATATTGAGTCCCTATTTCCTATATTCAATGTCCTTTCAAGCCCTAACTTTGTCCGGGTT

GAAGGCAAAGATCCAAATAATCACATTTGTCTTTGATAACTGAAACTGGGAGAACTGGGACTGTCTCAAGAGTTC

TACGTGACTGTAGGTTGCAAGTACTGTGGTTGCATCTCCAAATATTAACCAATCCCAGTGACAATTCAATGGGGT

CTCCTGAACCATGATCCTCATGTCTCCAGTGAAGGAAATGGGCAAAGGGGATTCAAAAATCCCTTTTGGAGGAAT

AGGAAACTTCTGCTTTCCTTCATTTCATAACATTTGCGATGGAACAAAGGCTTTTTTAGAATGGAGCAACCAGAT

CCTTTTTTGGGGGAATCAGCTTAAATGTCCCTTCTTCTCATACTACTTTTATCTATGTGATCCTATTCTTTTCTG

TTGTGGATTGAATCATGTCCCTCAAAAAGATTGAATTTAGAGTGTGCTCTAAATTCAATGTGGAGAAATTTGGAC

ACAGAGGCAGACACACAGGGAGAACCCCGTGTGACAATGGAGGAAGAGGATGCATTTATGCTGCCACAAGCCAAG

GAACACCAAAGATTGTCAGCAGCCACCAGAAGCTAGGATAAAGGCATGGCACATCACTCCCTCTGAGCCCCCAAA

AGGAGCCAAGACTGCTAATACTCTGATCTCGGACTTCTGGCCTGAAACAGTGAGAGAATAAGGTTCTGTTGTTTC

AAGCTACCCAGCTTGCGGTATTTTGTCACAGAAGCACAAGGAATCAAGTACATTTTCTTTCTCAGCACTTGTGAT

AATTTGATTTTTTCTTTACTCAGTGGTTGTTTCACACCTATGTCCCCATCAGACTGTAAGCTTAAAGAGACCTGG

ATCTGGTCTGTCTTCACCACTGTTGATTCATTACCAGCACAGTGCCTGGCCCATGGTCACTGAATAAACGTTTGT

TGAGAGAATGAATGTGCTTAACCAGAAGTACTATTGACCTATTAGGCCAAGTTCAAGGTGCCTAACAGCTCAGCT

GTGAAGGATACCTCTCCTTTCAGTCCTCTGTTACATATGTCCCTGATAGATGTGTTATTTGTATCTCCTCCTGGC

CCTCAAGTTTGTTTGAGGGCAGGACCCTTTTTTGTATATGTGTAGAGCTTCGTAGTACCTAAATACTACTTTGCA

TATATAATAAAGTTTCGATAAATATTCATTAAATAAAGAAATAAATGAAATGACTAAGTTTTCTAAGATGTTACA

ACTAGATTGAAGATATTTAGCTCATTATTTAACAAGAAAACTATGGTTAATTATGGTGTCCTGTGTGAAAATGGT

TATAGTTTGTTTTTTAATTAATATAAGCATGTATGTGCATTATCAGTATACACAATTTGTGGTATGAGTGTTTTG

TGTCCCTGCACACAGACCACGGAAATCCTGAGAAACAAACTGCCACCCCAGAGCAGGTGCCTAACACAGAGACTT

TTAATCCTTAAAGTTTTTCTATAACTAAGCAATGTTTTTTCAAATGCAATAACACTGATATGCAGACATATTGAT

TGTCCACTCACAAAGCCATTCCTCAATATCATTACAACATGCCTCTTTGAATGTCATTAAAAATAGATGTCTCAT

TTTTCTAGGACAAGTTGGCTGAAGTTCTGCTTGAAAACTGGTAATAGAAAATACAATTTCTCAACCCGCTTTGGC

CTTTTAATTCTGTTCTACAACCTTGCCAGTTCACTTTCAAAGTCAAGGGATGCATCTTGCAAAACCATGACATCT

TTTGAGTAACTCCTTCTGTTCTTAACACATATTCCCAGGAGCTTAATAAATATTGTTTTTGCAACTTGTTTAGTG

GCAAAATAATGAGTCCTTGGTGTATGCTTATCCTCTGCTTTGCTATTAGAGAAGATATATTCAGACTGTTTTAAA

CAAATTAATTCAAGGGCAGGGAACAGTCCTAAAACCTGTTAAAATTCAAATACTTGGTCACTGTATGTGCAGCAT

GTGTGTTCTAGAAAGTCCTATTATTTTAAAATATAAATTGAATCTTGTTGAGAAATTAATGTCATATGAATATAT

TAATAACTGAAATGCTGCCAAGTTTACAAAAAGCCCTCAATGAAACTGTGACCTTGTATAGACAAGGGCCTGTGG
```

-continued

```
AGGGACATTTTTAAACCATCTCTTTTTTTATTTCCTCATGAGATCTACAATGTAAGTGCATTAAAGTTGATGAAT
GAATTGCAGTGCAACTTTTCCTGCCTCTTTTGCCTTTCATTTGTCTATATTTCAAGCTTCACTGAAGTGATAGAT
TTTGGGCTTTGCCACATTGTCCTCTGATTGCTTCCCTCTGCTCCTCCTTTTCCTAGTGAATCTTTGTTTTACTGG
TGGAAAAATCTACATCTTTGTATCTTGGCATTTTACTTTCACATTATCTCATAGATTTTATTTCAAGTTGCTATA
AAGTTATCAACTTTTATTTTTAACTAATATTATTTTTAACAATTAGAAAATTGTTGACCAGGTAATTCCAGCACT
TTGGGAAGCTGAAGCGGGAGGATCACGTGAGCCCAGGAGCTCGAGACCAGCCTGGGCAATGCAAGGAGACTGTCT
CTACAAAATATAAAAATACATTAGCCAGGTTTGGCGGTGCATGCCTGGGGTCCAGCTATTCAGGAAGCTGAGGTG
GGAGGATCACTTGAGCTGGAGAGGTTGAGGCTGCAGTGAGCAGTGATCGCACCACTGCACTCCAGTCTGGGTGAC
AGAGGGAGACCCTATCTCGAAAAAAGGAAAAGAAGAGGATTTTGCTGGCAAGATGGCTGAATAGGAATAGCTCC
GTCTGCAGCTCCCAGTTGAGATCAATGCAGAAGGCAGGTGATTTCTGCATTTCCAACAGAGGTACCTGGTTCATC
TCACTGGGACTGGTTGGACGGTGGGTGCAGCCCATGGAGGGTGAGCAGAAGTAGGGTGGGGCGTTGCCTCACTCA
GGAAGTGCAAGGGGTCCCTCTTCTAGCCAAGTGAAGCCGTCAGGGACTGTGCCATAAGAACAGTGCACTCTGGTC
CAGGCTTTTCCCACAGTCTTTGCAACCCACAGACCAGGAGATAACAAGCGGTGCCTATGCCACCAGGGCCCGGGG
TTTCAAGCACAAAACTGGGTGGCCATTTGGGCAGACATCAAGCTAGCTGCAGGAGTTTTTATTTTCATACCCCAG
TGGTGCCTGGAACGCCAGTGAGACAGAACCGTTCACTCCCCTGGATAAGGGGCAGAATCCAGGGAGCCAAGTGGT
CTGGCTTGGCGGGTCCCACACCCACGGCGCCCAGCAAGCTAAGATCCACTGGCTTGAAACTCTCGCTTCCAGCAC
AGCAGTCTGAGGTCCACCTGAGACGCCCGGGCTTGGTGTGGGGAGGGGCATCCACCATTGCTGAGGCTTGAGTAG
GCGGTTTTACCCTCACGGTGTAAACAAAGCTGCCTGGAAGGTCCAGCTGGGCACAGCCCACCACAGCTCACCAAG
GCCGCTGTGGCCAGAGTGCCCCTCTGGATTCCTCCTCTCTGGGCAAGGCATCTCTGAAAAAAGGCAGCAGCGCC
AGTCAGAGACTTATAGATAAAACCCCCATCACCCTGGGACAGAGCACCTCAGGGAAGGAGTGGCTGTGGGTGCAG
TTTCAGCAGATTTAAACGTTCCTGCCTGACAGCTCTGAGAGAGCAACAGATCTCCCAGCACAGCGTTCAAGCTCT
TTTAAAGATCAGACTGCCTCCTCAAGTGGGTCCCTGACTCCCATGTCTCCTGATTGAGAGACACCTCCCAGTAGG
GGCTGACAAACACCTCATAAAGGAGAGCTCCAGCTGGCATCTGGCAGGTGCCCCTCTGGGACGAAGCTTCCAGAG
GAAGGAACAGGCAGCAATCTTTGCTGTTCTGCAGTCTCAGCTGATGATACCCAGTCAAACAGGTCCTGGAGTGGA
CCTCCAGCAAACTCCAGCAGACCTGCAGCAGAGGGGCCTGACCGTTAGAAGGAAAATTAACAAATAGAAAGGAAT
AGTATCAACATCAACAAAAAGGACGTCCACTCAGAGACCCCATCCAAAAGTCACCAACATCAAAGACCAAAGGTA
GATAAATCCACAAAGATGGGGAGAAACCAGTGCAAAAAAGTCTGAAAATTCCAAAAACCAGAACGCCTCTTCTCC
TCCAAAGAATCACCACTCCTCACTAGCAAGGTAACAAAACTGGACAGAGAATGAGTTTGACAAATTCACAGAATT
AGTGTTCAGAAGGTGGGCAATAACAAACTCCTCCAAGCTAACGGAGCATGCAAGGAAGCTAAGAACCTTGAAAAA
AGTTAGAGCAATTGCTAACTAGAATAACCAGTTTAGAGAAGAACATAAATGACCTGATGGAGCTGAAAAACACAG
CACGAGAACTTTGTGAAGCATACACAAGTATCAATAGCCAAATCGATCACGTGGAAGAAAGGATATCAGAGATTA
AAGATCAACTTAATGAAATAAATTGAGAAGACAAGATTAGAGAAAAAAGAATGAAAAGGAATGAACAAAGCCTCC
AAGCAATATAGGACTATGTGAAAAGACCAAATCTATGTTTGACTGGTGTACCAGAAAGTGACGGGGAGCATGGAA
CCAAGCTGGAAAACACTCTTCAGGATATTATCCAGGAGAACGTCCCCAACCTAGCAAAACAGGCCAACATTTAAA
TTCAAGAAATACAGACAACACCACAAAGATACTCCTCGAGAAGACCAACCCCAAGACACATAATCGTCAGATTCA
CCAAGGTTGAAATGAAGAAAAAAATGTTAAGGGCAGCCAGAGAGAAAGGTCAGGTTACCCACAAAGGAAGCCCAT
CAGACTAACAGCAGATCTCTCTGCAGAAACCCTACAAGCCAGAAGAGAGTGGGGGCCAATATTCAACATTTTTAA
AGAAAAGAATTTTCAACCCAGAATTTCATGTCCAGCCAAACTAAGCTTCATAAGTGAAGGAGAAATAAAATCCTT
TACAGACAACCAAATGCTGAGAGATTTTGTCAACAGCAAGCGTGCCTTACAAGAGCTCCTGAAGGAAGCACTAAA
CGTGGAAAGGAACAATCGGTACCAGCCACTGCAAAAGCACACCAAATTTTAAAGTCCATTGACACTATGAAAAAA
CTGCATCAACTAACAGGCAAAATAACCAGCTAGCATCATAATGACAGGATCAAATTAACCTTAATTAAGTTAGCC
```

-continued

```
TTAAATGTAAACGGGCTAAATGCCCCAGTTAAAAGACACAGACTGGCCACCTGTATAAAGAGTAAAGACCCATCA

GTGTGCTATATTCAGGAGACCCATCTCACATGAAAAGACACACATAGGCTCAAAATAAAGGGATGGAGGAATATT

TACTAAGCAAATGGGAAGCAAAGAAAACAAAAAGCAGGGGTTGCAATCCTAGTCTCTGATAAAACAGACTTTAAA

CCAACAAAGATCAAAATAGACAAACAAGGGCATTACATAATGGTAAAGGGATCAATGCAACAAGAACAGCTAACT

ATCCTAAATATATATGCACCCAATACAGGAGCACCCAGATTCATAAAGCAAGTTCTTAGAGACCTACAAAGAGAC

TTAGACTCCCACACAATAATAATGGGAGACTTTAACACTCCACTGTCAATATTAGACAGATCAATGAGATAGGAA

ATTAACAAGGATACTCAGGACTTGAACTCAGTTCTGGATCAAGTGGTCCTAATAGATACCTACAGAACTCTCCAC

CCCAAATCAACAGAATTTACATTCTTCTCAGCACCACATCGCACTTATTCTAAAATTCACCACATAGTTGGAAGT

AAAACACTCCTCAGCAAATGCAAAAGAACGGAAATCATAACAGTCTCTTAGACCACAGTGCAGTCAAATTAGAAC

TCAGGATTAAGAAACTCACTCAAAACCGCACAACTACATGGAAACTGAACCTGTTCCTGAATGACTACTGGGTAA

ATAATGAAATGAAGGGCAAAAAAGAAGTTCTTTTGAAACCAATGACAACAAACACACAATGTACCAGAATCTCT

GGGACACATTTAAAGCAGTGTTAAGAGGGAAATTTATAGCACTAGATGCCCAAAAAGAAAGCAGAAAAGATCTA

AAATCGACACCCTAGCATCACAATTAAAAGAACTAGAGAAGCAAGAGCAAACAAATTCAAAAGCTAGCAGAAGAC

AATAAATAAGATCAGAGCAGAACTGAAGAGGAGAGAGACATGAAAAACCCTTCAAAAAAATCAATGAATCCAGGA

GCTGGTTTTTTGAAGAGATTGACAAAACAGATAGACCACTAGCCAGACAATAAAGAAGGAGAGAAGAATCAAATA

GATGCAATAAAAAATGATAAAGGGGGTATCACCACTGATCCCACAGAAATACAAACTACCATCAGAGAGAATACT

ATAAACAACTACACAAATAAACTAGAAAATCTAGAAGAAATGGATAAATTCCTGGACACATACACCCTCCCAAGT

CTAAACCAGGAAGAAGTTGAATCCCTGAATAGACCAATAACAAGTTGTGAAATTCAGGTAGTAATTAATAGCCTA

CCAACCAAAAAAGTCCAGGACCAGACAGATTCACAGCCGAATTCTATCAGAGGTACAAACAGGAGCTGGTACCA

TTCCTTCTGAAACTATTCCAATAGAAAAGAGGGAATCCTCCCTAACTGATTGTATGAAGCCAGCATCATCGTGA

TACCAAAACCTGGCAGAGACACAACAAAAAAAAGAAATTTTCAGGCCAATATCCCTGATGAACATTGATGCGAAA

ATCCTCAATAAAATACTGGCAAGCGGAATCCAGCAGCGCATCAAAAAGCTTATCCGCCAGGATCAAGTCGGCTTC

ATCTCTGGGATGCAAGGCTGGTTCAACATACGCAAATCAATAAACCATCATTCTCAGCAAATTATCACAAGAACA

GAAAACCAAACACCGCATGTTTCTCACTCATAAGAGGGAGTTGAACAATGAGAACACGTGGACCCAAGGAGGGAA

CATCACATACTGCGGCCTGTCGAGGGATTTGGGGTTGAGGGAGTGATAGCATTAGGAGAAATACCTAATGTAGGT

AACAGGTTGATGGGTGCAGCAAACCACAATGCGATGTGTATACCTACCTAACAAACCTGCACGTTCTGCACATGC

ACTCCAGAACTTAAAGTATAATAATAAAAGGCGCTGCCTCAGGATGTAAAGTGTAACAAGGGGGCTGGGGTGGGC

AGCGTGGGCCTCTGAGACCTTTGGTTGCCCGTGTCCGCAGCTCGCCCCGCAGCCGGCTCCACAATGGTCCGCTCC

GTTTGCCACGTGCGGATTCGGGTTCCAGACTGAAGGCTGCGTGTTCTCTGCCGCCCACAGCCCAAGTTTATTGTG

GCAACCGCCGGAGCAGCCTTCCCCGCTGTGGAGGAGCCTGGGGCTACCCCTCAGCGGTATTTGGGGCTGGTCCTG

GGGGAGCTAAGCAGGGTTGTGGCAGCACTGCCTGAAAGTGTGAGACCAGACTCTAATCCTTATGGTTTTCCATGG

GAGTTGGTGATATGTGCAGCTGTACATGGATTTTTTGCTGTTCTCTTTTTTTGTGTGGAGAAGTTTTAGATCGGT

TGGGAGTCGGCTTTATGTGGGAAGAGAAAAAAAGCTTGCTGTAATGCTTTCTGGACTAATTGAAGAAAGCATAA

ACTACTTGAAAAATTTAGCCATGTTCAAAAAGAGTATGAAGGCTATGAAGTAGAGTCATCTTTAAAGAATGCCAG

CTTTGAGAAGGAGGCAACCTGTGAAAAGCTAAACAGGTCCAATTCTGAACTTGAGGATGAAATACTCTGTCTAGA

AAAAGAGTTAAAATAAGAGAAATCTAAACATTCTGAACAAGGTGAATTGATGGTGGATATTTGCAAAAGGATACA

GTCTCTAGAAGATGAGTCAAAATCCCTCAAATGACAAGTAGCTGAAGCCAAAATGAACTTGACGATATTTCAAAT

GAATGAAGAACGACTGAAGATAGCAATAAAAGATGCTTTGAATGAAAATTCTCAACTCCAGGAAAACGAGAGACA

GCTTTTGCAAGAAGCTGAGGTATGGAAAGAACAAGTGAGTGAACTTAATAAACAGAAAATAACATTTGAAGACTC

CAAAGTACATGCAGAACAAGTTCTAAATGATAAAGAAAATCACATCAAGACTCTGAACGCTTGCTAAAAATGAAA
```

```
GATCAGGCTGCTATGCTTGGAGAAGACATAACGGATGATGGTAACTTGGAATTAGAAATGAACAGTGAATCGGAA
AATGGTGCTTACTTAGATAATCCTCCGAAAGGAGCTCTGAAGAAACTGATTTATGCTGCTAAGTTAAATGCTTCT
TTAAAAACCTTACAAGGAGAAAGAAACCAAATTTATAGTCAGTTATCTGAAGTTGATAAAGGAAGAGCTTACAGA
GCATATTAAAAATCTTCAGACTGAACAAGCATCTTTGCAGTCAGAAAACACACATTTTGAAAGTGAGAATCAGAA
GCTTCAACAAAAACTTAAAGTAATGATTGAATTTTATCAAGAAATGAAATGAAACTCCAGAGGAAATTAACAGT
AGATGAAATTACCGGTTAGAAAAGGAAGAAAAACTTTCTAAAGTACACGAAAAGATCAGCCGTGCCACTGAAGAG
TTGGAGACCTATAGAAAGTGAGCCAAAGATCTTGAAGAAGAGTTGGCGAGAACTATTCATTCTTATCAAGGATGG
ATTATTTCCCACGAGAAAAAGCACATAATAATTGGTTGGCAGCTTGGACTGCTGAAAGAAACCTCAATGGTTTA
AGGAAAGAAAGTGCTCACAACAGACAAAAATTAACTGAAGCAGAGTTTAAATTTGAACTTTTAGAAAAAGATCCT
TATGCACTTCATGTTCCAAATACAGCATTTGGCAGAGAGCATTCCCCATATGGTCCCTCACCACTGGGTCGGCCT
TCATCCTAAACAAGAGCTTTTCTCTGAGGGCCCACTGAGACTCTCATCTTTGCTAACAGGAGGAGGAGGAAGAGG
CTCAAGAGGTCCAGGGAATCCTCTGGACCATCAGATTACCAATGAAAGAGGAGAATCAAGATGTGACAGGTTAAC
CAACCTCACAGGGCTTCTCTGACACTGGGTCCCTGTCACCTCCATGGGAACAGGACCGTAGGATGATGTTTTCTT
CCACCAGGACAATCATATCCTGATTCAGCTCTTCCTCCACAAAGGCAAGACAGATTTTATTCTAATTCTGGCACA
CTGTCTGGACCAGCAGAACTCAGAAGGTTTAATATGACTTCTTTGGATAAAGTGGATGGGTCAATGCTTTCAGAA
ATGGAATCCAGCAGAAATGATACCAAAGATGACCTTGGTAATTTAAATGTGCCTGATTCATCTCTCCCTGCTGAA
AATGAAGCAACTGGCCCTTACTTTTCTCCTCCACCTCTTGCTCCAATCAGAGGTCCATTGTTTCCGGGGGATACA
AGGAGCCTGTTCATGAGAAGAGGACCTCCTTTCCCCCCACCTCCTCCAGGAACCATGTTTGGAGCTTCTCAAGAT
TATTTTCCACCAAGGGATTTCCCAGATCCACCACATGCTCCATTTGCAATGAGAAATGTCTATCCAGCGAGGCGT
TTCCTCCTTACCTTCCCCCAAAACCTGGATTTTTCCCCATAAACCCCACATTCTGAAGGTAGAAGTGAGTTCCCT
GCAGGGCTGATTCTGCCTTCAAATGAGCCTGCTACTGAACATCCAGAACCACAGCAAGAAACCTGACAATATTTT
TGCTCTCTTCAAAAGTAATTTTGACTGATCTCATTTTCAGTTTAAGTAACTGCTGTTACTTAAGTGATTACACTT
TTGCTCCCACTGAAGCTTAATGGAATTATAATTCTCAGGATAGTGTTTTCTAAATAAAGATGATTTAAATATGAA
TCTTATGAGTAAATTATTTCCATTTTATGTTATTCTGGATAGTATAACTATTTTAATTTGATAAACTAATCCACG
ATTATATAAACAATAATGGGAGTTTTATATATGTAATCTTGCAGGTAGGGAGGCTTTAAATTATAAAGGTTGTGT
CTTTATGCCAAGAACTGTATTAACTGTGGTTGTAGACAAATGTGAAAGTAATTTTATGCTTCATTAAATAAATTT
TAGTTGATTTTTTTTAAAAAAAGAAAATGGTTAATCTATCATTTAGGTGCATCATCAGTTGTTTAACCATTCTC
TCTTACTGAACATTGGGTTGTTTAAAAAGTGTTGTTATTTTTGAATCATGGTTCAGTGAACAATTTTGGACACAT
AACTTTTTATCTGATGAGTTATTTCCTAAGGATCCAGCTCAGAAACTCAGCACATAAACCTAATAAGAAAAAAAC
AATTTGAAGTGGCTAACCTCTTATCCCAATAAAAATGTTGTATTTATGTTTGGATTTAGATGCCTTTCAGTGGTC
ATACCTTCACCTAACTTTTATGGATTCTACTTTTAACATGTAGAGTGACTGTTTAAATCACCTAAACTCACTGAG
TTTTAAGTTCCTTTTTATTCAACAAGACTGGATTGTATGTTCCAGCTCCTCAAACTTAGTTACCAACCACCATCC
TAGAGAAGTGAATTCACATGAGGCCTGTCCAGAAGAACAATCTCCCTTTCAGTGTCCTCATGCATGCAGTGACCA
GAGACCAACCTTGATAAATTATGGAAAAGTACAGCACATTCTGGAAGAGCCATGAAAGATCCAGATCATCTGGT
GCTGGATAAGAATATTAATGGACAGGCTGGGCGCGGTGGCTCACGCCTGTAATCCTAGCACTTTGGGAGGCCGAG
GCGGGCGGAACATGAGGTCAGGAGATCGAGACCATCCTGGCTAACACGGTGAAACCCCGTCTCTACTGAAAATAC
AAAAAATTAGCCGGGCATGGTGGCGGGCGCCTGTAGTCCCAGCTACACGAGAGGCTGAGGCAGGAGAATGGCGTG
AACCCGGGAGGCAGAGCTTGTAGTGAGCCCAGATGGCGCCATTGCACTTCAGCCTGGGCGACAGAGTGAGACTCC
GTTTCAAAAAAAAAAAAAAAAGAATATTAATGGACAAAAAGATTAATGAAAGAACATATTGAAGCATCCAATTAC
CTGGTGTCTGCTCAAATGAGGAATCGGTGAGATAGGTCAGTTAGCAGTCAAGATTTATAAAAGAGACGATGGCCT
TGGGAGGGGCTGCCCTACTCGACTTTTTAATGGCTAGAAGCTATTAAGGGCTAAGCCAGAACCCTTCAGTATGGT
```

-continued

```
TCAGTGAGGATCCCAATTTGGGGTCCAAAAGTAAATGACAACTCCCAGGAACCATTAAGAATAAAAATCATGGAG

CATTACTGAGAATTTATGTTATCTAAGTCTGAGGAAAATTAATGTTAAGGAAGCTTTCAAAAGTCTAATATTTAC

ACCGAATTCCAGGGCACCATGCTCTAAGACAAAGCACTCTGGTCCTGCCCCTCTCCTTTCCTCATGTTTTTTGGT

TCTTGGGATCCTTAAGGGTCAATGTTATTCTTAAAATACAGAGCATCCTGGAAACTAAAAAAGTGGAAGATATTC

AAATTCTAATGAATGTACTGGCAGTATTGTAGATCATGGAGTATAACATAAAGACAAGAATCCCTAGCCTCTTCC

ACCATACTTTGTAATGGTAAGGAGAAAGGATAGAATTTTGAGAAGTCTGGGAAGACAATGTATGATAACATCTGG

AGAAGCTCTGCATAAGTTACTTTTGTTCAGGCTTAAGAAAAATTCTAGCTTGCCCCTGCACTGTCATCAGGTATC

ATGAAAGTAAAAAAACCTTTAAAGATTCTTCAAGCCAGCAGACTTCTATCTTTCTCTATACTATCCTGTGATCCT

AAACTCTTAACAGTTACTACGTATAATTTCCCTACATTTGCTACTAGTATTTTATCATACACAATATTACACTCA

ATATTTCAAAAGTGGATGATTCATCTCCCGAAGAGACTGCAAAATTCATGAGTTAAGATTTGAGAATACTATTTT

AGACAAGATTTAGTCAGATTTTAGAGAGTTAGAAACCTGTAACAATTCTCTAACAATACTGCTTCTCCTTTTGTG

TATTAAGGAATTTTTGTCTATCAAAGATAGTACGAGGTAGACCAGAAGTAACTTGCCTTCAAAATGTCTGGAAT

GTAAAATGGCAACAGTAGTATTTGGGGACTTCGTAGGGGATGGCCAATATACACCCATTCTTAGAGGTACTGATG

ATATAATGTATAAGACAAAATCAAGTGGTCTCCATCACCATATAATGTTTAAAATGGCAAAGAGGGAGCAGAACA

AACACCCTTTGCAAATCTCTTCATAGAATCTACCGTAATAAACTTGTACTTGCTTAAAGTGTGTCTCTTCAGTGG

TCTTATTACCACTACTTTGGGGAAAATGAGGCTGCTTAAAAGATTAACAGACATTACATTTTACATATCTGTGGC

AGAGAAAACACTATGTATTCACCAAACCACTTCTTTTCCTTCCCAGTCACTCGGGAAGAGGTCATTTCTTTGTCC

CCTTTCATCTAATTGAGGTGCCGTGACTACTTCTAGACAGGCAATGTGAGCAGAAGGTATGCACGCCACGTATAG

GCCTGGTCTTCAAAAATCCCTCAGATATGATCTTCTTCTCGTCTCTTTCATGGACAAACTACAGGCCATGTAA

TAAGGATGGTGGGGTTCCAAACTGAAAGAGCCTGGATTTCTGATTTACTGTTTTGAGAAGAGTTCACCAGGGAAA

CAGCCTGGAAATACGCACAGGAAAATATGCACAGGACCCTGTGTGAGCAAGATATAAAGATCTATTACATGGTGC

CATTAAGGTGAGAGTATTGTGCTTATAGTATCCAGCATTAATTATCCTCACTACTACAACTTCTTTGTATCCATC

ATGTGGAAAAGTAGAGTATTTAATAAATGATTATTGAGTTTATTACCTTTTTTATATTCCAATCATTGCTAATTG

TACGTTACCTCATTTCAAGGTAAAGGTGACCAAGGGCTAAAGCAGTGCTATCCAAACCAAGCCAGACATCAAAAT

CACACAAAACCTTTTGAAAATACAACTTTGAAGATGCCATTCACATAGATATTTATTCAGTGGGTTTTCAAATGG

AACCCTGGAATCTACAGTCTTTAACAAGGCTTCCCAAGTTATTCTGATATACAGCAGGCAAATCTGAGAACCACT

GGACAAGAAGAAAATAAAGGCTATATCTTTCGACAACAAAGACAATGCCTTAAACATAGAATGTATTCAATTAAA

GCTTGTAGAAAGATAGGTTTGTGAACAGGCACAGGGACTAGCCTCGAGCAAATTAATAAGGGCAGCAATGTTTTT

CACTGAAACCATTATTCCCCCTATTTTATTTCTTCTGGGGCTCTGTGTTTCCTTTCTCCTATCAAAATCCATTCT

AAGGTTGGAGGTTGGGGGTATCTCTTGCCTACTCCATACAGCAAGGAATAAAATTAGTATTTCTCGAACTATCTG

TGACAGCAGACCCATTGTAGGCCAGTACTTTTGTAAAATGCAATAAAAATTAACTTCTAGAGAATGAAATTTTAA

AATCACAGACATTCAAAATACAAATTCCAATTTTTTTATTATTAACTGTAAGAAATTTAAAATTAAATCTCAATA

AATAAAATTAAAGCAAACATAAGATAGAAAAAAATAAGCATTATGGATTGGCCCAGTCTGCAAACTGTATACACT

TTGCCAAACATGGGCATAAATTACTAAGAAGCAAATCTTCCATCTGTAAACATTTCCATTTCCATTGACAATAT

GTGTGAGGGAAAGGAGGGATGCTTCTGTTTTAGAATGCCAGGCGTCAGCTAACAAGTGACAAATACGTATTGAGA

CTGAGATCTCCCCAGCCTCTCAGTAGTCAGCAAGAACATGTTGAGGCCTCTGTTTTTGACTAAAAAATTGGCCAG

TGCATGGGCAACATGCATAGGTCCTGAATGAAAAAAATAGCAGCAGCAGAAATTTAAAAGAATTTTCACAGCTAG

GCCACAGTAAATTCTCAAGCCCTTCATCAGAAGCCACTGTGGGGCCTCATTTATGCCTTTGTTTTTATTAAATTG

GATGTGATCTTAAGATTCTTCTGTCAAAATTCCACTAGCATGTGAAGGCACCAAAAGTTTAAAATGTAAAATTAA

CCCAAGTTAAGCTATTCCATTATTAAGCAATAGCAGATATATTTGTTATTATATGAGAAGAAAGTTAACAGGGAG
```

-continued

```
CTAAGATTGATGTTACTGATAAGAAACAGAAACAAGACTTTAAAATTAAATAAATGAATTATTTATTTAATAAGA

ACCAATTGACAGATTCTCGATAAAGACTGTAAGATGTCTTAAAACATTAGGTGTATGGAGATAACATTTGTAACT

TTGACAATTTATATGATGAGAAAAATCAAGGAATGTTATTGTTTATTGGCAGAGTTCTAGAATTACAATTCCATC

ATTCTGTTTTGGGGAAGTTTCCCTTGAAGTAAATGATAACAGGGCTTGAAATAGTACACCTCAGCATTTTGTTTA

TAAAACTGTGGAATAGGTAAGGTTTGTATTGTAACTGAACCCAGGTTCAGCTGCTTGCTGCTCTAAAGCTAGACA

TAAGAGAGGAAGGTTGGTGGGAGGAAAAGCGATTTTAATCGGAGAAGCAGCAAACCAAGAAGATGGTGAACAATA

GTCACAGAACCATCTTAAATTTTAAAATTTACCATAGAGTGTTCAAAGGAAAACTTGGTATGGGAGGCATGCAGG

AGGGGTGCAGGGGGCGGGGTCTGTGTGTCTTGTTCCAATGGCTATCTCAGATAGTCACCCATCTGGAGGTCTAGT

TGGTATTATTTTGAATTCAGCCCAGTGGTGGTGGACTGTCAGTGACTCCTCGCTAAGCAGGAGGATTCTGCACTC

AGGGCTCCATGCATGGTTTGTTTCAAGATTGGCCTCTGGAATTTCTCAAGCAAGAACATAATTAAATAAGCAGGC

ATTGCCAGAGGGGAGTGTCTGGAAAGGAAAGGAATGAAGAGATGAAAGGAAAGTGGGTGGTTAAACTATATTTTT

AAAACTGAGGTTCCCAGTTATAGTATGTTTCGCACGCTCCCCCCATTTTAGCACCCCTGACAGAATTTAGTAATC

TCCTCATCTTGTCCTCTACTTCAGGTCCCCTATCTGTCCTTGTACTCTCCAGGGTTTCCTTTTCTTCTTCACGAC

CTTCCTTCCCTGCAATTTTATAAGCTATTCCTATCCCAGTGATTTAGTTTCAGCTTATAAAACTGTGTCTTTGCC

ATTGTAATCAAATTGAAGGGCCTCTGCTTCATGGTTGGATTCTGTGACCAGGAGACTCTTACGAGGAGTTGGCCA

GGTCTCTGTTAGGAAAGCAAAAAGAACAATGGAGGCAATTATCCCATTGATTTCAGCTATAAATCCTATTTTGC

CTGAATTGTCTGAACGATGAGTATTCTGTGAAATGCTGCTCTCTAGTGCAATAGAACTGCAAATAATGCACATC

TATTTCTTATAATCTCATCCAACATACCCACAGAGATTCAGATCTAACAAAACAGAGGTGATTTGGTTATTGAAT

CATAATATAAATATGGGGAAGAGGAGGGAAATTTCAAGCCTGAGGAAACTGTAGTAGGAGTAAGTATGCTGTGTT

TAAGAGGTCACAGATAAAATTAATATTACCAATCCATCAATAGGCAATTACTAATAGCTTACTACACACACAGGA

ATAAAATGTGAAGACAGAGGAAGTGTAAAATGGAGCCGCCAACTCTACGGAGTTGTTTGCAATTTGGTCTGGTAG

AAAGCTATGAAATAAGGAAGTACATGATTGAGAGCTAGAGAATGTGGCACAGGCTCTGAACCCGGACCGTTCAAT

GTAGTAAGCTCTAGCCACACTGGACACTTGCAATGTGGCTTGTCCAAACTGACATGTGCTTTAAGTATAAAATAT

AATCCAGATTTCTAAGACTTCAAAAAAAATGGAAATATCTCATTAATAATCTTAAGTTTATTACAGGTAGAAATG

ATAGATTAAATAAACTATATTGTCAAAATTCATTTGATCTGTTTCTACAGTATAACAAACTTACTTGTGTGGTTT

GCATTTTATTTCTACTGGATAACATGGCTTTAAAAATGGTATTTTAGAGGAAGGAAAGCTTGGTAGAGAATGGAC

TAATCCGGATCCCTGGAAGAAATGGACCTTGAATGGGTCTTGATGACTTGGAGAGGCAGAGAGAGAAAAAGAAAA

GTCAAACATAGGGAATTGGTTGATAAAATGAAGGTGAGGGGAGAAGGAACAGAGGGAGGAGAAGATCCAGTTTGA

GGGATATTACAGCGAGCAGCCTGAGAAAGAAGGATAAGAAAGGAGAGAAAAAATGCAAGGGAAGTAACCCTTCAA

AGCCAGTCAGAAGTTTCTGGGTTCCTCAGCAGCCAGAAAAGAAGCCGTTGAAAAGATCTGAGTAACGGAGATTCT

GGACGAAAACTGAAGTTATGGAAGGGAAGTTTAGACATGGGTTATTAAACGCTTTAGCGCATTAGAAGTTTCTTA

TGTAATCACTAAATTCAGATCCTGAAATAATGCCACAAGAACTATACAGCTCAGCCACCCAATTCAATAAGAAGT

TACAGCACAGTCTCACACATATCCAATTAACCTTGGCCTTTAGTCAACATCTGGGTTCTTTTTGTCATTTTCAAA

TACTATCACCCAGAGGTGCTATGATTTATATTGGGGAGGGGATTAAAAGAAAATAAGTAAGTTGGTGATAAGAAA

AAGCTTTCAGATGATTCCATCTGAATTAACAGCCCTCTTTAGTTGTCTAGGAAAGAGGATGCTTTTTCTTGAAAG

TGCTTTGAAATGATGATGTGCTTGTTAGTAAACATCAATTATTTTCAAATCGTAATGTTTGCAAGTTTGTCTTCC

TGTAGCTCACCCTTTATGTAGGTCCAGAATATGATTGTCACAAATATCTGGGTGAGCAAGACTATGAAATGTGGT

CATAAAGTAAGTGATTATTTCTAAACTCATCTTTGTCACTCGTAGTGCTTCACAAAGCACCTTTTCCTGGACTAC

AATTCATTTTAATTGATCCCATCAGCACTATATCTGTATCCTGAGTGACTTCACAATACCCTCTATTTCAAGAGA

AACCAATCAGGTTATGGGTTTGTTAGTAATAAAAATTACCAAGGAGCAGTTTGTGGATGGTAAAAGCAATGCAAA

TTCTAAAGAGAAGTCATAAGAGCAATAATAAGCATCCTCCTCACTTCTTGGAAGTGAACAATTCCAAGCTCCCTG
```

-continued

```
AAGCAACACTTAACCTATCATATTAAACAGTAATGGACAAATATTAGAAATGTTGATGTCAGCTTTCAGAATCTG

TGGGCATCAAAACATCACTTAAGTTCTCCGAAGTATTCTCTGTCAAGTTTCCTTCTACAGTATTCTTTTCCTACT

AGGACAGAGCCTTAAGCCCTAGAAGAATAATTTTGCTTGTGTGTTAATTATTTGTTTACTGGTTCATTCCAGAGT

GTGAGCTGGAAAAAGGGGGAAGTGTCATAAATAGTTTTTTATGGCCCATGGTTTTTCAACTACGTCACTATTGGT

AGCAGTTTCCACTGCAGGATCTATTTGCAAAGCCTAGGAAATTAGCATTAAGCAAGCTGCTAGGAAGACTTCAAC

AGTAACTAGGCCACAGGCCTCACACATTTTTCCTCCACCCCAGCCTCCTCTGGAGAGTACTTGCTAAACCTCTGT

GACACATAATGAAGCAAAGAAAGTGATAGAACAACAGAATTACACGGGCAGATCCTTGTTTCTTCTTCTCTCTCT

AAAGAATTCCTTGGACTGAAAAGCAGTTTATTTTGGAGGAGTGAGAAAGTGGTGACAGAATTAGAAGGGCCTGGG

AGGGCTTCATTTTAGGAGACAGTTTTAGGCTGAAAAGAGATTTCATGAGTGTGATTTACCTGAGGTGACTTTTGG

GGGCTCTTATAAAAAGGAAGTTCATGCTGAATGGGAGGTGGCTTCTGAGATGCAGATTCTGGTGAGCTAAGAGGG

CTCGGTAAAGAGGAGGCAGGAGTTAAGTAGCGTGAACTATGCAGTAGCAGCCTTCTTCCCCCCTTGCTTGGGGCA

GGTCATCACAACCCTTCTCAATAAAGGGGTCCAGGAACCACTAGGAATAAATGGGCATTTGCACTTCAGGTGAAA

CCCATTTGTCATAACTGCTTGGACTTTAAGCTTACAAATAAAAGAACCACATATTTCCCTTTGCAGCTTGATTT

AGTTAATGTCATTTTGAGAAAGAAAGAAGACATTGTTATCCCGTCCCTTTTTTTTTTTTTTTTTTTTTATGA

AGAGACTGGGACTCAGAGAAGTCAAGTGATTTTCCCAGAACCAGAAAACACAGAAGTAGCAGAGCTGAGATGACT

ACTCCGGTCTTCTGATTCCAAATTCCAAATTCATTCTTCTAAGCGATTTCCCAAAACGGGAAATGGGTTTATCTT

CTATTTATGGGAAGTGATAGTGGTATTCTATTTAGAGAACTTATATAAAATCTTACTTTAAAATAAATAATATTT

CAAAAAGTAAGCTTAATTTAAAGAAAATAATCAAGAAAGTCTGGTATATTTTTACAAATATACCAAATGACCTTG

CTCTAAAATACATCTACTTTCCAGCAAGCCAAAGTGAAACAATTTGAAATAAGTGGCATTTACTGACCACTCCCT

AAAGTTCACACAAAGAGGTAGTACTCTAACTTAAATATACAAGGTGAAGAAATAGCTTACTCAGCCTGTTGGGC

TTCCTCTTCTACACTCTTGGGAAATGCCCTCCGTGTTAACCAAGAATTCTCAGGCCTTGGAGGGAGTTTTCCATT

CTCAGTAAACTGAGATTGCAGTTGCGGAAATTAAGAGGTATCTGTCCAGCACTTCATTCCCTTAAGGTCAGGATC

TGTGCTTTTAATAATGACAATTAGCTAACATATACAATTAAGCCATGCAAATGAAGTAAGAGAAAGCTAGAGGAG

AAATTCAGGAGCCAGTTGCCTTTTCCAGACATCTTGTACAAATAGTGTTCAAAGGACTAATTCAAAAGATGGGAT

TCTTCGCTTGAACCCAGGAGGTGGAGTTTGCAGTGAGCGGAGATCGCTCCACTGCACTCCAGCCTGGGTGACAAA

GTGAGACCCCATCCAAAAAAAAAAAAAAAAAAAAAAAAAAAAAAGATGGGATTCTTTTTTAAAAAATAAATTTTACT

GCGTATTTTTAAGGTATACAACGTGATGTTATAAGATGGATATAGATAGTGAAAAGGTAACTGTAGTGAAGCAAA

TTAACATATTCATCATCTCACATAGTTATCTTTTATTTGTTTTGTTTTGATGGGATTTTTAAGATAGTAGAAAGG

AATGGTAGACAATAAACATTTGAGGGAAAGTGGGGCTTTGTAGAACTCCTAAAATGACAGCACGCACAAATGTCC

CCATTATGTCTAAAGGGTAACTCGTTCCTACTTCTAGGGACAGCTGAGGGACATCAATGTAAATTTCTAAATGAC

TTCCTGAACTTTTTATTTTTATTTTTTGTATTTTTAGAGGAAATTATAATAACATCAAGCCACCTCTGGACCATA

TCGCTGCTGATATCATCAGCAAATGGCACTATTCCTAAATCCTAAGATGCACTTTTCCCTTCACATTTCAACATT

TGTGAAACTCGATTGTACCTACACCTGATTTTATATACAATGCAGCCTTTCCTTTTCTTCTGTCATTGCATCTTA

CGCCTGATTTCTCCTTGGAATTGAGTAAATATAATGCTTACATGTGTTAATAAGAATTGAGGTCACTCATAATTT

TTGAAATATGCCACCAAATATAAGCCTTTCTACATATTGTTGACTTTGAAGTCATTTCTTTTTTTAACTACTAAA

CAATAACACTTTTTGTTGAGAAAAATTGCATATGAACAAGAGACCAAGCAGGTAGAGAGAAAAAAACTTTTAATA

ATCAAGAGAATGTTACTGTGTCCCAAAGGCTAAAGTCACCTTACTATCAAGAGAGAAGGACAGGAACAGAGAGAA

CCAGGTAAATTACGAATTGAAAATTCCATGGTTCATTTATCTTTATTTTTAATAATTCCATTTGTGTGATTGTGT

TGACCACAAGGTCATAAGTTACTCTTCATACTGACTTCTCATGTAAATTATAAATAAGTTTTTTATGCTAATGAT

TTATGGAGTAAGCTATTCATCTTTCCGACAGAGAGTTACCTACAAAGAAATAATTATTCTACCTCTGAGATGAAA
```

```
TATCATGAAAGGAGTGGTTTCCAGATATTTTGACTTTAAAAGCTTAAAGAATATATGTAGTTATAAAATTCTAAA
GCAGGCAAAATTAATCCTTTTAGCAATCAAGATAGCGGCTACTTTTGGTGAGAAGGACAAGGTAGTGATAGAGAA
GGGGCTCAGGGGTCTTTCCTGAAGACAGTGAGGTGGGCAATGGTATTTTCCTTGACCTGGATGGTGATTAAACAG
ATGTGTTTACTTTGTGATAATTGACTAGGCTGTGCACCTATGAACTGCATACTTTTCCATATATGTACTGTATTC
TTATACTTAAAAAGAAGTTTAAAAATAAATGCAACAGATATAGGACTTCCTATATTACTCGTTGACCAAAAAAT
GGATTCATTTTTCTTTCAGGTAAAACGTACTAGTGGTTTTAATATTATATTGACCAGGGAGTAAATGTTTACCTT
AGGAACCTTAATCTTGATGTTCTCCAAAGTCATTATCTGTTCTTTCTGATTATCAGAATAGAGTATATCTCTATA
TAAATGAAAATTTCTGGTCATTCTCAAAAAATAACACTAAGCATGAAAATCAGAAATATTGATCTTGTTTTGTAA
TGATGTTTCTATTGATGTGAAGTAGTTTCTAGTAGAGTTGCTGTCCTAACACACAAATGAAATTGCACTGTTTGG
AAGACACAACTGTGAATGACTTGCTTCAGTAAGGAATTTCCAACATGATGGTTTAGGGATAGAGGTGCTCGATTC
CTCTGTCTCCGGTTACCCAGGTTATTGAGGACAGGGAGGTCAATAAGTAATGCCCTCCTCCCACCCATAGCACAA
AACAGAGCGGGGTTCAGAGAATAGGTAAGGCTTTGGCCAGGGTGTTGAGGAGACTTACATCCCTGGGAACCAGTC
AGAATGGGGGCGCTGAAAACAATGTTTTAAATTCTAGCACCCAGCAACATATGTGTGAAGATTAAATGTACTCGT
GCTAAATTCACTTGCTCCATTACTGAATTTGGGTGGTGTCTGTTAAAGATGGGAACAAAGGCATTCAGGTCCTGG
TATCTTCTACCACTCCCAGCATGAACAGACTCATGTCAGTGGGTAAGGGATGGTATTTCCCGAGAAGGCTTTGAA
CTCTTGTAGTGGGTCAAATAATGGCCCCCCACTTAAAAATGTTCATGTCCAAATCCCTGGAAGCTGTGAAAAGGG
GTTTTTGCACATGTAATTAAGTCAAAGATATTGAAATTAGATCATCCTGGATTACATAGGTGGGCCCTACATTTA
ATGACAAGTATCCTCATAACAGAAGAGGAGAAGGTGATGTGAGATTTGGAGCAGCAGAGATTGGAGTGATGTGGC
CACCAATCAAGGAAACCAAGGACTTCCAGCAGCCACCAGAAGCTGGAAGAGGCAAGGAAGGACTCTTCCCTAAAG
CCTTTAAAGGAGCACAGCCCTACTAACACCTTGCTTTTGGGCTCTGGCCCGCAAAACTGTGAAAGGATACATTGC
TGTTATTTGAAGCCACAGTTCGTAGTAAATTTATTACAGCAGCCCTAGAAACTGATACAACTCCTAAATACACCC
TTAGCAACACTGCTCAACAAGAAGTAGGCAATTTCCTCCTGACTGAAAAATACTGATACTGTTATGGGATCCTTG
GGGGTGTTGCTTTTCTGTCCAGAAACCTCTGTGGCGGTGGCACCTTTGCATGAGTTTTGCTCGGGTCCACTGGGC
CCACTCATCCTGGCAGGCTGCGCTCAGCTGACACTACTGGCGTGGATCCCATGCCTCCAAAGAGACTGGAGCGAA
GCGGTGAGGGATGTGTGAGGAAGTGAGCGTGGGGTCTGGCACACAGTCAGGCTCAATGGCTGCTACAGCGGGATG
GGCAGCTTCAGGTGCTGGCACGGGTGCTGGCTCACTGCAAGGCTGTGGCTGCACCAAGCAGCGCAGCAACGGAAC
GCATTGGTGCCTGGAAACTTGGAGACTCCAGGAACCTCAGGGCTCCAAAAGGCAAATCACAGCCCTAGCTTCGGG
AGCTCCCAGGTCTGGGCTGCCAAAGGGCTGCAGCTCTTCTCTCCTCTCTCTCTTCGCTCCTCTCCCTTTCTCT
CTTCACTCCTCCCTCTTTCTCTCTTCACTCCTCCTGTCGCCTATGAACAGCGAATTCAACCTTCCAGTTTTCAGA
CTAGGAATGCTGGAGTTGTCCTTGATTACTCTGAATTGTTCACTCCGCATATGGGCACTGAGGATACGTTGATGA
ACTACACAGACAAAAAGGATAGAAATTCCTGTCAAGACTACATTCAATAGGGATGAAGCAGGCAATAATGAATAA
ACATACTAAGTTGAATATGACTATTTAAATATATATAACACATATGACTTGTATAATGTTAAATATTTTAAGTTT
TTTAAATTCTTCCCTTCATAGATTTTACATTATAGTAGAAGAGGCATTTTTGTTGTTGTTCTTTTTGTTTTGGAT
TCAGAGGGTAAATGTGCGGGGTTGTTACATGGGTATATTGCATAATGCTGATGATGGTCCCATCACCCAGGTGGT
AAACATAGTACGTAATAGGTGAATTTTTAGCCCGTGCTTCCCTCTCCCATCTAGTCGTCCTGAGTGTTTATCGTT
GCTACGTTTATGTCAATGTGTATTCAATATTTAGCTCCCACTTATAATTGAGAATATGCAGTATTTCGTTTTTTG
TTCTCGTGTTAATTTGTTTAGGATAATGGCCTACAAAGAACATGATTTCATTATTTTTATGGACATGTAGTATTT
CATGGTGTATATGTACCACGGTTTCTTTATACAATCCCACTGTTGATGGGCACCTAGGTTGATTCTATTGCTGTT
GTGAATAGGGCTGCAATGAACATACAAGTGCATGTATCTTTTTGGTAACAAAAATTTTATATTTGGATTACCCAG
TAGAATTGCTGGGTTGAATAATAGTTTTGGTTTAAGTTCTCTGAGAAATCTCCAAACTGCTTTCCACAGTAGCTG
AACTAATTTACATTTCCACTAGCAGTGTATAAGCGTTCTCTTTTCTCCACAATCTTTTCACCAGCATCTGTTATG
```

-continued

```
TTTTGGCTTTTTAATAGCCTTTTGATGACTGTGAAATGGTATCTCACTGTGGTTTGGATTTCCATTTCTCTAATG

ATTAGTGAATGTTGAGCATTTTTTTCATATGTTTATTGGCCGTTTGTATGTCTTCTTTTGATAAGCGTCTGTTCA

TGTCCTTTACACATTTTCAATTAAAATATTTGTTTTTTGCTTGCTGATTTAAGTTCTTTGTATATTCTGGAAATT

AGATCTTTGTCAGATGCATAGTTTGCAAATATTTTCTCCCATTCTGTAGCCTGTTTACTCTGTTGGTAATTTCTT

TTGCTGTACAGAAACTCTTTAATTAGGTCCCACTTGCCTATTTTTAGTTTTGTTGCAATTATTCTCTGGAACTTA

GCCATAAATTGTTTGCCAAAGCCAACGTGGAGAAGGATATTTTCTAGGTTTTCTTCTAGGATTTATAGTTTAAG

TTTTACATTTAAATCTTTAATCCATCTTGAGTTAATTTTTGTATATGTTGAGAAGCAGGAGTCTAATTTCATTCT

TCTGCATAGGGCTAGCCATTATCTTGGCACCATTTATTGAATAGAGAGTCCTTTCCTTATTGCTTATTTCTGTCA

ATTTTGTTGAATATCAGATCGTCGTAGGTGTATGGGTCCATTTCTGGGTTTTCTATTCTGTTCTATTTGTCTCTG

TGTCTGTTTTTGTACCAGAACCATGCTGCTTGGTTACTGTAGCCTTTTAGTATAGTTTGAAGTTGGGTAATGTGA

TGTCTCTGGCTTCGTTCTTTTGCTTAGGATTGCTTTGGCTATTCAGGCTCCTTTTTGGTTCCATATGAATTTTA

GAATATTTTCTGATTCTGTGAAAAATGACTTGATATTTTGCTAGGGATAGCATTGGAGTGGTAACTTGCTTTGG

ACAGTGTGGCCATTTTAATGATATTGATTATTCCAATCCATGAGCATGGAGTATTTTTATATTTATTCAGTCATC

TTGATTTCTTTCAGCAGTGTTTTGTAGTTCACCCTGTAGAACATTTCACTTCCATGGTTAGATGTATTCCTATTT

TGTGGCTATTGTAAATGGCATTGTATTTTTTTTATTTGGCCCTAAACTAGAATGTTATTGGTGTATAGAATTGC

TACTGATTTTGTACATTGATTTTGTATCCTTAAACTTTACTGAAGTTATTTATCAGTTCTAGGAGACTTTTGGA

GAAGTCTTTAGGGTTTTCTATGTATGAAATCATATCATCAGCAAAGAGAGACAGTTTGACTTCTTCTTCTTTTTG

GATGCCATTTATTTCTTTCTCTTGCCTAGTTGCTCTGACTAGGACTTCCAGGGCAATGCTGAATAGGAGTGGTGA

GAGTGGGCATCCTTGTCTTGTTCCAGTACTCAAGAGAAATGCTTCCAGCATTTACCTGTTTAGTATGATGTTGGC

TGTGGTTTGTCATAGGTGGATCTTATTATTCTAAGGTATATTCCTTTGATGCCTAGCCTGTCGAGGGTTTTTAAT

CATGAATGGATATTGAATTTTATTGAAGGTTTTTTCTGAAACTATTGAGATGATCATATGGTTTTTGTTTTTTCA

TTCTGTTTATGTGGTGAATCACACTTATTGATTTGTTATGTTGAACCAGCCTTGCATCCCAGGAATAAAGCCTAC

TTGATTGTTGTGAATTAACTTTTTGATGTGCTTCTTGATTTAGTTTGCTCATATTTTGTTGAGGATTTTCGTGTT

TATGTTAATCAGAGATATTGTCCTGAAGTTTTCTTTTTTCATTGTGTCTCTGGCAGATTTTGATATCAGGATGAT

GCTGGCATTGTAGAATGAGTTAGGGAGGAGCCCCTCTCCTTAATATTATGGAATAGTTTCAGTAAGATTACTATC

AGTTCTTCTTTGTATGCTTGGTAGAATTCAGTGTGAATCCATCTGGTCCAGGGCTAAATTTGGTTGGTAGGTTT

TTATTACTGATTCAATTTTGGAACTTTGTTATAGGTCTGTTCAAGTTTTCACTTCCGTCCTGGTTCAATCTTGGG

AGGTTGTATGTTTCCAGGAATTTATCCATTTCCTCTAGATTTCCTACTTTGTGTGCATAGAGGTGTTCATAACGG

TCTCTGAAAATCTTTGGCATTTCTGTGGGATTGGTCGTAATGTCATTTTTGTCATTTCTTGTGCTTTTTGGAACT

TCTGTCTGTTTTTCCTCGTTTTTCTAGCTAGCAGTCTATTAGTCTTGTTTATTCTTATGAAAAACCAACTCTTTG

TTTCACTAACATTTTATGGACTTTTGCATCTCAATTTTATTTAGTCATTATCTGATTTTAGTTATGTCTTTTCCT

CTGCTAGCTGTGAGATTGAATTGTGCTCTTTTTTTCTAGTTCCTCTAGTGTTATGTTAGATTGTTTAGTTGAGAT

CTTTCTAACCTCTTGATGAAGGCATTTTAGCACTATAAACTTTCCTCTTAACACTGCTTTTGCTACATCCCAAAG

ATTTTGGAAAGTTGTGTCTCTATTTTCATTAATTTCAAATAATTTTTTGATTTCTGCCTTAATTTCATTGTTCAC

CCAACAGTTATTCGGGAGCATGTGGCTTAATTTCCATGCTTTTGTGTAGTTTTGAGAGATCTTCTTGGTATTGAT

TTCTATTGTTATTTCACTATGATTTGAGAGTGGCCTTTGTATGATTTTAATTTTTTTAATTTATTGAGACTTGC

TTTATGACTGAGCATGTGGGCAATCTTAGAATACGTTCCATGTGCATATGAGAAGAATGTGTGTTCTGTCATTG

TTGGCTTGAGTATCCTAGAGAGGTCTATTAGGTCCAACTGGTCAAGTGTCAAGTTTAATTCCAGAATTCCTTCGT

CAGTTTTCTGCCTCAGTGATCTGTCTAATGCTATCAGTGGAGTGATAAAGCCCCCACTAATATTGTGCTGCCATC

TACGTTTTATTGTAGGCCAATAATTTGTTTTATGAATCTGAGTGCTCCAGTGTTGGGTGCATATATGTTTAGAAT
```

-continued

```
AGTTAAGTCTTTTTGTTCAATTGAACCTTTTATCATTTTATAATGCCCTTCTTTGTCCTTCCTGATTGTTGTTGG
TTTAAAGTATGTTTTAATCTGATTTAAGGGTAGCAACTCCTGCTCTTTTTTGTTTTTCATTTGCATGGTAGATCT
TTCTTCATTCTTTCACTTTGAGCCTGTGAGTGTCATTCATGTAGGATGCATCTTCTGAAAACAGCAGACAGTTGT
GTCTTGTCTTTTTATCCAGCTTACCACTTTATGCATTTTAAAGGGAGAGTGTAGACTGTTTACATTTAGGGTTAG
CATTGACATGTGAGATTTTGCTCCTGTCATTGTGTTGTTTAGCTGGTTGTTTTGTAGACTTCATTGTGTAATAAG
TGTATTTTATTGGTAGCAGGTTTCGTCTTTCATTTCCATGTTTAGCAATCACTTACGGATTTCCTGTAAGAATC
ATCTGGTGGTAATGAATCTCCTTGGTGCTTGCTTGTCTGAGAAGGATTGTATTTCTCCTTCACTTATGAAACTCA
GTTTGGTGGGATATGAGTTCTTGGTTGAAATTTATTTTCTTTAATAATGCTGAAAATATAGGCCCCCCCATATCT
TCTGGCTTGTAAGGTTTCTGCTGACAGAACTGTTGCTGGCCTGATGAGGTTCTTTTTGTAGGTGACCTGACCTTT
CTCACTAGCTGCCTTAACAATTTTTTCTTTTGCATTGACCTTGGTGAATCTGATGACTATGTGACTTGGCAATGG
TTGTCTTGTATAGTGTCTCACAGGAGTTCTCTGTATTTCTTGAATTTGTATGCCCACCTCTCTGGTGAGATAGGG
GAAATTTTCATGGACTGCATCCTCAGATGTATGTTCTAAGTTGCTTACTCTCTTTCTCAGGAATGACTGTGAGTC
ATAGACTTGGTCTCTTTACATAACCTCATAAATCTTGAAGGTTTTGTTCATGTTTTAAATTCTTTTTTCTTTATT
TTTGTCCAACCAAGTTGATTCAAATAACTGGTCTTCAAACTCTGAGATTCTTTCCTCAGCTTGGTCTGTTCTGCT
GTTAATGCCTCTGACTATATTATGAAATTTTTGAAGTTGATCCCTCAATTTCTGAAGTTCAGTTTTGTTCTTTCT
TAAAATAGCTATTTCATCTTTAAGCTCTTTGATCATTTTTCTGGATTCCTTGAGTTCCTTGTATTGGGTTTCAAT
GATCTCCTGGATCTTGATGTACTTCCTTGCCATCCAGATTCTGAATTCTATGTATGTCATTTGAGTCATTTTAAT
CTGGTTAAAATCCTTTGCTGGAGGACTTGTGTGTTTGTCTGGAGGTAAGGAGACACCAGCTTTTTTGAATTGCTA
GAGTTCTTGAGATGACTCTTTAACATATGAGGGCTGGTGTTCCATTAACAATAGTGTACATTGAGTATAGTCAGT
TGGCTTCATTCTGAGTGCTTTCAAAGGGCCAAAGCTCTGTACAGCATCTTTATTTGTGGCTAGATTTTGCTTTA
GGTTTCACAGGTGCTGTATATTGGAAAAATGTTTTTGGTGTTGTCATTTGGGGTGCAATCCAGTAGGTGATGCTT
AAGAGTGGTAGCTGGCAGATAGGCTCTTACTCAGTCCACAGCTCTTTTGTATTTTGGTGCAGTCCTCAGTAGTGC
TCTGTGGTGGTAGGGAGAGATGACCCCCTCACCAGATACATTCCTGGGCCTTGGGGGAGCCCTCTCTTATTACTG
GCACTGCACCTGCATTTCATTTATTAGGTGTCCTGGGCTGCAGGGTGCCCTCAGGCAGAGGCTGCGGCTGGAAAA
TAGACCATACCCTTCCCTGGCTGGCCCTGCACAAGGAGGCACACCCTGTTCCTGAGCCAGTCCATGAACCCAGCT
GTCTCACCCCTCTCAGTGTTCTGAGAGTAGGGGATCCCCCACTGCTTGAGCACCATGAGCCCCTCCTGGCTACAG
GCAGTGGGGGTAGGTATAGTCTCTCAACCCACTGTCCAACTGATTTCCAGGGTAACAGAGAGCTGTGCCTGCCCA
CAGAGTTCAGGCAGAGGCCAGGCCATTGTGCTGGAAGCTGATGCTAAGCCTTGTCTGATGATGGGGAGTGAAGCA
ATGTAACGGCTCCCTAACTGTGGCTTCTCTCAGGGCTATGGCAGCTGGCATGAGACTGCTCCAGGTCCAAGGCCT
GTGGGACTTCCTGTGGACTTGAGTTTTGCCTCTGCAAACACTCCAGCAACTCTCTATGTCAGTCTAGAGGCCCAG
GGACACGGATCAGGTATTGGGATGAAGGGGTTCTCCAGTTCCCAGGATTTCACAGGTCCCTGTGGAAAGTGAGGA
TCCCCCAGGGGCTCTCACTCACTCACCCTTTCTCTATGTTGGGGAGCTTCCCCTGGCTCCATGCCCATCTTGGGT
GGCCAGCTGCCCAGCTTCACTCTTCCCTGTTCTCTGTGTCCCCTCACTCCCTTAATTGTCCTGATATCGTTCCTT
AGGTGATCTACTTGCAGAGGCAGTGTTTACTCGCCACTTGTTTTCTCTCTGTGAGAGTAGCACACACTAGCTGCT
ACTCATCTAGCATCTTGAATTCTTCCCATCTGAAAAAGTTTCAACTGCAATCACAGTTAAAGAAATACAAAAACA
ATAGCACCTAAGTTACAACTTCTCACCTATAGAATTCAAAAACATCCAAATGATTAACTAAACATTTTGTTTGGT
AGATCTGTGGGAAAACATGAATTCCTTGTGAATTACTGGAGAAAATGAAAATGATGCAACACTTATGGAAGAAAA
TTTGGGGATTTTTGGGGGGGAGGGGAACAATATATTTAAAACTATAAATGCATTTATCCTAGCAATTCTATGAAT
GGGGATTTATCTTAGGGTACACCTGCACACTTAGGAAATAATGTATGCAGTCATTCATTACAGAATTGTTTGTAA
TAGCAACAACCTGAAAAGCAACTCATATATCCATCCATCACACAGGGACTGGTTTCATGACTACGGTTCATGAAT
ACTCTGCAGCCCTTAGAAAGAATGAGGAAGTGGCCGGGCACGGTGGCTCATGCCTGTAATCCCAGCACTTTGGGA
```

-continued

```
GGCCGAGGCGGGTGGATCACGAGGTCAGGAGATCAAGACCATCCTGGCTAACACGGTGAAACCCCGTCTCTACTA

AAAACAATACAAAAAAATTAGCCAGGCAGGCGCCTATAGTCCCAGCTATTCGGGAGGCTGAGGCCGGAGAATGGC

ATGAACCCGGGAGGCAGAGCTTGCAGTGAGCCGAGATAACGCCACTGCACTCCATCCAGCCTGGGCGACAGAGCG

AGACTCCGTCAAAAAAAAAAAAAAGAGGAAGTTCTCTATGCGCTGACATGGAAGGAAGACAGATGGTTGAATGA

AAAAAGTACATAATTAGCCATAAAGTGTAAGACTTTTTGTCTAAAAAAGAAGGGTGATATAATTGCATATTTATA

TTTTCTTCCATTTATATTAAGAGATAATAAAGGTACACAAATTGGCTAGAATAAAGTGGTTTCCTATAAAGGGTA

AGAGTAATTGAGTGGATGAAGACTAGGGTTAGGGATAGATTTTCAGTTGTATTCATTTTAATATATGTATTCATT

TTATATATGTACTAATTTTTATATATGTATTTATTTTATATTTTGATTTTCTTAACATAAATATATTATTCCTTC

ATAAAATTAAACTTGATACATTTTTGATTACTAGATATGTAGAAAGCATTATGTTCAGTACCACAGTAATACTTT

CAAACCAGCTACAATTAGTATTTATGAGCATCTATGTGCCAGACATTGTGTTCTGCTTTGGTTGGTGGGGGTAGA

GGAGGAAAGGAAACCATGGCTTACATAGGAGTGGAAGTCTTGTCTTTCACTTTGCACCTCTCTCCTTCAGACCTA

GCATAAATATGACCTTAGGGGAGGCAGAACACATATGATAAAGAGATAACTAGCAAGAGACATAATAGTAGCTAA

ATAAATACTGAAGGAAAAATTCAGGAAGAGGTAGGAAGGATATGCCTCATCACTTCCACCTGTTAAGAAAAACTT

TAGACATTCTTGCCAATATTCCTTATTGCCTGTCTTTTGAACAAATGCCATTATCACTAGAGTGAAATGATATTT

CATTGTAGTTTTGATTTGCATTTCTCTCATGATCGGTGATGTTGAGCACCTTTTTATATACCTGTTTGCCATTTG

TATGTCTTCTCTTGAAAAATGTCTATTCAGATCTTTGCCCATTTTTAAATGGCGTAATACATTTTTTCCTATTGA

GTTGTTTGAGTTCTTTATATATTCTGGTTATTAATCCCTTGTCAGATGAATAATTTGCAAATATTTTCTCCCATT

CTGAGGATTACCAGAGGCTCAGAGGGGTAATGGTGGTGGGGGAGAATAAAAATGGTTAATGAGTACAAAAATATA

GATAGGAGTAATAAGATCTAGTATCTGATAGCACAACAGGGTAATTACAGCCAACAAAAATTTTATTGTGCATTT

AAAATAACTAAGAGTATAATTGGAATGTCTGTAACACAAAGAAGCAATAAATGCTTGAGGTGATGTGAGGGGATG

GATATCTAATTTACCTTGATGTGATTATTACATATTGTATGCCTGCATCAAAATAGCTCATGTATCTTATAAGTA

TATACACCTATTATGTACCCATTAAATTTTTTAAGAACTTTAAACAAATCAAATTTAACAGAGTTTAATTGGGCA

AAGAATGATTTGAGGATCAGGCAACCCCCAGAAACAGAAGAGGTTCAAAGCAACTCAGTGCTGTCACATGGTTGG

AGAGGATTTATGGGCAGAAAAGGGAAAGAGAGATACAGAAAATGGAAGTGAGGTACACAAACAGCTGGATTGGTT

ACAGCTTGCCATTTGCGTTATTTGAACATAATCTGAACAGTTGGCTGTCTTTGCTTGACCAAAACTTGGTGTTTG

GTACAAGAGCAGATTACAGTCTATTTACACATCCAGTTAGTTTTACAGTTCACTATACACGAAGAAGAAACCTTA

AGCAGAACTTAAAATATGCAAAGAGGAAGCTTTAAGTTAAACTTAATTTAACACACCCAATTATCAAAAAATGAG

TAGCTCTGCAAAAGTGGATTTTCCTGGTCATCTTTGGTACTTCCTTAAAAAAGAGAAAAGTAGTACTCACGATAA

AAAAAAAAAGTCCTCAAGTCTTTATTTTATTCCTTTCCAATTTAAAATGTTACATCATCTGAGGAAGGTTTTTC

CCTTTGACCGCTTTCATAGACATTTCTTCTGCATGGGTTGGCCAGAATCAGAAGAGTAATTGTAACTTTCTGTTC

TTGTCCTACAGTTACAAAGCGGTTTCACTTTGTAAATGCTCTTTGGATGGCAGGAACCAAGCAGCCATGAAAGA

GGAGTTACACCTTTAAAGGAGTCATTCCATCATGACTCTCAGGACTGGAACATGGAATACCTGAATGGCCTCTTT

GGCACAGATAGGCCACCCTTGAAAGGTGTTCCAAGCTAGGAACTCACTACCACTGTTACATCGATGCAACTCTGT

GAGAAGTTTTATCTGGTGATGGAAAATCTCATCTCTTCAACACACTGACTACTACCAGTCTCAGAACCCTGTAA

ACAAGATTCATTCATCTCAAATTGGGTTAAAGCAGTCACCCTGCCTTACATTAGTTTGGAATAAGGATGTGGGA

TGGTGGTAGAGGAGGGGAGTGGATGATGATTTTTTATTGTTATTTGATTCTAAAGAAACTTCTATACATTTTGC

ATTTAAAATAATTATGTTTTTAACAATGTTTGGATTAATTCAAAATAGGATATTATATCCTATTATATTAAATAT

ACTATTTAATCATCTTGTTGACCAAATGCAACTTAAACATGTAAAATGGTAAATAGCATAATAATTGTCTTCTAA

GCCTGCACTATAAAGTATTTCAGTGGCCTCATTATTAAAGGACCAAGGTGCCCAAAGAAACAAAATTTAGTAATC

ATAAACAAGAGACAAACCTACTTCTTTTCCCCCAGAGTTCTGGCCACATTGAAATAAGGTGTTTGAATGCTTAAT
```

```
AAGAATTATTTTGGCCCACACAGTGGCTCATGCCTGTAATCTCAGCACTTTGGGATGCCAAGGTGAGCAGATCAC

TTGAGGCCAGGAGTTCAAGACCAGCGTGGCCAACGTGGTGAAACCCCATCTCTACTAAAAATACAAAAATTAGCC

CGGTGTGGTGGTACACGCCTATAGTCCCAGCTACTCGGGAGACTGAGGTGGGAGAATCACTTGAACCCGGGAGGC

CAAGGCTGCAATATCGAGATCACACCACTGCACTCTAGCCTGGGCAACAGAGTGAGAGTGAGACTCTTTCTCGGA

AAAAAAAAAAAGAATTATTTTGAACAAAGTGCTGTCACCTAAGTTAGCAAAACTCCAAGCAAGGTTTTTGGCTC

TGTAAGGAAAGAATTAGCCTACTCATTTGGAAATTTAGTGGTGTTTGTAATGCAGAAAGTGACAGTGAGACTGGA

AAGGGATTGGCTTTGGGGCTTGTTCTGCTTTATAAATAATAATGAATCTTCTCCAACATGAAGTAATGTGAATTA

AAAAAAAAAAATCTGTCCTTAGAGTACAAAATTACTTCATAACCCAATCTGCATTTCTCCACTCCAAGCATATTT

TCTGGGAGTTCTACTTAGAGAGTGAAAGCTGCTGTGTGTGTGATAATTAATTTTAACAAACACTTGGCAAACTGA

GCTGGACTATGTATAAGCTACCCTAGACTAAGCATGAATTTGAACTGCACTTTTTATGGTGTTTTTTCCACAATG

ACATTATTTAGGCATTTAAAGTTATCTGAACTGCAATTTTTTGTTCTTTTTTTTTAATTTGACTTTTTAAAAAA

AATTATTCCTGAATAAAGAGGCAGTTTGTAAAAACTCGAGAACTGTGAGAGATAATTGGATCTTTGTGTAGCAAA

ACTAGAAGGGTGTTGGGTATCTGCTCTTTATCAAATGGACCACTTACTTTTCTTTTCTTTTTGCCCTGTGTTCA

GAAAACAAATGTGCGTGTCTCCTGATTTATAATGTATAGTTCATTAATGGAGAAAGTGCTTGAGAATTAGATCCT

AATGTCATTTCCCATGCAGCATCTTCATTCTTTTCTAAAGCACTATTTGGTAAAAACAACTGATAGTCGTCAGAG

GTGATCACCAATGTTTGAGCACTATTTCCTTTTTATATCCTGCACATGGAATATGGACAGGCAAACAAATCATTT

CCAAGTAAGAAAATAAATTTTGAGGGAGTTAATACTATAATTTGAAAGTAATAACCTCCTATTTATCCATCTAGT

TTGTTGTTCTGTACTAAATTATTTGTGCATGTCTCTGTGTCTATAATTTATGTGAAACTTTGCACAATCTTAAAT

AGGACAAAATAGACATTCTGTAATTTCCCAGGCAAGCTATTTAAGGTGACTATCTCTCTACATATTTGAGATGAA

AAACAATAACATGACAATCCATCCCTTCTTAGGTTTTTGTAAGCAGACTTACTACCTGTGACTCAGTTTTGTTCT

CACAGGGTACTAATTAATCCTTCACGATAATAACTTGTCAAATCCATTACTTCTGTAAAGGCAATACTTTTATAT

TTGTTTGTATTCAAATTTTAAACTGATGTTAAATGCCGTGGGTGCAACTGCAGGTTAAAAATATGTGTTTGAATC

TCTTATTCTTTTTGCTTGGCAATGTATGAAATAACTGCTCTTTCTAGAAATCTTGATGATGAAGTGGCCTGTTGT

TTTGTCACCTAAAAATGCAATAATGTTCAAATTAAGCTTTTCTTTATTAACATCACTTGATTGTGTGCCATATTT

AGAGCTTAGTGAAATTTTAATCTACACATTGATTAAATACATTTTATTTATTCTTGTTTCTAATGGGAACTTTCT

TTGTTTCTAATGGGAACTTTCTTAAATTAAATTACATCCAACATTTATTAAAGACCTAAAACATAGGCAATTACT

GTGCTTAGAGGAAAAGCGCAGACGAAAGTGAATCAGACAAGTTTCCCTGCCCTCCGGAAGCTTCAGTCTAGTGAT

GAGAAAGACGTATACACACCTTATGTTGATTTAAAAAAAAAAAAAGCTCTTACCTGGTTGCTGGCATATGAAAGT

GTTAGTTACAGATCTGCCCCAAACTAAAGGTGTCACCTCGAGTAAATCTCTTTCCCTTTCCCTTTCAATCTCTTC

ATCTATAAACTAGGGGTTGGGAATACATTTATTAACAAACACAAATTGAGCGTCTACCATGTGATAATAGTAGCT

AAACTTACTGAGCAATTACCATGGGGCAGGTATCAAGATAAACCCTTTATGATGGTAACCTCATTTAATCCTCAA

AGCAATTCCATTTTCAAGAGGAGGAAATTGAGGCTCAAAAATGTTAAGTAACTCCCCCAAGGATGCAAAGTGATT

GAGCCAGAATTCAAGACTAGGTTGGTTTGACTCCAAAACTCATGCCATTAAACCCTATTGTGTCACTGCAAACAA

CTCTAATAGTTTCAAATTATTAGTTCTATTAATATTATATTACCATTATTTGCCCCCAAAATGTAAAATGTAAAT

ACAAAGAGTTTGGTTTTTGTATTACTAGTGGAGGTTAAAGGTGCACAATGGAATTATTCAAACTGGGAAAATCCA

GGAAGACTTCATGGAGGAGGCAGCATATGGCTGCAGTTAATAAGGTTTGCTCACACAAAATGGAGAGGTGAGGAC

ATTTCAGGCAGAGAGAATTATATGAGAGGTTACAGAGCAGTAAACAGTCATGCGTCTGCAAGATCAAAGGGAAAG

GGCGGTAAGAGAGAAGCTTGAAAGTCAAGTGGAGCCAGATTGTGGAAAAACTAGAGAGTCATGCCAAGGACCTTG

ACATATAGAAAATGGGAAGCCCCTGAAAGGTGAAGAACATGAGAGTGAAATGATTAGTAACTTTTGGTTTAGGA

CTTGTTTCTTTTGTGTTTTGGTTGCTTTCTTGTTTTGCTTTGTTTGTGGTTTTTAAATTTACAACCAATAAGAAT

ATTTAGTAAGGTTTCCAAATACATCATGAATATATAAAACTAGCCTGACTCAAGGATAATAATTCTGGGTAGTTG
```

-continued

```
GAGTGAAGTTTCAATCAGCTACGTGGCATTTGCTAATCATCTGATATGAGCTAACAATAAAGGAGTTAACAAATA
AACTGTCAGCCTACAGTCCAGGGTCTCAAATAGCATGTGACATAGTTGAGAAGCAGTTTTCCATATCATACATGA
AATAACTAAAGAAACTACTTACAAAGCACTATACCAGTAACTACAATAAAATACAACTATACATGCAAATAATG
CTGAAAGCTGCAAGTAGAGGGGTAAAGCTAGGCCAGTTGCTCAGGGAACCATTCTGAAGTTGGATTGGGAAGTAT
GTCTAGAAGGGGAGCCATTGCTGTGAGAGTGCTGAGGCTCATCTGCTACTAGTCCCCCACTACTCAGGCATATGG
TAGGTCAGTAACAAAACCATCATTGTGCACTGTTCTTTCCATCTAAATTCCATCAAATTATGACCAACCTATCAA
GGTACTAGTTCAAATTCTCTCTTCCTCTATAAGCTAGTGGTCTTCTCTAAAATTTAAGAAGATCGTGCTCATCTT
CCTACTTCTTGTTCTCTTTCTTCTGTGTTTTCTGAGGCTGCAATGAACTAGGAACTTCCTCTCCCCAGAACTCTG
TATTCCAGGCCTTAGATCACTCAAAACTGTTGCTTATAAAGTGCAGAGAATCAACAGAGAAGGAATAGAGGTTAA
TGTCTGGTCAAAGATGTGATTCTCTTGTTGAAAAGTTCATTAGCTTATTATTTATAGAATCATAAGTCCCAGGAA
AAACCAAAAGGAAATATATATTGGATCCTAATGATATTCTCTTTTTTTCTTTTTTCTTTTCCCCCACTCCATTGC
CCAGGCTGGAGTGCAGTGGCATAATCTCAGCTCACTGCAACCTCCACCTCCCGGGTTCAAGGGACTCTCCTGCCT
CAGCCTTCCAAGTAGATGGGATTACAGGCATGTGCCACCACATCTGGCTAATTTTTTTTGTATTTTTAGTAGAG
ATGGGGTTTCACCATGTTAGTCAGGCTGGTGTTGAACTCCTGACCTCAAATGATCCACCAGCCTCGGCCTCCCAG
TGTGCTGGGATTGCAGGCGTGAGCCACCACACCCGGCCTGATATTCTCTTGCAAGGGCATTGTTTACATTGTCTA
TCATCAGAACTGTAGAGTGTTGGCTCCAGGCACAGAACCCCTAGAGTTTTGTAAACCATTTATATCACACTGGCA
ACCAGAAGTAACTTTATATACTCAAGAATCAAGATTTCACCTAGAAGTACCTCAGGTAGGTGTTGGTTCATTCAC
ATTCCAACCAAAAGATAATGTACCATAAAGTGCATACCGCCTAGTCCGTAATGATTAAGGCAACCACATAAAATC
TCATTATTTAAAAGAAATTAAGTCCAGGCACGGTGGCTCACACCTGTAATCTCAGCACTTCGGGAGGCCAAGGAG
GGCAGATCACCTGAGGTTGGGAGTTTGAGACCAGCCTGATCAACATGGAGAAATCCCATCTCTACTAAAAATACA
AAATTAGCGGGGCATGGTGGTGCATGCCTATAATCCCAGCTACTCAGGAGGCTGAGGCAGGAGAATCACTTGAAC
CCAGGAGGTGGAGGTTGAGATCGTGCCATTGCACTCCAGCCTGGACAACAAGAGTGAAACTCTGTCTCAAAAAG
AAAAAAAGAAAAAGAAATTAAATGCACTATGGTTTATGGAGCGGTATTCCTCCTCCATGTCCTACATAAGATCTT
TCACATGCCAGTCACAGTTAAATCTAATTTGCTGTAATCTGGATAAATGGGAGCTAATCAACAAGCTCTCAGCTC
TAGCTCTGAATCAGCAGCAGATATTGCATTTTTGAAATACACTAATAGCAAGAATGCCTTCCTGACAACAACTGG
CATTTTTGACACAGCAGGAAGTTTATCTGGATTCTGATATAATAGTTATTGGAATCATACATAGGTACATAGTTT
AAAAGGCTAATAAGTCATTTGTTATTGCTTTTATTATCTCTGCATAGTTAGTAAAATTGAGATTAGAACCACTTC
TCGAATGTACTGTTCTAAATCCTTAGCTTGCTTGATCACACATGACCCTCACAATGATCCTAGGAGAAATTATTC
TGCATGCCATTTTGTAGCTGGGAAACTGAGGCACAGAGAAATACAGTACTGCCCAAAATGTCATAACTAATCAA
AGGCAAAGACAATACTCACACCAGCTCTGATTCCAGAGCCCACTCTCTTAACCATATGCTTTTCTGCTTCCCTAG
TTGTAGAGTCTTTTTGTATGACTGCATTAATTATATGTGAAGAGTTCAAAAATTTCTATATAAGGTCTTTTAAGG
GTGTCATTCTGGTTGAAAATGGAGGACTAGGCTTCTCACTTGAAGACATATTTCTGTAGAAAAACCTATTTTCAT
TTAGATGCTACAGTTACTTGATGTGGTTAATAAACCAGTTAACAGAGTATGAAAAGGATAAGGGTTAAAGCCCTC
CCAAGCCATCTTTCATGCTGCTAATATGAATCACATTACTAGATACTTAAATATCATTTTCTCTTTGGTTCCCAG
AAGACTGCATATATGCTAGAATATTTGTCCTCCTCTTTTACCCTTTCAGGCAATAAAGTATTTTGGACCACTGTA
CTATGTTATAATTATTGTTTCTCTCCTGATTTTTTTGCTCCAATCTAATGAAAGACATACAAGCTACTATACTGC
TACACAATGACTAAATACCTGTTGGATTAGGTGGGGGGAAGATACACAGTCACTGGCTAGAAAGCATCATGCATA
CAGAGCCATTTTCACCATATATTTTATTTCTCATGATCATGTAGAATTTAGGCTTTGGTGTTGATTATTTCTCTC
TTAGGAAACATAGTTGTTTCAGGGTTGATATCACAAAAAAACAGAAAAACCTATTCGAGAAAAGGAAAATTATTT
GTCTGTAGGCCAAATTTTGAAGTAGGAAAACCTGCTTTTGGAGTTGTATTCCCCTCCCAGGCACTTAATCCAAGT
```

-continued

```
TCCAGTCTTATTCTAAACTGGGGATGCTAGTATTAACCACCATAGGAGTTATCTGAGATGAGTTATCATCAACTT
GGTACCAGGTTGTTGTCCTCTGGACTCAGTGAGCTCTAGAATTGCATGAAACTGGCCTAATTTATCAAAGTATGT
AGCCTTGGGTAAATAATTCAAGCTCTCAGAGGTCCAGTTATCTCCTCTGTAAAACATATCTACATCCTAGGGATG
ACAATATCTACATCCTAGAGATGTCAGGAGGATTAAGTTGTAATTTTTTTAATTGTATGTATTTAAAATGGGCAA
CATAATGTTTTGATATACACGTGTATAGTGATTACTACAGTCAAGCAAATTAACATATCCATCATTTCATAGCTA
CCTTTTATGTATGTGATAAGATTATCTAAAATCTATTCTCTTACCAAATTTCCAGTATACAATATTGATATGGTT
TGATCCATATCCCCATCCAAATCTCATGTTCAGTTGCAATCCCCAACGTTGGAGATGGAGCCTGGTTGGAGGTGA
TTGGATCACAGGGGTGGCTTCTAATGGTTCAGCACCATCCTTTCTTGGTACTGTATAGTGAGTAAGTTCTCACGA
GATCTGGTTGTTTAAAAGTGTGTAACACCTCCCCCACTTTCCCTCTCTGTTCCTCCTGCTCCCGCTATGTGAA
GTGCCAGCTCCCTCTTTGCCTTCCGCCATGATTGTAAGTTCTCTGAGGCATCCCCAGAAGCTGATGCTGCCATGC
TTCCTATACAGCCTGCAGAACCATGAGTCAATTAAACCTCTTTTCTTTGTAAATTACCCAGTCTCAAGTATTTCT
TTATAGCAATGCAAGAATGGACTAATACAGAAAATTGTTACTGAGAAGAAGGGCATTGCTATAAAGATACCTGAA
AATGTAGAAGTGACTTTGGAACCGGCTAACAGGCAGAAGTTGAAACATTTTAGAGGGCTCAGAAGAAGACAGAAA
GATGAGAGAAAGTTTGGAACTCGCTAGGAACTTGTTGAGTGGTTGTAACCAAAATACTGATAGTGATATAGACAG
TGAAGTCCAGGCTGAGGAGGTCTCAGATGGAAATGAGAAATTTATTGGGAATGAGTAAAGGTCAGGTTTGCTATG
CTTTAGCAAAGAGCTTAGCTGCATTGTTCCTCTGTTCTAGGGATCTGTGAAATCTTAGACTTAAGAATGATGATT
TAGGGTATCTGGCAGAAGAAATTTCTAAGCAGCAGAGTGTTCAAGAAGTAACCTAGCTGCTTCTAATAGCCTATG
CTCATAGGCATGAGCACAGAAATGACCTGAAATTGGAACTTACACTTAAAAGGGAAGCAGAGCATAAAAGTTTGT
AAATTTTGCAGCCTGGCCATGTGGTAGTAAAGAAAAGCTCGTTCTCAGGAGAGGAAGTCAAGCAGGCTGCATAAA
TTTGCATAACTAAAAGGAAGGCAAGGGCTGATAACCAAAACAATGGGGAGAAAGACTCATAGGACTAACAGGCAT
TTTATTTTTATTTATTTTTATTTTATTATTATTATACTTTAAGTTTTAGGGTACATGTGCACAATGTGCAGGTTA
GTTGCATATGTATACATGTGCCATGCTGGTGTGCTGCACCCATTAACTCGTCATTTAGCATTAGGTATATCTCCT
AATGCTATCCCTCCCCCCTCCCCCACCCCACAACAGTCCCCAGAGTGTGATGTTCCCCTTCCTGTGTCCATGTGT
TCTCATTGTTCAATTCCCACCTATGAGTGAGAACATGTGGTGTTTGGTTTTTGACCTTGCAATAGTTTACTGAG
AATGACGATTTCCAATTTCATCCATGTCCCTACAAAGGACATGAACTCATCATTTTTATGGCTGCATAGTATTC
CATGGTGTATATGTGCCACATTTTCTTAATCCAGTCTATCACTGTTGGACATTTGGGTTGGTTCCAAGTCTTTGC
TATTGTGAATAGTGCCACAATAAACATAGTGTGCATGTGTCTTTATAGCAGCAGGATTTATAGTCCTTTGGGTAT
ATACCCAGTGATGGGATGGCTGGGTCAAATGGTATTTCTAGTTCTAGATCCCTGAGGAATCGCCACACTGACTTC
CACAATGGTTGAACTAGTTTACAGTCCCACCAACAGTGTAAAAGTGTTCCTAATAGGCATTTTAGGCTTTCATGG
TGGTCCCTCTCATCACAGGCCCCGAGGCCTAGGAGGACTGAATCATTTCCTGGGCCAGGCCTAGGGCCCCTGCTC
CCTCTTACAGCCTTGGGACTCTGCTCCCTGAATCCCAGCTGCTCAAAGGGGCCCAGGTACTGTTACAGTAGGTAG
CTAATCAGGCATGAGTGGGGTAAGAGAGAAGTCCCCACCACCCACCAGGAATGTCAGGCAACCATCAGATGATGG
TCAGGCAGTTGTCATACTGCCTCTCTAAAATAGTAATTGGTTGCAGCCAGCACCAGGGAGAGGCAACTTCTCAAT
AGATAGAAACACCTGAAATTGGTAACTGGGCGCTTCCAATAAGATCTCAGGAACTGAGAGAGTGGGCTTAACATG
CACATTAAGAGGCAAAATGGTGAAGTATGACCTTTGGGGGCATTCCACCGGAAAAGGGAAGAAAGCCTCAGGTAA
GCATGTATACAACTCCAGTAAACACACTGCACACGCTCACCTTCCAAGTGCAAGCAGGGCACCATGCATGCGGCA
AGCTCACCCTTAGGGAAGGACCAAGGGAAAGGGGCACAAGATGTCAGAAGTAGGCCAGTGTATAAGATCCTAGGT
TCAAGGTCAAACAGGGCACTTGACCTCCAAGGTGCCCACTTGGGCCTCTTCCAAATGTACTTTCCTTTCATTCCT
GTTCTAAAGCTTTTTAATAAACTTTTACTCCTGCTCTGAAACTTGTCGCAGTCTCTTTTTCTGCCTTATGCCTCT
TGGTCAAATTCTTTCTTCTGAGGAGGCAAGAATTGAGGTTGCTGCAGACCCACATGGATTTGCAGCTGGTAACTC
AGATAACTTTCACCAGTAAGAATACAGTTCAGGCTGCTGCTTCACAGGGTGCCAGGCATAAGCCTTGGTGGCTTC
```

```
CATAAGCTGTGAAGCCGGGGGGCGCACATAATGCAAGAGTTGAGGCTTAAGAAGCTCTGCCTAGATTTTAGAGGA
TGTATGAAAAAGCCTGGATGTCCAGACAGAAGCCTGTTACTGGGGTGGAATCCTCATGGAGAACATCTACTAGGG
AAGCAAGGAGAAGAAATGTGGGGTTGCAGCCCCCACAGAGAGTCCCCTGGGGCACTGCCTAGCAGAGCTATGACA
AGACAGCCACCGTCCTCCAGACCCCAGAATGGTAGATCCACCAACAACTTGCACCCTGCAGCCTGGAAAAGCTGC
AAGCACTCAATGCTAGCCCATGAGAGCAGCTGTGGGAGATGAACCCTGGAAAACCACAGGGGTGGTTCTGCCCAA
GGTTTTGGGAGCCCACTCATTGCATCAGTGTTCCCTGGGTGTGAGTCAAAGGAGATTATTTCAGAGCTTTAACAT
TTAATGACTGCCCGGCTGGCTTTCAGACTTGCAATGGGGCCCTATAGCCTCTTTCTTTTGGCAGATTTCTCCCTT
TCGGAATGGCAGTATCTGCCCAATGCCTATACCCCCATTGTATCTTTGAAGCAATTACCTTGTTTTTGATTTTAC
AGGTTCATAGGTAGAAGGGACTAGCTTCGTCTCAGGTGAGACTTGGGACTTTGGACTTTTGAATGAATGCTGGAT
CGAGTTAAGACTTTGGGGAACTGTTGGTAAGGCACGACAGTATTTTGCAATATGAGAAGGACATTAGATTTGGGA
GGGGCCAGAGTTGGAATAACATGGTTTGGATCTCTGTCCCCACCCAAATCTCATGTTCAACTGTAATCCCCAGTG
TTGGAGGTTGGGCCTGGTGGGAGGTGAGTGGATTATGGGGTGGCTTCTAATGGTTTTGTACAGTCCCCTCTTGGT
ACTATATAGTGAGTTCTGACAAGATCTAGTTGTTTAAACGTATGTAGCACCTCCCATTTCTCTCTTCCCCCAGTT
CCTGCCATGTGAAGTCTGGGGTCTCCCTATGCCTTCCATCATGATTTTAAGTTCCCTATGGCCTGCCCAGAAGCT
GATCCAGCCATGCTTCTTGTACAGCCTGCAGAACTGTGAGCCATTAAACTTTTCTTTATAAATTACCCAGTTTCA
GTTATTTCTTTATAGCAGTGTAAGAATGGACTAACACAATTATTAACGCTAGTCCTCATGTTGTACATTAAATCT
CTAGATGTATTAGACGTAACTGCAACTTTGTACCCTACCCTACAATTTTCTTTCCCCCCAAGCCCCCCAACCAAG
GGTCTACTCTGTTTCTATAAATTCAGTTGTTTTTTAATTCCACGTATAAGTGAAGTACAACTCAGTGTAGAAACT
TGGTAAATGCTAGCTACTTGTTATAAGCTGTCAGTCAAAATAAAAATACAGAGATGAATCTCTAAATTAAGTGAT
TTATTTGGGAAGAAAGAATTGCAATTAGGGCATACATGTAGATCAGATGGTCTTCGGTATATCCACACAACAAAG
AAAAGGGGGAGGTTTTGTTAAAAAAGAGAAATGTTACATAGTGCTCTTTGAGAAAATTCATTGGCACTATTAAGG
ATCTGAGGAGCTGGTGAGTTTCAACTGGTGAGTGATGGTGGTAGATAAAATTAGAGCTGCAGCAGGTCATTTTAG
CAACTATTAGATAAAACTGGTCTCAGGTCACAACGGGCAGTTGCAGCAGCTGGACTTGGAGAGAATTACACTGTG
GGAGCAGTGTCATTTGTCCTAAGTGCTTTTCTACCCCCTACCCCCACTATTTTAGTTGGGTATAAAAAGAATGAC
CCAATTTGTATGATCAACTTTCACAAAGCATAGAACAGTAGGAAAAGGGTCTGTTTCTGCAGAAGGTGTAGACGT
TGAGAGCCATTTTGTGTATTTATTCCTCCCTTTCTTCCTCGGTGAATGATTAAAACGTTCTGTGTGATTTTTAGT
GATGAAAAGATTAAATGCTACTCACTGTAGTAAGTGCCATCTCACACTTGCAGATCAAAAGGCACACAGTTTAA
AAAACCTTTGTTTTTTTACACATCTGAGTGGTGTAAATGCTACTCATCTGTAGTAAGTGGAATCTATACACCTGC
AGACCAAAAGACGCAAGGTTTCAAAAATCTTTGTGTTTTTTACACATCAAACAGAATGGTACGTTTTTCAAAAGT
TAAAAAAAAACAACTCATCCACATATTGCAACTAGCAAAAATGACATTCCCCAGTGTGAAAATCATGCTTGAGAG
AATTCTTACATGTAAAGGCAAAATTGCGATGACTTTGCAGGGGACCGTGGGATTCCCGCCCGCAGTGCCGGAGCT
GTCCCCTACCAGGGTTTGCAGTGGAGTTTTGAATGCACTTAACAGTGTCTTACGGTAAAAACAAAATTTCATCCA
CCAATTATGTGTTGAGCGCCCACTGCCTACCAAGCACAAACAAAACCATTCAAAACCACGAAATCGTCTTCACTT
TCTCCAGATCCAGCAGCCTCCCCTATTAAGGTTCGCACACGCTATTGCGCCAACGCTCCTCCAGAGCGGGTCTTA
AGATAAAAGAACAGGACAAGTTGCCCCGCCCCATTTCGCTAGCCTCGTGAGAAAACGTCATCGCACATAGAAAAC
AGACAGACGTAACCTACGGTGTCCCGCTAGGAAAGAGAGGTGCGTCAAACAGCGACAAGTTCCGCCCACGTAAAA
GATGACGCTTGGTGTGTCAGCCGTCCCTGCTGCCCGGTTGCTTCTCTTTTGGGGGGGGGTCTAGCAAGAGCAGG
TGTGGGTTTAGGAGGTGTGTGTTTTTGTTTTTCCCACCCTCTCTCCCCACTACTTGCTCTCACAGTACTCGCTGA
GGGTGAACAAGAAAAGACCTGATAAAGATTAACCAGAAGAAAACAAGGAGGGAAACAACCGCAGCCTGTAGCAAG
CTCTGGAACTCAGGAGTCGCGCGCTAGGGGCC (GGGGCC)$_n$
```

-continued

```
GGGGCCGGGGCGTGGTCGGGGCGGGCCCGGGGGCGGG

CCCGGGGCGGGGCTGCGGTTGCGGTGCCTGCGCCCGCGGGGGGGGAGGCGCAGGCGGTGGCGAGTGGGTGAGTGA

GGAGGCGGCATCCTGGCGGGTGGCTGTTTGGGGTTCGGCTGCCGGGAAGAGGCGCGGGTAGAAGCGGGGGCTCTC

CTCAGAGCTCGACGCATTTTTACTTTCCCTCTCATTTCTCTGACCGAAGCTGGGTGTCGGGCTTTCGCCTCTAGC

GACTGGTGGAATTGCCTGCATCCGGGCCCCGGGCTTCCCGGGGGGGCGGCGGCGGCGGCGCAGGGACAAGG

GATGGGGATCTGGCCTCTTCCTTGCTTTCCCGCCCTCAGTACCCGAGCTGTCTCCTTCCCGGGGACCCGCTGGGA

GCGCTGCCGCTGCGGGCTCGAGAAAAGGGAGCCTCGGGTACTGAGAGGCCTCGCCTGGGGGAAGGCCGGAGGGTG

GGCGGCGCGCGGCTTCTGCGGACCAAGTCGGGGTTCGCTAGGAACCCGAGACGGTCCCTGCCGGCGAGGAGATCA

TGCGGGATGAGATGGGGGTGTGGAGACGCCTGCACAATTTCAGCCCAAGCTTCTAGAGAGTGGTGATGACTTGCA

TATGAGGGCAGCAATGCAAGTCGGTGTGCTCCCCATTCTGTGGGACATGACCTGGTTGCTTCACAGCTCCGAGAT

GACACAGACTTGCTTAAAGGAAGTGACTATTGTGACTTGGGCATCACTTGACTGATGGTAATCAGTTGTCTAAAG

AAGTGCACAGATTACATGTCCGTGTGCTCATTGGGTCTATCTGGCCGCGTTGAACACCACCAGGCTTTGTATTCA

GAAACAGGAGGGAGGTCCTGCACTTTCCCAGGAGGGGGGCCCTTTTCAGATGCAATCGAGATTGTTAGGCTCTGG

GAGAGTAGTTGCCTGGTTGTGGCAGTTGGTAAATTTCTATTCAAACAGTTGCCATGCACCAGTTGTTCACAACAA

GGGTACGTAATCTGTCTGGCATTACTTCTACTTTTGTACAAAGGATCAAAAAAAAAAAAGATACTGTTAAGATAT

GATTTTTCTCAGACTTTGGGAAACTTTTAACATAATCTGTGAATATCACAGAAACAAGACTATCATATAGGGGAT

ATTAATAACCTGGAGTCAGAATACTTGAAATACGGTGTCATTTGACACGGGCATTGTTGTCACCACCTCTGCCAA

GGCCTGCCACTTTAGGAAAACCCTGAATCAGTTGGAAACTGCTACATGCTGATAGTACATCTGAAACAAGAACGA

GAGTAATTACCACATTCCAGATTGTTCACTAAGCCAGCATTTACCTGCTCCAGGAAAAAATTACAAGCACCTTAT

GAAGTTGATAAAATATTTTGTTTGGCTATGTTGGCACTCCACAATTTGCTTTCAGAGAAACAAAGTAAACCAAGG

AGGACTTCTGTTTTTCAAGTCTGCCCTCGGGTTCTATTCTACGTTAATTAGATAGTTCCCAGGAGGACTAGGTTA

GCCTACCTATTGTCTGAGAAACTTGGAACTGTGAGAAATGGCCAGATAGTGATATGAACTTCACCTTCCAGTCTT

CCCTGATGTTGAAGATTGAGAAAGTGTTGTGAACTTTCTGGTACTGTAAACAGTTCACTGTCCTTGAAGTGGTCC

TGGGCAGCTCCTGTTGTGGAAAGTGGACGGTTTAGGATCCTGCTTCTCTTTGGGCTGGGAGAAAATAAACAGCAT

GGTTACAAGTATTGAGAGCCAGGTTGGAGAAGGTGGCTTACACCTGTAATGCCAGAGCTTTGGGAGGCGGAGGCA

AGAGGATCACTTGAAGCCAGGAGTTCAAGCTCAACCTGGGCAACGTAGACCCTGTCTCTACAAAAAATTAAAAAC

TTAGCCGGGCGTGGTGATGTGCACCTGTAGTCCTAGCTACTTGGGAGGCTGAGGCAGGAGGGTCATTTGAGCCCA

AGAGTTTGAAGTTACCGAGAGCTATGATCCTGCCAGTGCATTCCAGCCTGGATGACAAAACGAGACCCTGTCTCT

AAAAAACAAGAAGTGAGGGCTTTATGATTGTAGAATTTTCACTACAATAGCAGTGGACCAACCACCTTTCTAAAT

ACCAATCAGGGAAGAGATGGTTGATTTTTAACAGACGTTTAAAGAAAAAGCAAAACCTCAAACTTAGCACTCTA

CTAACAGTTTTAGCAGATGTTAATTAATGTAATCATGTCTGCATGTATGGGATTATTTCCAGAAAGTGTATTGGG

AAACCTCTCATGAACCCTGTGAGCAAGCCACCGTCTCACTCAATTTGAATCTTGGCTTCCCTCAAAAGACTGGCT

AATGTTTGGTAACTCTCTGGAGTAGACAGCACTACATGTACGTAAGATAGGTACATAAACAACTATTGGTTTTGA

GCTGATTTTTTCAGCTGCATTTGCATGTATGGATTTTTCTCACCAAAGACGATGACTTCAAGTATTAGTAAAAT

AATTGTACAGCTCTCCTGATTATACTTCTCTGTGACATTTCATTTTCCCAGGCTATTTCTTTTGGTAGGATTAAA

ACTAAGCAATTCAGTATGATCTTTGTCCTTCATTTTCTTTCTTATTCTTTTTGTTTGTTTGTTTGTTTTTT

TCTTGAGGCAGAGTCTCTCTCTGTCGCCCAGGCTGGAGTGCAGTGGCGCCATCTCAGCTCATTGCAACCTCTGCC

ACCTCCGGGTTCAAGAGATTCTCCTGCCTCAGCCTCCCGAGTAGCTGGGATTACAGGTGTCCACCACCACACCCG

GCTAATTTTTTGTATTTTTTAGTAGAGGGGGGTTTCACCATGTTGGCCAGGCTGGTCTTGAGCTCCTGACCTCAG

GTGATCCACCTGCCTCGGCCTACCAAAGAGCTGGGATAACAGGTGTGACCCACCATGCCCGGCCCATTTTTTTTT

TCTTATTCTGTTAGGAGTGAGAGTGTAACTAGCAGTATAATAGTTCAATTTTCACAACGTGGTAAAAGTTTCCCT
```

-continued

```
ATAATTCAATCAGATTTTGCTCCAGGGTTCAGTTCTGTTTTAGGAAATACTTTTATTTTCAGTTTAATGATGAAA

TATTAGAGTTGTAATATTGCCTTTATGATTATCCACCTTTTTAACCTAAAAGAATGAAAGAAAAATATGTTTGCA

ATATAATTTTATGGTTGTATGTTAACTTAATTCATTATGTTGGCCTCCAGTTTGCTGTTGTTAGTTATGACAGCA

GTAGTGTCATTACCATTTCAATTCAGATTACATTCCTATATTTGATCATTGTAAACTGACTGCTTACATTGTATT

AAAAACAGTGGATATTTTAAAGAAGCTGTACGGCTTATATCTAGTGCTGTCTCTTAAGACTATTAAATTGATACA

ACATATTTAAAAGTAAATATTACCTAAATGAATTTTTGAAATTACAAATACACGTGTTAAAACTGTCGTTGTGTT

CAACCATTTCTGTACATACTTAGAGTTAACTGTTTTGCCAGGCTCTGTATGCCTACTCATAATATGATAAAAGCA

CTCATCTAATGCTCTGTAAATAGAAGTCAGTGCTTTCCATCAGACTGAACTCTCTTGACAAGATGTGGATGAAAT

TCTTTAAGTAAAATTGTTTACTTTGTCATACATTTACAGATCAAATGTTAGCTCCCAAAGCAATCATATGGCAAA

GATAGGTATATCATAGTTTGCCTATTAGCTGCTTTGTATTGCTATTATTATAAATAGACTTCACAGTTTTAGACT

TGCTTAGGTGAAATTGCAATTCTTTTTACTTTCAGTCTTAGATAACAAGTCTTCAATTATAGTACAATCACACAT

TGCTTAGGAATGCATCATTAGGCGATTTTGTCATTATGCAAACATCATAGAGTGTACTTACACAAACCTAGATAG

TATAGCCTTTATGTACCTAGGCCGTATGGTATAGTCTGTTGCTCCTAGGCCACAAACCTGTACAACTGTTACTGT

ACTGAATACTATAGACAGTTGTAACACAGTGGTAAATATTTATCTAAATATATGCAAACAGAGAAAAGGTACAGT

AAAAGTATGGTATAAAAGATAATGGTATACCTGTGTAGGCCACTTACCACGAATGGAGCTTGCAGGACTAGAAGT

TGCTCTGGGTGAGTCAGTGAGTGAGTGGTGAATTAATGTGAAGGCCTAGAACACTGTACACCACTGTAGACTATA

AACACAGTACGCTGAAGCTACACCAAATTTATCTTAACAGTTTTTCTTCAATAAAAAATTATAACTTTTTAACTT

TGTAAACTTTTTAATTTTTAACTTTTAAAATACTTAGCTTGAAACACAAATACATTGTATAGCTATACAAAAAT

ATTTTTTCTTTGTATCCTTATTCTAGAAGCTTTTTTCTATTTTCTATTTTAAATTTTTTTTTTACTTGTTAGTC

GTTTTTGTTAAAAACTAAAACACACACTTTCACCTAGGCATAGACAGGATTAGGATCATCAGTATCACTCCCT

TCCACCTCACTGCCTTCCACCTCCACATCTTGTCCCACTGGAAGGTTTTTAGGGGCAATAACACACATGTAGCTG

TCACCTATGATAACAGTGCTTTCTGTTGAATACCTCCTGAAGGACTTGCCTGAGGCTGTTTTACATTTAACTTAA

AAAAAAAAAAGTAGAAGGAGTGCACTCTAAAATAACAATAAAAGGCATAGTATAGTGAATACATAAACCAGCAA

TGTAGTAGTTTATTATCAAGTGTTGTACACTGTAATAATTGTATGTGCTATACTTTAAATAACTTGCAAAATAGT

ACTAAGACCTTATGATGGTTACAGTGTCACTAAGGCAATAGCATATTTTCAGGTCCATTGTAATCTAATGGGACT

ACCATCATATATGCAGTCTACCATTGACTGAAACGTTACATGGCACATAACTGTATTTGCAAGAATGATTTGTTT

TACATTAATATCACATAGGATGTACCTTTTTAGAGTGGTATGTTTATGTGGATTAAGATGTACAAGTTGAGCAAG

GGGACCAAGAGCCCTGGGTTCTGTCTTGGATGTGAGCGTTTATGTTCTTCTCCTCATGTCTGTTTTCTCATTAAA

TTCAAAGGCTTGAACGGGCCCTATTTAGCCCTTCTGTTTTCTACGTGTTCTAAATAACTAAAGCTTTTAAATTCT

AGCCATTTAGTGTAGAACTCTCTTTGCAGTGATGAAATGCTGTATTGGTTTCTTGGCTAGCATATTAAATATTTT

TATCTTTGTCTTGATACTTCAATGTCGTTTTAAACATCAGGATCGGGCTTCAGTATTCTCATAACCAGAGAGTTC

ACTGAGGATACAGGACTGTTTGCCCATTTTTTGTTATGGCTCCAGACTTGTGGTATTTCCATGTCTTTTTTTTTT

TTTTTTTTTTGACCTTTTAGCGGCTTTAAAGTATTTCTGTTGTTAGGTGTTGTATTACTTTTCTAAGATTACTT

AACAAAGCACCACAAACTGAGTGGCTTTAAACAACAGCAATTTATTCTCTCACAATTCTAGAAGCTAGAAGTCCG

AAATCAAAGTGTTGACAGGGGCATGATCTTCAAGAGAGAAGACTCTTTCCTTGCCTCTTCCTGGCTTCTGGTGGT

TACCAGCAATCCTGAGTGTTCCTTTCTTGCCTTGTAGTTTCAACAATCCAGTATCTGCCTTTTGTCTTCACATGG

CTGTCTACCATTTGTCTCTGTGTCTCCAAATCTCTCTCCTTATAAACACAGCAGTTATTGGATTAGGCCCCACTC

TAATCCAGTATGACCCCATTTTAACATGATTACACTTATTTCTAGATAAGGTCACATTCACGTACACCAAGGGTT

AGGAATTGAACATATCTTTTTGGGGGACACAATTCAACCCACAAGTTGTCAGTCTCTAGCTGAGCCTTTCCCTCC

TGTTTTTCTCCTTTTTAGTTGCTATGGGTTAGGGGCCAAATCTCCAGTCATACTAGAATTGCACATGGACTGGAT
```

```
ATTTGGGAATACTGCGGGTCTATTCTATGAGCTTTAGTATGTAACATTTAATATCAGTGTAAAGAAGCCCTTTTT
TAAGTTATTTCTTTGAATTTCTAAATGTATGCCCTGAATATAAGTAACAAGTTACCATGTCTTGTAAAATGATCA
TATCAACAAACATTTAATGTGCACCTACTGTGCTAGTTGAATGTCTTTATCCTGATAGGAGATAACAGGATTCCA
CATCTTTGACTTAAGAGGACAAACCAAATATGTCTAAATCATTTGGGGTTTTGATGGATATCTTTAAATTGCTGA
ACCTAATCATTGGTTTCATATGTCATTGTTTAGATATCTCCGGAGCATTTGGATAATGTGACAGTTGGAATGCAG
TGATGTCGACTCTTTGCCCACCGCCATCTCCAGCTGTTGCCAAGACAGAGATTGCTTTAAGTGGCAAATCACCTT
TATTAGCAGCTACTTTTGCTTACTGGGACAATATTCTTGGTCCTAGAGTAAGGCACATTTGGGCTCCAAAGACAG
AACAGGTACTTCTCAGTGATGGAGAAATAACTTTTCTTGCCAACCACACTCTAAATGGAGAAATCCTTCGAAATG
CAGAGAGTGGTGCTATAGATGTAAAGTTTTTTGTCTTGTCTGAAAAGGGAGTGATTATTGTTTCATTAATCTTTG
ATGGAAACTGGAATGGGGATCGCAGCACATATGGACTATCAATTATACTTCCACAGACAGAACTTAGTTTCTACC
TCCCACTTCATAGAGTGTGTGTTGATAGATTAACACATATAATCCGGAAAGGAAGAATATGGATGCATAAGGTAA
GTGATTTTTCAGCTTATTAATCATGTTAACCTATCTGTTGAAAGCTTATTTTCTGGTACATATAAATCTTATTTT
TTTAATTATATGCAGTGAACATCAAACAATAAATGTTATTTATTTTGCATTTACCCTATTAGATACAAATACATC
TGGTCTGATACCTGTCATCTTCATATTAACTGTGGAAGGTACGAAATGGTAGCTCCACATTATAGATGAAAAGCT
AAAGCTTAGACAAATAAAGAAACTTTTAGACCCTGGATTCTTCTTGGGAGCCTTTGACTCTAATACCTTTTGTTT
CCCTTTCATTGCACAATTCTGTCTTTTGCTTACTACTATGTGTAAGTATAACAGTTCAAAGTAATAGTTTCATAA
GCTGTTGGTCATGTAGCCTTTGGTCTCTTTAACCTCTTTGCCAAGTTCCCAGGTTCATAAAATGAGGAGGTTGAA
TGGAATGGTTCCCAAGAGAATTCCTTTTAATCTTACAGAAATTATTGTTTTCCTAAATCCTGTAGTTGAATATAT
AATGCTATTTACATTTCAGTATAGTTTTGATGTATCTAAAGAACACATTGAATTCTCCTTCCTGTGTTCCAGTTT
GATACTAACCTGAAAGTCCATTAAGCATTACCAGTTTTAAAAGGCTTTTGCCCAATAGTAAGGAAAAATAATATC
TTTTAAAAGAATAATTTTTTTTTACTATGTTTGCAGGCTTACTTCCTTTCTCACATTATGAAACTCTTAAAATCA
GGAGAATCTTTTAAACAACATCATAATGTTTAATTTGAAAAGTGCAAGTCATTCTTTTCCTTGTTGAAACTATGC
AGATGTTACATTGACTGTTTTCTGTGAAGTTATCTTTTTTTCACTGCAGAATAAAGGTTGTTTTGATTTTATTTT
GTATTGTTTATGAGAACATGCATTTGTTGGGTTAATTTCCTACCCCTGCCCCCATTTTTTCCCTAAAGTAGAAAG
TATTTTTCTTGTGAACTAAATTACTACACAAGAACATGTCTATTGAAAAATAAGCAAGTATCAAAATGTTGTGGG
TTGTTTTTTTAAATAAATTTTCTCTTGCTCAGGAAAGACAAGAAAATGTCCAGAAGATTATCTTAGAAGGCACAG
AGAGAATGGAAGATCAGGTATATGCAAATTGCATACTGTCAAATGTTTTTCTCACAGCATGTATCTGTATAAGGT
TGATGGCTACATTTGTCAAGGCCTTGGAGACATACGAATAAGCCTTTAATGGAGCTTTTATGGAGGTGTACAGAA
TAAACTGGAGGAAGATTTCCATATCTTAAACCCAAAGAGTTAAATCAGTAAACAAAGGAAAATAGTAATTGCATC
TACAAATTAATATTTGCTCCCTTTTTTTTTCTGTTTGCCCAGAATAAATTTTGGATAACTTGTTCATAGTAAAAA
TAAAAAAATTGTCTCTGATATGTTCTTTAAGGTACTACTTCTCGAACCTTTCCCTAGAAGTAGCTGTAACAGAA
GGAGAGCATATGTACCCCTGAGGTATCTGTCTGGGGTGTAGGCCCAGGTCCACACAATATTTCTTCTAAGTCTTA
TGTTGTATCGTTAAGACTCATGCAATTTACATTTTATTCCATAACTATTTTAGTATTAAAATTTGTCAGTGATAT
TTCTTACCCTCTCCTCTAGGAAAATGTGCCATGTTTATCCCTTGGCTTTGAATGCCCCTCAGGAACAGACACTAA
GAGTTTGAGAAGCATGGTTACAAGGGTGTGGCTTCCCCTGCGGAAACTAAGTACAGACTATTTCACTGTAAAGCA
GAGAAGTTCTTTTGAAGGAGAATCTCCAGTGAAGAAAGAGTTCTTCACTTTTACTTCCATTTCCTCTTGTGGGTG
ACCCTCAATGCTCCTTGTAAAACTCCAATATTTAAACATGGCTGTTTTGCCTTTCTTTGCTTCTTTTTAGCATTG
AATGAGACAGATGATACTTTAAAAAAGTAATTAAAAAAAAAAAACTTGTGAAAATACATGGCCATAATACAGAACC
CAATACAATGATCTCCTTTACCAAATTGTTATGTTTGTACTTTTGTAGATAGCTTTCCAATTCAGAGACAGTTAT
TCTGTGTAAAGGTCTGACTTAACAAGAAAAGATTTCCCTTTACCCAAAGAATCCCAGTCCTTATTTGCTGGTCAA
TAAGCAGGGTCCCCAGGAATGGGGTAACTTTCAGCACCCTCTAACCCACTAGTTATTAGTAGACTAATTAAGTAA
```

-continued

```
ACTTATCGCAAGTTGAGGAAACTTAGAACCAACTAAAATTCTGCTTTTACTGGGATTTTGTTTTTTCAAACCAGA

AACCTTTACTTAAGTTGACTACTATTAATGAATTTTGGTCTCTCTTTTAAGTGCTCTTCTTAAAAATGTTATCTT

ACTGCTGAGAAGTTCAAGTTTGGGAAGTACAAGGAGGAATAGAAACTTAAGAGATTTTCTTTTAGAGCCTCTTCT

GTATTTAGCCCTGTAGGATTTTTTTTTTTTTTTTTTTGGTGTTGTTGAGCTTCAGTGAGGCTATTCATTCA

CTTATACTGATAATGTCTGAGATACTGTGAATGAAATACTATGTATGCTTAAACCTAAGAGGAAATATTTTCCCA

AAATTATTCTTCCCGAAAAGGAGGAGTTGCCTTTTGATTGAGTTCTTGCAAATCTCACAACGACTTTATTTTGAA

CAATACTGTTTGGGGATGATGCATTAGTTTGAAACAACTTCAGTTGTAGCTGTCATCTGATAAAATTGCTTCACA

GGGAAGGAAATTTAACACGGATCTAGTCATTATTCTTGTTAGATTGAATGTGTGAATTGTAATTGTAAACAGGCA

TGATAATTATTACTTTAAAAACTAAAAACAGTGAATAGTTAGTTGTGGAGGTTACTAAAGGATGGTTTTTTTTA

AATAAAACTTTCAGCATTATGCAAATGGGCATATGGCTTAGGATAAAACTTCCAGAAGTAGCATCACATTTAAAT

TCTCAAGCAACTTAATAATATGGGGCTCTGAAAAACTGGTTAAGGTTACTCCAAAAATGGCCCTGGGTCTGACAA

AGATTCTAACTTAAAGATGCTTATGAAGACTTTGAGTAAAATCATTTCATAAAATAAGTGAGGAAAAACAACTAG

TATTAAATTCATCTTAAATAATGTATGATTTAAAAAATATGTTTAGCTAAAAATGCATAGTCATTTGACAATTTC

ATTTATATCTCAAAAAATTTACTTAACCAAGTTGGTCACAAAACTGATGAGACTGGTGGTGGTAGTGAATAAATG

AGGGACCATCCATATTTGAGACACTTTACATTTGTGATGTGTTATACTGAATTTTCAGTTTGATTCTATAGACTA

CAAATTTCAAAATTACAATTTCAAGATGTAATAAGTAGTAATATCTTGAAATAGCTCTAAAGGGAATTTTTCTGT

TTATTGATTCTTAAAATATATGTGCTGATTTTGATTTGCATTTGGGTAGATTTATACTTTTATGAGTATGGAGGT

TAGGTATTGATTCAAGTTTTCCTTACCTATTTGGTAAGGATTTCAAAGTCTTTTTGTGCTTGGTTTTCCTCATTT

TTAAATATGAAATATATTGATGACCTTTAACAAATTTTTTTATCTCAAATTTTAAAGGAGATCTTTTCTAAAAG

AGGCATGATGACTTAATCATTGCATGTAACAGTAAACGATAAACCAATGATTCCATACTCTCTAAAGAATAAAAG

TGAGCTTTAGGGCCGGGCATGGTCAGAAATTTGACACCAACCTGGCCAACATGGCGAAACCCCGTCTCTACTAAA

AATACAAAAATCAGCCGGGCATGGTGGCGGCACCTATAGTCCCAGCTACTTGGGAGGATGAGACAGGAGAGTCAC

TTGAACCTGGGAGGAGAGGTTGCAGTGAGCTGAGATCACGCCATTGCACTCCAGCCTGAGCAATGAAAGCAAAAC

TCCATCTCAAAAAAAAAAAAGAAAAGAAAGAATAAAAGTGAGCTTTGGATTGCATATAAATCCTTTAGACATGT

AGTAGACTTGTTTGATACTGTGTTTGAACAAATTACGAAGTATTTTCATCAAAGAATGTTATTGTTTGATGTTAT

TTTTATTTTTTATTGCCCAGCTTCTCTCATATTACGTGATTTTCTTCACTTCATGTCACTTTATTGTGCAGGGTC

AGAGTATTATTCCAATGCTTACTGGAGAAGTGATTCCTGTAATGGAACTGCTTTCATCTATGAAATCACACAGTG

TTCCTGAAGAAATAGATGTAAGTTTAAATGAGAGCAATTATACACTTTATGAGTTCTTTGGGGTTATAGTATTAT

TATGTATATTATTAATATTCTAATTTTAATAGTAAGGACTTTGTCATACATACTATTCACATACAGTATTAGCCA

CTTTAGCAAATAAGCACACACAAAATCCTGGATTTTATGGCAAAACAGAGGCATTTTTGATCAGTGATGACAAAA

TTAAATTCATTTTGTTTATTTCATTACTTTTATAATTCCTAAAAGTGGGAGGATCCCAGCTCTTATAGGAGCAAT

TAATATTTAATGTAGTGTCTTTTGAAACAAAACTGTGTGCCAAAGTAGTAACCATTAATGGAAGTTTACTTGTAG

TCACAAATTTAGTTTCCTTAATCATTTGTTGAGGACGTTTTGAATCACACACTATGAGTGTTAAGAGATACCTTT

AGGAAACTATTCTTGTTGTTTTCTGATTTTGTCATTTAGGTTAGTCTCCTGATTCTGACAGCTCAGAAGAGGAAG

TTGTTCTTGTAAAAATTGTTTAACCTGCTTGACCAGCTTTCACATTTGTTCTTCTGAAGTTTATGGTAGTGCACA

GAGATTGTTTTTGGGGAGTCTTGATTCTCGGAAATGAAGGCAGTGTGTTATATTGAATCCAGACTTCCGAAAAC

TTGTATATTAAAAGTGTTATTTCAACACTATGTTACAGCCAGACTAATTTTTTATTTTTTGATGCATTTTAGAT

AGCTGATACAGTACTCAATGATGATGATATTGGTGACAGCTGTCATGAAGGCTTTCTTCTCAAGTAAGAATTTTT

TTTTTCATAAAAGCTGGATGAAGCAGATACCATCTTATGCTCACCTATGACAAGATTTGGAAGAAAGAAAATAAC

AGACTGTCTACTTAGATTGTTCTAGGGACATTACGTATTTGAACTGTTGCTTAAATTTGTGTTATTTTTCACTCA
```

-continued
```
TTATATTTCTATATATATTTGGTGTTATTCCATTTGCTATTTAAAGAAACCGAGTTTCCATCCCAGACAAGAAAT
CATGGCCCCTTGCTTGATTCTGGTTTCTTGTTTTACTTCTCATTAAAGCTAACAGAATCCTTTCATATTAAGTTG
TACTGTAGATGAACTTAAGTTATTTAGGCGTAGAACAAAATTATTCATATTTATACTGATCTTTTTCCATCCAGC
AGTGGAGTTTAGTACTTAAGAGTTTGTGCCCTTAAACCAGACTCCCTGGATTAATGCTGTGTACCCGTGGGCAAG
GTGCCTGAATTCTCTATACACCTATTTCCTCATCTGTAAAATGGCAATAATAGTAATAGTACCTAATGTGTAGGG
TTGTTATAAGCATTGAGTAAGATAAATAATATAAAGCACTTAGAACAGTGCCTGGAACATAAAAACACTTAATAA
TAGCTCATAGCTAACATTTCCTATTTACATTTCTTCTAGAAATAGCCAGTATTTGTTGAGTGCCTACATGTTAGT
TCCTTTACTAGTTGCTTTACATGTATTATCTTATATTCTGTTTTAAAGTTTCTTCACAGTTACAGATTTTCATGA
AATTTTACTTTTAATAAAAGAGAAGTAAAAGTATAAAGTATTCACTTTATGTTTCACAGTCTTTTCCTTTAGGCT
CATGATGGAGTATCAGAGGCATGAGTGTGTTTAACCTAAGAGCCTTAATGGCTTGAATCAGAAGCACTTTAGTCC
TGTATCTGTTCAGTGTCAGCCTTTCATACATCATTTTAAATCCCATTTGACTTTAAGTAAGTCACTTAATCTCTC
TACATGTCAATTTCTTCAGCTATAAAATGATGGTATTTCAATAAATAAATACATTAATTAAATGATATTATACTG
ACTAATTGGGCTGTTTTAAGGCTCAATAAGAAAATTTCTGTGAAAGGTCTCTAGAAAATGTAGGTTCCTATACAA
ATAAAAGATAACATTGTGCTTATAGCTTCGGTGTTTATCATATAAAGCTATTCTGAGTTATTTGAAGAGCTCACC
TACTTTTTTTGTTTTAGTTTGTTAAATTGTTTTATAGGCAATGTTTTAATCTGTTTTCTTTAACTTACAGTG
CCATCAGCTCACACTTGCAAACCTGTGGCTGTTCCGTTGTAGTAGGTAGCAGTGCAGAGAAAGTAAATAAGGTAG
TTTATTTTATAATCTAGCAAATGATTTGACTCTTTAAGACTGATGATATATCATGGATTGTCATTTAAATGGTAG
GTTGCAATTAAAATGATCTAGTAGTATAAGGAGGCAATGTAATCTCATCAAATTGCTAAGACACCTTGTGGCAAC
AGTGAGTTTGAAATAAACTGAGTAAGAATCATTTATCAGTTTATTTTGATAGCTCGGAAATACCAGTGTCAGTAG
TGTATAAATGGTTTTGAGAATATATTAAAATCAGATATATAAAAAAAATTACTCTTCTATTTCCCAATGTTATCT
TTAACAAATCTGAAGATAGTCATGTACTTTTGGTAGTAGTTCCAAAGAAATGTTATTTGTTTATTCATCTTGATT
TCATTGTCTTCGCTTTCCTTCTAAATCTGTCCCTTCTAGGGAGCTATTGGGATTAAGTGGTCATTGATTATTATA
CTTTATTCAGTAATGTTTCTGACCCTTTCCTTCAGTGCTACTTGAGTTAATTAAGGATTAATGAACAGTTACATT
TCCAAGCATTAGCTAATAAACTAAAGGATTTTGCACTTTTCTTCACTGACCATTAGTTAGAAAGAGTTCAGAGAT
AAGTATGTGTATCTTTCAATTTCAGCAAACCTAATTTTTTAAAAAAAGTTTTACATAGGAAATATGTTGGAAATG
ATACTTTACAAAGATATTCATAATTTTTTTTGTAATCAGCTACTTTGTATATTTACATGAGCCTTAATTTATAT
TTCTCATATAACCATTTATGAGAGCTTAGTATACCTGTGTCATTATATTGCATCTACGAACTAGTGACCTTATTC
CTTCTGTTACCTCAAACAGGTGGCTTTCCATCTGTGATCTCCAAAGCCTTAGGTTGCACAGAGTGACTGCCGAGC
TGCTTTATGAAGGGAGAAAGGCTCCATAGTTGGAGTGTTTTTTTTTTTTTTAAACATTTTTCCCATCCTCCA
TCCTCTTGAGGGAGAATAGCTTACCTTTTTATCTTGTTTAATTTGAGAAAGAAGTTGCCACCACTCTAGGTTGAA
AACCACTCCTTTAACATAATAACTGTGGATATGGTTTGAATTTCAAGATAGTTACATGCCTTTTTATTTTTCCTA
ATAGAGCTGTAGGTCAAATATTATTAGAATCAGATTTCTAAATCCCACCCAATGACCTGCTTATTTAAATCAAA
TTCAATAATTAATTCTCTTCTTTTTGGAGGATCTGGACATTCTTTGATATTTCTTACAACGAATTTCATGTGTAG
ACCCACTAAACAGAAGCTATAAAAGTTGCATGGTCAAATAAGTCTGAGAAAGTCTGCAGATGATATAATTCACCT
GAAGAGTCACAGTATGTAGCCAAATGTTAAAGGTTTTGAGATGCCATACAGTAAATTTACCAAGCATTTTCTAAA
TTTATTTGACCACAGAATCCCTATTTTAAGCAACAACTGTTACATCCCATGGATTCCAGGTGACTAAAGAATACT
TATTTCTTAGGATATGTTTATTGATAATAACAATTAAAATTTCAGATATCTTTCATAAGCAAATCAGTGGTCTT
TTTACTTCATGTTTTAATGCTAAAATATTTTCTTTTATAGATAGTCAGAACATTATGCCTTTTTCTGACTCCAGC
AGAGAGAAAATGCTCCAGGTTATGTGAAGCAGAATCATCATTTAAATATGAGTCAGGGCTCTTTGTACAAGGCCT
GCTAAAGGTATAGTTTCTAGTTATCACAAGTGAAACCACTTTTCTAAAATCATTTTTGAGACTCTTTATAGACAA
ATCTTAAATATTAGCATTTAATGTATCTCATATTGACATGCCCAGAGACTGACTTCCTTTACACAGTTCTGCACA
```

-continued

```
TAGACTATATGTCTTATGGATTTATAGTTAGTATCATCAGTGAAACACCATAGAATACCCTTTGTGTTCCAGGTG
GGTCCCTGTTCCTACATGTCTAGCCTCAGGACTTTTTTTTTTTAACACATGCTTAAATCAGGTTGCACATCAAA
AATAAGATCATTTCTTTTTAACTAAATAGATTTGAATTTTATTGAAAAAAAATTTTAAACATCTTTAAGAAGCTT
ATAGGATTTAAGCAATTCCTATGTATGTGTACTAAAATATATATATTTCTATATATAATATATATTAGAAAAAAA
TTGTATTTTTCTTTTATTTGAGTCTACTGTCAAGGAGCAAAACAGAGAAATGTAAATTACCAATTATTTATAATA
CTTAAAGGGAAGAAAGTTGTTCACCTTGTTGAATCTATTATTGTTATTTCAATTATAGTCCCAAGACGTGAAGAA
ATAGCTTTCCTAATGGTTATGTGATTGTCTCATAGTGACTACTTTCTTGAGGATGTAGCCACGGCAAAATGAAAT
AAAAAAATTTAAAAATTGTTGCAAATACAAGTTATATTAGGCTTTTGTGCATTTTCAATAATGTGCTGCTATGAA
CTCAGAATGATAGTATTTAAATATAGAAACTAGTTAAAGGAAACGTAGTTTCTATTTGAGTTATACATATCTGTA
AATTAGAACTTCTCCTGTTAAAGGCATAATAAAGTGCTTAATACTTTTGTTTCCTCAGCACCCTCTCATTTAATT
ATATAATTTTAGTTCTGAAAGGGACCTATACCAGATGCCTAGAGGAAATTTCAAAACTATGATCTAATGAAAAAA
TATTTAATAGTTCTCCATGCAAATACAAATCATATAGTTTTCCAGAAAATACCTTTGACATTATACAAAGATGAT
TATCACAGCATTATAATAGTAAAAAAATGGAAATAGCCTCTTTCTTCTGTTCTGTTCATAGCACAGTGCCTCATA
CGCAGTAGGTTATTATTACATGGTAACTGGCTACCCCAACTGATTAGGAAAGAAGTAAATTTGTTTTATAAAAT
ACATACTCATTGAGGTGCATAGAATAATTAAGAAATTAAAAGACACTTGTAATTTTGAATCCAGTGAATACCCAC
TGTTAATATTTGGTATATCTCTTTCTAGTCTTTTTTTCCCTTTTGCATGTATTTTCTTTAAGACTCCCACCCCCA
CTGGATCATCTCTGCATGTTCTAATCTGCTTTTTTCACAGCAGATTCTAAGCCTCTTTGAATATCAACACAAACT
TCAACAACTTCATCTATAGATGCCAAATAATAAATTCATTTTTATTTACTTAACCACTTCCTTTGGATGCTTAGG
TCATTCTGATGTTTTGCTATTGAAACCAATGCTATACTGAACACTTCTGTCACTAAAACTTTGCACACACTCATG
AATAGCTTCTTAGGATAAATTTTTAGAGATGGATTTGCTAAATCAGAGACCATTTTTTAAAATTAAAAAACAATT
ATTCATATCGTTTGGCATGTAAGACAGTAAATTTTCCTTTTATTTTGACAGGATTCAACTGGAAGCTTTGTGCTG
CCTTTCCGGCAAGTCATGTATGCTCCATATCCCACCACACACATAGATGTGGATGTCAATACTGTGAAGCAGATG
CCACCCTGTCATGAACATATTTATAATCAGCGTAGATACATGAGATCCGAGCTGACAGCCTTCTGGAGAGCCACT
TCAGAAGAAGACATGGCTCAGGATACGATCATCTACACTGACGAAAGCTTTACTTCCTGATTGTACGTAATGCTC
TGCCTGCTGGTACTGTAGTCAAGCAATATGAAATTGTGTCTTTTACGAATAAAAACAAAACAGAAGTTGCATTTA
AAAAGAAAGAAATATTACCAGCAGAATTATGCTTGAAGAAACATTTAATCAAGCATTTTTTTCTTAAATGTTCTT
CTTTTTTCCATACAATTGTGTTTACCCTAAAATAGGTAAGATTAACCCTTAAAGTAAATATTTAACTATTTGTTTA
ATAAATATATATTGAGCTCCTAGGCACTGTTCTAGGTACCGGGCTTAATAGTGGCCAACCAGACAGCCCCAGCCC
CAGCCCCTACATTGTGTATAGTCTATTATGTAACAGTTATTGAATGGACTTATTAACAAAACCAAAGAAGTAATT
CTAAGTCTTTTTTTTCTTGACATATGAATATAAAATACAGCAAAACTGTTAAAATATATTAATGGAACATTTTTT
TACTTTGCATTTTATATTGTTATTCACTTCTTATTTTTTTTTAAAAAAAAAAGCCTGAACAGTAAATTCAAAAGG
AAAAGTAATGATAATTAATTGTTGAGCATGGACCCAACTTGAAAAAAAAAATGATGATGATAAATCTATAATCCT
AAAACCCTAAGTAAACACTTAAAAGATGTTCTGAAATCAGGAAAAGAATTATAGTATACTTTTGTGTTTCTCTTT
TATCAGTTGAAAAAAGGCACAGTAGCTCATGCCTGTAAGAACAGAGCTTTGGGAGTGCAAGGCAGGCGGATCACT
TGAGGCCAGGAGTTCCAGACCAGCCTGGGCAACATAGTGAAACCCCATCTCTACAAAAAAAAAAAAGAATTTATT
GGAATGTGTTTCTGTGTGCCTGTAATCCTAGCTATTCCGAAAGCTGAGGCAGGAGGATCTTTTGAGCCCAGGAGT
TTGAGGTTACAGGGAGTTATGATGTGCCAGTGTACTCCAGCCTGGGGAACACCGAGACTCTGTCTTATTTAAAAA
AAAAAAAAAAAAATGCTTGCAATAATGCCTGGCACATAGAAGGTAACAGTAAGTGTTAACTGTAATAACCCAGG
TCTAAGTGTGTAAGGCAATAGAAAAATTGGGGCAAATAAGCCTGACCTATGTATCTACAGAATCAGTTTGAGCTT
AGGTAACAGACCTGTGGAGCACCAGTAATTACACAGTAAGTGTTAACCAAAAGCATAGAATAGGAATATCTTGTT
```

-continued

```
CAAGGGACCCCCAGCCTTATACATCTCAAGGTGCAGAAAGATGACTTAATATAGGACCCATTTTTTCCTAGTTCT

CCAGAGTTTTTATTGGTTCTTGAGAAAGTAGTAGGGGAATGTTTTAGAAAATGAATTGGTCCAACTGAAATTACA

TGTCAGTAAGTTTTTATATATTGGTAAATTTTAGTAGACATGTAGAAGTTTTCTAATTAATCTGTGCCTTGAAAC

ATTTTCTTTTTTCCTAAAGTGCTTAGTATTTTTTCCGTTTTTTGATTGGTTACTTGGGAGCTTTTTTGAGGAAAT

TTAGTGAACTGCAGAATGGGTTTGCAACCATTTGGTATTTTTGTTTTGTTTTTTAGAGGATGTATGTGTATTTTA

ACATTTCTTAATCATTTTTAGCCAGCTATGTTTGTTTTGCTGATTTGACAAACTACAGTTAGACAGCTATTCTCA

TTTGCTGATCATGACAAAATAATATCCTGAATTTTTTAAATTTTGCATCCAGCTCTAAATTTTCTAAACATAAAA

TTGTCCAAAAAATAGTATTTTCAGCCACTAGATTGTGTGTTAAGTCTATTGTCACAGAGTCATTTTACTTTTAAG

TATATGTTTTTACATGTTAATTATGTTTGTTATTTTTAATTTTAACTTTTTAAAATAATTCCAGTCACTGCCAAT

ACATGAAAAATTGGTCACTGGAATTTTTTTTTGACTTTTATTTTAGGTTCATGTGTACATGTGCAGGTGTGTTA

TACAGGTAAATTGCGTGTCATGAGGGTTTGGTGTACAGGTGATTTCATTACCCAGGTAATAAGCATAGTACCCAA

TAGGTAGTTTTTTGATCCTCACCCTTCTCCCACCCTCAAGTAGGCCCTGGTGTTGCTGTTTCCTTCTTTGTGTCC

ATGTATACTCAGTGTTTAGCTCCCACTTAGAAGTGAGAACATGCGGTAGTTGGTTTTCTGTTCCTGGATTAGTTC

ACTTAGGATAATGACCTCTAGCTCCATCTGGTTTTTATGGCTGCATAGTATTCCATGGTGTATATGTATCACATT

TTCTTTATCCAGTCTACCATTGATAGGCATTTAGGTTGATTCCCTGTCTTTGTTATCATGAATAGTGCTGTGATG

AACATACACATGCATGTGTCTTTATGGTAGAAAAATTTGTATTCCTTTAGGTACATATAGAATAATGGGGTTGCT

AGGGTGAATGGTAGTTCTATTTTCAGTTATTTGAGAAATCTTCAAACTGCTTTTCATAATAGCTAAACTAATTTA

CAGTCCCGCCAGCAGTGTATAAGTGTTCCCTTTTCTCCACAACCTTGCCAACATCTGTGATTTTTTGACTTTTTA

ATAATAGCCATTCCTAGAGAATTGATTTGCAATTCTCTATTAGTGATATTAAGCATTTTTTCATATGCTTTTTAG

CTGTCTGTATATATTCTTCTGAAAAATTTTCATGTCCTTTGCCCAGTTTGTAGTGGGGGGGTTGTTTTTTTGCTT

TTAATTAGTTTTAAGTTCCTTCCAGATTCTGCATATCCCTTTGTTGGATTACATGGTTTGCAGATATTTTTCTCC

CATTGTGTAGGTTGTCTTTTACTCTGTTGATAGTTTCTTTTGCCATGCAGGAGCTCGTTAGGTCCCATTTGTGTT

TGTTTTTGTTGCAGTTGCTTTTGGCGTCTTCATCATAAAATCTGTGCCAGGGCCTATGTCCAGAATGGTATTTCC

TAGGTTGTCTTCCAGGGTTTTTACAATTTTAGATTTTACGTTTATGTCTTTAATCCATCTTGAGTTGATTTTGT

ATATGGCACAAGGAAGGGGTCCAGTTTCACTCCAATTCCTATGGCTAGCAATTATCCCAGCACCATTTATTGAAT

ACGGAGTCCTTTCCCCATTGCTTGTTTTTTGTCAACTTTGTTGAAGATCAGATGGTTGTAAGTGTGTGGCTTTAT

TTCTTGGCTCTCTATTCTCCATTGGTCTATGTGTCTGTTTTTATAACAGTACCCTGCTGTTCAGGTTCCTATAGC

CTTTTAGTATAAAATCGGCTAATGTGATGCCTCCAGCTTTGTTCTTTTTGCTTAGGATTGCTTTGGCTATTTGGG

CTCCTTTTTGGGTCCATATTAATTTTAAAACAGTTTTTTCTGGTTTTGTGAAGGATATCATTGGTAGTTTATAGG

AATAGCATTGAATCTGTAGATTGCTTTGGGCAGTATGGCCATTTTAACAATATTAATTCTTCCTATCTATGAATA

TGGAATGTTTTTCCATGTGTTTGTGTCATCTCTTTATACCTGATGTATAAAGAAAAGCTGGTATTATTCCTACTC

AATCTGTTCCAAAAAATTGAGGAGGAGGAACTCTTCCCTAATGAGGCCAGCATCATTCTGATACCAAACCTGGC

AGAGACACAACAGAAAAAGAAAACTTCAGGCCAATATCCTTGATGAATATAGATGCAAAATCCTCAACAAAAT

ACTAGCAAACCAAATCCAGCAGCACATCAAAAAGCTGATCTACTTTGATCAAGTAGGCTTTATCCCTGGGATGCA

AGGTTGGTTCAACATACACAAATCAATAAGTGTGATTCATCACATAAACAGAGCTAAAAACAAAACCACAAGAT

TATCTCAATAGGTAGAGAAAAGGTTGTCAATAAAATTTAACATCCTCCATGTTAAAAACCTTCAGTAGGTCAGGT

GTAGTGACTCACACCTGTAATCCCAGCACTTTGGGAGGCCAAGGCGGGCATATCTCTTAAGCCCAGGAGTTCAAG

ACGAGCCTAGGCAGCATGGTGAAACCCCATCTCTACAAAAAAAAAAAAAAAAAAAATTAGCTTGGTATGGTGAC

ATGCACCTATAGTCCCAGCTATTCAGGAGGTTGAGGTGGGAGGATTGTTTGAGCCCGGGAGGCAGAGGTTGGCAG

CGAGCTGAGATCATGCCACCGCACTCCAGCCTGGGCAACGGAGTGAGACCCTGTCTCAAAAAAGAAAAATCACAA

ACAATCCTAAACAAACTAGGCATTGAAGGAACATGCCTCAAAAAAATAAGAACCATCTATGACAGACCCATAGCC
```

-continued

```
AATATCTTACCAAATGGGCAAAAGCTGGAAGTATTCTCCTTGAGAACCGTAACAAGACAAGGATGTCCACTCTCA

CCACTCCTTTTCAGCATAGTTCTGGAAGTCCTAGCCAGAGCAATTCAGGAAAGAGAAAAAAGAAAGACATTCAGA

TAGGAAGAGAAGAAGTCAAACTATTTCTGTTTGCAGGCAGTATAATTCTGTACCTAGAAAATCTCATAGTCTCTG

CCCAGAAACTCCTAAATCTGTTAAAAATTTCAGCAAAGTTTTGGCATTCTCTATACTCCAACACCTTCCAAAGTG

AGAGCAAAATCAAGAACACAGTCCCATTCACAATAGCCGCAAAACGAATAAAATACCTAGGAATCCAGCTAACCA

GGGAGGTGAAAGATCTCTATGAGAATTACAAAACACTGCTGAAAGAAATCAGAGATGACACAAACAAATGGAAAT

GTTCTTTTTTAACACCTTGCTTTATCTAATTCACTTATGATGAAGATACTCATTCAGTGGAACAGGTATAATAAG

TCCACTCGATTAAATATAAGCCTTATTCTCTTTCCAGAGCCCAAGAAGGGGCACTATCAGTGCCCAGTCAATAAT

GACGAAATGCTAATATTTTTCCCCTTTACGGTTTCTTTCTTCTGTAGTGTGGTACACTCGTTTCTTAAGATAAGG

AAACTTGAACTACCTTCCTGTTTGCTTCTACACATACCCATTCTCTTTTTTTGCCACTCTGGTCAGGTATAGGAT

GATCCCTACCACTTTCAGTTAAAAACTCCTCCTCTTACTAAATGTTCTCTTACCCTCTGGCCTGAGTAGAACCTA

GGGAAAATGGAAGAGAAAAAGATGAAAGGGAGGGGGGCCTGGGAAGGGAATAAGTAGTCCTGTTTTGTTTGTGTG

TTTGCTTTAGCACCTGCTATATCCTAGGTGCTGTGTTAGGCACACATTATTTTAAGTGGCCATTATATTACTACT

ACTCACTCTGGTCGTTGCCAAGGTAGGTAGTACTTTCTTGGATAGTTGGTTCATGTTACTTACAGATGGTGGGCT

TGTTGAGGCAAACCCAGTGGATAATCATCGGAGTGTGTTCTCTAATCTCACTCAAATTTTTCTTCACATTTTTTG

GTTTGTTTTGGTTTTTGATGGTAGTGGCTTATTTTTGTTGCTGGTTTGTTTTTGTTTTTTTTGAGATGGCAAG

AATTGGTAGTTTATTTATTAATTGCCTAAGGGTCTTCTACTTTTTTAAAAGATGAGAGTAGTAAAATAGATTGA

TAGATACATACATACCCTTACTGGGGACTGCTTATATTCTTTAGAGAAAAAATTACATATTAGCCTGACAAACAC

CAGTAAAATGTAAATATATCCTTGAGTAAATAAATGAATGTATATTTTGTGTCTCCAAATATATATATCTATATT

CTTACAAATGTGTTTATATGTAATATCAATTTATAAGAACTTAAAATGTTGGCTCAAGTGAGGGATTGTGGAAGG

TAGCATTATATGGCCATTTCAACATTTGAACTTTTTTCTTTTCTTCATTTTCTTCTTTTCTTCAGGAATATTTTT

CAAGATGTCTTACACAGAGACACTCTAGTGAAAGCCTTCCTGGATCAGGTAAATGTTGAACTTGAGATTGTCAGA

GTGAATGATATGACATGTTTTCTTTTTAATATATCCTACAATGCCTGTTCTATATATTTATATTCCCCTGGATC

ATGCCCCAGAGTTCTGCTCAGCAATTGCAGTTAAGTTAGTTACACTACAGTTCTCAGAAGAGTCTGTGAGGGCAT

GTCAAGTGCATCATTACATTGGTTGCCTCTTGTCCTAGATTTATGCTTCGGGAATTCAGACCTTTGTTTACAATA

TAATAAATATTATTGCTATCTTTTAAAGATATAATAATAAGATATAAAGTTGACCACAACTACTGTTTTTTGAAA

CATAGAATTCCTGGTTTACATGTATCAAAGTGAAATCTGACTTAGCTTTTACAGATATAATATATACATATATAT

ATCCTGCAATGCTTGTACTATATATGTAGTACAAGTATATATATATGTTTGTGTGTGTATATATATATAGTACGA

GCATATATACATATTACCAGCATTGTAGGATATATATGTTTATATATTAAAAAAAAGTTATAAACTTAAAACC

CTATTATGTTATGTAGAGTATATGTTATATATGATATGTAAAATATATAACATATACTCTATGATAGAGTGTAAT

ATATTTTTATATATATTTTAACATTTATAAAATGATAGAATTAAGAATTGAGTCCTAATCTGTTTTATTAGGTG

CTTTTTGTAGTGTCTGGTCTTTCTAAAGTGTCTAAATGATTTTTCCTTTTGACTTATTAATGGGGAAGAGCCTGT

ATATTAACAATTAAGAGTGCAGCATTCCATACGTCAAACAACAAACATTTTAATTCAAGCATTAACCTATAACAA

GTAAGTTTTTTTTTTTTTGAGAAAGGGAGGTTGTTTATTTGCCTGAAATGACTCAAAAATATTTTTGAAACA

TAGTGTACTTATTTAAATAACATCTTTATTGTTTCATTCTTTTAAAAAATATCTACTTAATTACACAGTTGAAGG

AAATCGTAGATTATATGGAACTTATTTCTTAATATATTACAGTTTGTTATAATAACATTCTGGGGATCAGGCCAG

GAAACTGTGTCATAGATAAAGCTTTGAAATAATGAGATCCTTATGTTTACTAGAAATTTTGGATTGAGATCTATG

AGGTCTGTGACATATTGCGAAGTTCAAGGAAAATTCGTAGGCCTGGAATTTCATGCTTCTCAAGCTGACATAAAA

TCCCTCCCACTCTCCACCTCATCATATGCACACATTCTACTCCTACCCACCCACTCCACCCCCTGCAAAAGTACA

GGTATATGAATGTCTCAAAACCATAGGCTCATCTTCTAGGAGCTTCAATGTTATTTGAAGATTTGGGCAGAAAAA
```

```
ATTAAGTAATACGAAATAACTTATGTATGAGTTTTAAAAGTGAAGTAAACATGGATGTATTCTGAAGTAGAATGC

AAAATTTGAATGCATTTTTAAAGATAAATTAGAAAACTTCTAAAAACTGTCAGATTGTCTGGGCCTGGTGGCTTA

TGCCTGTAATCCCAGCACTTTGGGAGTCCGAGGTGGGTGGATCACAAGGTCAGGAGATCGAGACCATCCTGCCAA

CATGGTGAAACCCCGTCTCTACTAAGTATACAAAAATTAGCTGGGCGTGGCAGCGTGTGCCTGTAATCCCAGCTA

CCTGGGAGGCTGAGGCAGGAGAATCGCTTGAACCCAGGAGGTGTAGGTTGCAGTGAGTCAAGATCGCGCCACTGC

ACTTTAGCCTGGTGACAGAGCTAGACTCCGTCTCAAAAAAAAAAAAAAATATCAGATTGTTCCTACACCTAGTGC

TTCTATACCACACTCCTGTTAGGGGGCATCAGTGGAAATGGTTAAGGAGATGTTTAGTGTGTATTGTCTGCCAAG

CACTGTCAACACTGTCATAGAAACTTCTGTACGAGTAGAATGTGAGCAAATTATGTGTTGAAATGGTTCCTCTCC

CTGCAGGTCTTTCAGCTGAAACCTGGCTTATCTCTCAGAAGTACTTTCCTTGCACAGTTTCTACTTGTCCTTCAC

AGAAAAGCCTTGACACTAATAAAATATATAGAAGACGATACGTGAGTAAAACTCCTACACGGAAGAAAAACCTTT

GTACATTGTTTTTTGTTTTGTTTCCTTTGTACATTTTCTATATCATAATTTTTGCGCTTCTTTTTTTTTTTTT

TTTTTTTTTTTCCATTATTTTTAGGCAGAAGGGAAAAAAGCCCTTTAAATCTCTTCGGAACCTGAAGATAGACC

TTGATTTAACAGCAGAGGGCGATCTTAACATAATAATGGCTCTGGCTGAGAAAATTAAACCAGGCCTACACTCTT

TTATCTTTGGAAGACCTTTCTACACTAGTGTGCAAGAACGAGATGTTCTAATGACTTTTTAAATGTGTAACTTAA

TAAGCCTATTCCATCACAATCATGATCGCTGGTAAAGTAGCTCAGTGGTGTGGGGAAACGTTCCCCTGGATCATA

CTCCAGAATTCTGCTCTCAGCAATTGCAGTTAAGTAAGTTACACTACAGTTCTCACAAGAGCCTGTGAGGGGATG

TCAGGTGCATCATTACATTGGGTGTCTCTTTTCCTAGATTTATGCTTTTGGGATACAGACCTATGTTTACAATAT

AATAAATATTATTGCTATCTTTTAAAGATATAATAATAGGATGTAAACTTGACCACAACTACTGTTTTTTGAAA

TACATGATTCATGGTTTACATGTGTCAAGGTGAAATCTGAGTTGGCTTTTACAGATAGTTGACTTTCTATCTTTT

GGCATTCTTTGGTGTGTAGAATTACTGTAATACTTCTGCAATCAACTGAAAACTAGAGCCTTTAAATGATTTCAA

TTCCACAGAAAGAAAGTGAGCTTGAACATAGGATGAGCTTTAGAAAGAAAATTGATCAAGCAGATGTTTAATTGG

AATTGATTATTAGATCCTACTTTGTGGATTTAGTCCCTGGGATTCAGTCTGTAGAAATGTCTAATAGTTCTCTAT

AGTCCTTGTTCCTGGTGAACCACAGTTAGGGTGTTTGTTTATTTTATTGTTCTTGCTATTGTTGATATTCTATG

TAGTTGAGCTCTGTAAAAGGAAATTGTATTTTATGTTTTAGTAATTGTTGCCAACTTTTTAAATTAATTTTCATT

ATTTTTTGAGCCAAATTGAAATGTGCACCTCCTGTGCCTTTTTCTCCTTAGAAAATCTAATTACTTGGAACAAGT

TCAGATTTCACTGGTCAGTCATTTTCATCTTGTTTTCTTCTTGCTAAGTCTTACCATGTACCTGCTTTGGCAATC

ATTGCAACTCTGAGATTATAAAATGCCTTAGAGAATATACTAACTAATAAGATCTTTTTTTCAGAAACAGAAAAT

AGTTCCTTGAGTACTTCCTTCTTGCATTTCTGCCTATGTTTTGAAGTTGTTGCTGTTTGCCTGCAATAGGCTAT

AAGGAATAGCAGGAGAAATTTTACTGAAGTGCTGTTTTCCTAGGTGCTACTTTGGCAGAGCTAAGTTATCTTTTG

TTTTCTTAATGCGTTTGGACCATTTTGCTGGCTATAAAATAACTGATTAATATAATTCTAACACAATGTTGACAT

TGTAGTTTTACACAAACACAAATAAATATTTTTATTTTAAAATTCTGGAAGTAATATAAAAGGGAAAATATATTT

GAAAGGGATAAAGGTAATAGAGCCCTTCTGCCCCCCACCCACCCAAATTTACACAACAAAATGACATGTTCGAATG

TGAAAGGTCATAATAGCTTTCCCATCATGAATCAGAAAGATGTGGACAGCTTGATGTTTAGACAACCACTGAAC

TAGATGACTGTTGTACTGTAGCTCAGTCATTTAAAAAATATATAAATACTACCTTGTAGTGTCCCATACTGTGTT

TTTTACATGGTAGATTCTTATTTAAGTGCTAACTGGTTATTTTCTTTGGCTGGTTTATTGTACTGTTATACAGAA

TGTAAGTTGTACAGTGAAATAAGTTATTAAAGCATGTGTAAACATTGTTATATATCTTTTCTCCTAAATGGAGAA

TTTTGAATAAAATATATTTGAAATTTTGCCTCTTTCAGTTGTTCATTCAGAAAAAAATACTATGATATTTGAAGA

CTGATCAGCTTCTGTTCAGCTGACAGTCATGCTGGATCTAAACTTTTTTAAAATTAATTTTGTCTTTTCAAAGA

AAAAATATTTAAAGAAGCTTTTATAATATAATCTTATGTTTTAAAAAAACTTTCTGCTTTTAACTCTCTGGATTT

TGATTTTTCAAATTATATATTAATATTTCAAATGTAAAATACTATTTAGATAAATTGTTTTTAAACATTCTTATT

ATTATAATATTAATATAACCTAAACTGAAGTTATTCATCCCAGGTATCTAATACATGTATCCAAAGTAAAAATCC
```

-continued

```
AAGGAATCTGAACACTTTCATCTGCAAAGCTAGGAATAGGTTTGACATTTTCACTCCAAGAAAAAGTTTTTTTTT
GAAAATAGAATAGTTGGGATGAGAGGTTTCTTTAAAAGAAGACTAACTGATCACATTACTATGATTCTCAAAGAA
GAAACCAAAACTTCATATAATACTATAAAGTAAATATAAAATAGTTCCTTCTATAGTATATTTCTATAATGCTAC
AGTTTAAACAGATCACTCTTATATAATACTATTTTGATTTTGATGTAGAATTGCACAAATTGATATTTCTCCTAT
GATCTGCAGGGTATAGCTTAAAGTAACAAAAACAGTCAACCACCTCCATTTAACACACAGTAACACTATGGGACT
AGTTTTATTACTTCCATTTTACAAATGAGGAAACTAAAGCTTAAAGATGTGTAATACACCGCCCAAGGTCACACA
GCTGGTAAAGGTGGATTTCATCCCAGACAGTTACAGTCATTGCCATGGGCACAGCTCCTAACTTAGTAACTCCAT
GTAACTGGTACTCAGTGTAGCTGAATTGAAAGGAGAGTAAGGAAGCAGGTTTTACAGGTCTACTTGCACTATTCA
GAGCCCGAGTGTGAATCCCTGCTGTGCTGCTTGGAGAAGTTACTTAACCTATGCAAGGTTCATTTTGTAAATATT
GGAAATGGAGTGATAATACGTACTTCACCAGAGGATTTAATGAGACCTTATACGATCCTTAGTTCAGTACCTGAC
TAGTGCTTCATAAATGCTTTTTCATCCAATCTGACAATCTCCAGCTTGTAATTGGGGCATTTAGAACATTTAATA
TGATTATTGGCATGGTAGGTTAAAGCTGTCATCTTGCTGTTTCTATTTGTTCTTTTTGTTTTCTCCTTACTTTT
GGATTTTTTATTCTACTATGTCTTTTCTATTGTCTTATTAACTATACTCTTTGATTTATTTTAGTGGTTGTTTT
AGGGTTATACCTCTTTCTAATTTACCAGTTTATAACCAGTTTATATACTACTTGACATATAGCTTAAGAAACTTA
CTGTTGTTGTCTTTTTGCTGTTATGGTCTTAACGTTTTTATTTCTACAAACATTATAAACTCCACACTTTATTGT
TTTTTAATTTTACTTATACAGTCAATTATCTTTTAAAGATATTTAAATATAAACATTCAAAACACCCCAATTAAA
AGTCAGAGATTGTTAATACCACATGATCTCACTTACACACAGAATTGAAAAACTTGGAACTCATAGAAGCAGAGA
GTAAAAACATGGTTACCAGGTGCTGGGGAGAGGCGGTGGGCTGGGGAGATGTTGGTCAAAGTTAGACAGGAGGAA
TAAGTTCAAGAGATCTATTGTACAACTTATTCAGTTAGATAGGAGGAATAAGCTAAAGATCAAGAGATCTATTGT
ACAATGTGACTATAACCAACAACATATATTGTACACTTGAAAATTGCTAACAGTATCTTTTAAGTGTTCTCTCTA
CAAATAAATATGTGAGGTAATGTATATATTAATTAACTGTAGTCATTTCACAATGTATACTTATTTCAAAACATC
ATATTGTATGCTATAAATATATACAACTTTTTATTTTCAATTTTAGAAATGTCCTTAAAAAATCAGATTTTCAGA
TCAGATAAAAAAGCAAGACCCAACTATATGCTGCCAACAGGAAACACACCTTAAAAATAAAGGACGAACAAACAG
ATTAAAAGTAAAAGGATGGAGAAAAGATACATCATATTGGTAATTAGAAGAAAACTGGAGTGACAATATGAAACA
AAATAGATTTCAGAGCAAAGAATATTACCAGGGGTAAAAATGATCATTTTATAATGATAAAAGAGTCAGTTCAGC
AAAAGGATATAACAGTCCTAAATGTTTTTTCACCTCATAGCTGTGTCAAAATAGATGAAGCAAAAACTGATAGAA
CTGTAAGAAGTAGACAAGTCCACAATTATGTTTGGAGATTTTTTTTTTTTTTTTTTGTCGCCCAGGCTGGAGT
GCAGTGGCAGGATCTCAGCTCACTGCAAGCTCCGCCTCCCAGGTTCACGCCATTCTCCTGCTTCAGCCTCCCCAG
TAGCTGGGACTACAGGCGGCCACCACCACGCCTGGCTAATTTTTTGTATTTTTAGTAGAGACGGGGTTTCACCG
TGTTAGCCAGGATGGTCTCGATCTCCTGACCTCGTGATCTGCCTGCCTCGGCCTCCCAAAGTGCTGGGATTACAG
GCATGAGCCACTGCACGCAGCCTGGAGATTTTAATATCCTTTCAATGTTTAGTAGAACAAGAATACACAAAATCA
GTAAGGATATAGAAGATTAGAACAAGACTATCAAACAATTTGACTTAAATGACATTTGTAGAGCACAGCAGTCCC
CAACAACAATAAATCACACATTCTTTCCAAGAGTACATGAAACATGTACCAAGATAGACCGTATTTTGAGCCATG
AAACAAATCTTGATAAATTTAAAAGGATTCAAGTCATAGAAAATATGTTCTCTGACCACAATGGAATTAAATTAT
TAACCAATAACAAATATCTGGGAAAACCTCAAAAACTTGGACACCAGCGCTTTTAAAAGACTAAATAATTTCTAA
ATTATGTGTGTTGGGGGAAAAGAGAAATGGATTAGAGAGCAAAAAGGGTATCAGAGTGCTGTGGTACGATTTTT
ATGAAGAGTGGAACAGAATCTGCCTTTGGCGTTTCCCCACTACAGCCCATTCTTCACATTGATAACAGCATGATC
CTTCTAAAATTAAATCTAACGATCACTTCTGCTTAATGGCTCTCCAACACTTACAGAATTAGGTCCAAAATTCTA
GCACAGTTTCTGTTCATCTTTCTAACCTTTCTTCCCACAGGTCTAGCTAGTACGTATTTCTTTTATTGCATTTAT
TACACTATTCCTTTGCTTATCTATCTCCCCACCTAGGCTAAAGAACAAGATTCTTGTCTTTTTCATTTTGTGTC
```

-continued

```
TCAGTGCCTAGCATGGTGCCAGGCACACAGCATGCTTCCAGTAAATGTTAGCTGGATGGATGTAATGAGTATATT
AAATATTAATTTATTTGTTTTTCCCCAAAAAGAATTATTTCCTGCAAATCAAGGAAATTGCTTTCTTTATATAAT
CAAAAACTTATTTTCCCAGAAGATTCTTCATTAAAAATTAAGCCTATGCACAACCTAGCTCTAAAGTTTCAAAGA
TTTTAGGCAGCAATTTTTCAATCTTTTTGAAGTAATACATTTGAATCTTTTCAAATTTCTGTTTCTGCATTTGTG
CCACACCATCTCATCTCTTGCTGAAATGTTTTTGTTAAATTAATTGCTTGATAAATTGCTAAGTACTTTTCATCA
GACCAATTAGGACAATAGTAAGTATCCATCTGTGGAGCGCGGACATTCAAGAAATCTGATCCAGTATTTAGAAAG
TCATTCCTGAGCTGAGTTGGCTCAAACTGGCACCTTCTGGCATTTGCTTGTGGGTGGGGAATGTGGAATGCTTTG
AAAGCTGAATGAGTTTGTCAAGTTTTAAAATTCCCTTATGGCTAAAGGAAAACAACATTCATTGTTTAAAAACAC
CATTGTTTGTTTTTTCTGCTTTTTTGTTCTTTGGAGCCTGAATCTGCAAAAACACTCACACCCAGCATTTTGCTT
CATGTACCACTCCTAAGATGTTTTTAGAGACTTGAATAGTGTCTCCGCACTACTTTTTATTGTGATTGTTCAGAA
TGTTCATAACAAATGGTAAAAAGTCAGTTTTAGTGCTCAAATTGAGTTTTATGGAGAAAGACCATAATTTATGTT
TGTCATTGTAAATTGATAGGAGAATTTTTGGAAGTTTGCGTCCTAGAACCAGATTTCCAAGGCTCAGATCCTTAT
TTTCTCACTTCCTAGCTGTGTGACCTTAGACAAGGTATTAAACCTGTCTGTGCTGCCTCAGTGTCCTCATCTATT
CTTTAAGAGTAAGAATAGAACCTACCCGATAGAGTCACTTGAAGATTAAGTGGGTTAGTAAATTCAGAATGCTTG
GAACAGTAACTAGCACAGAATAAGTGTCCAATAAAATTGGGTTGCAGCTATTATCAGTATTATTCCTGTCATAAT
CATCATCACCATTAAGCAATTAAATGTAGAGTTCCAAAATTTGATTATGAAACTACAGTTATACAGCCATGATTC
CCGGTGATACCACGTCAGTAACAAGATTATTTCCTTAGCTTGAGCCAGTCACTACCTCATTGCATGTGGCAGAGT
GTGTTGCCGTAGGCAAATGTCATTGTAGGGAATGAAAAAAAAATTGCCTGTGAGCTGCTCTCCAGAGGCCTCATC
CCATTTTCCCATCGTCCACTTTACTCCATCTCCACTGCCACTATTAGGACCTTATCATTTCTTGTCTAGATTAAT
TCAACAGCTTCCTTCCTTCTAGTCTCCATGATTTCACCCACTAGCCATCCCCTCCCCTTTGCCCAATTTTCTCCA
TTTATGGTAGAGTGATCTTTCTAATAGGAAACTCCTGACTTGCCTTAAAAAGCCCTCATTGAGGCCGGACGTGGT
GGCTCATGCCTGTAATCCCAGCACTTTGGGAGGCCGAGGCAGGTGGATCACGAGGTCAAGAGATTGAGACCATCG
TGACTAACACAGTGAAACCCCATCTGTACTAAAAATACAAGAAATTAGCCAGGCGTGGTGGGGGGTGCCTGTAGT
CGCAGCTACTTGGGAGGCTGAGGCAGGAGAATGGCGTGAACCCGGGAGGCAGAGCTTGCAGTGAGCCGAGATTGC
GCCACTGCACTCCAGCCTGGGCGACAGAGTGAGACTCCGTCTCAAAAAAAAAAAGCCCTCATTGACAACCTTCAA
CCCACAATCCATGGTGAAGCACAGGAGCCTTGGGGATCTGCCCCCAGCACACCTCTCCACCCTTGTCTCTCACTG
CTCCTGCCTTCATGGAGAGCCCTGATGAACTATTTGTAGTTTCCCCTGACTCACCTTGCTGTTACTGGGCCTGTG
TGCGTGTTGCTCCCACTACCTGCAATACGCTTACCCACTTCACCTGGGTGAACTTTACTTAGGATTCACCTTAGG
TGGGCATCATGTTCTTCCAGGCCCCTCCTCTAACTTTTAGTTGAGAGTATTCCAGACTTAAGGCTCCATGGGATA
GGGATCTTGTCTATGCACCAGCTTATTCCCAACTGCCTGGCACGTAATGCATTTATTAAATATATATTGAATTGA
TTACCCTACTTGGGGCTCTTGTTTGCTTCTACACTTACAGTTCTAGCATAGCACTTAACTCATTATCATGCATCA
TTATTATGGGTTTGTTTTGTCTCCCATTAGACTGTGAGCTCCACAAGGCTGTGTCCTTGTCTTATACATCATTGT
ATTTCCAGCTTCCAACATAGTGCTTGCCATGACACAGGAAGTCAGTAAGCTCTGAATGAATGAATAGTATCTACA
TACCATTAATCTGAGGTTTAAAGTTTCCCCAAATTCTGAAGCAAGGGGATTTACGGACTTCCCTGACAATTTTTG
GATGTCATCCCAATGATACCACTAACATTTTAAGGGACAGCTTGCATATATACATTTTTCTGGATGGCAGTTTTT
TTTCCCACAGGCTTCATCAGATATTTCTCCATAGCCTTCCTCAGATTCTCAAAGGGGTCTCTGATTCCCCCAAAA
GATAAGAAACTGTCATAAAAAATTATTTCTAAATATCAATTGTTAAATAAAATGTTTGCAAAGCAGCCTGATGAA
TCATTTCAGGCCACTTGACCCCGATGAGTTAGAGAGTTTGTGCTCTGCAATCTGACTGCTTCCAGCAGTCTCACT
GCTGCTGGACTGTGGCACTTCCAATTGGCAGCAGGGCAAGTTTCTTCTGGATGAATATTCTGTCATAGGGGTCCC
CCTTCCACACATACCTGTAGGAGCAGTTTGAAACTCATATGCATGGTCTTCCTGGTTCTAGGCACATGAGTCATT
TAAGCTGCTGGAGCCAGGACCAGCTAGTATGCTAGCCCGGCATTCAGAAAGTTAAAATTTGGGGTCAAAACTGAG
```

-continued

```
AACCTTCTTTGATCCACCTTGGCCAGACATTTTCTCTGGCTTCCATTAATAGCCTCAACATTTTTTTTTTTCTG

GCCTAGACCCACACAGGCAAGAGACCAGAGCTTCTCTAAGGAGCTAAGGGAAAGCACATTTTAAAAATAACTTGA

GCAAATGAATTCATCTGGCAAAAGCAACCCCACTACGTAAAATAAACCTTTTTAGTTTCGCAATAGCAGTTCCTG

AAAATGTAAACAACCTCAGGGTCTACATGCACTGAATCATTTGCTGAACAGAAAGTCCCTGGTCCAAATTCTGCA

AGAATAAACACCTTACAAAACTAGGGGTCAATGACCTTCATATGGGAACAAGGAGGGTGTGGGGGGCAGCAACCC

ACCCTGAGGACAATGAGAAAGTCTTGAGACTTGATATTCAAAATGCTGGCTTTCTAAACCAAAAACTGGCATGAG

TGGAGGGAGAAGGGGAGGGTGGGCACAGTCTATGCCTCAGGCTCTTGCTCAGACCCTACCAGGCCCCTGCCTTCC

CTAGGGAAAGCGAGAGTCTACTCACTGTCATGAAGCCAGAGGAAGGCCCTGCAGGTTTCACTGTGTGTTCTGTTG

ACAAGATGATGGTTCCATTGAAACTGTAATAACATACTTGGCCAACTAAGCCCATACGATCGTAGTAACTTTGTA

CCCAGTCCTAGCTTTTCAAACATAATGATAATATGTTCTTTCTAATGTGGCCCATACTGTTCTAATGAACTTATG

CTGAGTTTTTCTGAGTACTAGAATAATATTCGCCATAAATAATAGATATAATTATTCTCATTTAATATTTGCGTA

GCTCTTCTTTAAAGCAGAAAGTATTTTCTCATTCCTTACTAGAACCTTTCTGTGTGAGGAGCACTGAGCTAGAAC

CCATATCTTAGAATGGTCAGAATTTGGAGAAATTCAGGGAAAAGGCACTGGACTCATTTTTAAAGACTAGAAAAT

GCAACCTCCAGAAAAAGATTCAAGAGTTTTTTACTCCCAGAGATGTAGGAAAGATTGGAGTAAATCTTAATATTA

TATTTCAGGTAAACAAAGGATCACTGTCAAAATAGCAGCATTTATTGAGTAATGGCTGTGTGCCAGGTACTTTAC

AGTTTCACATTTAACCCTCATAATAACCTTGTAAAGTGGATATCCCCTCAGTACATGATGAGAACACTGAAGCTT

AGGTTAAATGATTGTCCAAATCGGACAATCATTTTCAAAATCTCCCCCTTTTTTCTCCTTTCTTATCTGCAAGG

CAGATTGCCCTTTCCCTTTCAGTGAAACTTGTGCATGACCACATGACTCTCTTTGGCCAATGAAACATGAACAAG

CAGCGTTTATCACTTTCAGATGGAAGGCTTTGCATGAGCTTTGCCTCCTTTTCACTCTGCCACAGTGGCCACTAA

CATTCCAGATAGTGGCGCTCTGCAGGCTAGGTCCTATAGTGGGAGCTATGGGCAGAGCCCCCTTTCCCACCCCCA

TCAAGATGTGCATGCTGCATAAGCCATGCATTAATCTTTGCAGTTTTAAGCCACTAAGTTTTGGAGTTATATTAA

TCATTAATCATGGTTCTCAAGAGAAACAGAGTGGGGAGTGGTATTCATTATGGGAATTGGCTTACATGATTATG

GAAGCTGAGTAGTCCCCCAGTCTGCTGTTTTGAGCTGGAGAACTAGAGGAGCCAGTTGGTATAATTCAGCCCAAG

CCTGAAGGCCTGAGAAATGGGATGGGGGAATTGGGAGGGTGGGTGTGCTAGGGTAGGATAAGTCCTGAAGTTCAA

AGGCCAGCCAGAAGGTGGATGTTTCAGCACCAGAAGAGAGAGCAAATTCGCTTTTCTTCTGCCTTTTTGTCCTCT

CTGGGCCCTCAATGGATTGGATGATGCCCTCCCACATTGGTAAGGGTGGATCTTCTATACTCAGTCTGCTAATTT

CTTCCAGAAACATCTTCACAGACACATCCAGAAATAATGTTTTACCAGCTATCTCGGTATCCCTTAGCCTAGTCC

ATATTTAAAAATTAATGATCACAAGCAGTTGTTTGTTTCCACAGCAAAACCTGGGTGACAGACCAAGTGACCCAG

ATGACTAGAATTTGACCTTTCTTTGTTGCCCACACCATACTCTGAACTAACATGCTGTGCTGCCTTCCAAGTGGA

GAATGATGGCTAAGTATCTTCTACCTAATTTGAGTCACAGAAAAAAAAAAAAAAGGTTATTAACTGCAGTGACAA

GAATTGTGATTCCCCAGGGGGCAGATCAAGACTGATAGATAAGAGAAGTGAGGAACATCTGGGGAATGTCCATTG

AAAATTTACTCAGAAGAGAAGAATAATTAATATAATAATATGATATATTGAATTATAATAAATAATATTTTGATG

TATTTCCTTCCAGGCATGTTTAAGTTATAGACTTTGAGTATATTTTCTCAAAGGGGTTCTATGTAAGAGACTAT

TTCTTAATATAGTTCCTAGCTTGGAATTGCTCTTGCTGGTTTAAGCTGAGCTTATTTTATTACAGACTTCACAAC

AATAACGTTTTCCTTCACTAGTCAGTACACAAGATGGTCTTCATTTCCAGTTTGGAATCCCACACTATCAGAGCC

TGAGACAAGGACTAGTATGCAGTTAGTTTGTTTGGGAGGTGATTCCAGGAAGTGGGAATGAGAGATCAGTCAGCC

TGCAACACGAAGGAGGAAAAGTCAATATAAGGATGAATTTGGCAATTGGCCGTTTCATGCAACTGGGGCTAAATT

TTGCTTGGCTCTCTAAGAAATGTAAAGAATGCCTCCCGTAATTGCTCACCTCAAGTATTTATTCATTGGCTCTCA

TGCTCCATTGGTTGTCCATGAGAACTTTAGCCCTCCCTCGCTGCAGCACAGACACTGTGCTTTCTCCTAGGCTGA

GCAAGCTCCTGCATCTGTGGAAACCGTCCCGGGGCAGATAGTGAAATAATGACTGCTGCGTGCTTGAGATCTGGG
```

-continued

```
AAAGAGGCCACATCATAAGTGCACTGAAATCAGAGATGTGTCAAGAGATGTGACACAGGGCATCTGAGGTGTCTA
CTGCACCAGCTATAACTCCCTAAACGCTAATCTCAGTTCTTACAGAGGGGATGGATGCAAGGGAACAGTCATGAT
TGAGAGCACCGAAGAAGCTCTGTATGAACCTTAGGCAAGTTTCCTAATCTCCAAAATGAAGGTAATAATACCCAC
CATCCAAGATCTTCGGGAGGAATAGATGAACTAATGTATGTGAAAATGTCCAGCACAGGTCCTAACCCATAGTAG
GTGCTCACCAAATGTTAGTTCCCTGCCCTCCACGTTGTGTGTATCCGGAGCTGCACTAGATGCTGAGGCAAATGG
TCTCAAATGTACTTTAACACTTAATGACTGAGATTTTTTCTGAGCTGCCTACAGGTTATTGACTATATTCATTAT
TAATAATAATATATGGCCACTTCAGGCAACTGGGGCTAAATTTTGCTTGGCTCTCTAAGAAATGTAAAGAATG
CCTCCTGTAATTGCTCACCTCAAGTATTTATTCATTGGCTCTCGTGCTTTATTGGTTGTCCCTGAGGACTTTAGC
CCTCTCTCACTGCAGCACAGACACTGTGCTTTCTCCTAGTTTCTGTGGCAAGTGACAGGAGCCCACCTCAAACTA
AAGCAAAAGGGACTTCATTGGCTCTTGTAGCTAGGAATTCCAGGGTTGGCACTGGCTTTGGGCACTACTGGATGC
AGGAATTCAAACAATGTCTTCAACTCTTTCTTTTGGTGTTTCTCTCAGCTGTGCTTCTCTTGTCGTTTCTTTTTC
CCATTTTACAGATAAGTTCATCCGTAACTGAGAGAGGTGAAAAGGGGATGGCTGCAGAGAACTCTGGCTTATATC
ATCCTTGCTTGCTGACCTCAAGGTCCATGTATAAATTCTCAGAGAAGAAGCCCTCTGGTTGGTGATGCTTGGAAC
ATGCCCTGGAGGGTGGGCCCCTTGAAGTGGAGCTTGCTGGAACCACATGGGCTGGAGCAAGGCGCTAGGGCCAGA
AGAGAGAGGTAGGCAGGGCTGCTGGCCAGGCACTCTTCACCAAGACAAGGCAAGAGGAGGGGCATGATTGAGGCA
GTGATACAGAAAGCAGACAGTAGAGGTCGTGGCAAGTGTGCCGTTACTTGCTACCTGTGGTTGATGGGAGAGTCA
CACCACATTTAGGAGGAGAATCCATTTGCCACTTCTGACAATGCCACAAGAATCACATATTTCATCCAGAGGT
TGAATTTGGCCCATGCTGAGCTTTAAAATACAGAGCTGTCTTGGAACAATGGCTCAGTACATTCATTTGGTGTCC
AACAAAGCCTGCCTCTGTTGCCTTCCCTCTCTGTGTGCCCTTCAAGATCTTCATTGTGCTTTGGGGAGAGAAA
GAGAAAATGTCATATCAGGGTAGCTCACCCCATGTGTCCTGGACTCAGGAAAAGAGTATCTTATCACCTTACTCT
TTTGTTATTATAAAAAAAAAGTTGAACGTCTTCAAATAAAATAAAGAAGTATAGAAAAAATTTTTAAATTAACCT
GTTATGATTCTACCTAGAGAACCATTGTCAACATCTTGGTATATGTACTTCCAGATACTTTCCTATGAATATATA
CATTGTAGATTTTTTAATATTAAAAGGCTATCATGCTGCTTTGTATACAGGCTTTCTTTACTGATATGTAATATA
ATACACAGACAAATATACAAATCCTAAGCCATCAACTCATTGAATTTTATTCATTGTTTTTTAATACCTGCATTG
TGTTCCATTGTTAGGCTATGTCACAACATATTTTAATTAAGCCCCTATTGATGAATATTAATTACTCTATTTGCC
AGTTCATTCCAGTCCAACATTTATTGAGTGTCTACTTACGGGCCAGGCACTCTTGTATTCATCAAGATCACCACA
TTATCTGTATCAGTTATTTATTGCCACAATAAAACTGCATAACAAATCACTCCAAAATGTAGCACCTTAAAACTA
CAACTACTTATTATTTCTCAAGAGTCAATGGGTCAGCTGAGCAGTTCTGCCGATAGGGGTCAAGGTCAACACATT
TCAACTAGACTACTTGTAAAAAAGAATGAGTGTCTGGGTAGGTGTGTTCTTCTAAAAATAAAACAAGGAATGAGG
AAATTGCAGGTAGGATAAGAGGGGGGTTTGGCAACCAAACCCCACAAAAGGCAGACAAATTTTAAGGAAACATAA
TGCCAGACTCCTATGTCATCATCCAAGTAGATGCAGTGAAGTATAACCTGGGGCGTAGTAGGGTAGGAGTGGGGA
GAGCAGAGGAGAAGGAAGGGAGATTGCTTTTCATCACTTTTGGATTCCCTAATAACAGACATGACTGCCAGTATT
AAAATTTAACAAAGGATATCTGATCATTAATTTTCCTGTATAAGTCACTGGTGATCTTCAACATCTCTCCCTCCC
TTCCTCCCTTCCTTCCTCCCACCCTCCCTTCCTTCCTTCTTTCCTCTTTTGCTTTCAACTTCCTTTTCTCGTTTC
CTTTTGCTTTCTTTCTCTTCTCCCTTTTTTCTGTCACTCTGGGCGTATGTAGTAGTGTAAAAAGGTTGACAGAGA
AATCAAATATAACAGGAGCAGGGCCCTGAGAAAAGCACCTGGCATCCTGTAGGCAAACCATTGTTTCTAAAAGAA
GGGACTGAGAGATTGAGGAGCTCAGGACATTGCCAAATGAACAAGGCAAGCACATTTATTCAGTACCAAACAAAC
GGAAAACGGCCTTTCCAAATAACTGACCTATAAAACAGCCTTTTCACAAGAGTACCGTAATTACTGGCCAACAGC
AACAATGAAAAACAACTCCCAAACAAAGAAATATTTCTGGATTAAAAGCCATGAGATCTGGATTCTAACAAGCTG
TGCTCCTCAAACTACAAGTACAAAATCTGGCTCTAAACTAACAAGCTATGAGCCTCAAACTGATGACTGGCATGT
TTGGGTCTCCATCTCCTTCTTGGGGGTTGGGGTCTTAGAGACCCTTTTCCACGCCCTGATTCTCTTACTAGTGTG
```

-continued

```
TATGCTTTCCTTTTGACTTCTCATGCTGACCGTCTGAGCAGGAGTGAGAAGCAATTTCAAAGGAAAACATCGTTT

ATCATCTGCTGAAAGAAACCAAAAAGAACACAGGAAAACAAAAAGACAAGGAAAGGGAATGAAAATGTAATTCAT

TTTATTAAAAGAAGAATTATTCTTCTGGGACACTGGATAGAAACCTTAATGAGTTACCTAGCTATCATAAATCC

TCTAACAGAGAAGAGAAGAGAAAGAAACAAAGACGGAAGAGGGCAGGATAAAAGAAAGAAAAAAGGAAGGGAAAA

ATGAAGGAAGGAAGTTATCTATTCATTTCTACAGAGACTCTGCTGAGCAGTAGACAAGAAGACTTGGGAAAAATT

TAACTGAAACTTTTCCAAAAATCTTTTCAGAGGGATTTTTTCCCTCTGAAAAGCATCATTAGAGGCTGTTCAATA

CCCAAGGCAAGCCTCTTTCATATTACTTACTGTACATGAAACACTCATGCAATTGAGGCTAGCCAGAGGCCATTT

AGAAATTCAATAATTATTCAACCCAAGGGGCTTTCCAAATGGTGAAGTAGCTTCTTAAGAGGAAATTAATATTGA

GCAGTATAGCAAACCTAATTGGAATCTTGAGAAAATAGTTCTGTGTCGTTAGAACAGCTAGAGGCTAAAGAAGAT

CAGGTTGGATGATACCTTCATTTTGTCTCTTTCCTTAATTATGATGTAAAGGGAAAAATCTTGTTTATTTTCTA

TGCCAGGAGGGTAGAGGGTGATTTGGAGAGGTTCCAAGTTTATCAAAATCTACCTTCAGTCTGGCAGTAGAAAAG

TTTACTTCCTTCATTTCTTTCCTATAGACATTCAAAGAGAGCTAAGGAGATCCAAAAACCTTTTTTTCTATATTT

GCAATGCAAGGCAGTTGGGAATTAATGACTGATTTGTTGGTGAGGGCAGTGGGCATTGATCACAAAAGCAGTAAA

GCTGTGTTTCTCAAAGAGAGAAAGTCTCTTTGAGATCTTCATTATTTTACTATTTAGAAGAGAAAGGGGCGTTAT

ATCACGTTGGAAGCATCCATGAGTCACTAGTCTCTTCTCTATCTTTCTATGCCTTTCTGTATTAATTACTTTGAA

AGCACAACATTCCAAACCCATTGAGCACACAGTGGTCTGATTTCTCCACTTGTGAAAGGTGCTAAAGTCTCACTG

TAGGATTAATTTGGGGGTCCAGGCTATGGGCTTGTAGATATGACTACCTTAGACTTTGGTTCTCCTGGCAACTAA

CCCTTTTTGGATCGTATCTAAGTTGACCTGTTTCACAGTGAGAGAACTCCTCTCCATTACTCAGAATACTGAGGC

AGATCACAAGTGTACCACACCTGGCTAATGTTAAGCCAGACAGAAACATCAGGCTCATCTCTTGAGAAGAAGGGT

CGCTTATTAAGGATACAAACTATTTTTTTTTTTTTTTTGAGACAGGGTCTCATTGCCCAGGTTAGAGTGCAGT

GGTGCAATCATAGCTCACTGCAGCCTCAACCACATGGGTATTTTAAATAAGAAAAAAATACCATCTGATAGATA

TGAAGGAGCATTGGGTCACTATAAACAAAACAGATTCTAAGAGCAGGAAGAAAGAGTACAGTCTCTTTTCAATAA

TTTTTTTTTAAACTTGGGAAAGAACACTCACTCTATTCCTATAGACCAGAAAGCAGATAATTGTCCATTATGATT

CCACATGACACTATCTTGTTCAGCTGTCACTGAAACAACTTTGAACACTGTCATATGTTCTTCCCAGCTCCTGAA

CTCTGACCTTTTTATGCCTTAGTTCCACTTTCACAAAAAGGGATTGATGTAATGTGCATTTCAGAGGAAACGACT

ATAGACATTTAGTGTCATTATAAATGTTGAGAAGTATGCTGGCAGAAATTATGCCTTAAGATCATATATGGATTC

TTGTATGGTTTGAAATTGCTTAAAAGATATATATGATCTCTAAAATGTGTGTGTATATATATATGATGTCTTCTT

ATATATCTATATGTGATATATTTATATATATATAAATCTGTGTATATCACATATATAAATTTGCTGTTATTTGAA

TTGCCATTACCTCAGTGCTTAGGGGAAGCCATGCACGTTTGTTTCTTTTCAGTACCCAGAGTTAATTAACATAAG

TTATCACAGAAGCTCCCATAAGCATTGAGACAATTTCTCTATACCTGTGACTATTTAAGGTTTTGAAAACAAAAC

AGAAGCAGGTAAGGAGGAAGTACGCTTTACTATTGAAGATTTATTAGGTACACATTTAGATTTGTGAACTCACAT

TGCTTAGGATGAAAGGGACTCTTGAGGATGTCTGCTGTTTGTTAGTGAACTGCCTGTAACAATTACAATTAGCAC

ACACATGAGCACAATGAACTGGGTAGTCAGACTCAGCCAAAATGAATAGAAATAGCCTCTTACCAAATTTACTTT

GAGTAGCCCTTGGACTCTGAGCACTGCTGCCCAGAGCAATATGACTGTAGGTCCAAGTTTGTCAATGACTATGCA

AATGTGCTTTCTTCGCTTTTACTCTATTGTCATCTGTCTATTACAATGTTGCTATGGTGACACCTTTCCAATATC

CCTGTGCTTCTTTGGTATCCTCTAAGGGGAAGCTGTAATGAAGTGGCTTGGCAAAAGAATCCTCTTGGAATTTTT

TTTTTTTCATATGCTACTGAAAACCAGCATGATTTTCCTCTTATGGGAAATGTATAAAGTATGAGTTGGAAATGA

TGGAAATTAATCTGTACTGACTTGGGCAAGGAATGTGAATGTTATTCATTCTGTTCCAAACTACCTGAAAATATT

CTCTTTCTGTTCCTACTTTCCAGGAGATAACATCTTAAGGGACACTGAAGCTTGTGCGTGTGTGAGTAGAACACG

TGCTGGGGGCTCTTGAGCTCATGAGGGAGGGGCTACATGTCGGTGGGGTGATAACTGTATGCTGGAAACAATGAT
```

-continued

```
AGGGGTGACCCTGGAGCACTTACCATGTGACAGGTGTTATGCTAAGCATGTTTGTATGCATTCCTTCATTGAATG

ACACCTACCTATATTATCCTCATTTTATAAGATGAGGTAACAGAGCTTCAGAAAGGTTAGACTCAGCTGCTATGG

GTCTGTCTGACTCTGGTGTTCTTCCTCTTAAAAACTGGGGCACTTTGGAAATGAGATTCCTCGGTGATGAACAGA

AATATTGCTTAGCGGCTGTATTTTTGTATCTGGCAGTTTTCCCATATTTGAGTCTTATATTCACAATCGGTATCT

TTACATTACACAAAAGTGACACAGAATTAGAGTCATTTAATCCAGGGTTGATATCATTAAGTCATGACTATTTAT

TAAATGTTTCTTACAATATCTGAGATGATATTGCAAAAGATGTAAGTGATTTTAGAAGTTCTCACTTCGTAGTTA

GTTGCAGAAACCTCTTTTGGAGGAGGGATGTTTTCTCTATATATCCTAATTTCTACTTAATATATTTCCACACCT

CTTTGAAGTGTGTAGTAAGAATGGTAAAATGCAGTACTTCGTCATTTGGTACAGTTCAATCAATATGCATTAAGA

TGTGATCATATGGGTAATAGAAAAATGTGAAAGATCCAATTCTTTTTCTCCAGAAGGCAGGAAGCTCATATTTGA

TTTCTGTTACTATAAACTATAAAAACGTTTCAAATGTAGTTTACCCGTAACCATCACCCTGCAAGGGTGATATTG

CTCCCCGCCAATTTACGGAGGAGAATACTGAGGCTTTAAGGTTGTAGATAGACCAAGACCACACAAGTAGAGAGT

GGCGGGCTGTGGGTTGAGCTTTAAAATCCAGGTTCATCCATGACTCCCAGTGTGTTCTAGTAAATCCACTAGAAT

CTGAGTATTTTCCAATGATTTATGCTCCGCTCTGTGTCAGGCAGTTCATGGTATTTTTCAACAATCAGAAAATCC

TGGGGAAGGCAAACTGTTTCCCCCTCTCTAGGTGCCTTGGAAGTGGCCGTTGTGGACCCAGAGATCATCCTTTCT

GATCTGACACCTTCTTCACTGCCCTGGCCCAGTGTCTTTTCTGCAAGGCTGGAAGCCCCCTTAGACTGGTCATGT

CCCATCTCTTTCCGGAGGGAAGATGATCCCAAAGACGACTTTTCTCTCCACGGTGCTGCCATACCGCAGGCGGCC

GCCAGGGGTCCCCGCTCGGCGTCCCCGCGAGACAGTCGAGCCCCGGCCGGCTGCGCGGCGCGCTGGGTGCATGAG

GGGGCTGCTCCGGAGCGACGGCGGCTGCAGCTGGAGCCAGGCGCTCGCCCGTCCGCCGGTTGGCTCGCCGGGACC

TCGCGCACCGGCGGCAGAGTCCCTTGCGTGGATTGGCAAGCGACGCCCCACCTGCCCCGAGCTTCACCATTTCTT

TCGCGCTGGCTGCAGCTGACCCGGCGAAGGGAGCCGACCGGGCCCTGGGCTGGAGGTAAAACCCCACGGTGAGTA

AGAACCCGCTCCAAGCTAGGGGAGGCGGCGCAGCCCGGTGGCTGCTCGCTCCCGATCTCGCCCGGGGGGGGGGGG

AGGTTTGGGGCGCACCTGGGCGCGGGTGCAAGAAGGTGCGGGAGGCGGCGGACCGGTCTTCTGCCCGCCGGCCAC

GGGCTTCCGGGGCTGGAGTCCTCTTCAGACCCCTGCCGGCGCCTGGGTTTCTGGCCGGCTCCTCGTGTGCACTTC

CCGGCAGGAACAAGGGTCGCCCACTTTCCACCCCGGGATCTTGATTTGTCCTTGATTTGAAAAGATATAAATCAA

TAAGATCGTCCTTCTTTCGGGGTGCAAGACTCCGAGCCCATCCCCAGCCGCGGACGCCTGCAGGGTGCGTGTTGG

GCTGTGGGTGGCGGGAAGACAAACTTTTACAAAAGTGCGCCTGGGCTGGGGGACAACGCTTGGGCGTCCTGATCC

TGAGGGAGGAGTCTCGGCTTGGGGCAGCGTAGGGGAAGTCCGCACCGTCAGCCAGGTCGCCCCCGGGGCTGACGA

TGCCTCACGGAGGTGGGGAGCGTGTAAAGGCCGTACAAATCGCGCTTAACTTTGGGGCCAACAACTGTCAAACAT

CTGGAATCCCAGCCCCTCCCTTTCCCTGAACTGGGGAAGAAGGTGAAAACCCTTCAAGTTTTCTTTGATTGCCCC

TTCCCACCTTCAGACCCCTGCTGGGAGGGTAAAGCGCCGACCCCTGGTGCCTGGCAAGTACCAGAGACTCTAAAT

CTCTCGGGATCCCCCCCCTCGCGCTCTTTCCTGACCCTCTCCCCTAACCCTCCCCACAGAGATCTCTCTACGCAG

CCGACTGAGATCGTGGCGAATGGCCTTTTGTTTCTCCGCGTTTCCCCTATTGTTTGCCTTTCCAACATCTGGCGG

GGCTTGGGGAGAGAAGGAAGCCCCTCTGGTCCCCCTCCCCGGCCCCACGCCAGCTCCGGCAGGGGATCCCAGCT

GGGAAAGTGGAGGAGCCCGACCCCAGCGAGGCCGCCCCACCCCGCCCTTGTGGTTAGAGGGCGGAGGGAAAGTTG

TTCCTTCCCCGCCTCCGCTGCTGCCTGTGGCCCAGGGCGCATTTCTCAGATCTCAGCCCAGGCGCGCCGCAAAGG

CTCAAATCCGAGAAGGTGCTGCTTTCGAGACAGTGGAAGCGCGTTCCGCCCCAATCCAGAGCGTCCAGTGGTTGG

TTCCAGAGGATTTCAATCTCTAGCCAAAGGCGTTGGGGCTGGGCCGCTGCTAGGGCAGTGGGAGGGGATCGGGGC

ACCTTTGGTAGGCGGAAAGCTGAGATTCTGGGGTCCACAAGTTTCCAAGGGCGGGAGGGCAGGCTAGTCGCCAAA

AAGAGAACGAAGATGCAAATAACGAGGAAGCCTTATGACGTTGCCTGGAAATAGTAGTGTGGTGGTTCACTCCGG

AATGAACGTGGAGTTCTGGCTTTGAGTACCGCTCCAAGTTTAAATCCAAGTCCCCTTTCTTCATTGTAGAAAAA

GAGGACTCAGACGACGCAACACAGATACGGCTAGAGCACAGTTCCTGCTTCCACGTCCCAGAGAACAAGTGGCTT
```

-continued

```
AGGATGGTCCCGAGTTCCCCTGTGGGTGCGCTTGTTGGGTTGCAGGCGGCCCTGTTTCCCTGCACAAGTCAGATG

CTTACACATTGTGTTCATTCTTAGTGTGGATTATTGATTAAAGAACTGGGGCAAAAGCAAAGTAGCTACTCTGAG

AAGTCAGGGTCCCCAGATGGTGCCCAGCGAGTTGTCTTGCCTCTGAGGGGAGGCTGACTGAGACTGTGCACCTGT

TAGAACCTATGCTACCCCATAGCCTTGCAGTTGACTTGCTGTTGCCAGCTTTTCCTGTGGGATCCCCAATGAGTC

CCTCTTCCAAGGAAGCTCAATTACACTTTTGATTCCTCCTCAACCCAGGGGAAGAAAGAGGCTTCTGTAGGAACA

TTATGATCTATGTACCCACTCAGACATTGTCAGTGGATACCAGAAGCTTGGCTCTGCACAGCTCTGAGAGTTTTC

CCTTTGCGAACTCAACAGAACTTTTGAGTTTCCATTTAACATAAAAGAAGTGAGACTGCTAAGCCAGGAATGCGA

CACATAGAGCACTTTCTCTAGTGATTTCTGGGTATTATATCTCTTTACCTTCCCAACGGTGGAACCAGGAAAAGA

AAAAAAAGCAACATCTTTGAAGTACTGCAAGGCACTTTACAAACATTTCATTATGAAAATGATCCCCAAGGAAGG

ATTCCTTTGAAATTTAGCAGCAGCAACCCAGAAGCAACAAAAAAGACCAAAGTTACTCAAGAAGTACCCAAAGGC

ATCATTAACAAAATAAAAGAGCATTTCTTGTCTTGGCCTACCCCGCTAAGGAAAACAGGGTAATTATAGTGGAAG

TTAAGCTTG
```

In some embodiments, the human C9ORF72 gene and flanking sequences comprise a sequence that is, e.g., at least 75, 80, 85, 90, 95, 96, 97, 98, or 99% identical to the sequence above. As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence.

In some embodiments, the number of GGGGCC hexanucleotide repeats (e.g., $(GGGGCC)_n$ in SEQ ID NO: 63) is 300-800, 300-700, 400-600, or 500-600. In some embodiments, the number of GGGGCC hexanucleotide repeats (e.g., $(GGGGCC)_n$ in SEQ ID NO: 63) is 500-600. In some embodiments, the number of GGGGCC hexanucleotide repeats (e.g., $(GGGGCC)_n$ in SEQ ID NO: 63) is greater than 300, 400, 500, 600, 700 or 800. In some embodiments, the number of GGGGCC hexanucleotide repeats (e.g., $(GGGGCC)_n$ in SEQ ID NO: 63) is greater than 500. In some embodiments, the transgenic mouse is an FVB, balb-C or C57B/6 strain mouse. In some embodiments, the transgenic mouse is an FVB strain mouse. In some embodiments, the mouse can be used to screen for therapies for the treatment of ALS or FTD, e.g., a therapy described herein or a candidate therapeutic agent.

A transgenic mouse as described herein can be made using any method known in the art or described herein, e.g., Example 4 (see also, e.g., PCT Publication Number WO2001010199 and WO2013022715; and US Publication Number US20110113496 and 20060031954, each of which are incorporated by reference herein). For example, a transgenic mouse described herein may be produced by introducing transgenes (e.g., the human C9ORF72 gene, optionally with flanking sequences) into the germline of the mouse. Embryonal target cells at various developmental stages can be used to introduce transgenes. Different methods are used depending on the stage of development of the embryonal target cell. The specific line(s) of any animal used to practice this disclosure are selected for general good health, good embryo yields, good pronuclear visibility in the embryo, and good reproductive fitness. In addition, the haplotype is a significant factor. For example, when, transgenic mice are to be produced, strains such as C57BL/6 or FVB lines are often used (Jackson Laboratory, Bar Harbor, Me.). The line(s) may themselves be transgenics, and/or may be knockouts (e.g., obtained from animals which have one or more genes partially or completely suppressed). The transgene construct may be introduced into a single stage embryo. The zygote is the preferred target for micro-injection. The use of zygotes as a target for gene transfer has a major advantage in that in most cases the injected DNA will be incorporated into the host gene before the first cleavage (Brinster et al. (1985) PNAS 82:4438-4442). Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, the exogenous genetic material should be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane.

Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter. Any technique which allows for the addition of the exogenous genetic material into nucleic genetic material can be utilized so long as it is not destructive to the cell, nuclear membrane, or other existing cellular or genetic structures. Introduction of the transgene nucleotide sequence into the embryo may be accomplished by any means known in the art such as, for example, microinjection, electroporation, or lipofection. The exogenous genetic material is preferentially inserted into the nucleic genetic material by microinjection. Microinjection of cells and cellular structures is known and is used in the art. In the mouse, the male pronucleus reaches the size of approximately 20 micrometers in diameter which allows reproducible injection of 1 –2pl of DNA solution. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

Aspects of the disclosure also relate to polynucleotides, e.g., a bacterial artificial chromosome (BAC) vector, comprising SEQ ID NO: 63.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Figures 2A, 2B:
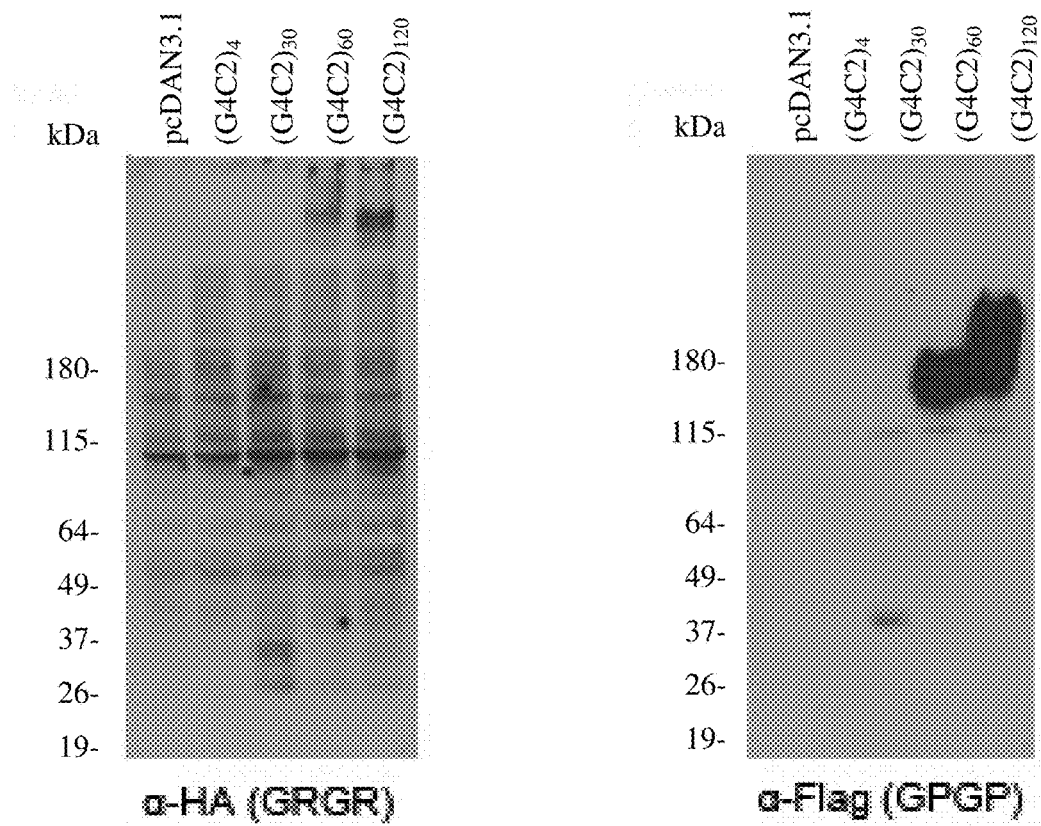
FIG. 2A is a diagram of an expression vector for expressing RAN translation proteins in cells. CMV=cytomegalovirus promoter. 6xStop=6 stop codons, two in each frame. (GGGGCC)exp=a GGGGCC repeat sequence that extends for 4, 30, 60, or 120 repeats. (GR) HA-(GP)Flag-(GA)Myc=a HA, flag or myc tag that corresponds to the poly-(Gly-Arg), poly-(Gly-Pro), and poly-(Gly-Ala) repeat proteins, respectively. SV40 poly(a)=transcription terminator and poly A signal.
FIG. 2B is a photograph of a western blot depicting that GR and GP RAN translation proteins are expressed in cells transfected with 30, 60 or 120 GGGGCC repeat sequences.
Figure 3:
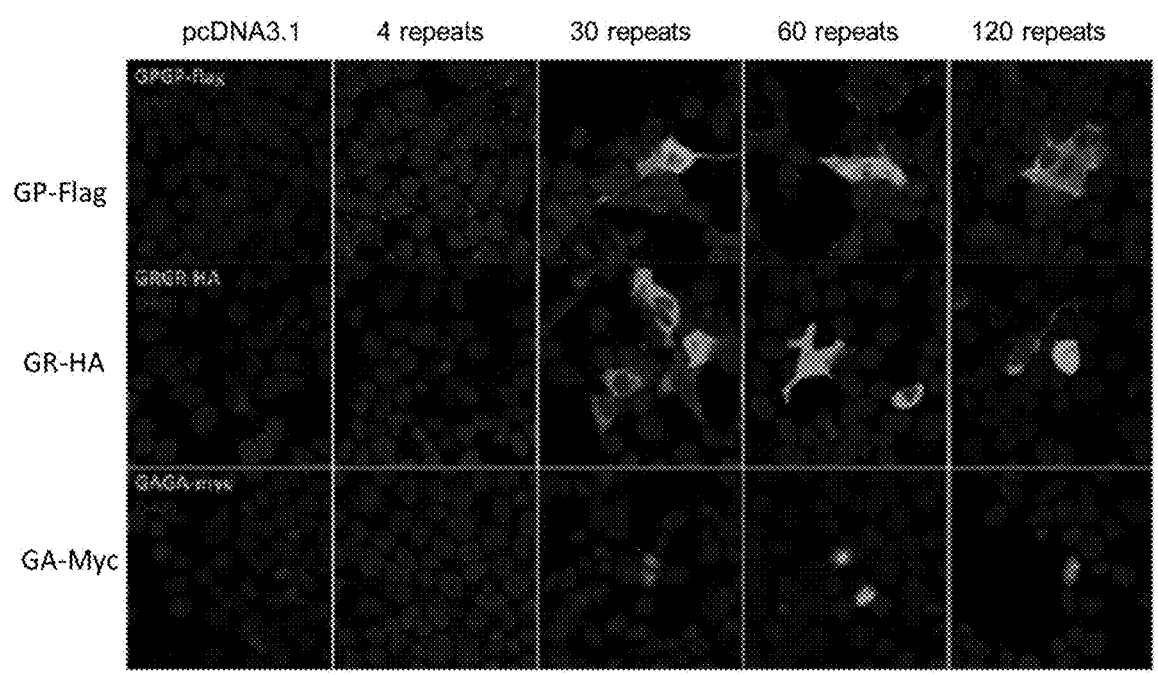
FIG. 3 is a photograph of an immunofluorescence staining of cells expressing GP, GR, or GA RAN proteins in cells transfected with 30, 60 or 120 GGGGCC repeat sequences.

A construct containing a CMV promoter, a (GGGGCC) expansion motif containing either 4, 30, 60, or 120 repeats of GGGGCC, and an HA, FLAG, or MYC tag were transfected into cells (FIG. 2A). It was shown by western blot that poly-(GR) and poly-(GP) proteins were produced in cells transfected with constructs containing 30, 60 or 120 repeats of GGGGCC (FIG. 2B). It was further shown using immunofluorescence of cells that GP-flag, GR-HA, and GA-Myc proteins were expressed in cells transfected with constructs containing 30, 60 or 120 repeats of GGGGCC (FIG. 3). These results show that GGGGCC repeat regions are capable of initiating translation independent of an AUG start codon (repeat-associated non-ATG (RAN) translation), and that poly-(GP), -(GR), and (GA)-repeat proteins are produced.

Figure 4:
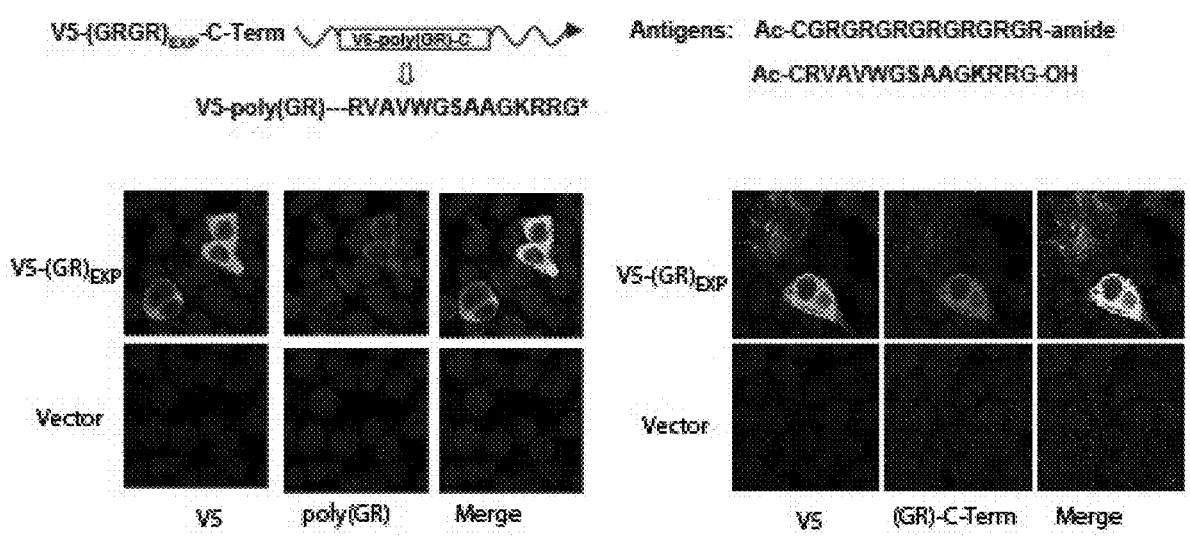
FIG. 4 is a diagram of the poly-(GR) and GR-c-terminus antigens and a series of photographs of immunofluorescence staining showing that the poly-(GR) and (GR)-c-terminal antibodies detect poly-(GR) RAN proteins.

Antibodies to a poly-(GR) sequence or to the C-terminus of the poly-(GR)-repeat protein were generated. Fluorescent staining using these antibodies showed that these antibodies were capable of detecting the poly-(GR) repeat protein (FIG. 4).

Figure 5:
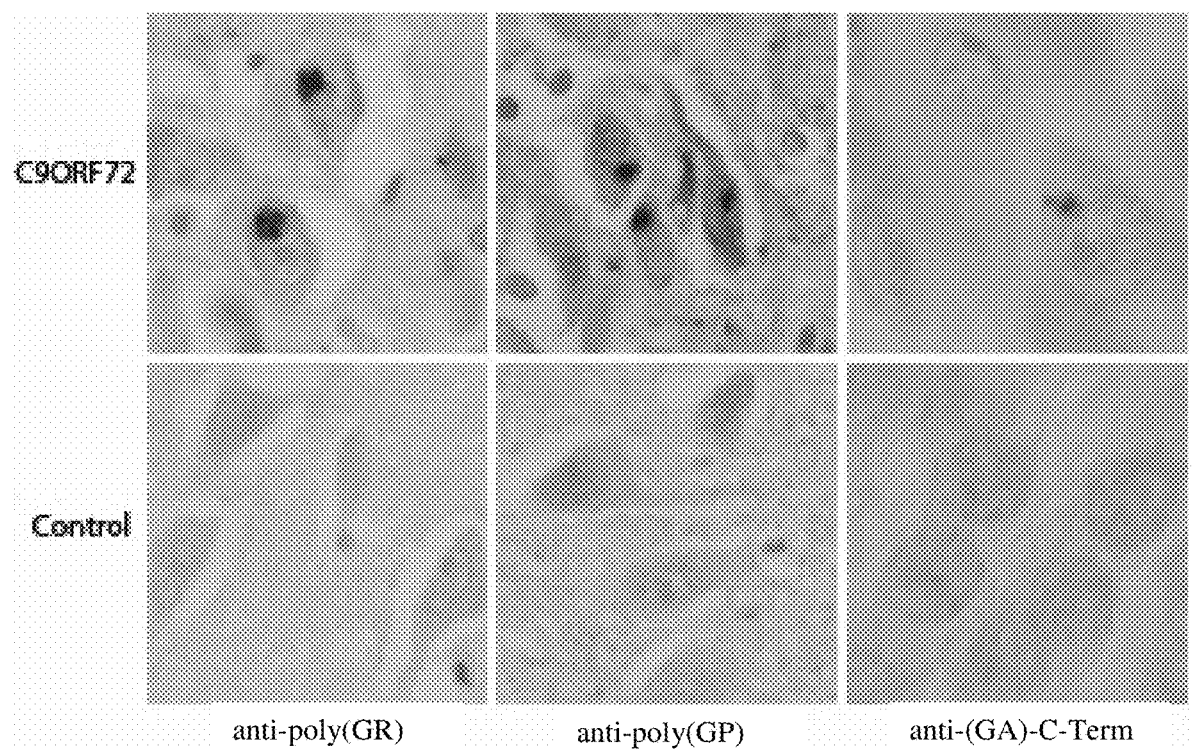
FIG. 5 is a series of photographs of tissue from C9ORF72 ALS patients or control patients showing that poly-(GR), poly-(GP), and poly-(GA) di-amino acid-repeat-containing proteins are expressed by C9ORF72 ALS patients.

Antibodies were further generated to a poly-(GP) sequence and the C-terminus of the poly-(GA)-repeat protein. The anti-poly-(GR), anti-poly-(GP), and anti-poly-(GA)-C-term antibodies were then used to stain sections of brain tissue from patients with C9ORF72 ALS or controls (FIG. 5).

Figure 6:
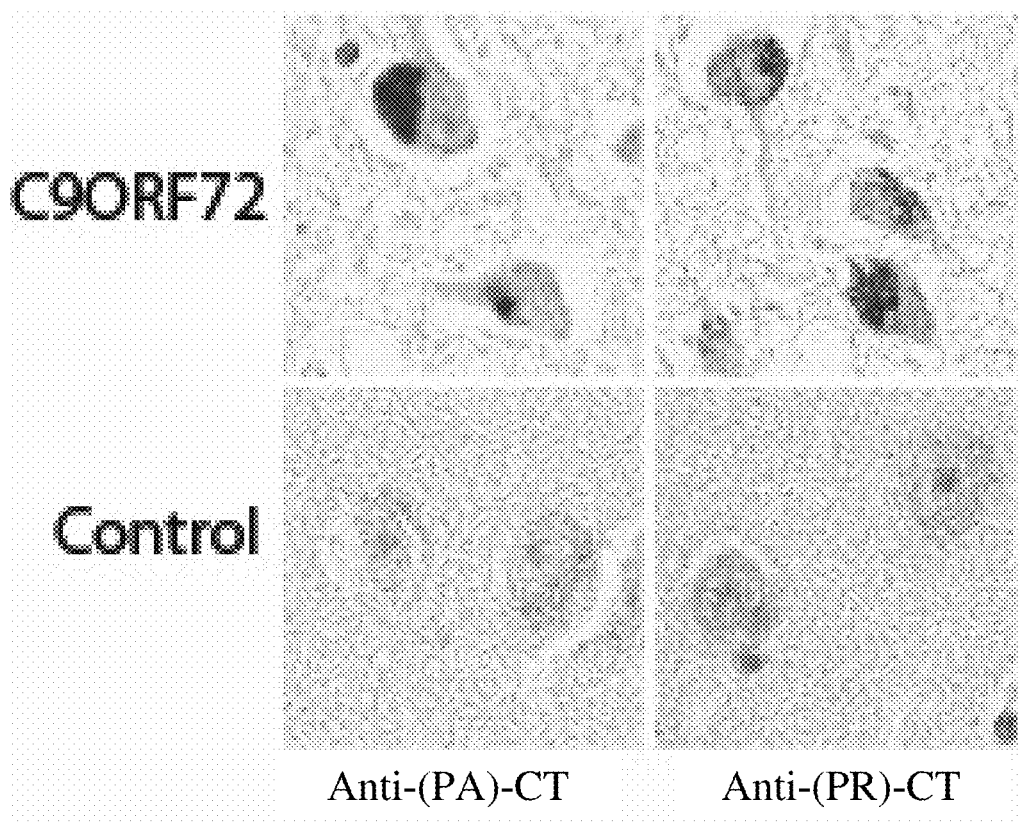
FIG. 6 is a series of photographs of tissue from C9ORF72 ALS patients or control patients showing that poly-(PA) and poly-(PR) di-amino acid-repeat-containing proteins are expressed by C9ORF72 ALS patients.

It was then hypothesized that transcripts of C9ORF72 may be produced in both a sense and anti-sense direction (see FIG. 1). It was further hypothesized that these antisense transcripts may also undergo RAN translation to produce further repeat proteins from the 5'-GGCCCC-3' repeats present in the anti-sense transcript. As shown in FIG. 6, both poly-(PA) and poly-(PR) proteins were detectable in brain tissue samples from patients with C9ORF72 ALS but not in controls. These results indicate that di-amino acid-repeat-containing proteins, such as RAN proteins are produced from both a sense and anti-sense transcript produced from the C9ORF72 locus.

Figure 7A:
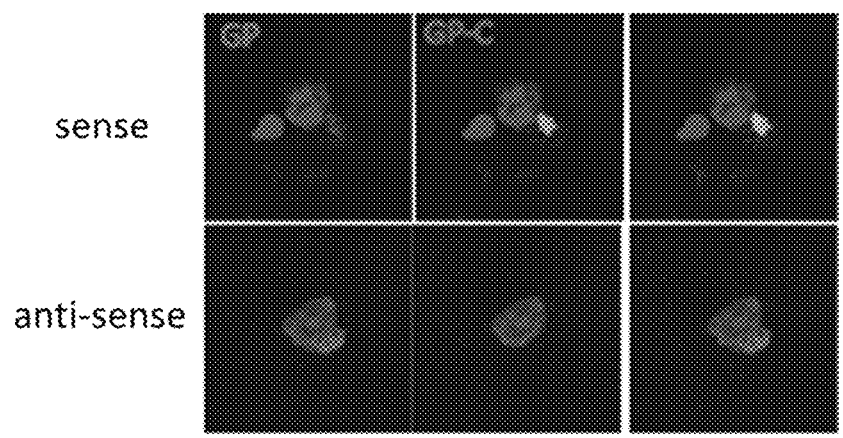
FIG. 7A is a series of photographs of immunofluorescence staining showing antibodies generated to recognize the GP repeat motif (GP) or the unique C-terminal region of the same GP-RAN proteins (GP-C) colocalize in 20% of patient cells. Cells that stain for and GP-C and GP express GP-RAN protein in the sense direction and that cells showing only GP staining express RAN-GP or Met . . . GP from the anti-sense strand.
Figure 7B:
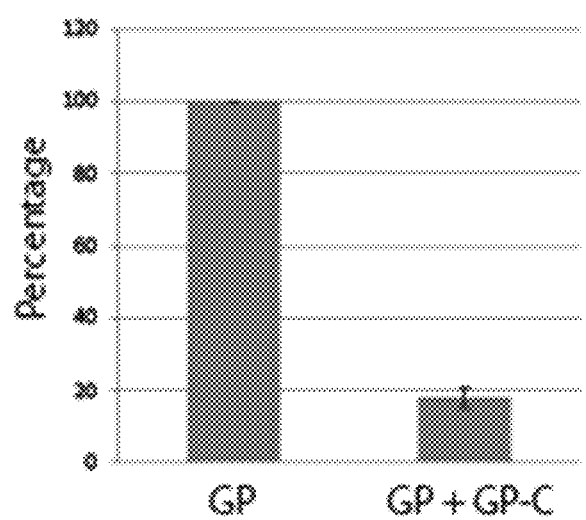
FIG. 7B is a graph depicting the percentage of GP and GP+GP-C in patient cells.

FIG. 7 shows that approximately 20% of aggregates detected with the anti-GP antibody (GP) also co-localize with antibodies directed against the unique C-terminus of the sense GP protein (GP-C). Consistent with the increases levels of antisense transcripts that seen in affected brains, these co-localization data suggest the more ~80 percent of the GP dipeptide aggregates are expressed from C9ORF72 antisense transcripts.

Figure 12:
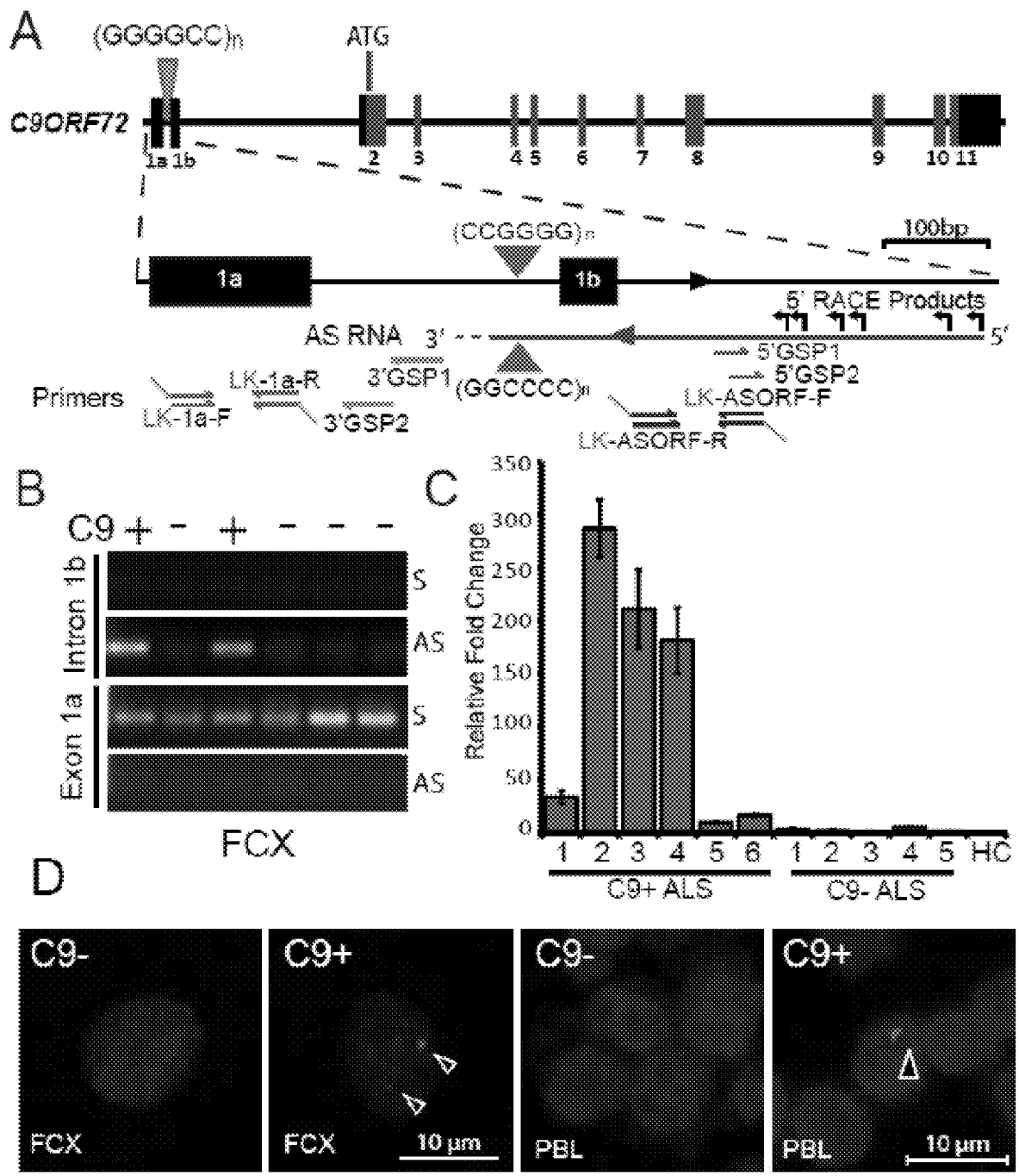
FIG. 12 is a series of schematics, graphs and images showing that G2C4 antisense transcripts are elevated by strand specific RT-PCR and accumulate as RNA foci in C9ORF72 patient tissues. (A) Schematic diagram of C9ORF72 gene and antisense transcripts and relative location of primers for strand-specific RT-PCR and RACE primers. (B) Strand-specific RT-PCR of sense(S) and antisense (AS) transcripts (across intron 1b and exon 1) from frontal cortex of C9(+) and C9(−) ALS patients. (C) strand-specific qRT-PCR showing elevated antisense mRNA in C9(+) compared to C9(−) ALS patients. (D) In situ hybridization with G4C2-Cy3 probe showing G2C4 antisense RNA foci (arrowheads) in C9(+) frontal cortex and peripheral blood leukocytes (PBLs) which are absent in C9(−) cases. Nuclear foci in FCX are indicated by arrow heads. FCX=frontal cortex. PBL=peripheral blood leukocytes.

Additionally, the anti-sense transcript was found to be dramatically elevated in subjects with ALS compared to controls (FIG. 12). The primers for the qPCR assay for detecting the anti-sense transcript levels are shown in the table below.

| ORF F2 | AGTCGCTAGAGGCGAAAGC (SEQ ID NO: 36) | primer in c9orf72 antisense orf |
|---|---|---|
| ORF R2 | CGAGTGGGTGAGTGAGGAG (SEQ ID NO: 37) | |
| ORF F2 + IK | CGACTGGAGCACGAGGACACT GAAGTCGCTAGAGGCGAAAGC (SEQ ID NO: 38) | |
| ORF R2 + Ik | CGACTGGAGCACGAGGACACT GACGAGTGGGTGAGTGAGGAG (SEQ ID NO: 39) | for RT 1st strand |

-continued

| Linker | CGACTGGAGCACGAGGACACT GA (SEQ ID NO: 40) | for RT- pcr with ORF F1 and F2 |

Further, di-amino acid repeat-containing proteins were found to be present in the blood (including in the serum and plasma) and in the brain of subjects with ALS (FIGS. 9 and 10) but not in control subjects.

Example 2

Figure 8:
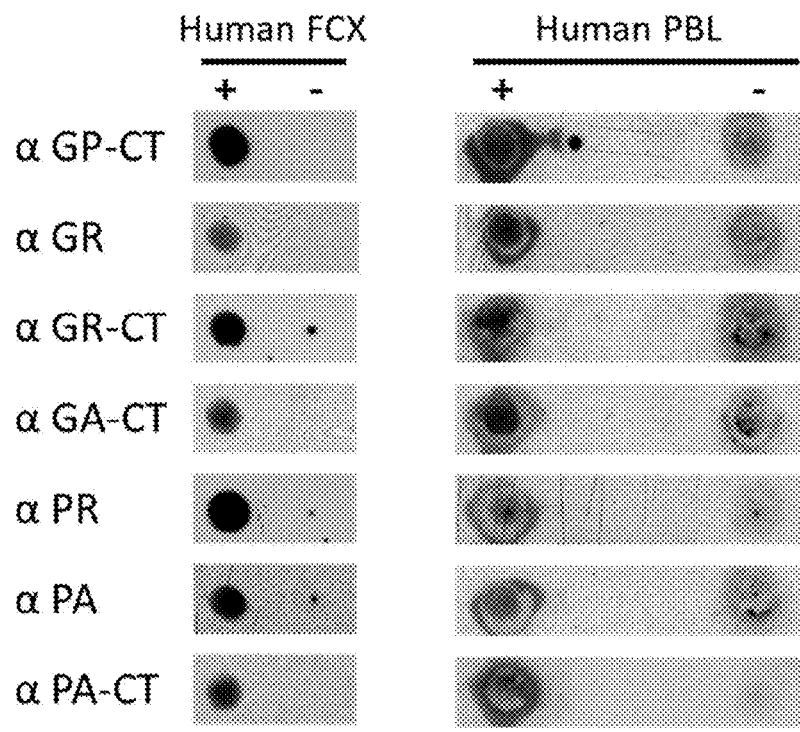
FIG. 8 is a picture of a dot blot showing that di-amino acid repeat-containing proteins are found in the blood (PBL) and the brain (FCX, frontal cortex) of subjects with ALS, but not controls.
Figure 9:
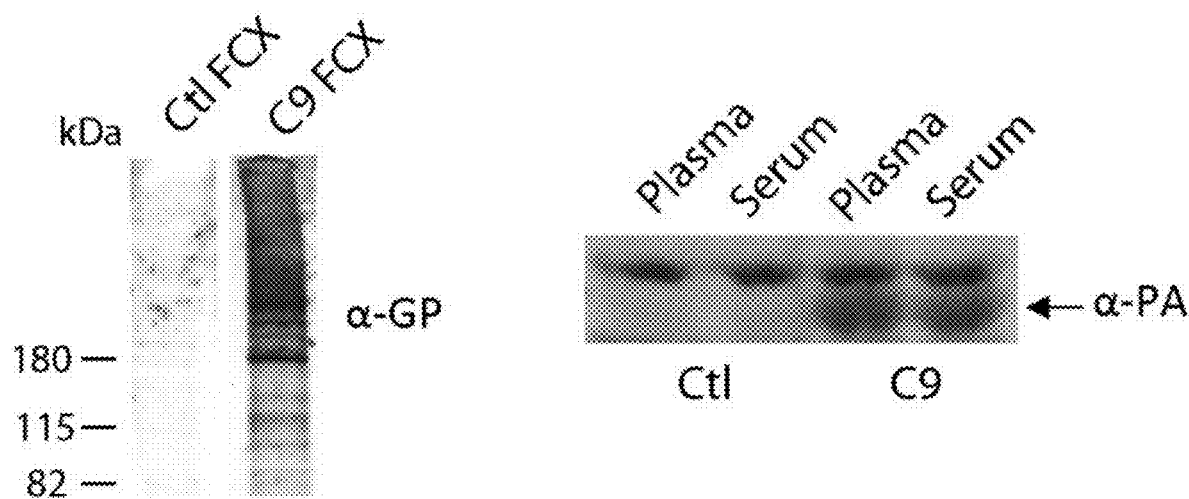
FIG. 9 is a photograph of a western blot showing that GP-repeat proteins are present in the brain (FCX) of subjects with ALS but not controls and that PA-repeat proteins are present in the plasma and serum of subjects with ALS but not controls.

According to some aspects of the disclosure, di-amino acid repeat-containing protein (such as RAN protein) accumulation in blood and cerebral spinal fluid (CSF) substantively contribute to C9ORF72 ALS/FTD and that plasmapheresis and bone marrow transplantation will reverse progression of the disease. According to some aspects of the disclosure, di-amino acid repeat-containing protein accumulation in blood and circulating CSF infiltrates the brain parenchyma and leads to protein accumulation, neuroinflammatory changes, CNS dysfunction and neuronal death. Aspects of the disclosure are based in part on the following. First, blood brain barrier (BBB) impairment is an early feature of disease in ALS patients (4, 5) and higher rates of ALS and other neurological diseases are found in patients who have had traumatic brain injuries (6). In some embodiments, without wishing to be bound by theory, ALS is in part caused by BBB disruptions that allow for the CNS entry of immune cells and other harmful substances that accelerate ALS/FTD. Secondly, as described herein di-amino acid repeat-containing proteins were found to accumulate in ALS patient blood samples (FIGS. 8 and 9).

Although plasmapheresis and bone marrow transplants have been tested as therapeutic strategies for ALS in the past, it is not clear if any of these cases were C9ORF72 positive or if treatment was early enough to have an effect. Accordingly, in some embodiments, ALS treatment (e.g., plasmapheresis or BMT) is initiated when above-normal levels of one or more di-amino acid repeat-containing proteins are detected in the blood of a subject.

The data presented herein on di-amino acid repeat-containing protein accumulation in C9ORF72 ALS patient tissues and blood indicates that reduction of blood (and perhaps also CSF) di-amino acid repeat-containing-protein load may help treat ALS in C9ORF72 ALS patients. According to some aspects of the disclosure, reduction may be achieved, for example, using plasmapheresis or a bone marrow transplant.

Methods

A detailed evaluation is performed on gene carriers from a C9ORF72 family (CNSA-1) and patients in the clinic including a gene-positive patient with early signs of motor neuron disease or fronto-temporal cognitive dysfunction, or both. Di-amino acid repeat-containing protein expression is correlated with repeat length in CNSA family samples and additional samples collected in clinic. Di-amino acid repeat-containing protein expression in blood is determined in longitudinally collected samples and correlated with disease onset and clinical severity. These methods are expected to characterize di-amino acid repeat-containing protein expression in C9ORF72 positive expansion study subjects and to determine if di-amino acid-repeat-containing protein expression occurs throughout life or increases with age and if di-amino acid repeat-containing protein levels quantitatively correlate with disease severity.

Plasmapheresis is tested to determine if lower di-amino acid repeat-containing-protein load in the blood and CSF reverses signs of the disease. Plasmapheresis is performed on five C9ORF72 positive individuals with early signs of the disease. Six plasmaphereses, each with 2-litter exchange with normal human albumin, is performed over two weeks, followed by one plasmapheresis weekly for the next six months. The study may be prolonged, if required. The primary outcome measure is the Appel ALS Rating Scale (AALSRS). Clinical evaluations including neurological examination, speech evaluation, neuropsychological testing, the ALS Functional Rating Scale (ALSFRS), EMG, and needle muscle biopsy for immunohistopathological evaluations of the vastus lateralis muscle are performed to assess disease progression immediately before and after the treatment period. Venipuncture and lumbar puncture are also performed before and after the 6-month (or if applicable, also after the prolonged) treatment period to assess the concentration of serum and CSF levels of RAN translation and ATG-translation products.

Bone marrow transplant in an animal model is tested to determine if BMT prevents di-amino acid repeat-containing-protein accumulation in blood and the brain. In a first cohort of animals, bone marrow from RANT-positive mice are ablated and replaced with wild-type donor marrow to test if protein aggregate load in the brain decreases. In a parallel set of experiments, RANT-negative animals are transplanted with RANT-positive bone marrow to test if CNS protein accumulation occurs in animals that only express the transgene in hematopoietic cells. Both groups of treated animals are compared to wild-type and untreated RANT control animals using a combination of behavioral, functional and neuropathological assessments.

Figure 10:
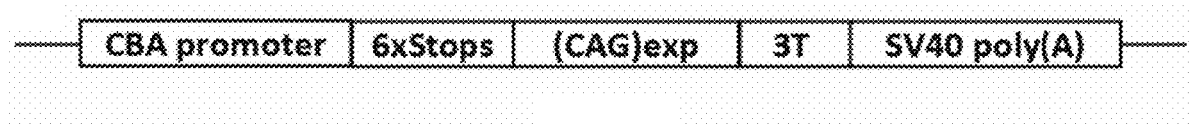
FIG. 10 is a schematic of the RAN translation mouse model construct containing 6X stops, a CAG repeat region, tags for detecting each CAG repeat frame, and a terminator sequence.
Figure 11:
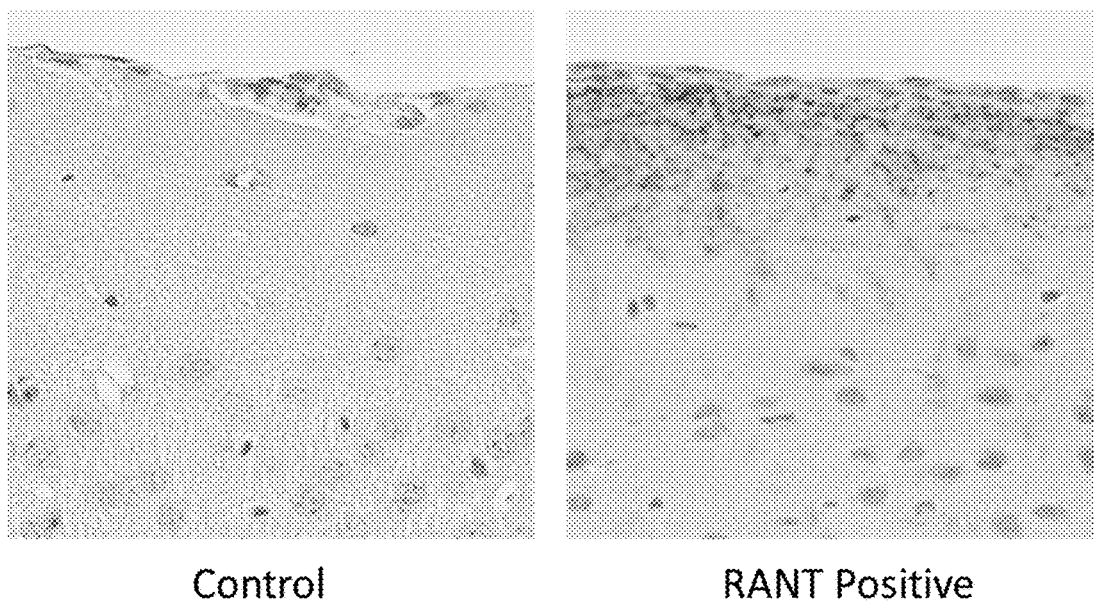
FIG. 11 depicts two photographs showing that poly-Gln proteins accumulated in the brain of RAN translation (RANT) mice containing the construct in FIG. 10, but not in control mice.

A RAN translation mouse model has been generated. Transgenic mice were generated using a construct containing 6 stop codons (two in each reading frame) immediately upstream of a CAG expansion mutation and followed by 3 separate epitope tags in each reading frame (FIG. 10). The CAG repeat generates poly-Gln RAN proteins, which have been previously associated with diseases in humans such as fragile X syndrome. The RANT mouse model produced poly-Gln RAN proteins, which were found to localize at high levels under the pia surface in the brain which is exposed to the cerebral spinal fluid (FIG. 11). This RANT mouse model is used in the studies outlined in Example 2. Accordingly, detection of poly-amino acid repeat containing proteins (e.g., mono- or di-amino acid repeat containing proteins) may be indicative of a risk for a brain disorder associated with the poly-amino acid repeat containing proteins. Accordingly, methods described herein may be used to detect or treat other neurological diseases.

Example 3

Introduction

The chromosome 9p21-linked form of ALS/FTD, the most common cause of familial FTD and ALS identified to date, is caused by an expanded GGGGCC ($G_4C_2$) hexanucleotide repeat in intron 1 of chromosome 9 open reading frame 72 (C9ORF72) (1, 2). The C9ORF72 mutation is found in 40% of familial and 7% of sporadic ALS cases and 21% of familial and 5% of sporadic FTD patients (3). The discovery of the C9ORF72 expansion has generated substantial excitement because it connects ALS and FTD to a large group of disorders caused by microsatellite expansion mutations (4).

Traditionally, microsatellite expansion mutations located in predicted coding- and noncoding regions were thought to cause disease by protein gain-, or loss-, of-function or RNA gain-of-function mechanisms (4). Protein loss-of-function has been proposed to underlie C9ORF72-driven ALS/FTD because the expansion mutation leads to decreased levels of variant 1 transcripts and potential decreases in C9ORF72 protein expression (1, 2). Additionally, because the C9ORF72 G4C2 expansion mutation is located in an intron, several studies have pursued the hypothesis that C9-linked ALS-FTD results from a toxic RNA gain-of-function mechanism in which G4C2 expansion RNAs sequester important cellular factors in nuclear RNA foci. Multiple G4C2 RNA binding proteins have been identified, but so far there is no demonstration that any of these candidates directly bind endogenous expansion transcripts or co-localize with RNA foci observed in patient cells or autopsy tissue (5-8).

In this mechanism, hairpin-forming microsatellite expansion transcripts express proteins in one or more reading frames without an AUG-initiation codon (9). While a variety of names have recently been ascribed to these RAN translated proteins (e.g. homopolymeric, dipeptide, RANT), it is proposed that all proteins expressed across microsatellite expansion mutations in the absence of an ATG-initiation codon be referred to as RAN proteins to prevent confusion as additional expansion mutations that undergo RAN translation are identified.

Here it is shown that C9ORF72 ALS/FTD antisense transcripts containing the GGCCCC ($G_2C_4$) expansion accumulated in patient brains as nuclear, and infrequent cytoplasmic, foci. Additionally, a novel panel of antibodies directed to both the repeat motifs and unique C-terminal regions was developed and both sense and antisense RAN proteins were demonstrated to accumulate in C9ORF72 patient CNS autopsy tissue. The discovery of antisense $G_2C_4$ RNA foci and three novel antisense RAN proteins in C9ORF72 patient brains suggests that bidirectional transcription and RAN translation are fundamental pathologic features of C9ORF72 ALS/FTD.

Results

Antisense RNA Foci in C9ORF72-Expansion Patients

Figure 19D:
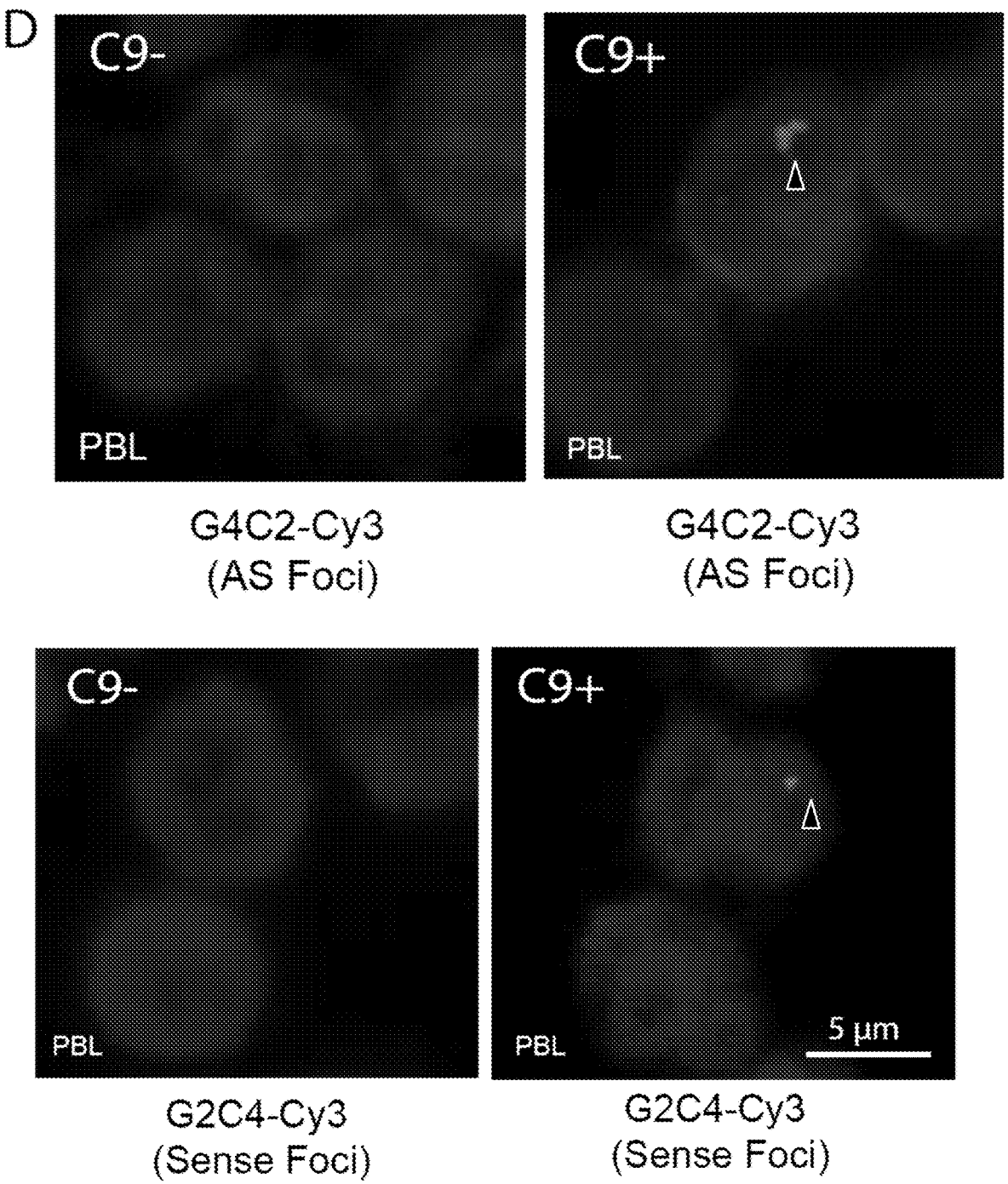

A series of experiments was performed to test the hypotheses that antisense (AS) C9ORF72 expansion transcripts form AS G2C4 RNA foci and express AS proteins by RAN translation or from short AS open-reading frames (AS-ORFs). First, it was confirmed that C9ORF72 antisense transcripts are expressed using a linkered strand-specific RT-PCR strategy to compare expression of the sense and antisense transcripts in intron 1b, 5' of the antisense $G_2C_4$ expansion, and exon 1a. For the antisense strand in intron 1b, strand-specific RT-PCR was performed using LK-ASORF-R primer for the RT reaction and ASORF-F and the LK for PCR to specifically amplify antisense-cDNAs (FIG. 12A). Similar strategies were used to amplify sense transcripts from the same region of intron 1b and sense and antisense transcripts in exon 1a. Intron 1b antisense transcripts were detected by RT-PCR in frontal cortex from C9(+) ALS/PTD patients but not C9(−) ALS/FTD or normal controls (FIG. 12B) and qRT-PCR shows these transcripts are dramatically increased among six C9(+) ALS/FTD cases (FIG. 12C). In contrast, intron 1b sense transcripts were not detected by RT-PCR (FIG. 12B) in frontal cortex. In blood, both intron 1b sense and antisense transcripts are detectable and the dramatic C9(+) elevation of the intron 1b antisense transcripts was not observed. 5' RACE showed intron 1b AS transcripts begin at varying sites 251-455 basepairs (bp) upstream of the G2C4 repeat (FIGS. 12A, 19B). In contrast, 3'RACE, using 3'GSP1 or 3'GSP2 primers located 40 and 90 bp 3' of the G2C4 repeat, did not detect transcripts. These data showed that the 3' end of the AS transcript does not overlap the sense exon 1a region, located 170 bp 3' of the antisense (2C4 repeat. Consistent with this result, sense but not antisense transcripts are detected by strand specific linkered-RT-PCR using primers overlapping exon 1a (FIG. 12B). To determine if antisense transcripts include the G2C4 repeat expansion, RNA fluorescence in situ hybridization (FISH) was performed using a Cy3-labelled (G4C2) 4 probe to detect putative antisense $G_2C_4$ RNA foci. The results showed nuclear (FIG. 12D) and rare cytoplasmic (FIG. 19C) $G_2C_4$ RNA foci accumulate in C9(+) but not C9(−) ALS frontal cortex. The detection of foci in the cytoplasm showed that antisense expansion transcripts can be found in the same cellular compartment as the protein translation machinery, presumably where RAN translation occurs. Because RNA foci in peripheral tissues may provide biomarkers of the disease, peripheral blood leukocytes (PBLs) were examined and both sense and antisense RNA foci were detected in C9(+) but not C9(−) PBLs (FIG. 12D, FIG. 19D). It was discovered that the RNA-FISH signal from the Cy3-G4C2 probe detecting AS-foci may be competed with excess unlabeled G4C2 oligo, and these foci were resistant to DNase I and sensitive to RNase I digestion (FIG. 19E, F). Taken together, this shows that C9ORF72 antisense transcripts are elevated in the frontal cortex in C9(+) ALS but not C9(−) ALS or normal controls. It was also shown for the first time that antisense transcripts containing the $G_2C_4$ expansion mutation are expressed and accumulate in nuclear and rare cytoplasmic RNA foci in C9(+) frontal cortex. Additionally, it was shown that sense and antisense foci accumulate in blood, providing potential biomarkers of C9ORF72 ALS/FTD in a readily accessible tissue.

RAN Translation of GGCCCC Repeat Expansion In Vitro

To test if the antisense $G_2C_4$ expansions undergo RAN translation, a triply tagged $G_2C4$ minigene was generated, $(G_2C_4)_{EXP}$-3T, lacking an ATG initiation codon, by inserting a 6X STOP codon cassette (two stops in each frame) upstream of $G_2C_4$ expansions of 40 or 70 repeats and three different C-terminal epitope 8 tags to monitor protein expression in all reading frames [e.g., ($G_2C_4$EXP transcripts translated in three frames results in Gly-Pro (GP), Pro-Ala (PA) and Pro-Arg (PR) RAN proteins] (FIG. 13A). Immunoblotting detected two epitope-tagged RAN proteins, PR-Myc and GP-Flag, but not PAHA (FIG. 13B). The (PR) 40- and (PR) 70-3xMyc proteins migrated at approximately their predicted sizes of 20 and 27 kDa, respectively. In contrast, the (GP) 40- and (GP) 70-3xFlag proteins migrated substantially higher than their predicted sizes (10-15 kDa) at 50 and 75 kDa, respectively (FIG. 13B). The faint lower molecular weight bands on this blot may result from repeat contractions seen during bacterial culture or differences in translational start site. Immunofloresence (IF) showed antisense RAN proteins are expressed in all three reading frames (FIG. 13C). The detection of PA-HA by IF but not western blotting may be caused by a lower frequency of cells expressing RAN PA-HA from these constructs. Additionally, recombinant GP-Flag and PA-HA proteins had a cytoplasmic localization whereas PR-Myc proteins were distributed in both the nucleus and cytoplasm. These localization differences may result from different properties of the repeat motifs or the C-terminal flanking sequences found in this epitope tagged construct. In an additional series of experiments also it was shown that sense G4C2-expansion constructs containing 30, 60 and 120 repeats express GP-Flag, GR-HA and GA-Myc RAN proteins (FIG. 20). In summary, these data showed that recombinant G2C4 and $G_4C_2$ expansion transcripts express RAN proteins in all six reading frames.

Dual Immunological Strategy to Detect RAN Proteins

Figure 23C:
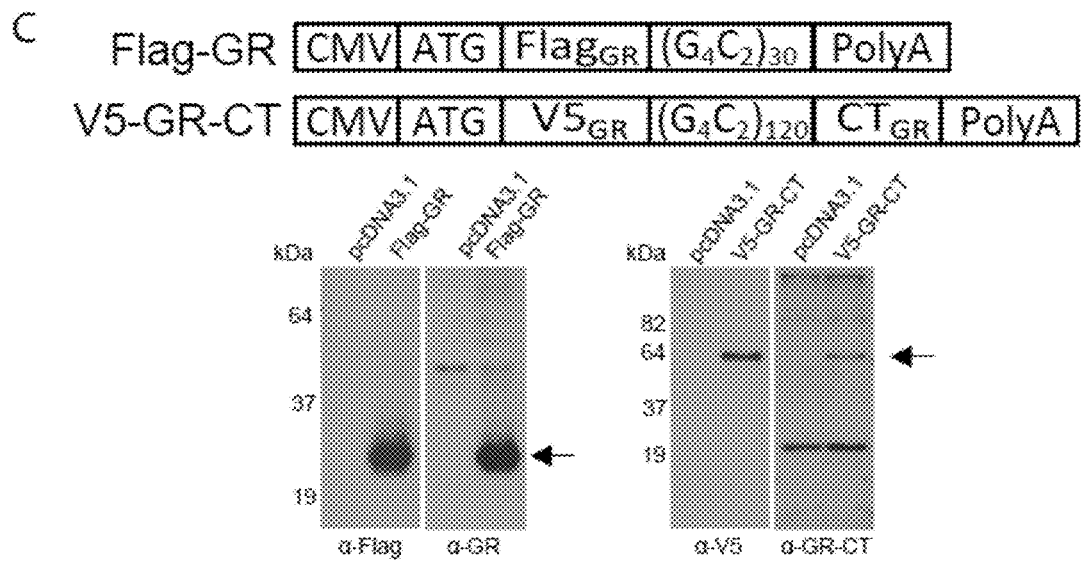

Since amino acid repeats can be found in a range of different proteins, a dual immunological strategy was used and antibodies that recognize the predicted repeat motifs described herein or their corresponding unique C-terminal regions were developed. A schematic diagram showing eight putative C9ORF72 RAN proteins is shown in FIGS. 13D and 21. Predicted proteins include six putative RAN proteins and two putative proteins with additional ATG-initiated N-terminal sequence. Unique C-terminal regions are predicted in five of the six predicted reading frames. To test for the accumulation of these proteins in vivo a series of polyclonal antibodies against the predicted repeat motifs or available corresponding C-terminal regions, were developed (FIGS. 13D, 21). Antibodies to test for putative antisense proteins [rabbit α-PA, α-PA-CT, α-PR, α-PR-CT, α-GP α-GP-CT (sense), and mouse α-GP] were generated and their specificities demonstrated in cells transfected with constructs expressing epitope-tagged recombinant protein by western blot and IF detection (FIGS. 13E, 22). Additional antibodies detecting repeat and C-terminal regions expressed in the sense direction are characterized in FIG. 23.

Antisense $G_2C_4$ RAN Proteins Accumulate in Brain

Figure 24:
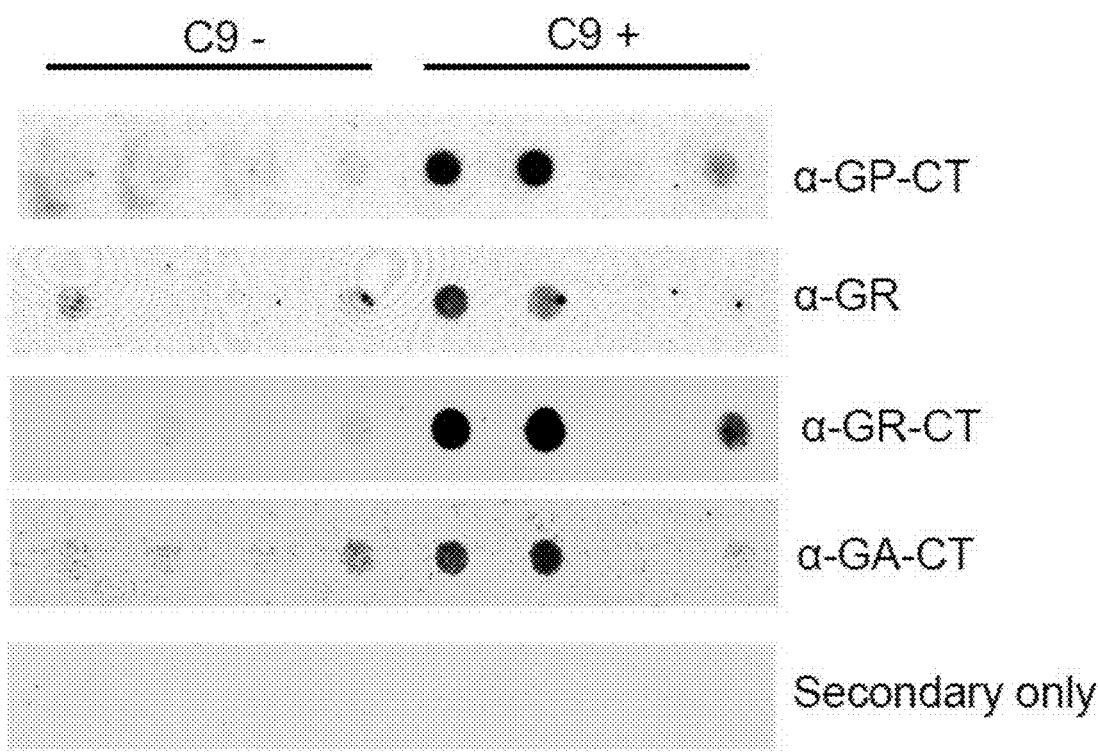
FIG. 24 is a series of images of immunoblots of 2% soluble lysates from C9(+) and C9(−) ALS frontal cortices with α-GP-CT, α-GR, α-GR-CT and α-GA antibodies.
Figure 25:
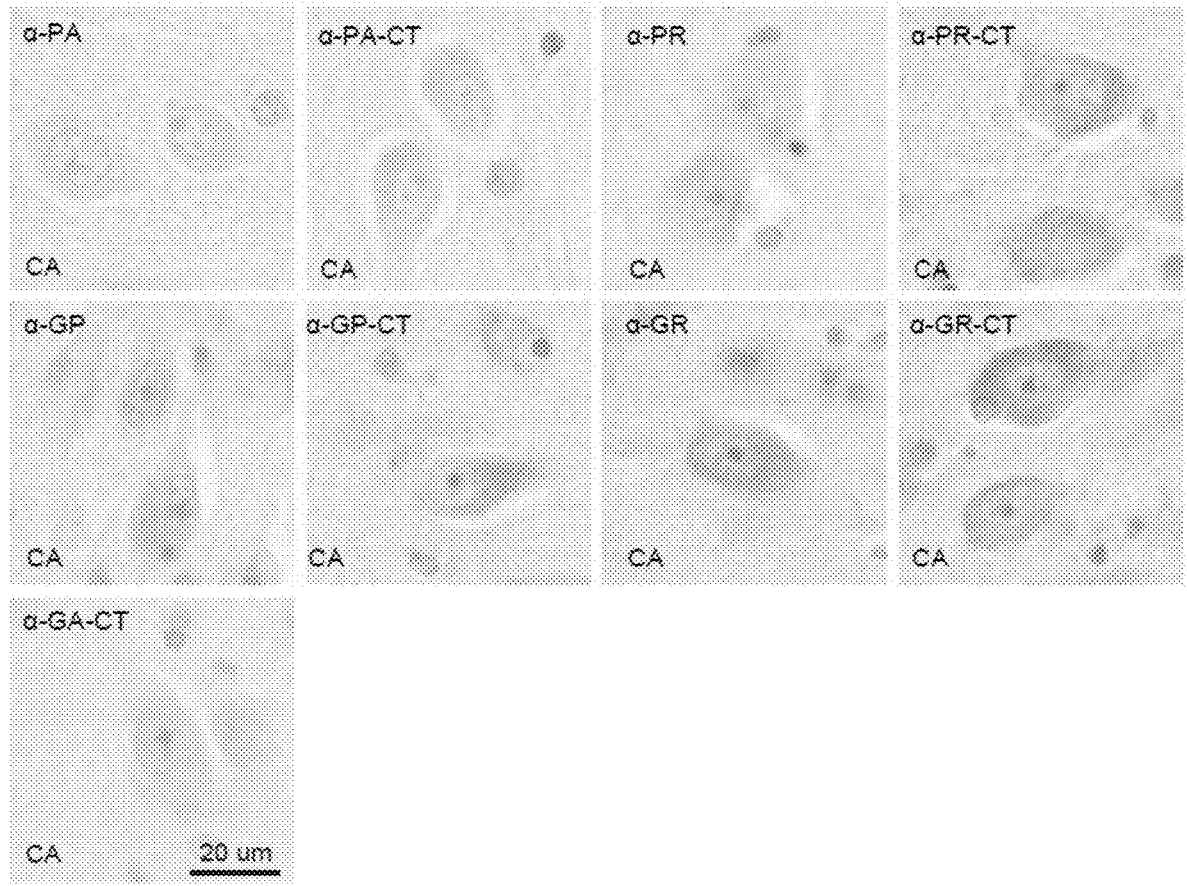
FIG. 25 is a series of images showing negative IHC staining of C9(−) ALS/FTD hippocampal sections with antibodies against sense and antisense proteins.

Several approaches were used to determine if novel antisense (AS) proteins are expressed in C9ORF72 expansion positive autopsy tissue. To overcome the obstacle that aggregated proteins are difficult to isolate from human brain, a sequential protein extraction protocol (23) was used on frozen C9(+) and C9(−) ALS frontal cortex autopsy samples. Antisense PA and PR proteins were detected with α-PA, α-PA-CT, α-PR, α-PR-CT on immuno-dot blots of 1% Triton-X100 insoluble, 2% SDS soluble extracts from a subset of C9(+) but not C9(−) ALS patients (FIG. 14A). Additional immuno-dot blots showing evidence for sense-RAN protein (GP, GR, GA) 10 accumulation in C9(+) ALS/FTD frontal cortex are shown in FIG. 24. α-PA, α-PR and α-GP antibodies also detected high molecular weight smears in 2% SDS insoluble fractions from C9(+) ALS frontal cortex samples after resuspending the pellets in sample buffer containing 8% SDS (23) (FIG. 3B). The differences in migration pattern seen for the recombinant proteins (FIG. 13B), which migrate as one or more bands, and the smears observed in patient tissue extracts (FIG. 14B) reflect differences in the RAN proteins due to much longer repeat tracts in patient samples and their extraction from highly insoluble aggregates. Immunohistochemistry (IHC) was next used to show that protein aggregates were detectable in the perikaryon of hippocampal neurons from C9(+) ALS/FTD autopsy tissue but not in C9(−) ALS patients or control subjects using antibodies against the repeat motifs (α-PA, α-PR, α-GP) as well as antibodies directed to predicted C-terminal sequences beyond the PA and PR repeat tracts (α-PA-CT and α-PR-CT) (FIG. 14C, 25). Previous studies using antibodies directed against the GP repeat motif, detected aggregates, which were assumed to be expressed from the sense strand (10, 11). It is noted that GP repeat-containing proteins are predicted to be expressed from both sense and antisense transcripts (FIG. 13D) In the sense direction the predicted RAN GP protein contains a unique C-terminal (CT) sequence. In contrast, the antisense GP protein has a stop codon immediately after the repeat. To distinguish sense-GP RAN proteins from antisense-GP proteins, a double label IF experiments was performed on C9(+) human hippocampal autopsy sections using rabbit α-GP-CT to detect the CT region of the sense-GP protein and mouse α-GP to detect both sense and antisense GP expansion proteins. Double labeling showed two types of inclusions: a) putative sense inclusions double labeled with mouse α-GP and rabbit α-GP-CT sense and; b) putative antisense inclusions singly labeled with mouse-α-GP (FIG. 14D). Approximately 18% of inclusions showed the sense pattern with double labeling and 82% 11 of inclusions showed the antisense pattern and were positive for α-GP and negative for α-GP-CTsense (FIG. 14E,F). These data showed the importance of characterizing protein aggregates with both repeat and C-terminal antibodies. Taken together, these results show that insoluble, aggregate-forming antisense-RAN proteins are expressed from all three antisense reading frames.

$G_2C_4$ Expansions and RAN Proteins are Toxic to Cells

Figure 13:
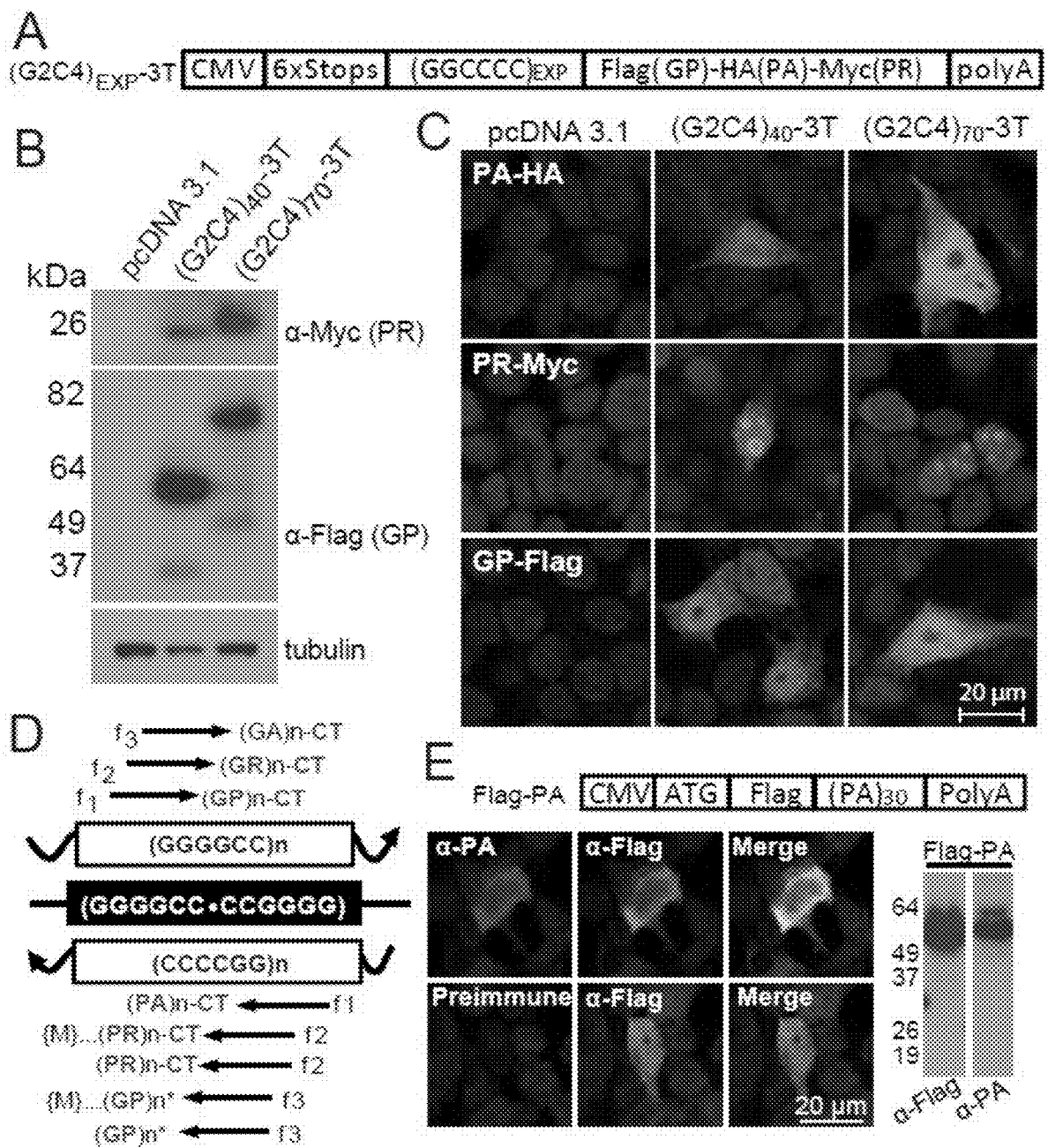
FIG. 13 is a series of schematics, graphs and images showing in vitro evidence for RAN translation of antisense G2C4 expansion and dual immunological detection strategy. (A-C) Immunoblots (B) and IF staining (C) of HEK293T cells 48 hours post-transfection with the (G2Ca) Exp-3T construct (A). (B) PR and GP expansion proteins detected by western and (C) PA, PR and GP detected by IF in transfected cells. (D) Diagram of putative proteins translated from sense and antisense transcripts. CT=C-terminal, f1-3: reading frame 1-3. (E) Abbreviated example of validation of α-PA rabbit polyclonal antibody. IF staining of HEK293T cells transfected with constructs with 5' Flag epitope tagged PA protein and corresponding immunoblots. See FIGS. 22 and 23 for additional controls and validation of eight additional antibodies generated against repeat motifs and CT regions.
Figure 14A:
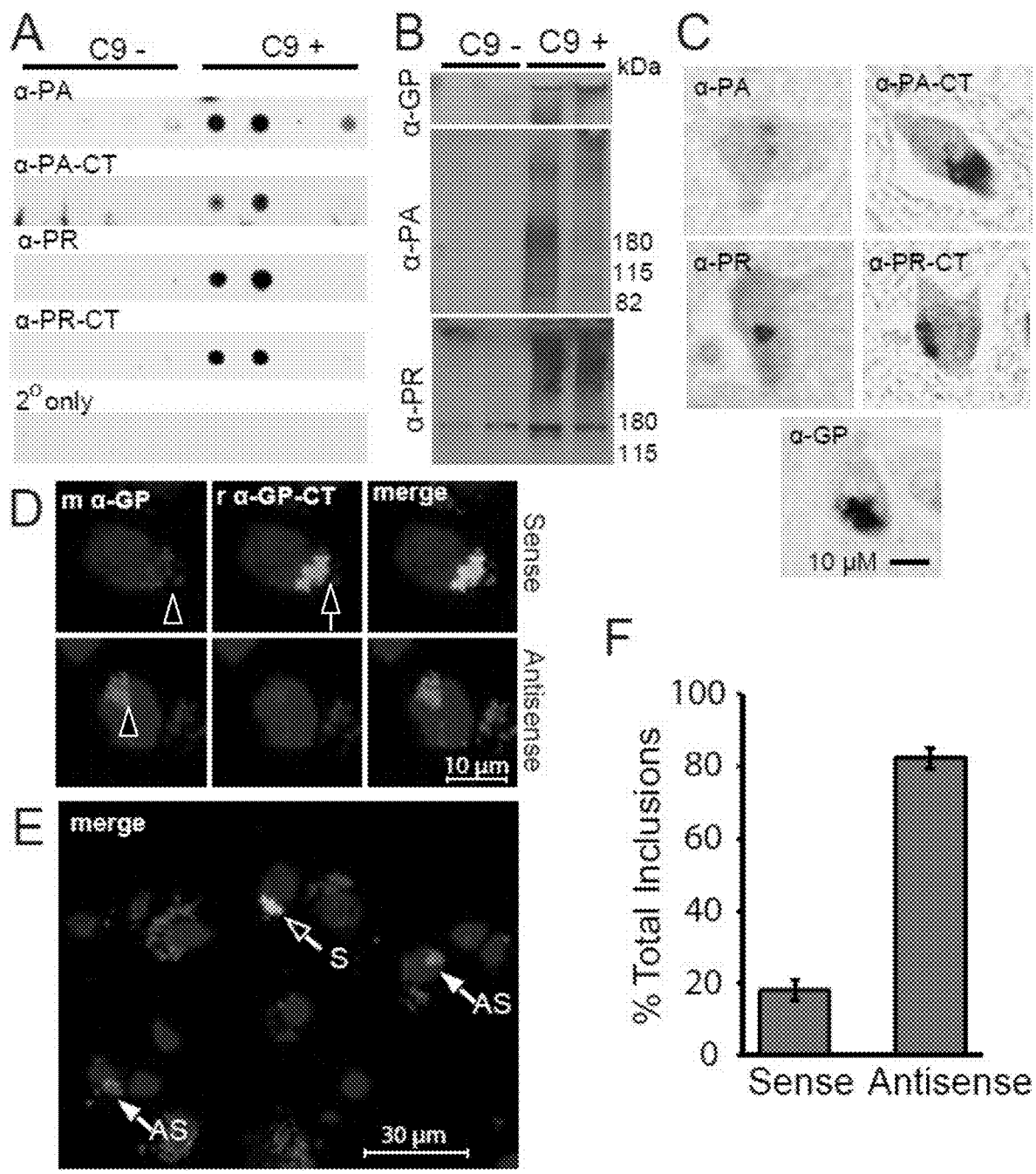
FIGS. 14A and 14B are a series of images and graphs showing in vivo evidence for RAN-translation of the G2C4 AS repeat and toxicity studies. (A) Dot blot of C9(+) and C9(−) frontal cortex lysates probed with α-PA. α-PA-CT, α-PR, α-PR-CT antibodies. (B) Immunoblots of C9(+) and C9(−) ALS frontal cortex lysates. (C) IHC detection of PA, PR and GP protein aggregates in hippocampal neurons from C9(+) ALS patients detected with α-PA, α-PA-CT, α-PR, α-PRCT and α-GP antibodies. (D) IF staining with mouse α-GP (arrowhead) and rabbit α-GP-CT (arrow) of C9(+) hippocampal tissue with sense inclusions positive for both antibodies (upper panel) and antisense inclusions positive for only GP repeat antibody (lower panel). (E) IF staining of larger region showing sense(S) and antisense (AS) staining. (F) Quantitation of double (sense) and single (antisense) labeled aggregates. (G-J) RAN and PR toxicity studies (G) G2C4 expansion constructs (+/−ATG-PR-3T)+/−ATG initiation codon in PR frame and 3'epitope tags. (H) Protein blots showing levels of PR and GP in cells transfected with constructs in (G). (I) LDH and (J) MTT assays of transfected HEK293T cells.
Figure 14B:
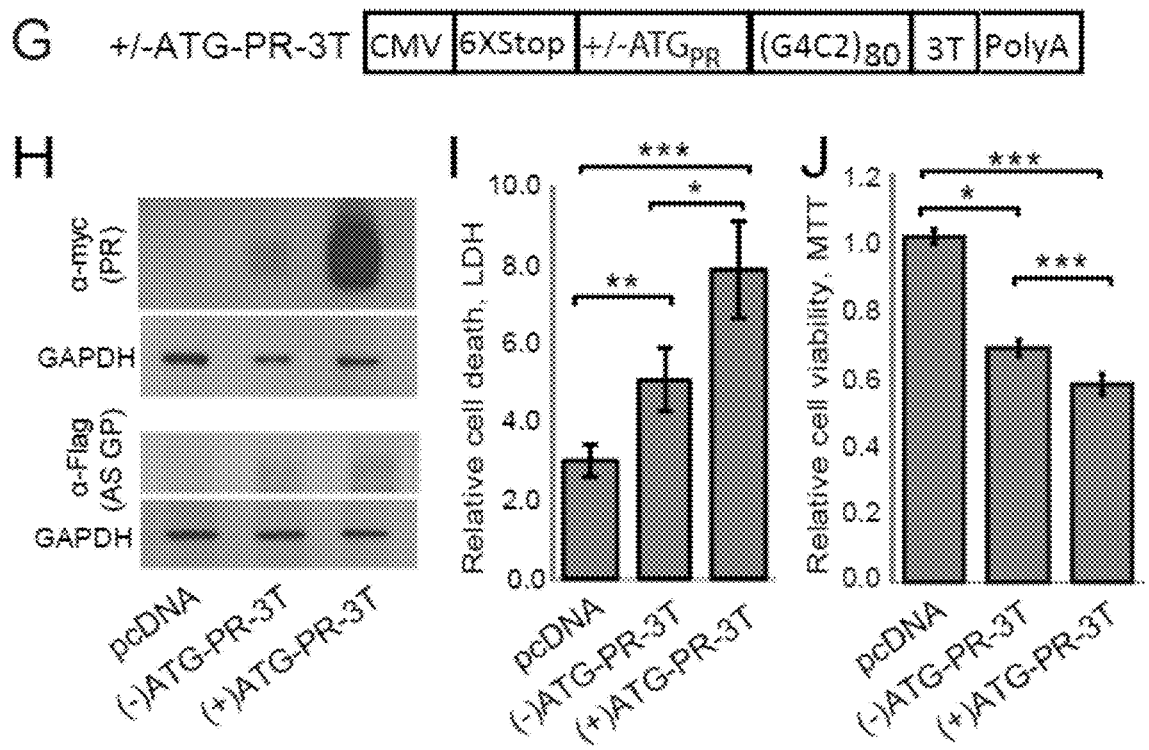
Figure 26A:
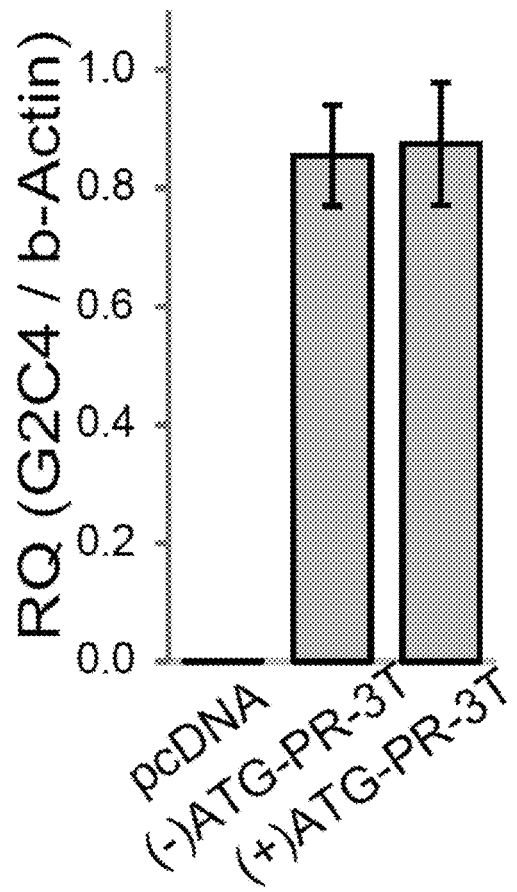
Figure 26D:
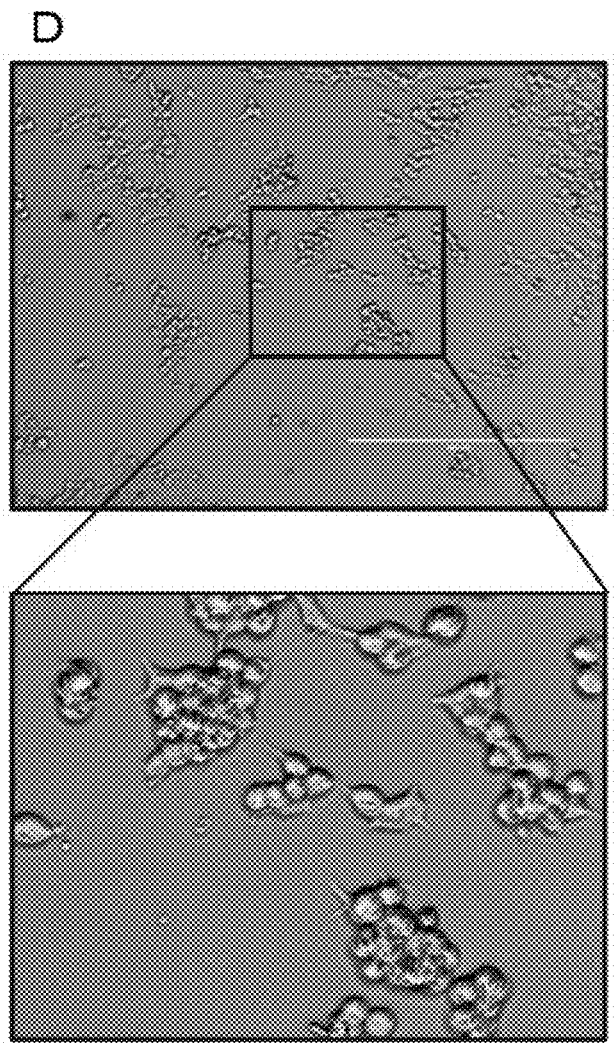

In addition to antisense GP and PR RAN proteins expressed by RAN translation, two of the antisense reading frames have upstream ATG initiation codons that may result in both ATG-initiated GP and PR proteins (M-GPAS and M-PRAS) (FIGS. 13D and 21). It was shown that the presence of an ATG-initiation codon does not prevent RAN translation from also occurring in all three reading frames (9). Therefore antisense GP and PR proteins may be expressed by both AUG-initiated and/or RAN translation. To explore the effects that an ATG-initiation codon has on RAN protein expression for the $G_2C_4$ expansion, an additional minigene construct was generated by placing an ATG initiation codon in front of the $G_2C_4$ repeat (FIG. 14G). The PR frame was selected for analysis because an ATG initiation codon naturally occurs in this reading frame. Western blotting shows that HEK293T cells transfected with (+) ATG-PR-3T express substantially higher levels of PR protein compared to (−) ATG-PR-3T transfected cells (FIG. 14H). In contrast, qRT-PCR and Western blotting showed transcript levels (FIG. 26A) and levels of RAN-translated GP (FIG. 14H) were comparable. Similar to FIG. 13, RAN-translated PA was not detectable by Western blot. The effects of these constructs on cell viability was then tested using complementary assays; lactate dehydrogenase (LDH) detection and methylthiazol tetrazolium (MTT). For the LDH assay, cells transfected with the (−) ATG-PR-3T or (+) ATG-PR-3T construct showed 1.9 and 2.9 fold increases in cell death compared to vector control cells (p=0.008 and 0.001), respectively. Additionally, (+) ATG-PR-3T transfected cells, which express elevated levels of PR protein showed a 1.5 fold increase in cell 12 death compared to cells transfected with the (−) ATG-PR-3T construct (p=0.034). The MTT assay showed similar results. Cells transfected with (−) ATG-PR-3T and +ATG-PR-3T constructs showed dramatic decreases in the number of metabolically active cells, 33% (p<0.00001) and 43% (p<0.00001), respectively compared to untreated cells or empty vector controls (FIG. 14.1). Additionally, elevated PR expression in cells transfected with (+) ATG-PR-3T had significantly lower levels of metabolic activity compared to (−) ATG-PR-3T cells (p<0.05). By light microscopy cell detachment and changes in cell morphology were evident in-ATG-PR-3T compared to control cells and these phenotypes worsened in (+) ATG-PR-3T cells which express elevated levels of PR (FIG. 26B-D). Taken together, these data demonstrated that: 1) the $G_2C_4$ expansion mutation is toxic to cells—this toxicity may be caused by effects of the DNA. $G_2C_4$ RNA and/or RAN-translated PR, GP or PA proteins; 2) increased PR protein expressed in cells transfected with the (+) ATG-PR-3T construct increases cell toxicity and death above levels caused by the DNA, G$_2$C$_4$ RNA and RAN protein effects. Therefore the PR protein was shown to be intrinsically toxic to cells.

All Six RAN Proteins Form Aggregates in the Brain

Figure 15A:
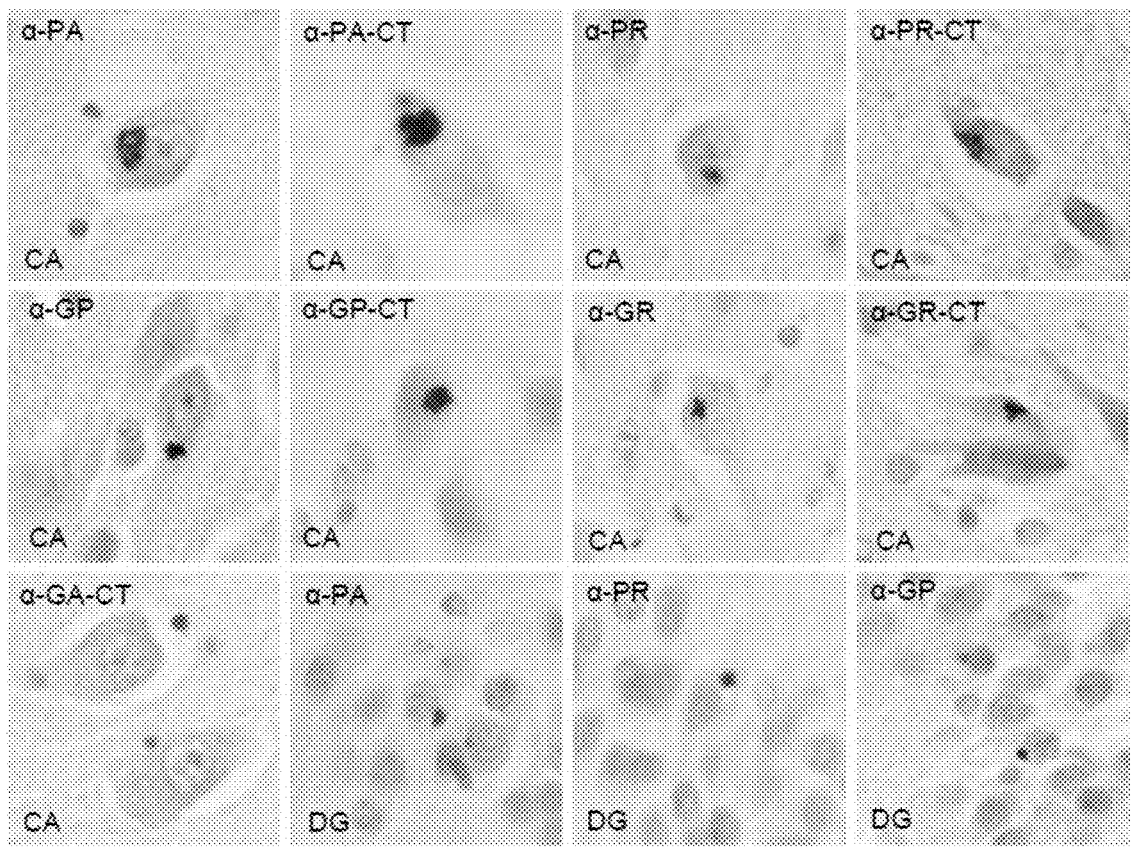
FIGS. 15A and 15B are a series of images showing in vivo evidence for RAN translation in both antisense and sense directions of C90RF72. Cytoplasmic inclusions detected by IHC using antibodies against sense (α-GR, α-GR-CT, α-GA, α-GP-CT) and antisense (α-PA, α-PA-CT, α-PR, α-PR-CT) and α-GP which recognizes GP proteins made in both the sense and antisense directions. Aggregates were found in neurons of cornu ammonis (CA) and dentate gyrus (DG) regions of the hippocampus and the motor cortex (MC) of C9(+) ALS autopsy tissue.
Figure 15B:
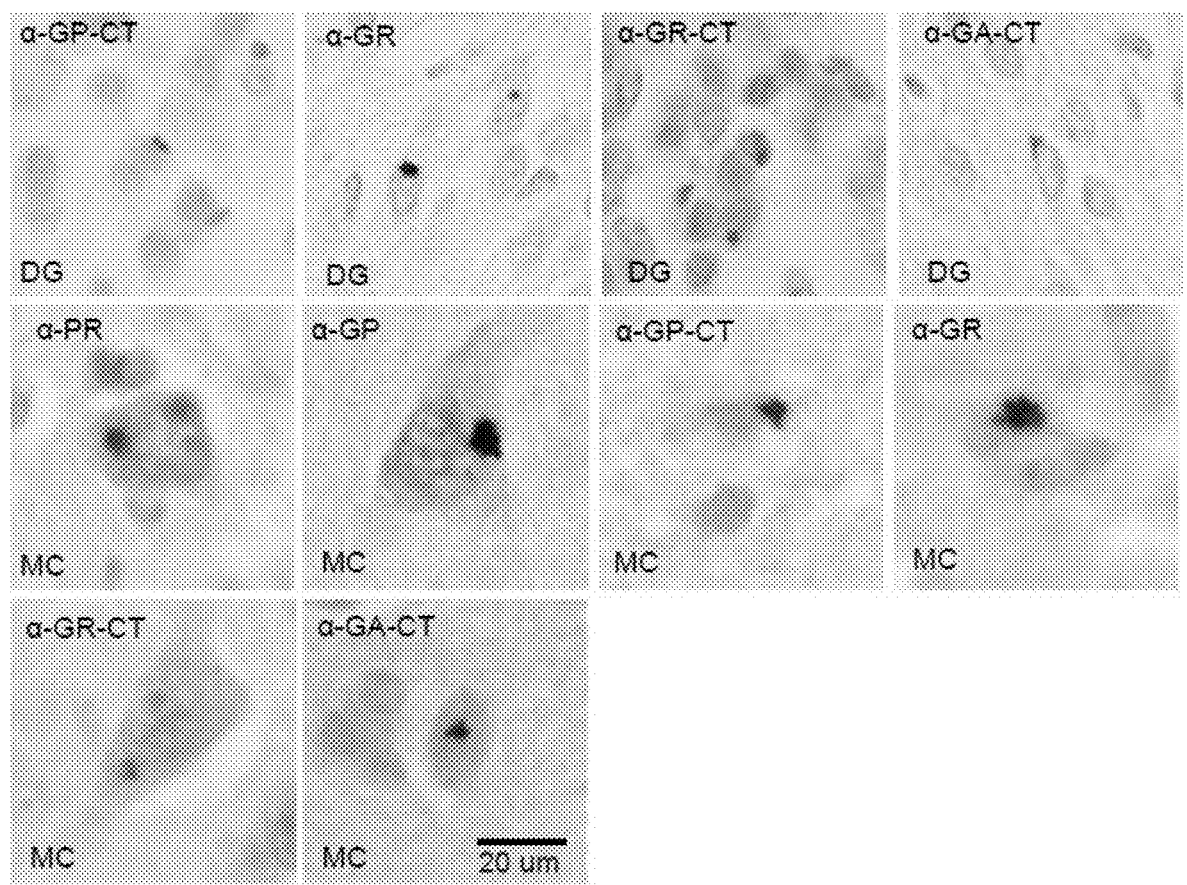

To determine if all six RAN proteins from both sense and antisense RNA strands are expressed in C9(+) ALS patients, IHC staining was performed on sections of paraffin-embedded brain tissues using nine polyclonal antibodies against repeat-expansion and/or C-terminal sequences of these proteins. In C9(+) cases there were abundant globular and irregular-shaped neuronal cytoplasmic inclusions (NCIs) in the hippocampus, the majority of which were in the dentate gyrus and in pyramidal cells in the CA regions. These RAN inclusions were also detected in C9(+) motor cortex (FIG. 15). GP positive inclusions were detected in all examined C9(+) cases but not in C9(−) cases or normal control sections in the hippocampus as well as in the motor cortex using α-GP. In the CA regions of the 13 hippocampal and in the motor cortex, clusters of aggregates were frequently found in C9(+) cases with aggregates in >20% of neurons (FIG. 27). Fewer aggregates were detected with the α-GP-CT sense antibody, consistent with double labeling experiments (FIG. 14D-F) that showed most GP aggregates are translated from C9ORF72 antisense strand. PA inclusions were detected in hippocampus in four out of six C9(+) cases tested and in one out of two motor cortex samples (FIG. 27). In C9(+) cases, the frequency of PA inclusions were significantly lower in the hippocampus and motor cortex compared with GP inclusions, but high-intensity regional staining with extremely large PA inclusions found in >50% of neurons were found in one patient (FIG. 27). PR positive inclusions were also seen in hippocampus in all C9(+) cases examined and in motor cortex in one out of two C9(+) cases tested. Similar to the PA staining, PR inclusions are less frequent but intense regional staining was occasionally observed. In the sense direction, GR positive inclusions were found in the hippocampus and motor cortex in all C9(+) cases examined, but appeared less frequent than the GP aggregates. GA inclusions were only occasionally detected by IHC as small perinuclear inclusions in hippocampus and in motor cortex (FIG. 15, 27). The apparent differences in the frequency of various types of aggregates may result from differences in protein conformation and epitope availability or differences in the affinities of these antibodies, which were designed to different epitopes. Taken together, this data showed that all six RAN proteins form aggregates in the C9(+) autopsy brains.

Inclusions of RAN Proteins in Upper and Lower Motor Neurons

Figure 16A:
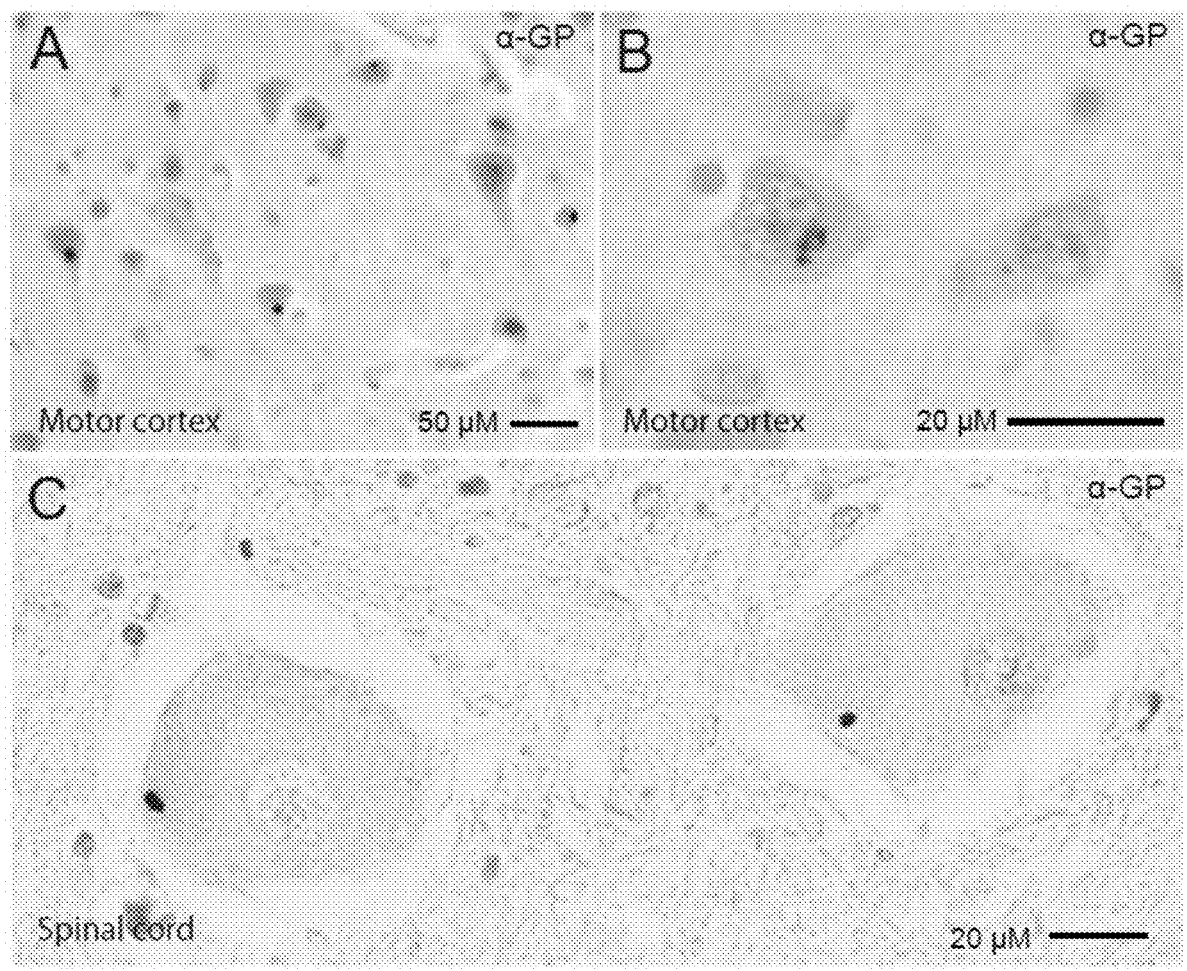
FIGS. 16A and 16B are a series of images of clustered RAN protein aggregates and RAN aggregates in motor neurons. IHC showing cytoplasmic α-GP aggregates in: (A) in layer Ill of motor cortex. (B) upper motor neuron in layer V of the motor cortex; (C) lower motor neurons in the spinal cord (L-S.C). (D) in cornu ammonis, CA. (E) and dentatus gyrus, DG regions of the hippocampus. (F and G) IHC showing abundant PA and PR cytoplasmic inclusions in the pre-subiculum (PrSub) from one patient.
Figure 16B:
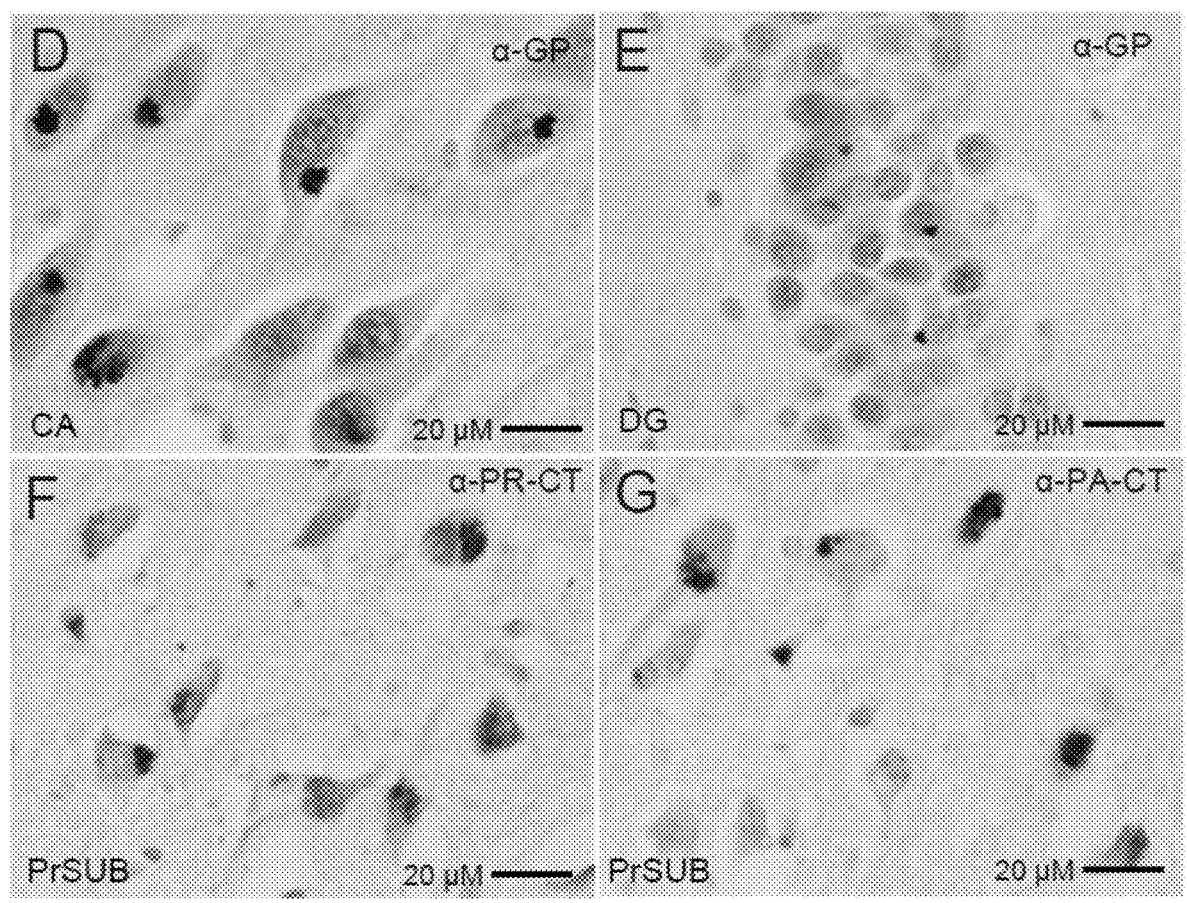

A central feature of ALS is the gradual degeneration and death of upper motor neurons in motor cortex and lower motor neurons in the brain stem and spinal cord. To test if RAN proteins accumulate in upper and lower motor neurons, IHC was performed using all nine antibodies against predicted proteins in both sense and antisense directions. In C9(+) cases, abundant GP-positive neuronal cytoplasmic inclusions were seen in all layers of motor cortex, with frequent GP aggregates in pyramidal neurons of layer III and throughout layer V (FIG. 16A). Although cell death and atrophy made motor-neurons in layer V difficult to identify, GP inclusions in remaining upper motor neurons were found (FIG. 16B). Additionally, PA-, PR-, GR- and GA-positive inclusions were also found in the motor cortex (FIG. 15, 27). Using a similar series of experiments performed in spinal cord sections, GP aggregates in all three cases examined and aggregates in lower motor neurons in two out of three C9(+) patients were detected, but not in C9(−) ALS cases or normal controls (FIG. 16C). This is the first report of RAN protein accumulation in motor neurons. The discovery of GP-aggregates in both upper and lower motor neurons links C9 RAN-protein accumulation to the neurons selectively vulnerable in ALS.

High Density Clustering of RAN-Protein Aggregates

Figure 17:
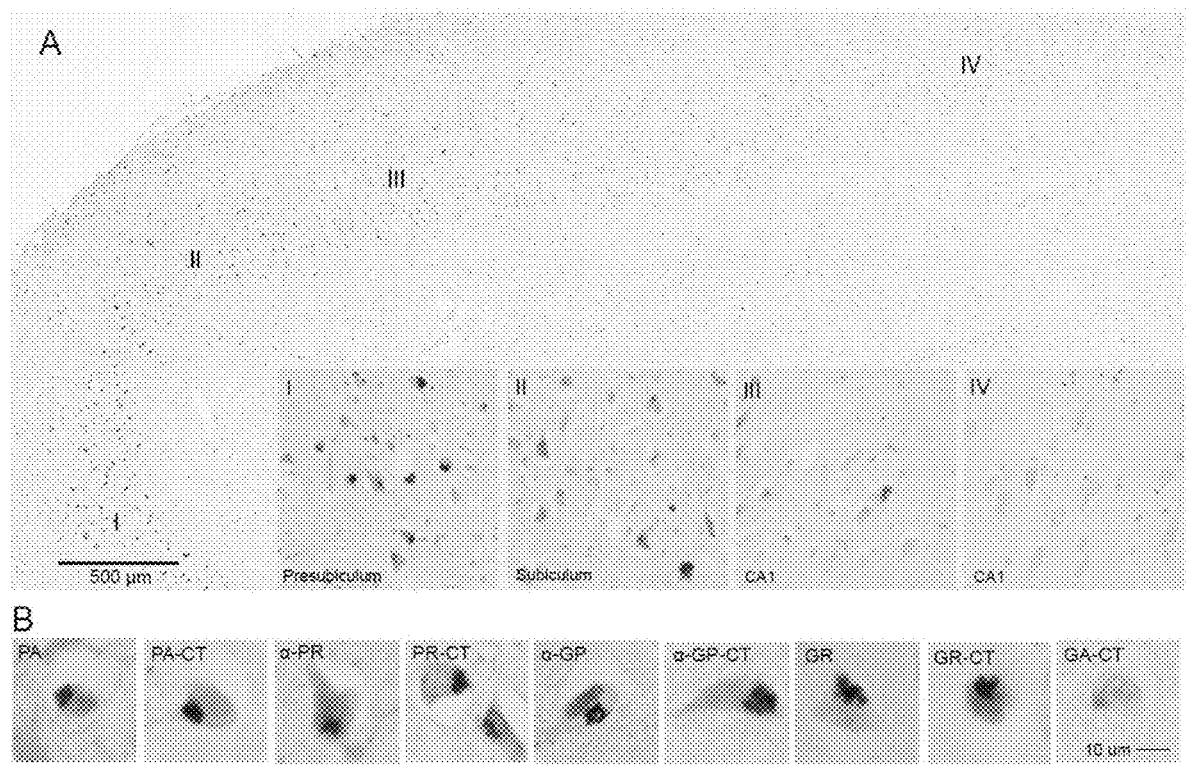
FIG. 17 is a series of images of clustered staining of RAN proteins. (A) Low power image of IHC staining with α-PA-CT shows variations in staining intensity (dark spots are positive) in regions I-IV with insets showing higher-power images. (B) Examples of aggregates from region I show immunoreactivity against all nine antibodies with similar staining for antibodies against repeat and unique C-terminal epitopes.

Both sense and antisense proteins accumulated in neurons of C9ORF72 autopsy brains. In general, two types of aggregation patterns were observed: 1) isolated cytoplasmic aggregates and 2) high-density clustered cytoplasmic aggregates in which ~10 to more than. 50% of neurons were positive. Clustered aggregates were most frequently detected for GP and were found in the dentate gyrus (DG) and CA1-4 of the hippocampus (FIG. 16D, E). The clustered GP aggregates in DG were smaller and less frequent than the large cytoplasmic aggregates in CA regions. Additional clustered GP aggregates were frequently found in subiculum and presubiculum of the hippocampus as well as 15 the motor cortex. Immunostaining of serial sections showed that multiple proteins are often found in the same region. For example, intense clustered staining for PA, PR, GP, GA and GR proteins was found in the same region of the presubiculum in serial sections from one C9(+) patient (see FIG. 16F,G). Immunostaining for PA showed that some brain regions have abundant aggregates whereas other regions in the same section are relatively spared. For example, FIG. 17A illustrates a gradient of PA inclusions (presubiculm>subiculum>CA1) across hippocampal regions in a single section in one patient. PA inclusions in this patient were numerous (>50% of neurons) in presubiculum (I), moderate in subiculum (II), and rare in CA1 hippocampal regions (Ill and IV). Consistent with the focal regional staining seen in this section, PA staining was not detected in sections from a separate block of hippocampal tissue taken from the same patient. These data shows that expression of the PA RAN protein is variable from cell to cell or that aggregation of PA in one cell triggers aggregation in neighboring cells as has been proposed in a mouse model of Parkinson's disease (24). Next, serial sections from this C9(+) case were used to show that antibodies directed against both the repeat motifs (α-PA, α-PR, α-GP, α-GR) and corresponding C-terminal regions (α-PA-CT, α-PR-CT, α-GP-CT, α-GR-CT α-GA-CT) detect aggregates in the same densely staining region of the presubiculum (region I) (FIG. 17B). These results showed that both sense and antisense RAN protein aggregates accumulate in this region. The detection of similar aggregates in using antibodies that recognize either the repeat motifs or specific C-terminal regions confirms that these antibodies are recognizing proteins expressed across both the G2C4 and G$_4$C$_2$ expansion transcripts and provides new tools to understand the biological impact of RAN translation in C9ORF72 ALS/FTD.

Discussion

There has been much excitement about the discovery that an intronic microsatellite expansion mutation in C9ORF72 causes a common form of both familial and sporadic ALS/FTD (1, 2). The three major pathological mechanisms being considered for this disease include haploinsufficiency (1, 2), RNA gain-of-function (5-8), and RAN translation (9, 11-13). To date, efforts to understand the molecular mechanisms of this disease have focused exclusively on understanding the consequences of the C9ORF72 expansion mutation in the sense direction. The results reported here show that C9ORF72 expansion mutation is also expressed in the antisense direction and show that antisense RNA foci and antisense RAN proteins contribute to C9ORF72 ALS/FTD. We show for the first time: 1) antisense C90RF72 but not sense transcripts are elevated in C9(+) autopsy tissue; 2) antisense G2C4 expansion transcripts form RNA foci that accumulate in C9+ brain and blood; 3) RAN translation occurs across antisense $G_2C_4$ expansion constructs in cell culture; 4) that sense and antisense RAN proteins accumulate in C9(+) autopsy brains using a dual immunological approach with both repeat and C-terminal antibodies; 5) RAN protein aggregates accumulate in upper and lower motor neurons linking RAN translation directly to the key pathologic feature of ALS. Since the initial report that $G_4C_2$ RNA foci accumulate in C90RF72 ALS/FTD patient tissues (1, 2), a leading hypothesis is that $G_4C_2$ sense transcripts sequester and dysregulate RNA binding proteins similar to the sequestration of MBNL proteins in DM1, DM2 and SCA8 (4). Several groups have already reported $G_4C_2$ binding proteins and are testing their potential role in disease (5-8). The discovery that antisense $G_2C_4$ foci also accumulate in patient cells shows that G2C4 antisense RNAs and binding proteins may play a role. Additionally, the discovery of sense and antisense foci in C9(+) peripheral blood may prove useful as an easily accessible biomarker of C90RF72 ALS/FTD. Biomarkers that monitor both sense and antisense transcripts may be particularly important as therapies that decrease expression of one strand may increase expression of the other strand. Using a dual immunological approach it was shown that $G_2C_4$ antisense transcripts express novel antisense proteins (PA, PR, GP) by RAN translation and/or from two short ORFs (Met-AS-PR and Met-AS-GP).

Materials and Methods cDNA constructs. $CCCGGGGCC(GGGGCC)_2 GGGGCCC$ (SEQ ID NO: 64) and $CCCGGGGCC(GGGGCC)_{28}GGGGCCC$ (SEQ ID NO: 65) fragments that contain upstream 6xStop codons were synthesized and cloned into pIDTSmart vector by Integrated DNA Technologies. 6xStops-$(GGGGCC)_4$-3T and 6xStops-$(GGGGCC)_{30}$-3T constructs were generated by subcloning NheI/XhoI fragment into pcDNA3.1 vector containing triple epitopes. To expand the size of the GGGGCC repeats, SmaI/XhoI fragment was subcloned into PspOMI blunted with T4 DNA polymerase/XhoI of pcDNA-6xStops-(GGGGCC) EXP-3T. To reverse the orientation of GGGGCC repeats in pcDNA-6xStop-3T construct, SmaI/I/ClaI fragment was subcloned into pBluescript SK+ to generate pBluescript-(GGGGCC) Exp. The AfeI/XhoI fragment pBluescript-(GGGGCC) EXP was subcloned into pcDNA-6xStop-3T to make pcDNA-6xStop-$(GGCCCC)_{EXP}$-3T construct.

RT-PCR. 1) Strand-specific RT-PCR in autopsy tissues: Total RNA was isolated from Frontal cortex autopsy tissues and peripheral blood lymphocytes (PBL) of ALS patients and healthy controls with TRIzol (Invitrogen). To detect transcripts from both strands, cDNA was generated from 0.25 µg of total RNA using the SuperScript III system (Invitrogen) with linkered strandspecific reverse primers and PCR with strand specific forward and linker (LK) primers. The PCR reactions were done as follows: 94° C. for 3 min, then 35 cycles of 94° C. for 45 s, 58° C. for 45 s and 72° C. for 1 min followed by 6 min at 72° C. Bands were cloned and sequence to verify their specificity of the PCR amplification. 2) RT-PCR for toxicity assay in 293T cells: Total RNA from cells was extracted using miRNeasy Mini kit (Qiagen) according to the manufacturer's protocol. Total RNA was reverse transcribed using the Superscript III RT kit (Invitrogen) and random-hexamer primers. The expression of the different G4C2-3XTag constructs were analyzed by RT-PCR and qPCR using primer set: 3xTag-Fw and 3xTag-Rv. β-Actin expression was used as a reference gene amplified with primer set ACTB3 and ACTB4. Primer sequences are listed in FIG. 27.

Real time RT-PCR. Two step quantitative PCR was performed on a MyCycler Thermal Cycler system (Bio-Rad) using SYBER Green PCR Master Mix (Bio-Rad) and ASORF strand-specific cDNA and primer sets. Control reactions were performed with human beta-actin primers ACTB3 and ACTB4 using oligo d'T synthesized total cDNA as template. Two stage PCR was performed for 40 cycles (95° C. 30 s. 60° C. 30 s) in an optical 96 well plate with each sample cDNA/primer pair done in triplicate. The relative fold changes were generated by first normalizing each experimental Ct value to their beta actin Ct value and then normalized to the healthy control antisense ΔΔCt. Primer sequences are listed in FIG. 28.

Rapid Ampliciation of 5' and 3' cDNA ends (5' and 3' RACE). Four µg of total RNA from 2 C9(+) ALS patients and 2 C9(−) ALS patients frontal cortex autopsy tissues were used for 5' and 3' RACE (5' RACE systems and 3' RACE; Life Technologies). In 5'RACE, Primer ASORF R was used for gene specific first strand cDNA synthesis and nested reverse primers are 5'GSP1 and 5'GSP2. In 3'RACE, nested forward primers are 3'GSP1 and 3'GSP2. The 3' RACE and 5' RACE products were gel-extracted, cloned with TOPO TA Cloning (Invitrogen) and sequenced. Primer sequences are listed in FIG. 28.

Production of polyclonal antibodies. The polyclonal rabbit antibodies were generated by New England Peptide and the polyclonal mouse antibody was generated by the Interdisciplinary Center for Biotechnology Research (ICBR) at the University of Florida. In sense strand $(GGGGCC)_n$ antisera were raised against synthetic poly (GP), poly (GR) peptides and C terminal regions of predicted GP, GR, and GA RAN proteins (FIG. 21). In antisense strand (GGCCCC), antisera were raised against synthetic poly (PA), poly (PR) peptides and the C terminal regions of predicted PA and PR RAN proteins. Peptides used to generate antibodies to both antisense and sense proteins and their use for Western blot, immunofluorescence (IF) and immunohistochemistry (IHC) is summarized in Table S3.

Cell culture and transfection. HEK293T cells were cultured in DMEM medium supplemented with 10% fetal bovine serum and incubated at 37° C., in a humid atmosphere containing 5% CO2. DNA transfections were performed using Lipofectamine 2000 Reagent (Invitrogen) according to the manufacturer's instructions.

Human Samples. Frozen frontal cortex tissue samples for biochemical and histological analysis included samples from six C9(+) ALS, five C9(−) ALS controls and one normal control were used in this research. Additionally, paraffin embedded fixed tissues from C9(+) ALS/FTD and C9(−) ALS/FTD cases as well as a normal control. Peripheral blood lymphocytes (PBL) were isolated from the buffy coat of freshly collected whole blood following brief centrifugation at 2000×g. Red blood cells (RBC) were preferentially lysed and removed using RBC Lysis Buffer (Roche), PBLs centrifuged, washed once with PBS and dried on slides. This study was conducted in compliance with the Declaration of Helsinki. Institutional review boards of the University of Florida and Johns Hopkins University approved the study. Written, informed consent was obtained from participants or relevant parties at the time of enrollment.

Immunofluorescence. The subcellular distribution of polymeric proteins was assessed in transfected HEK293T cells by immunofluorescence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum in PBS for 30 min. After blocking, the cells were incubated for 1 hour at RT in blocking solution containing the rabbit anti-Myc (Abcam), mouse anti-HA (Covance), mouse anti-Flag (Sigma), rabbit anti-GR and rabbit anti-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen).

RNA-FISH. Slides with cells were fixed in 4% PFA in PBS for 10 min and incubated in prechilled 70% ethanol for 30 min on ice. Following rehydration in 40% formamide in 2×SSC for 10 min, the slides were blocked with hybridization solution (40% formamide, 2×SSC, 10 mg/ml BSA, 100 mg/ml dextran sulfate and 10 mg/ml yeast (RNA) for 10 minutes at 55° C., and then incubated with 200 ng/ml denatured RNA probe in hybridization solution at 55° C. for 2 hours. After hybridization the slides were washed 3 times with 40% formaminde in 2×SSC and briefly washed one time in PBS. Autofluorescence of lipofuscin was quenched by 0.25% of Sudan Black B in 70% ethanol and the slides were mounted with mounting medium containing DAPI (Invitrogen). The specificity of the RNA foci was determined by treating cells prior to FISH detection with either RNAse (100 µg/mL in 2×SSC), DNase (1 U/ul in DNaseI buffer) or Protease K (120 ug/mL in 2 mM CaCl2, 20 mM Tris, pH 7.5). Treated cells were incubated at 37° C. for 30 minutes, washed 3 times with PBS then 3 times with 2×SSC. Subsequent FISH detected was performed as described above. Antisense foci specificity was determined using standard FISH detection to first hybridize slides with 10-fold excess unlabeled (G4C2) 4 oligo followed by hybridization with either G4C2-cy3 (antisense probe) or $G_2C_4$-cy3 (sense probe). Subsequent treatment and detection were performed as described above.

Western blotting. Transfected cells in each well of a six-well tissue-culture plate were rinsed with PBS and lysed in 300 µL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham). Sequential extraction of patient frontal cortex autopsy tissue was performed as follows: tissue was homogenized in PBS containing 1% Triton-X100, 15 mM MgCl2, 0.2 mg/ml DNase I and protease inhibitor cocktail and centrifuged at 16,000×g for 15 min at 4° C. The supernatant was collected. The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS. 62.5 mM Tris-HCl pH 6.8, 10% glycerol and 20% 2-Mercaptoethanol for protein blotting (25).

Protein slot blot. 1% Triton-X100 soluble fraction and 2% SDS soluble fraction from the sequential extraction was immobilized onto nitrocellulose membranes with Bio-Dot 96-well microfiltration system (Bio-Rad) under vacuum. The membranes were washed in PBS-T and blotted with each rabbit polyclonal antibody (1:2000) using the same protocol as western blotting.

Immunohistochemistry. Ten-micrometer sections were deparaffinized in xylene and rehydrated through graded alcohol, incubated with 95-100% formic acid for 5 min, and washed with distilled water for 10 min. HIER was performed by steaming sections in citrate buffer, pH 6.0, at 90° C. for 30 min. To block nonspecific immunoglobulin binding, a serum-free block (Biocare Medical) was applied for 30 min. Rabbit polyclonal antibodies were applied at a dilution of from 1:5000 to 1:15,000 in serum-free block (Biocare Medical) and incubated overnight at 4° C. Linking reagent (streptavidin and/or alkaline phosphatase, Covance) was applied for 30 min at room temperature. These sections were incubated in 3% $H_2O_2$ for 15 min to bleach endogenous peroxidase activity. Then labeling reagent (HRP, Covance) was applied for 30 min at room temperature. Peroxidase activity was developed with NovaRed substrate (Vector) and sections were counterstained with hematoxylin.

Cell toxicity assays. All the transfection experiments were performed using Lipofectamine 2000 (Invitrogen), according to the manufacturer's instruction and at a 60% cell confluence. 500 ng of each vector was transfected in 35 mm wells. Cell death was determined by measuring Lactate dehydrogenase (LDH) cell release, using CytoTox 96 non-radioactive cytotoxicity assay (Promega) according to the manufacturer's instructions. Absorbance was recorded at 490 nm and total LDH release was measured by lysing the cells with 1% Triton X-100. In each experiment, determinations were performed in quintuplicates for each experimental condition and average data calculated. Statistical significance was determined using the two tailed unpaired Student t test for single comparisons ($p<0.05$) and the analysis of variance (ANOVA) when multiple pairwise conditions were compared.

Cell viability assays. HeK293T cells were transfected in 96 well plates and cell viability was determined 42 hours post-transfection with the 3-(4,5-dimethythiazol-2-yl)-2,5-diphenyl tetrazolium bromide (MTT) assay. MTT was added to cell culture media at 0.5 mg/mL final concentration and incubated for 45 minutes at 37° C. Cells were then lysed with 100 µL of DMSO upon medium removal and absorbance was measured at 595 nm. In each experiment, determinations were performed in quintuplicates. Statistical significance was determined using Student's t test ($p<0.05$).

Example 4. BAC Transgenic Mouse Model of C9ORF72 ALS to Test the Hypothesis that Both Sense and Antisense Transcripts Contribute to ALS/FTD Rationale: A mouse model of C9ORF72 ALS/FTD that recapitulates the sense and antisense transcripts is critical for modeling this disease. BAC clones were isolated from a human patient which contain ~800 G4C2 repeats. These BAC clones were used to generate 8 founder lines. These mice are useful, for example, to answer the following questions: Does both RAN protein expression and RNA gain of function contribute to C9ORF72 ALS/FTD? Are sense and antisense mechanisms both important in C9ORF72 pathogenesis?

Figure 30:
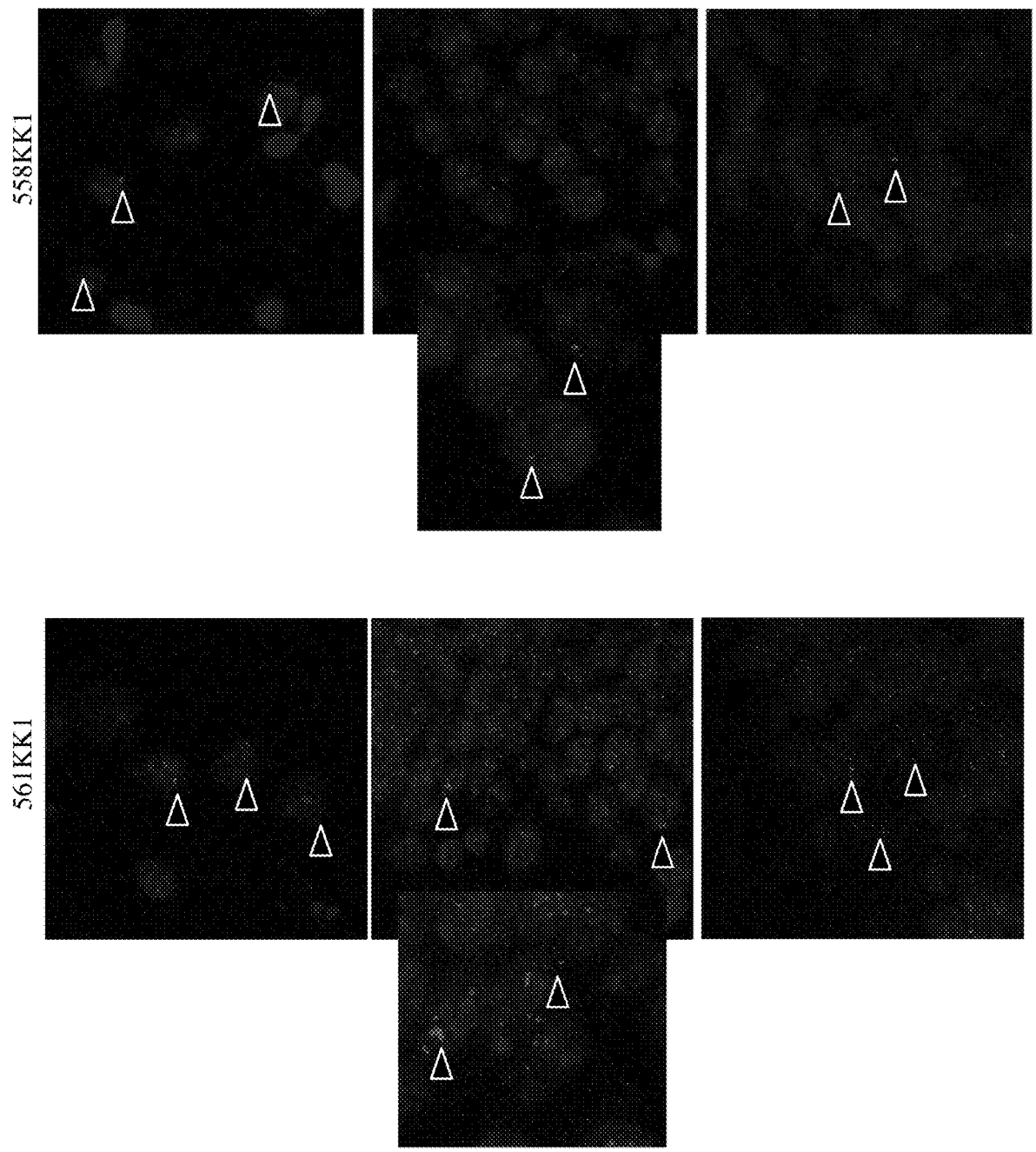
FIG. 30 is a series of photographs showing sense RNA foci in transgenic mice expressing a human C9ORF72 gene containing GGGGCC repeats. Exemplary foci are indicated by arrowheads.
Figure 31:
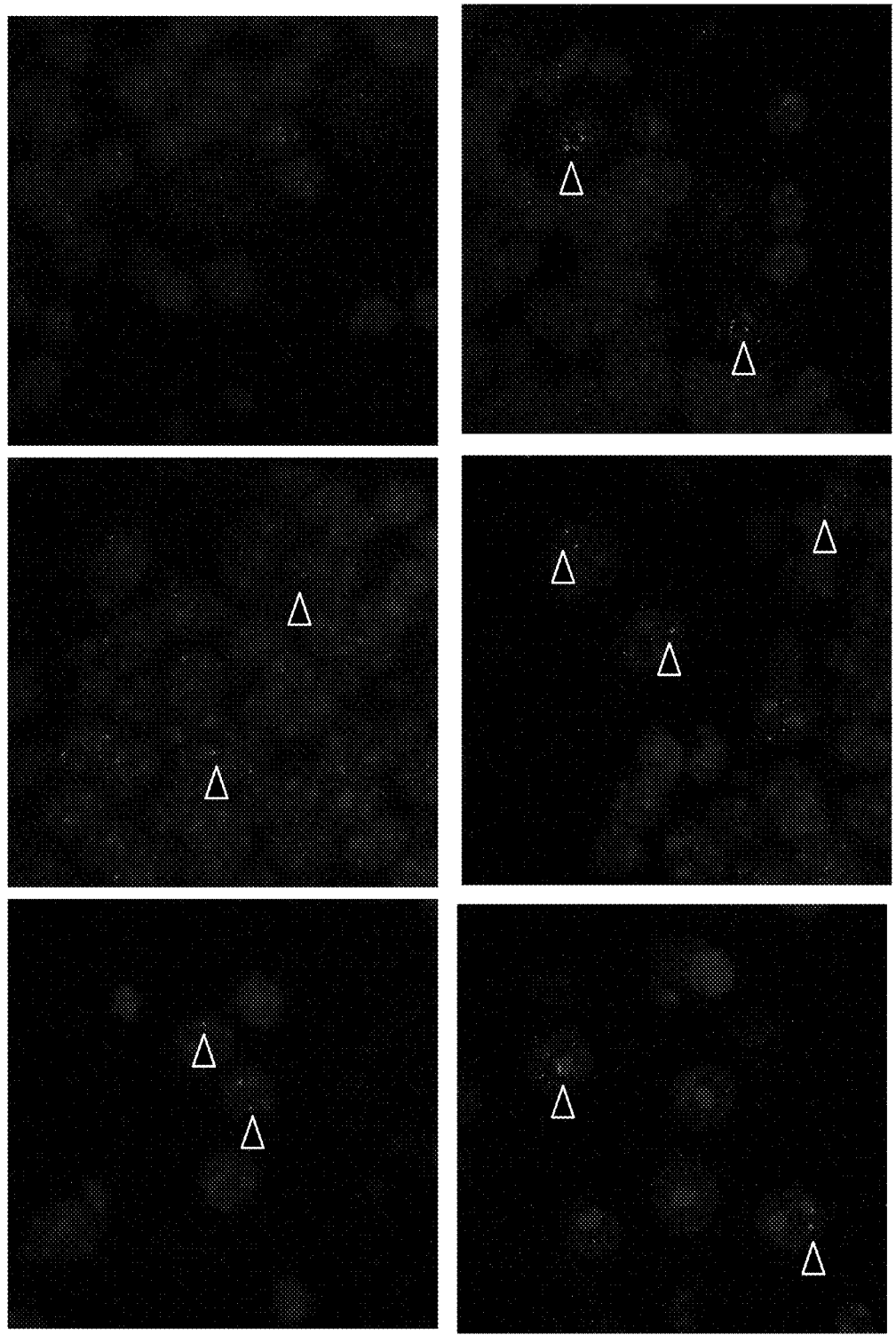
FIG. 31 is a series of photographs showing anti-sense (AS) RNA foci in transgenic mice expressing a human C9ORF72 gene containing GGGGCC repeats. Exemplary foci are indicated by arrowheads.

Approach: BAC clones containing the full human C9ORF72 gene plus flanking sequences were isolated from a human patient with ~800 GGGGCC repeats and inserted into the pCCIBAC™ plasmid (Epicentre®)). The BAC insert chosen for use in the mouse extended from bp27,625,470 to 27,527,137 of human genome reference sequence on Chromosome 9 (FIG. 29). The coordinates above do not include extra repeats from this patient. It was found that the BAC insert DNA contained about 800 repeats in some clone preps but was very unstable. Pronuclear injections were performed and 8 FVB founder lines were generated-2 independent lines which were confirmed expansion mutations. The BAC repeat size in the mice was ~500 repeats but varied between progeny and may grow or shrink in size as the mouse colony is expanded and additional generations of mice are propagated in the laboratory. BAC expansion mice expressed both sense and antisense versions of the C9ORF72 gene. Sense and anti-sense GGGCC RNA foci were present in mice that had the GGGGCC repeats, but not in control mice (FIGS. 30-31).

At least two expansion and two control lines are selected for detailed characterization. Behavioral characterization includes rotorod analysis, grip strength, balance beam and open field assessments. Molecular characterization of sense and antisense transcripts and RAN proteins are performed by RT-PCR, RACE, immunoblot, immunohistochemistry and immunofluorescence. Immunohistochemistry, immunofluorescence and FISH studies are performed to correlate sites of RNA foci and C9-RAN proteins accumulation with pathological changes. RAN-protein accumulation in the CNS, CSF, muscle, blood and other tissues are examined at various times during development.

Relevance: Results from these studies will lead to a better understanding of the role that RAN translation plays in C9ORF72 ALS/FTD. Additionally, these studies will help to prioritize individual protein targets by determining which proteins are found most frequently in autopsy tissue and identifying overt differences in the toxicities of individual RAN proteins. Information from cellular and mouse models will also inform future studies on the effectiveness of various treatment strategies.

REFERENCES

1. DeJesus-Hernandez M, et al. (2011) Expanded GGGGCC hexanucleotide repeat in noncoding region of C9ORF72 causes chromosome 9p-linked FTD and ALS. *Neuron* 72 (2): 245-256.
2. Renton A E, et al. (2011) A hexanucleotide repeat expansion in C9ORF72 is the cause of chromosome 9p21-linked ALS-FTD. *Neuron* 72 (2): 257-268.
3. Majounie E, et al. (2012) Frequency of the C9orf72 hexanucleotide repeat expansion in patients with amyotrophic lateral sclerosis and frontotemporal dementia: a cross-sectional study. *Lancet Neurol* 11 (4): 323-330.
4. Nelson D L, Orr H T, & Warren S T (2013) The unstable repeats—three evolving faces of neurological disease. *Neuron* 77 (5): 825-843.
5. Reddy K, Zamiti B, Stanley S Y, Macgregor R B, Jr., & Pearson C E (2013) The disease-associated r (GGGGCC) n repeat from the C9orf72 gene forms tract length-dependent uni and multimolecular RNA G-quadruplex structures. *J Biol Chem* 288 (14): 9860-9866.
6. Mori K, et al. (2013) hnRNP A3 binds to GGGGCC repeats and is a constituent of p62-positive/TDP43-negative inclusions in the hippocampus of patients with C9orf72 mutations. *Acta Neuropathol* 125 (3): 413-423.
7. Xu Z, et al. (2013) Expanded GGGGCC repeat RNA associated with amyotrophic lateral sclerosis and frontotemporal dementia causes neurodegeneration. *Proc Natl Acad Sci USA* 110 (19): 7778-7783.
8. Almeida S, et al. (2013) Modeling key pathological features of frontotemporal dementia with C9ORF72 repeat expansion in iPSC-derived human neurons. *Acta Neuropathol*.
9. Zu T, et al. (2011) Non-ATG-initiated translation directed by microsatellite expansions. *Proc Natl Acad Sci USA* 108 (1): 260-265.
10. Ash P E. et al. (2013) Unconventional translation of C9ORF72 GGGGCC expansion generates insoluble polypeptides specific to c9FTD/ALS. *Neuron* 77 (4): 639-646.
11. Mori K, et al. (2013) The C9orf72 GGGGCC Repeat Is Translated into Aggregating Dipeptide-Repeat Proteins in FTLD/ALS. *Science*.
12. Todd P K, et al. (2013) CGG repeat-associated translation mediates neurodegeneration in fragile X tremor ataxia syndrome. *Neuron* 78 (3): 440-455.
13. Ash PEA, et al. (2013) Unconventional Translation of C9ORF72 GGGGCC Expansion Generates Insoluble Polypeptides Specific to c9FTD/ALS *Neuron*.
14. Strausberg R L, et al. (2002) Generation and initial analysis of more than 15,000 full-length human and mouse cDNA sequences. *Proc Natl Acad Sci USA* 99 (26): 16899-16903.
15. Venter J C, et al. (2001) The sequence of the human genome. *Science* 291 (5507): 1304-1351.
16. Beausoleil S A, Villen J, Gerber S A, Rush J, & Gygi S P (2006) A probability-based approach for high-throughput protein phosphorylation analysis and site localization. *Nat Biotechnol* 24 (10): 1285-1292.
17. Sopher B L, et al. (2011) CTCF regulates ataxin-7 expression through promotion of a convergently transcribed, antisense noncoding RNA. *Neuron* 70 (6): 1071-1084.
18. Chung D W, Rudnicki D D, Yu L, & Margolis R L (2011) A natural antisense transcript at the Huntington's disease repeat locus regulates HTT expression. *Hum Mol Genet* 20(17): 3467-3477,
19. Wilburn B, et al. (2011) An antisense CAG repeat transcript at JPH3 locus mediates expanded polyglutamine protein toxicity in Huntington's disease-like 2 mice. *Neuron* 70 (3): 427-440.
20. Ladd P D, et al. (2007) An antisense transcript spanning the CGG repeat region of FMRI is upregulated in premutation carriers but silenced in full mutation individuals. *Hum Mol Genet* 16 (24): 3174-3187.
21. Moseley M L, et al. (2006) Bidirectional expression of CUG and CAG expansion transcripts and intranuclear polyglutamine inclusions in spinocerebellar ataxia type 8. *Nat Genet* 38 (7): 758-769.
22. Cho D H, et al. (2005) Antisense transcription and heterochromatin at the DM1 CTG repeats are constrained by CTCF. *Mol Cell* 20 (3): 483-489.
23. Li H, Wyman T, Yu Z X, Li S H, & Li X J (2003) Abnormal association of mutant huntingtin with synaptic vesicles inhibits glutamate release. *Hum Mol Genet* 12 (16): 2021-2030.
24. Luk K C, et al. (2012) Pathological alpha-synuclein transmission initiates Parkinson-like neurodegeneration in nontransgenic mice. *Science* 338 (6109): 949-953.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method of producing an antibody, the method comprising administering to a subject a poly-(Gly-Ala) di-amino acid repeat-containing protein.

2. The method of claim 1, wherein the poly-(Gly-Ala) di-amino acid repeat-containing protein comprises 2-10,000 di-amino acid repeats.

3. The method of claim 1, wherein the poly-(Gly-Ala) di-amino acid repeat-containing protein comprises:
   (i) the amino acid sequence (GA)$_x$WSGRARGRARG-GAAVAVPAPAAAEAQAVASG (SEQ ID NO: 8); or
   (ii) the amino acid sequence (AG)$_x$AWSGRARGRARG-GAAVAVPAPAAAEAQA VASG (SEQ ID NO: 9),
   wherein X represents the number of di-amino acid repeats and is 2-10,000.

4. The method of claim 1, wherein the poly-(Gly-Ala) di-amino acid repeat-containing protein comprises the sequence set forth in SEQ ID NO: 26.

5. The method of claim 1, further comprising the step of isolating the antibody.

6. The method of claim 1, wherein the antibody specifically binds an antigen comprising poly-(Gly-Ala) di-amino acid repeats.

7. The method of claim 1, wherein the antibody specifically binds an antigen comprising a C-terminal sequence of the poly-(Gly-Ala) di-amino acid repeat-containing protein.

8. The method of claim 1, wherein the poly-(Gly-Ala) di-amino acid repeating-containing protein comprises 10-200 di-amino acid repeats.

9. The method of claim 1, wherein the antibody is a polyclonal antibody.

10. The method of claim 1, wherein the antibody is a monoclonal antibody.

11. The method of claim 1, wherein the antibody is a humanized antibody.

12. The method of claim 1, wherein the subject is a mammalian subject.

13. The method of claim 1, wherein the subject is a mouse.

14. The method of claim 1, wherein the subject is a rabbit.

* * * * *